United States Patent
Hartmann et al.

(10) Patent No.: US 9,504,530 B2
(45) Date of Patent: *Nov. 29, 2016

(54) METHOD AND APPARATUS FOR SURGICAL NAVIGATION

(71) Applicant: Medtronic Navigation, Inc., Louisville, CO (US)

(72) Inventors: Steven L. Hartmann, Superior, CO (US); Bruce M. Burg, Louisville, CO (US); Andrew Bzostek, Boulder, CO (US); Matthew W. Koenig, Denver, CO (US); Brad Jacobsen, Erie, CO (US); Bradley A. Jascob, Broomfield, CO (US); Paul Kessman, Lakewood, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 146 days.

This patent is subject to a terminal disclaimer.

(21) Appl. No.: 14/171,346

(22) Filed: Feb. 3, 2014

(65) Prior Publication Data

US 2014/0148692 A1 May 29, 2014

Related U.S. Application Data

(63) Continuation of application No. 12/770,181, filed on Apr. 29, 2010, now Pat. No. 8,644,907, which is a continuation-in-part of application No. 11/247,848, filed on Oct. 11, 2005, now Pat. No. 8,057,407, which (Continued)

(51) Int. Cl.
*A61B 5/05* (2006.01)
*A61B 19/00* (2006.01)

(Continued)

(52) U.S. Cl.
CPC .......... *A61B 19/5244* (2013.01); *A61B 5/062* (2013.01); *A61B 34/20* (2016.02); *A61B 90/39* (2016.02); *A61B 2017/0046* (2013.01); *A61B 2017/00477* (2013.01);

(Continued)

(58) Field of Classification Search
CPC .............. A61B 19/5244; A61B 19/54; A61B 2017/0046; A61B 2017/00477; A61B 2019/5251
See application file for complete search history.

(56) References Cited

U.S. PATENT DOCUMENTS

| 1,576,781 A | 3/1926 | Phillips |
| 1,735,726 A | 11/1929 | Bornhardt |

(Continued)

FOREIGN PATENT DOCUMENTS

| CA | 964149 | 3/1975 |
| DE | 3042343 A1 | 6/1982 |

(Continued)

OTHER PUBLICATIONS

"AxiEM Electromagetic Navigation," tri-fold brochure, Medtronic Navigation (2005) 2 pages.

(Continued)

*Primary Examiner* — Baisakhi Roy
(74) *Attorney, Agent, or Firm* — Harness, Dickey

(57) ABSTRACT

Disclosed is a surgical navigation system for tracking an instrument relative to a patient. The system can track a portion of the patient, an instrument, and/or both relative to image data, a coordinate system, an atlas, a morphed atlas, or combinations thereof. The system can include a tracking device on the instrument to provide six degree of freedom information regarding the location of the instrument.

22 Claims, 49 Drawing Sheets

Related U.S. Application Data is a continuation of application No. 10/289,869, filed on Nov. 7, 2002, now Pat. No. 7,007,699, which is a continuation of application No. 09/428,721, filed on Oct. 28, 1999, now Pat. No. 6,499,488, application No. 14/171,346, which is a continuation of application No. 12/770,181, filed on Apr. 29, 2010, now Pat. No. 8,644,907, which is a continuation-in-part of application No. 11/179,044, filed on Jul. 11, 2005, now Pat. No. 8,239,001, which is a continuation-in-part of application No. 10/941,782, filed on Sep. 15, 2004, now Pat. No. 7,751,865, which is a continuation-in-part of application No. 10/688,068, filed on Oct. 17, 2003, now Pat. No. 7,366,562.

(51) Int. Cl.
*A61B 5/06* (2006.01)
*A61B 17/00* (2006.01)

(52) U.S. Cl.
CPC ............. *A61B 2034/2051* (2016.02); *A61B 2034/2068* (2016.02); *A61B 2034/2072* (2016.02); *A61B 2090/3983* (2016.02); *A61B 2090/3987* (2016.02)

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Zehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,150 A | 5/1971 | Alden |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,445,106 A | 4/1984 | Shah |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,671,287 A | 6/1987 | Fiddian-Green |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |

(56) References Cited

U.S. PATENT DOCUMENTS

| | | |
|---|---|---|
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,226,423 A | 7/1993 | Tenerz et al. |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,403,321 A | 4/1995 | DiMarco |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |

(56) References Cited

U.S. PATENT DOCUMENTS

| | | |
|---|---|---|
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,484,437 A | 1/1996 | Michelson |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,581 A | 10/1996 | Smale et al. |
| 5,566,681 A | 10/1996 | Manwaring et al. |
| 5,568,384 A | 10/1996 | Robb et al. |
| 5,568,809 A | 10/1996 | Ben-haim |
| 5,571,109 A | 11/1996 | Bertagnoli |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,632,432 A | 5/1997 | Schulze et al. |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,772,661 A | 6/1998 | Michelson |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |

(56) References Cited

U.S. PATENT DOCUMENTS

| | | |
|---|---|---|
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,868,789 A | 2/1999 | Huebner |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,930,741 A | 7/1999 | Kramer |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,002,378 A | 12/1999 | Harada et al. |
| 6,006,126 A | 12/1999 | Cosman |
| 6,006,127 A | 12/1999 | Van Der Brug et al. |
| 6,011,987 A | 1/2000 | Barnett |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,021,343 A | 2/2000 | Foley et al. |
| 6,024,408 A | 2/2000 | Bello et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,063,031 A | 5/2000 | Cundari et al. |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,106,464 A | 8/2000 | Bass et al. |
| 6,106,486 A | 8/2000 | Tenerz et al. |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,173,199 B1 | 1/2001 | Gabriel |
| 6,175,756 B1 | 1/2001 | Ferre et al. |
| 6,178,345 B1 | 1/2001 | Vilsmeier et al. |
| 6,190,330 B1 | 2/2001 | Harhen |
| 6,194,639 B1 | 2/2001 | Botella et al. |
| 6,201,387 B1 | 3/2001 | Govari |
| 6,203,497 B1 | 3/2001 | Dekel et al. |
| 6,211,666 B1 | 4/2001 | Acker |
| 6,223,067 B1 | 4/2001 | Vilsmeier et al. |
| 6,226,548 B1 | 5/2001 | Foley et al. |
| 6,233,476 B1 * | 5/2001 | Strommer ............ A61B 5/0066 600/424 |
| 6,236,875 B1 | 5/2001 | Bucholz et al. |
| 6,246,231 B1 | 6/2001 | Ashe |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,304,769 B1 | 10/2001 | Arenson et al. |
| 6,314,310 B1 | 11/2001 | Ben-Haim et al. |
| 6,332,089 B1 | 12/2001 | Acker et al. |
| 6,336,906 B1 | 1/2002 | Hammarstrom et al. |
| 6,341,231 B1 | 1/2002 | Ferre et al. |
| 6,347,240 B1 | 2/2002 | Foley et al. |
| 6,348,058 B1 | 2/2002 | Melkent et al. |
| 6,351,659 B1 | 2/2002 | Vilsmeier |
| 6,370,411 B1 | 4/2002 | Osadchy et al. |
| 6,381,485 B1 | 4/2002 | Hunter et al. |
| 6,424,856 B1 | 7/2002 | Vilsmeier et al. |
| 6,427,079 B1 | 7/2002 | Schneider et al. |
| 6,427,314 B1 | 8/2002 | Acker |
| 6,428,547 B1 | 8/2002 | Vilsmeier et al. |
| 6,432,041 B1 | 8/2002 | Taniguchi et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,447,448 B1 | 9/2002 | Ishikawa et al. |
| 6,447,488 B2 | 9/2002 | Estabrook et al. |
| 6,468,265 B1 | 10/2002 | Evans et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,491,699 B1 | 12/2002 | Henderson et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,551,325 B2 | 4/2003 | Neubauer et al. |
| 6,572,624 B2 | 6/2003 | U et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,694,162 B2 | 2/2004 | Hartlep |
| 6,701,179 B1 | 3/2004 | Martinelli et al. |
| 6,796,963 B2 | 9/2004 | Carpenter et al. |
| 6,926,674 B2 | 8/2005 | Tenerz et al. |
| 6,951,549 B1 | 10/2005 | Beyerlein |
| 6,977,575 B2 | 12/2005 | Bernier |
| 7,007,699 B2 | 3/2006 | Martinelli et al. |
| 7,152,608 B2 | 12/2006 | Hunter et al. |
| 7,366,562 B2 | 4/2008 | Dukesherer et al. |
| 7,697,972 B2 | 4/2010 | Verard et al. |
| 7,751,865 B2 | 7/2010 | Jascob et al. |
| 7,818,044 B2 | 10/2010 | Dukesherer et al. |
| 7,840,253 B2 | 11/2010 | Tremblay et al. |
| 7,966,057 B2 | 6/2011 | Macaulay et al. |
| 7,971,341 B2 | 7/2011 | Dukesherer et al. |
| 8,057,407 B2 | 11/2011 | Martinelli et al. |

(56) References Cited

U.S. PATENT DOCUMENTS

| | | |
|---|---|---|
| 8,239,001 B2 | 8/2012 | Verard et al. |
| 8,271,069 B2 | 9/2012 | Jascob et al. |
| 8,359,730 B2 | 1/2013 | Burg et al. |
| 8,549,732 B2 | 10/2013 | Burg et al. |
| 8,644,907 B2* | 2/2014 | Hartmann .......... A61B 19/5244 600/424 |
| 2001/0007918 A1 | 7/2001 | Vilsmeier et al. |
| 2001/0044578 A1 | 11/2001 | Ben-Haim et al. |
| 2002/0087101 A1 | 7/2002 | Barrick et al. |
| 2002/0095081 A1 | 7/2002 | Vilsmeier |
| 2002/0147497 A1 | 10/2002 | Belef et al. |
| 2003/0009169 A1 | 1/2003 | Young et al. |
| 2003/0066538 A1 | 4/2003 | Martinelli et al. |
| 2003/0069588 A1 | 4/2003 | Vilsmeier et al. |
| 2003/0078003 A1 | 4/2003 | Hunter et al. |
| 2003/0097061 A1 | 5/2003 | Ferre et al. |
| 2003/0114778 A1 | 6/2003 | Vilsmeier et al. |
| 2003/0184285 A1 | 10/2003 | Anderson et al. |
| 2003/0187347 A1 | 10/2003 | Nevo et al. |
| 2004/0024309 A1 | 2/2004 | Ferre et al. |
| 2004/0097805 A1 | 5/2004 | Verard et al. |
| 2004/0199071 A1 | 10/2004 | Lardo et al. |
| 2004/0215071 A1 | 10/2004 | Frank et al. |
| 2005/0075632 A1 | 4/2005 | Russell et al. |
| 2005/0085715 A1 | 4/2005 | Dukesherer et al. |
| 2005/0085720 A1 | 4/2005 | Jascob et al. |
| 2005/0105212 A1 | 5/2005 | Sato |
| 2005/0107882 A1 | 5/2005 | Stone et al. |
| 2005/0215887 A1 | 9/2005 | Ben-Haim et al. |
| 2005/0245817 A1 | 11/2005 | Clayton et al. |
| 2006/0025677 A1 | 2/2006 | Verard et al. |
| 2006/0036189 A1 | 2/2006 | Martinelli et al. |
| 2006/0084867 A1 | 4/2006 | Tremblay et al. |
| 2007/0016006 A1 | 1/2007 | Shachar |
| 2007/0052507 A1* | 3/2007 | Zaitsu ................ G01R 33/3815 335/216 |
| 2008/0171937 A1 | 7/2008 | Dukesherer et al. |
| 2008/0172069 A1 | 7/2008 | Dukesherer et al. |
| 2009/0264863 A1* | 10/2009 | Bloom .............. A61M 25/0054 604/524 |
| 2009/0290771 A1 | 11/2009 | Frank et al. |
| 2010/0210939 A1 | 8/2010 | Hartmann et al. |
| 2010/0274124 A1 | 10/2010 | Jascob et al. |
| 2010/0312096 A1* | 12/2010 | Guttman ................ A61B 5/418 600/411 |
| 2011/0160568 A1* | 6/2011 | Seeley ................ A61B 19/5244 600/424 |
| 2011/0258842 A1 | 10/2011 | Dukesherer et al. |
| 2011/0258843 A1 | 10/2011 | Dukesherer et al. |
| 2012/0310080 A1* | 12/2012 | Cunningham ......... A61B 5/055 600/423 |

FOREIGN PATENT DOCUMENTS

| | | |
|---|---|---|
| DE | 3508730 | 9/1986 |
| DE | 3717871 | 12/1988 |
| DE | 3831278 A1 | 3/1989 |
| DE | 3838011 | 7/1989 |
| DE | 4213426 A1 | 10/1992 |
| DE | 4225112 C1 | 12/1993 |
| DE | 4233978 C1 | 4/1994 |
| DE | 19631303 | 2/1998 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 | 11/2002 |
| DE | 20311919 U1 | 10/2003 |
| DE | 10335388 | 2/2005 |
| EP | 0062941 | 10/1982 |
| EP | 0119660 | 9/1984 |
| EP | 0155857 A2 | 9/1985 |
| EP | 0319844 A1 | 6/1989 |
| EP | 0326768 | 8/1989 |
| EP | 0350996 A1 | 1/1990 |
| EP | 0419729 A1 | 4/1991 |
| EP | 0427358 | 5/1991 |
| EP | 0456103 | 11/1991 |
| EP | 0469966 A1 | 2/1992 |
| EP | 0581704 | 2/1994 |
| EP | 0651968 | 5/1995 |
| EP | 0655138 | 5/1995 |
| EP | 0894473 A2 | 2/1999 |
| EP | 0908146 | 4/1999 |
| EP | 0930046 | 7/1999 |
| EP | 1523951 | 4/2005 |
| FR | 2417970 | 9/1979 |
| FR | 2618211 B1 | 11/1991 |
| GB | 2094590 | 9/1982 |
| GB | 2164856 A | 4/1986 |
| JP | 62327 | 6/1983 |
| JP | 61-94639 A | 10/1984 |
| JP | 63240851 A | 10/1988 |
| JP | 2765738 T | 4/1991 |
| JP | 3267054 | 11/1991 |
| WO | WO-8809151 | 12/1988 |
| WO | WO-8905123 A1 | 6/1989 |
| WO | WO-9005494 A1 | 5/1990 |
| WO | WO-9103982 | 4/1991 |
| WO | WO-9104711 | 4/1991 |
| WO | WO-9107726 A1 | 5/1991 |
| WO | WO-9203090 | 3/1992 |
| WO | WO-9206645 A1 | 4/1992 |
| WO | WO-9404938 A1 | 3/1994 |
| WO | WO-9423647 | 10/1994 |
| WO | WO-9424933 | 11/1994 |
| WO | WO-9507055 | 3/1995 |
| WO | WO-96/05768 | 2/1996 |
| WO | WO-9611624 A2 | 4/1996 |
| WO | WO-9632059 A1 | 10/1996 |
| WO | WO-9632060 A1 | 10/1996 |
| WO | WO-9729684 A1 | 8/1997 |
| WO | WO-9729710 A1 | 8/1997 |
| WO | WO-9736192 A1 | 10/1997 |
| WO | WO-9749453 A1 | 12/1997 |
| WO | WO-9808554 | 3/1998 |
| WO | WO-9838908 | 9/1998 |
| WO | WO-9915097 | 4/1999 |
| WO | WO-9921498 A1 | 5/1999 |
| WO | WO-9923956 | 5/1999 |
| WO | WO-9926549 | 6/1999 |
| WO | WO-9929253 | 6/1999 |
| WO | WO-9933406 | 7/1999 |
| WO | WO-9937208 A1 | 7/1999 |
| WO | WO-9938449 | 8/1999 |
| WO | WO-99/27839 A9 | 10/1999 |
| WO | WO-9952094 | 10/1999 |
| WO | WO-9960939 | 12/1999 |
| WO | WO-0130257 | 5/2001 |
| WO | WO-0130437 | 5/2001 |
| WO | WO-03002012 A1 | 1/2003 |

OTHER PUBLICATIONS

"Prestige Cervical Disc System Surgical Technique", 12 pgs., undated.

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

(56) References Cited

OTHER PUBLICATIONS

Benzel et al., "Magnetic Source Imaging: a Review of the Magnes System of Biomagnetic Technologies Incorporated," Neurosurgery, vol. 33, No. 2 (Aug. 1993), pp. 252-259.
Bergstrom et al. Stereotaxic Computed Tomography, Am. J. Roentgenol, vol. 127 pp. 167-170 (1976).
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Brown, R., M.D., A Stereotactic Head Frame for Use with CT Body Scanners, Investigative Radiology .Copyrgt. J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure [Mar. 1997] (2 pages).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical RoboticsandComputer-Assisted Surgery, Grenoble, France, pp. 459-466 (Mar. 19-22, 1997).
Champleboux et al., "Accurate Calibration of Cameras and Range Imaging Sensors: the NPBS Method," IEEE International Conference on Robotics and Automation, Nice, France, May 1992.
Champleboux, "Utilisation de Fonctions Splines pour la Mise au Point D'un Capteur Tridimensionnal sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Cutting M.D. et al., Optical Tracking of Bone Fragments During Craniofacial Surgery, Second Annual International Symposium on Medical Robotics and Computer Assisted Surgery, pp. 221-225, (Nov. 1995).
European Office Action mailed Nov. 24, 2010 for EP1523951 claiming benefit of U.S. Appl. No. 10/688,068, filed Oct. 17, 2003 and U.S. Appl. No. 10/941,782, filed Sep. 15, 2004.
European Search Report completed Jul. 6, 2005 for European Application No. EP 04 02 4680.
European Search Report mailed Feb. 23, 2011 for EP10183063 which claims benefit of European Serial No. 040246803 filed Oct. 15, 2004; which claims benefit of U.S. Appl. No. 10/941,782, filed Sep. 15, 2004 and U.S. Appl. No. 10/688,068, filed Oct. 17, 2003.
European Search Report mailed Nov. 29, 2010 for European Application No. EP10183187 claiming benefit of EPSN 040246803, filed Oct. 15, 2004; which claims benefit of U.S. Appl. No. 10/941,782, filed Sep. 15, 2004; which claims benefit of U.S. Appl. No. 10/688,068, filed Oct. 17, 2003.
European Search Report mailed Nov. 29, 2010 for European Application No. EP10183240 claiming benefit of EPSN 04024680.3, filed Oct. 15, 2004; which claims benefit of U.S. Appl. No. 10/941,782, filed Sep. 15, 2004; which claims benefit of U.S. Appl. No. 10/688,068, filed Oct. 17, 2003.
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Galloway, R.L., Jr. et al, Optical localization for interactive image-guided neurosurgery, SPIE, vol. 2164, pp. 137-145 (undated, the date is May 1, 1994.
German Office Action mailed Jan. 5, 2009 for German Publication No. 100851371 claiming benefit of PCT/US00/29880, filed Oct. 27, 2000; which claims priority of U.S. Appl. No. 09/428,721, filed Oct. 28, 1999.
Germano, "Instrumentation, Technique and Technology", Neurosurgery, vol. 37, No. 2, Aug. 1995, pp. 348-350.
Gildenberg et al., "Calculation of Stereotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. 1996, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).
Gueziec et al., "Registration of Computed Tomography Data to a Surgical Robot Using Fluoroscopy: A Feasibility Study," Computer Science/Mathematics, Sep. 27, 1996, 6 pages.
Guthrie, B.L., Graphic-Interactive Cranial Surgery: The Operating Ann System, Handbook of Stereotaxy Using the CRW Apparatus, Chapter 13, pp. 193-211, undated.
Hamadeh et al, "Kinematic Study of Lumbar Spine Using Functional Radiographies and 3D/2D Registration," TIMC UMR 5525-IMAG (1997).
Hamadeh et al., "Automated 3-Dimensional Computed Tomograhic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, "Reference-Display System for the Integration of CT Scanning and the Operating Microscope," Thesis, Thayer School of Engineering, Oct. 1984, pp. 1-189.

(56) References Cited

OTHER PUBLICATIONS

Hatch, et al., "Reference-Display System for the Integration of CT Scanning and the Operating Microscope", Proceedings of the Eleventh Annual Northeast Bioengineering Conference, Mar. 14-15, 1985, pp. 252-254.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Homer et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
International Preliminary Examination Report mailed Dec. 28, 2001 for PCT/US00/29880 filed Oct. 27, 2000 claiming benefit of U.S. Appl. No. 09/428,721, filed Oct. 28, 1999.
International Search Report and Written Opinion mailed Jul. 19, 2011 for PCT/US2011/033163 claiming benefit of U.S. Appl. No. 12/770,181, filed Apr. 29, 2010.
International Search Report mailed Feb. 26, 2001 for PCT/US00/29880 filed Oct. 27, 2000 claiming benefit of U.S. Appl. No. 09/428,721, filed Oct. 28, 1999.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kall, B., The Impact of Computer and Imgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, pp. 635-638 (undated), 1996.
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique for Accurate Transpedicular Screw Fixation Using CT Data and a 3-D Optical Localizer," TIMC, Faculte de Medecine de Grenoble (1995).
Lavallee et al., "Image guided operating robot: a clinical application in stereotactic neurosurgery," Proceedings of the 1992 IEEE Internation Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, "VI Adaption de la Methodologie a Quelques Applications Cliniques," Chapitre VI, pp. 133-148, undated.
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, Jr., et al, Registration of Head CT Images to Physical Space Using a Weighted Combination of Points and Surfaces, IEEE Trans. on Med. Imaging, vol. 17, No. 5, pp. 753-761 (Oct. 1998).

(56) References Cited

OTHER PUBLICATIONS

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Medtronic Navigation, "StealthStation.RTM. AXIEM.TM. Electromagnetic Navigation . . . ", 2005, www.stealthstation.com/physician/spine/library/axiem.sub.--ent.jsp, printed Aug. 19, 2006 (2 pages).

Merloz, et al., "Computer Assisted Spine Surgery", Clinical Assisted Spine Surgery, No. 337, pp. 86-96, 1997.

Ng, W.S. et al., Robotic Surgery—A First-Hand Experience in Transurethral Resection of the Prostate Surgery, IEEE Eng. in Med. and Biology, pp. 120-125 (Mar. 1993).

Partial European Search Report completed Mar. 16, 2005 for European Application No. EP 04 02 4680.

Partial European Search Report completed Nov. 26, 2007 for European Application No. EP 06 11 6892.

Partial European Search Report completed Nov. 8, 2006 for European Application No. EP 06 11 6892.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 133-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989. (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, Hans. F., Neuronavigation: A Ten-Year Review, Neurosurgery, pp. 329-341, (1996).

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS 1995, pp. 185-192.

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

The Laitinen Stereotactic System, E2-E6, undated.

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," pp. 119-128, undated.

Written Opinion mailed Aug. 14, 2001 for PCT/US00/29880 filed Oct. 27, 2000 claiming benefit of U.S. Appl. No. 09/428,721, filed Oct. 28, 1999.

\* cited by examiner

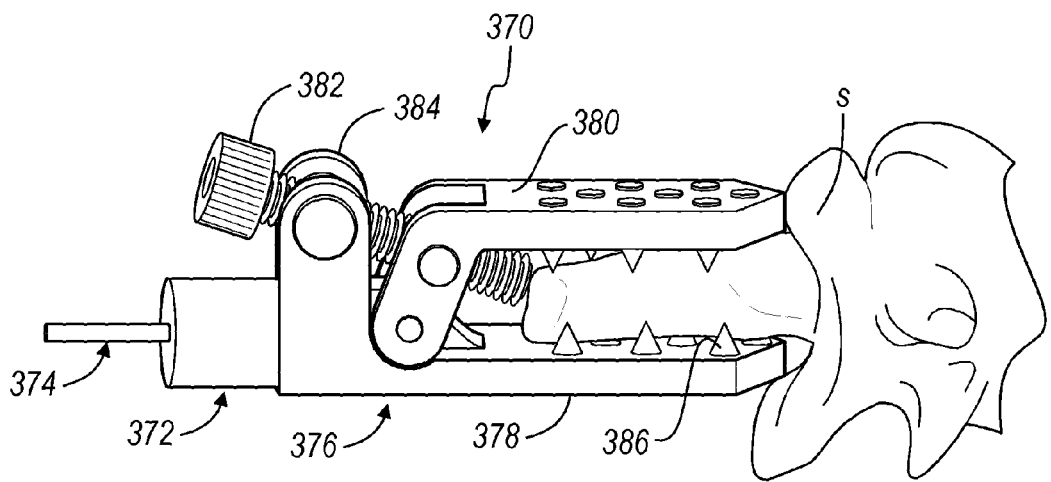
FIG. 20
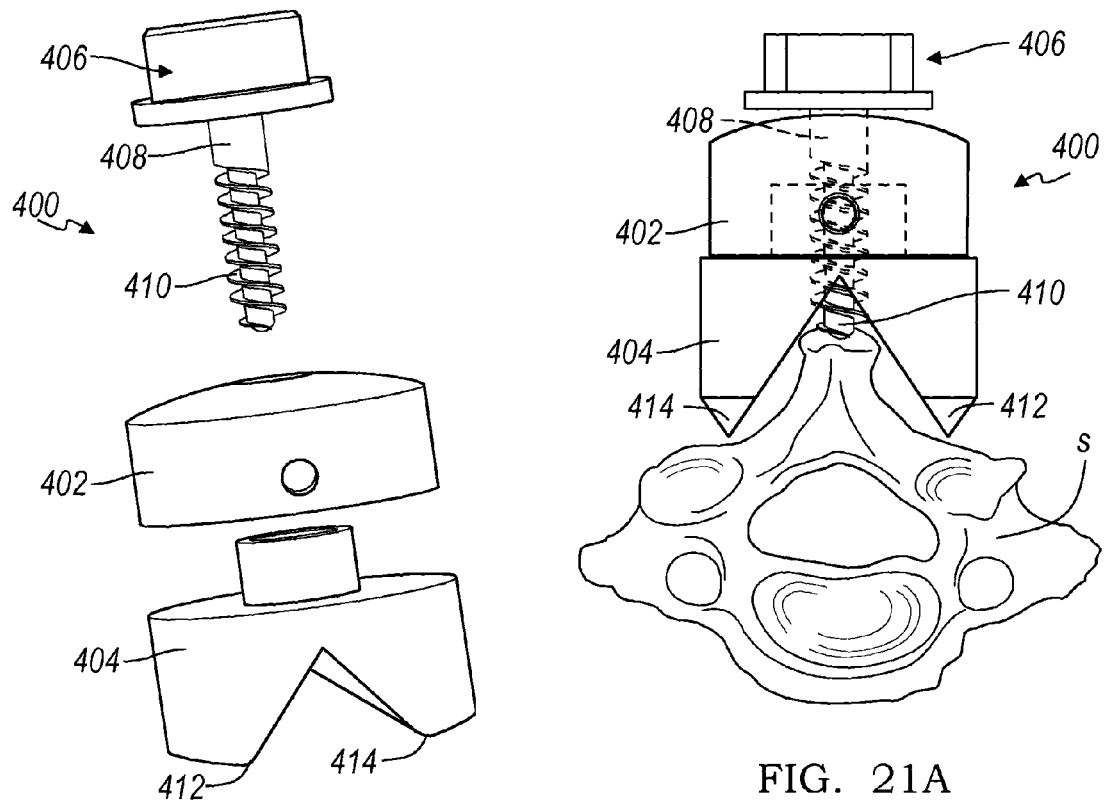
FIG. 21
FIG. 21A

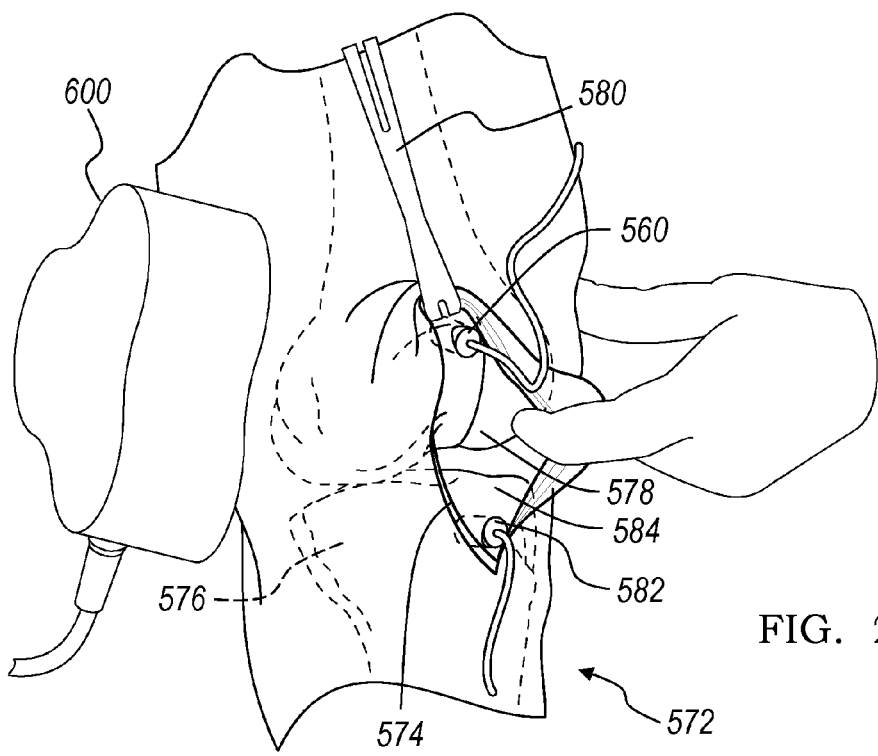
FIG. 28D
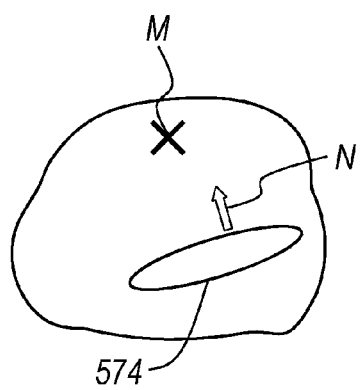
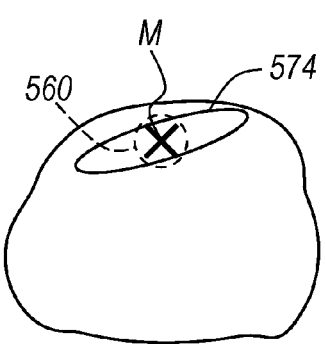
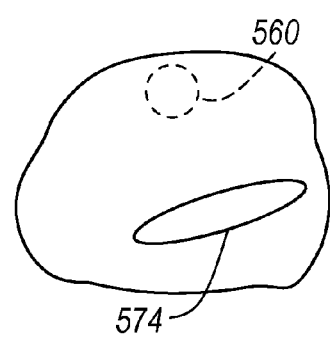
FIG. 28A     FIG. 28B     FIG. 28C

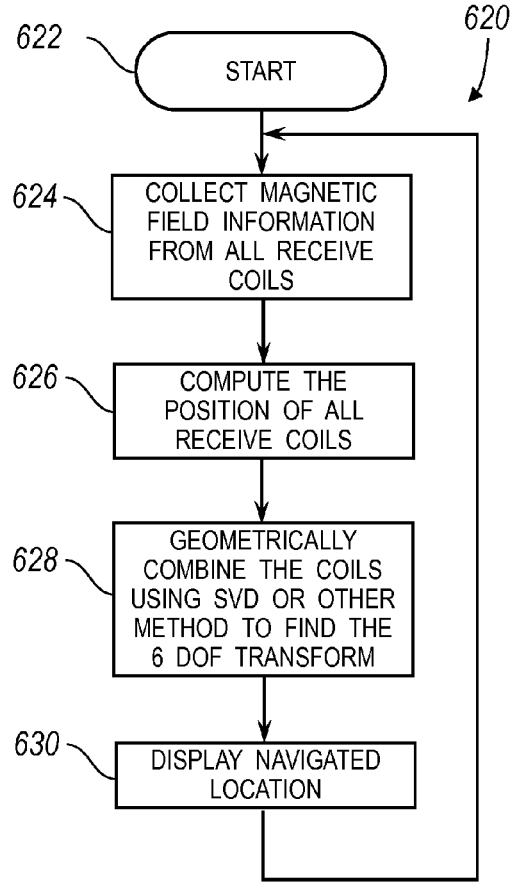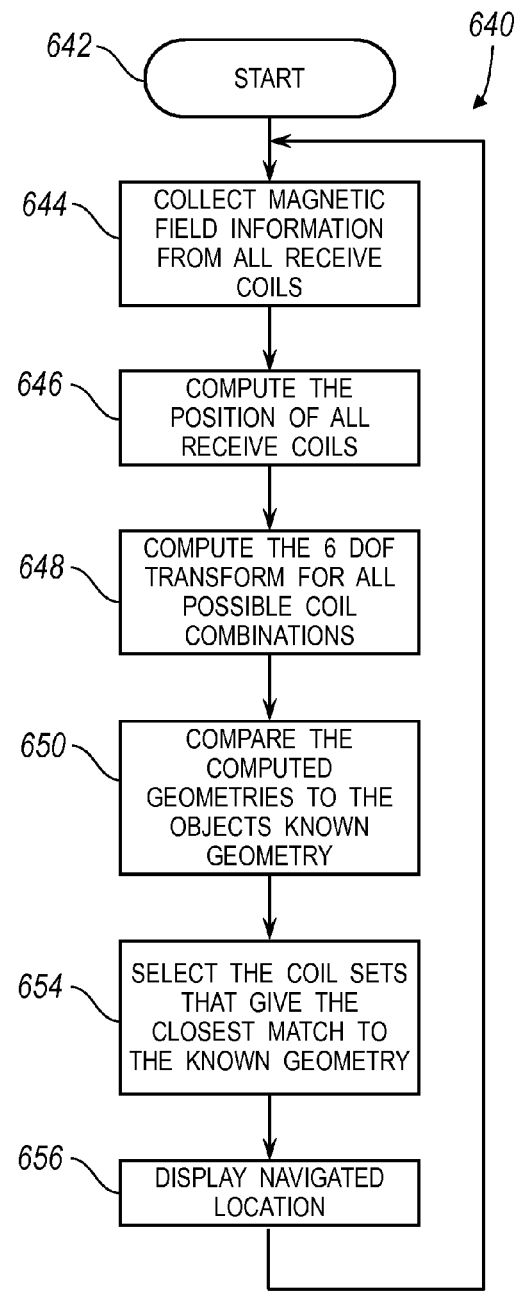
FIG. 31
FIG. 32

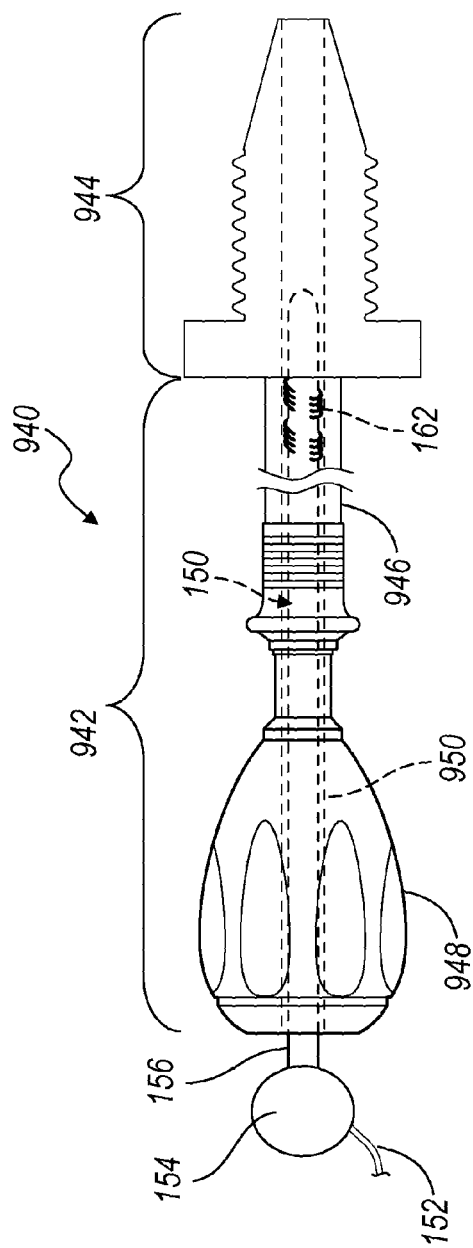
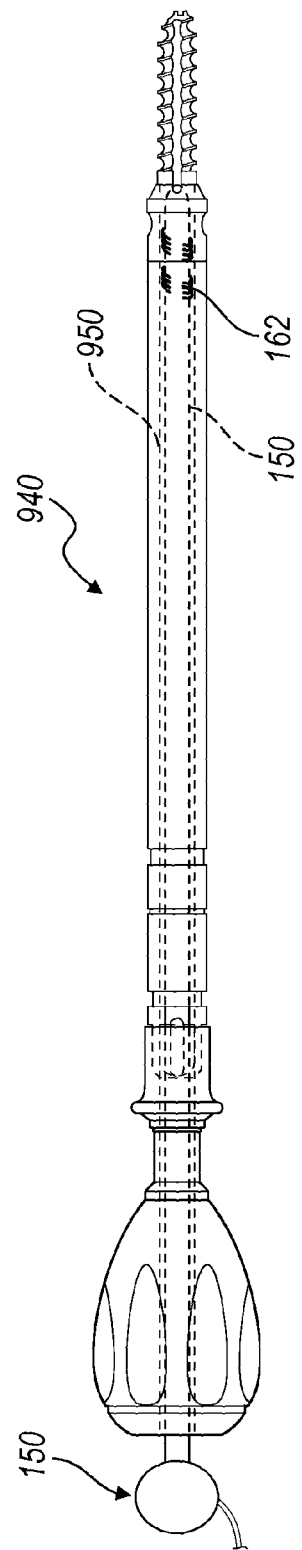
FIG. 37
FIG. 38

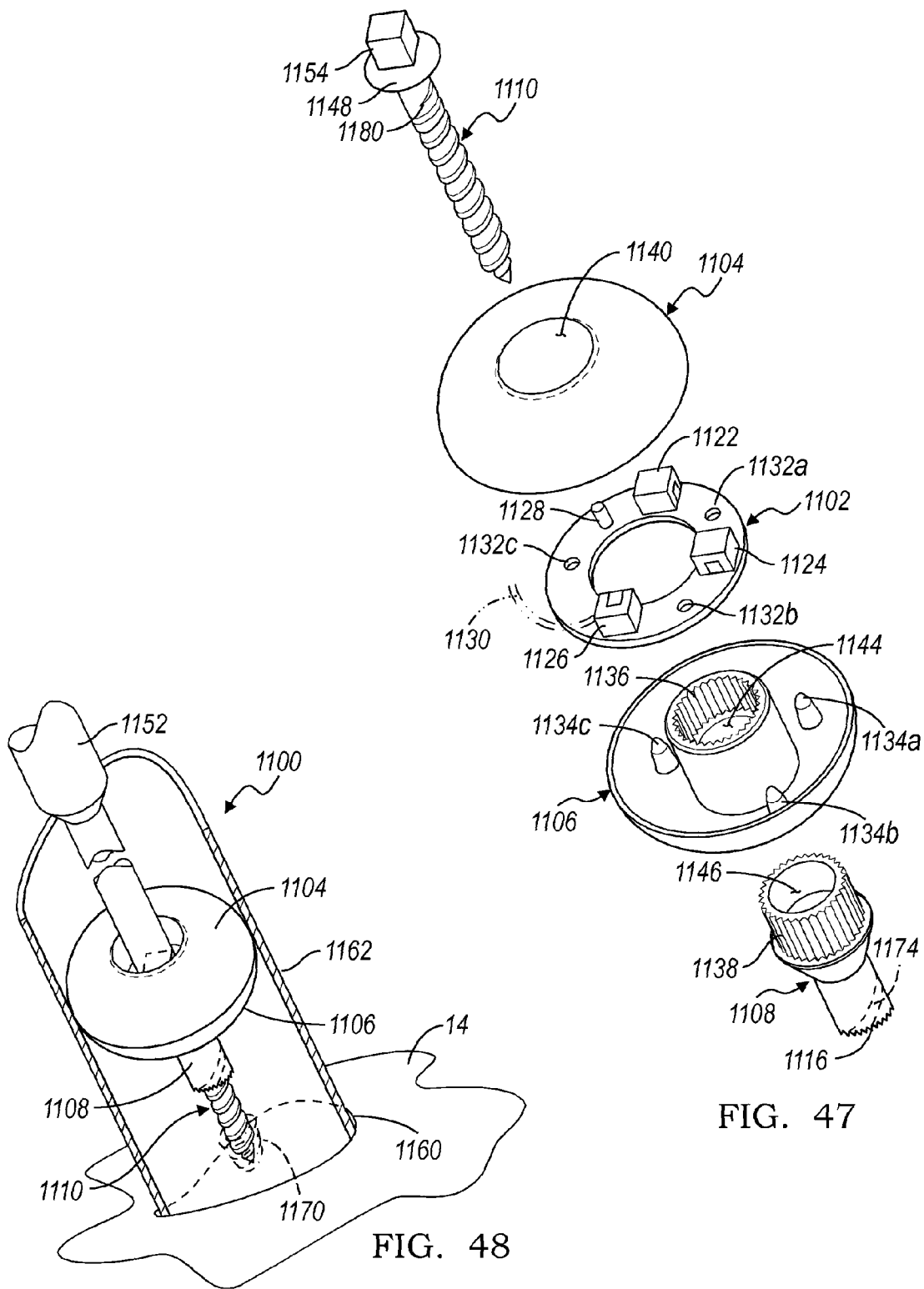

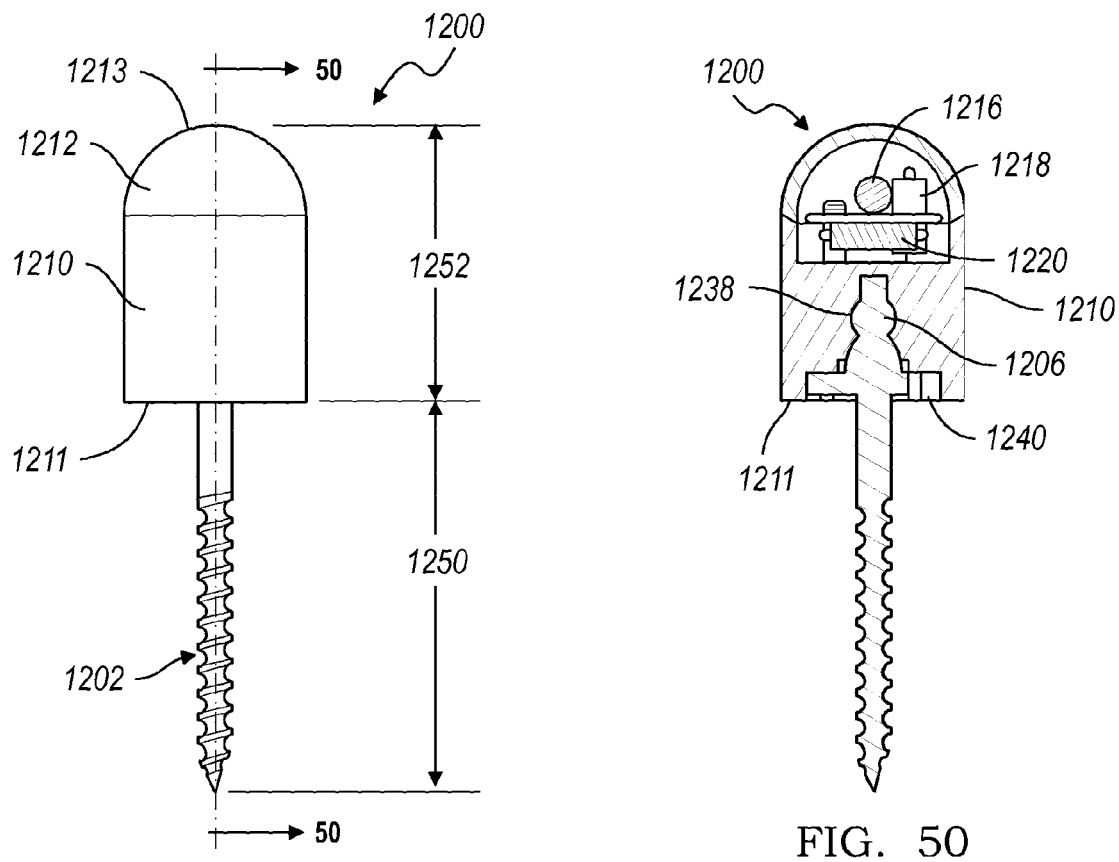
FIG. 49
FIG. 50
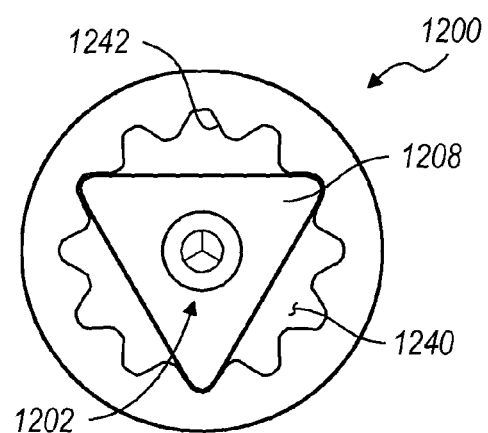
FIG. 51

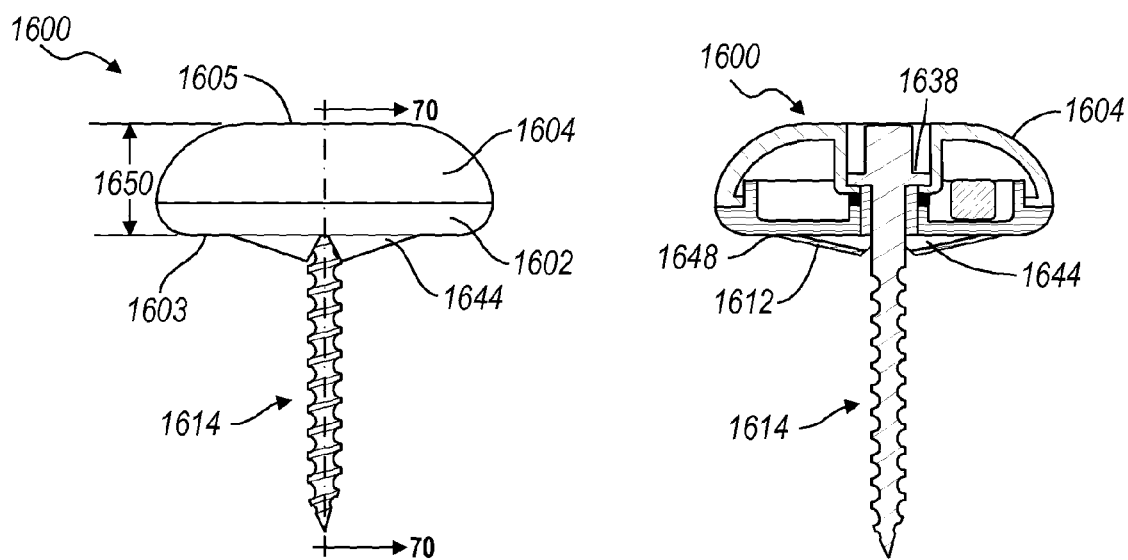
FIG. 69
FIG. 70
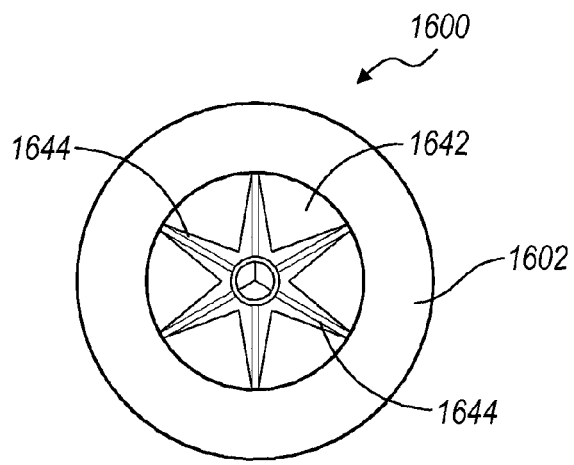
FIG. 71

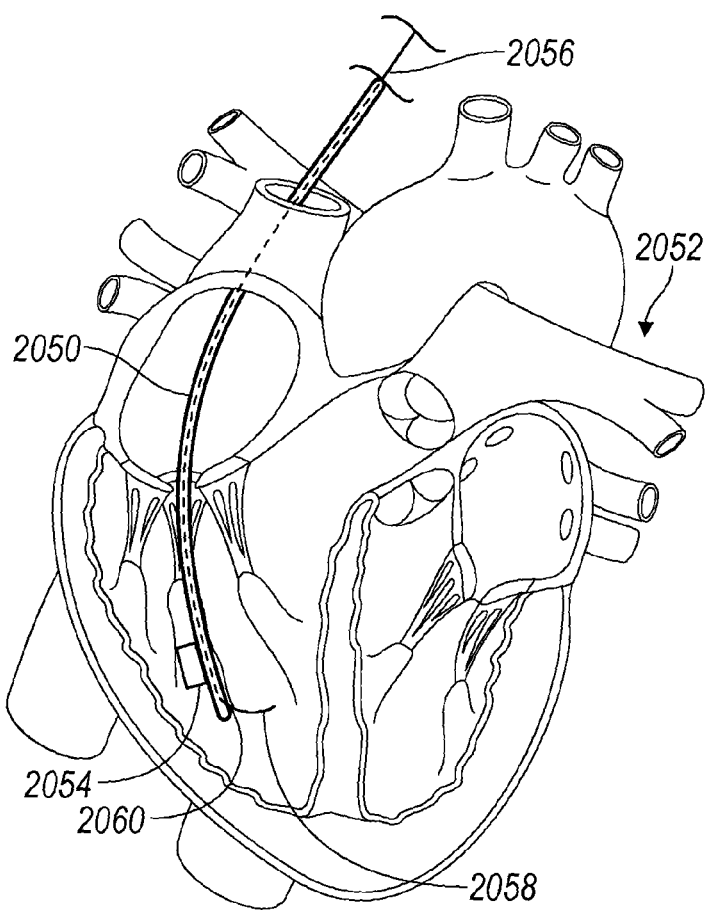
FIG. 92
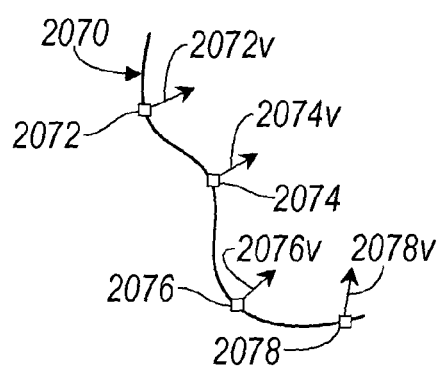
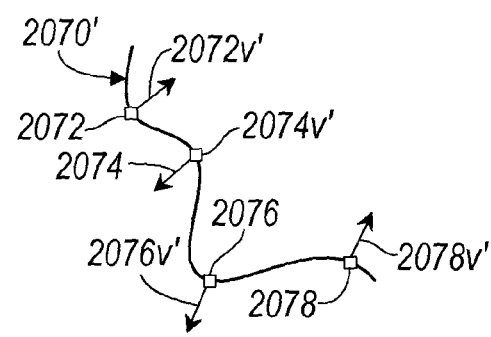
FIG. 93A                    FIG. 93B

METHOD AND APPARATUS FOR SURGICAL NAVIGATION

CROSS-REFERENCE TO RELATED APPLICATIONS

This application is a continuation of U.S. patent application Ser. No. 12/770,181 filed on Apr. 29, 2010, which is a continuation-in-part of U.S. patent application Ser. No. 11/247,848 filed on Oct. 11, 2005, now U.S. Pat. No. 8,057,407 filed on Nov. 15, 2011, which is a continuation of U.S. patent application Ser. No. 10/289,869 filed on Nov. 7, 2002, now U.S. Pat. No. 7,007,699 issued on Mar. 7, 2006, which is a continuation of U.S. patent application Ser. No. 09/428,721 filed on Oct. 28, 1999, now U.S. Pat. No. 6,499,488 issued on Dec. 31, 2002. The disclosures of the above applications are incorporated herein by reference.

This application is a continuation of U.S. patent application Ser. No. 12/770,181 filed on Apr. 29, 2010, which is also a continuation-in-part of U.S. patent application Ser. No. 11/179,044 filed on Jul. 11, 2005, now U.S. Pat. No. 8,239,001 issued on Aug. 7, 2012, which is a continuation-in-part of U.S. patent application Ser. No. 10/941,782 filed on Sep. 15, 2005, now U.S. Pat. No. 7,751,865 issued on Jul. 6, 2010, which is a continuation-in-part of U.S. patent application Ser. No. 10/688,068 filed on Oct. 17, 2003, now U.S. Pat. No. 7,366,562 issued on Apr. 29, 2008. The disclosures of the above applications are incorporated herein by reference.

FIELD

The present teachings relate generally to navigated surgery, and more specifically, to systems and methods for using instruments and systems to assist in navigating surgical procedures in internal body structures.

BACKGROUND

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in image guided medical procedures.

Typical image guided navigation systems generally require dynamic reference frames to track the position of the patient should patient movement occur during the assisted procedure. The dynamic reference frame is generally affixed to the patient in a generally permanent or immovable fashion. The dynamic reference frame may also be used as a fiducial marker and may, therefore, be attached to the patient during the acquisition of pre-operative images. This enables the image space to be aligned with patient space during the navigated procedure. For example, with relation to a cranial procedure, the dynamic reference frame can be attached to the skull by a bone screw. For other procedures the dynamic reference frame may be fixed to other boney portions also with bone screws. Regardless, the dynamic reference frame may include a portion that is fixed to the patient during the acquisition of the pre-operative images and remains attached until the procedure is complete to insure proper and accurate correlation between image space and patient space. Requiring that the dynamic reference frame be attached to the patient during the time that the pre-acquired images are acquired until the procedure actually takes place may be uncomfortable.

The dynamic reference frame may, then be used to assure that images of a patient, such as pre-acquired or atlas images, may be registered to the patient space. Generally this registration also allows for tracking of various instruments during a procedure. The tracked instruments will generally include portions that may be tracked and superimposed over acquired or modeled images of the patient.

Various instruments may be used during an operative procedure that are desired to be tracked. Even if images are acquired, either intra-operatively or pre-operatively, the instrument is generally illustrated, and superimposed on the captured image data to identify the position of the instrument relative to the patient space. Therefore, the instrument may include detectable portions, such as electromagnetic coils or optical detection points, such as LEDs or reflectors, that may be detected by a suitable navigation system.

Size considerations generally make it difficult to position the tracking sensors near a portion of the instrument to be positioned within the patient, such as the distal tip. Because of this, the tracking sensors are generally positioned within the handle of the instrument. Therefore, complex calculations and a degree of error may exist to determine the exact position of a distal end of the instrument relative to the position of the detectable sensors. Also the instruments may flex unexpectedly so that the known dimensions are no longer true dimensions of the instrument. Therefore, it may be desirable to provide sensors substantially near the distal tip or end of an instrument positioned within a patient.

The tracking of various sensor portions, such as electromagnetic coils, may require the transmission of a current or a voltage to or from the sensors. Therefore, an electrical potential is provided to an instrument that is often positioned within a portion of the patient's anatomy, which may include various portions such as the cardiac area, neurological area, and other areas of the patient. In order to provide separation of these potentials from the patient, it may also be desirable to isolate the potentials from the patient.

SUMMARY

An instrument can be tracked during a procedure, such as a surgical procedure. The instrument, because it is tracked, can be illustrated on a display device with image data for illustrating the location of the instrument. The location of the instrument can include both its 3-dimensional position (x,y, z) and its 3 degrees of orientation (yaw, pitch, and roll). These six variables can provide 6 degree of freedom information regarding the position and orientation (herein referred together as location) of the instrument. This can be achieved by providing one or more tracking devices on a long instrument wherein the navigated orientation of the tracking device is at an angle to the shaft around which it is round, which is also at an angle to the tracking device's long axis.

A surgical navigation system for navigating a region of a patient includes a non-invasive dynamic reference frame and/or fiducial marker, sensor tipped instruments, and isolator circuits. The dynamic reference frame may be repeatably placed on the patient in a non-invasive manner and in a precise location for guiding the instruments. The instruments may be precisely guided by positioning sensors near moveable portions of the instruments. The patient may be electrically isolated from various sources of current during the procedure.

According to various embodiments a surgical navigation system includes a method of forming an electromagnetic sensing coil in a medical instrument. The method may include forming a core of a conductive material and forming a coil about the core. The core is covered with a first layer of a material and a second layer of a material may also cover the core, and at least part of the first layer. The coil may be substantially electrically isolated from the core.

According to various embodiments a surgical navigation system for a substantially minimally invasive dynamic reference frame is disclosed. The dynamic reference frame may include a body portion selectively attachable to a portion of the anatomy. It may also include a navigation portion to at least one of sense and transmit a characteristic. A holding section is able to hold the body portion relative to the portion of the anatomy. The holding section may substantially non-invasively holds the body portion relative to the portion of the anatomy.

According to various embodiments a surgical navigation system for navigating a procedure relative to a patient having an electrical isolating portion. The navigation system may include an electrical source and an instrument including a conducting element disposable near the patient. A transmission medium may interconnect the electrical source and the instrument. An electrical isolator may electrically isolate the instrument from the electrical source.

According to various embodiments, a navigation system for determining the location of a member relative to an anatomy may include a tracking system and a sensor to be sensed by the tracking system. An anti-rotation mechanism may be provided to interconnect the sensor with the anatomy. The anti-rotation mechanism contacts at least two points on the anatomy to resist rotation of the sensor relative to the anatomy.

According to various embodiments a navigation system for determining a position of a sensor relative to a portion of an anatomy including soft tissue may include a localizer operable to produce a field relative to the anatomy and a tracking sensor for sensing the field produced relative to the tracking sensor to determine a position of the tracking sensor in the field. A housing may include and/or house the sensor. The housing is operable to allow movement of the sensor relative to the soft tissue when affixed to the anatomy subcutaneously.

According to various embodiments a method of navigating a procedure relative to an anatomy with a tracking system including a localizer and a tracking sensor positioned relative to the anatomy includes providing a plurality of coils in the tracking sensor in a fixed geometry. The tracking sensor may be positioned at a location relative to the anatomy and the position of each of the plurality of coils may be determined. At least one of the plurality of the coils positioned may be determined based at least in part on the determined sensed position of the plurality of coils. Wherein determining the position includes determining a geometry of each of the coils and comparing the determined geometry to the fixed geometry.

According to various embodiments a method of navigating a procedure relative to an anatomy with a tracking system including a localizer and a tracking sensor positioned relative to the anatomy is disclosed. The method may include providing a plurality of coils in the tracking sensor and positioning the tracking sensor at a location relative to the anatomy. A position of each of the plurality of coils may be determined and averaging each of the determined position of the plurality of coils. The position of the tracking sensor may be determined based at least in part on the averaging of each of the determined positions.

According to various embodiments a method of navigating a procedure relative to an anatomy with a tracking system including a localizer and a tracking sensor positioned relative to the anatomy may include providing a plurality of coils in the tracking sensor and positioning the tracking sensor at a location relative to the anatomy. Data regarding the position of the plurality of coils may be collected with a weight datum for each of the plurality of coils. A weight for the data collected regarding each of the plurality of coils may be determined along with a position of each of the plurality of coils.

According to various embodiments a method of using a tracking system to assist in reduction of interference in relation to the tracking system may include forming a field with a mobile localizer. An interference member may be determined and the mobile localizer may be moved to reduce the affect of the interference member.

According to various embodiments a method of navigating an anatomical position of an anatomy with an ultrasound system may include positioning the ultra-sound system relative to a selected portion of the anatomy and determining a plurality of points relative to a first portion of the anatomy subcutaneously. A first point may be selected within the determined plurality of points relative to the first portion of the anatomy. Also, a plurality of points may be determined relative to a second portion of the anatomy subcutaneously and a second point may be selected within the determined plurality of points relative to the second portion of the anatomy. A relationship between the first point and the second point may be determined.

According to various embodiments a system for navigating a tool may include a tracking system. A tracking sensor operable to be tracked by the tracking system may also be provided. An engagement member may interconnect the tracking sensor with a tool. The tracking system may be operable to track the tool.

Further areas of applicability will become apparent from the detailed description provided hereinafter. It should be understood that the detailed description and various examples, while indicating various embodiments, are intended for purposes of illustration only and are not intended to limit the scope of the description or the appended claims.

BRIEF DESCRIPTION OF THE DRAWINGS

The present teachings will become more fully understood from the detailed description and the accompanying drawings, wherein:

FIG. 20 is a perspective view of a DRF including an anti-rotational mechanism according to various embodiments;

FIG. 21 is an exploded perspective view of a DRF including an anti-rotational mechanism according to various embodiments;

FIG. 21A is an elevational environmental detail view of the DRF of FIG. 21;

FIG. 28A-C is an exemplary use of a DRF according to various embodiments;

FIG. 28D is a detail environmental view of a use of the DRF of FIG. 27;

FIGS. 31-33 are flow charts illustrating methods of determining a position of a sensor according to various embodiments.

FIG. 37 is a detail plan view of an instrument including a tracking sensor on a stylet according to various embodiments;

FIG. 38 is a plan view of an instrument including a tracking sensor on a stylet according to various embodiments;

FIG. 47 is a top perspective exploded view of a DRF according to various embodiments;

FIG. 48 is a detailed environmental view of a DRF being positioned relative to a patient according to various embodiments;

FIG. 49 is a side plan view of a DRF according to various embodiments;

FIG. 50 is a cross-sectional view of a DRF taken along line 50-50 of FIG. 49;

FIG. 51 is a bottom plan view of a DRF according to various embodiments;

FIG. 69 is a side plan view of a DRF according to various embodiments;

FIG. 70 is a across-sectional view of a DRF taken along line 70-70 of FIG. 69;

FIG. 71 is a bottom plan view of a DRF according to various embodiments;

FIG. 92 is an environmental/display device view of an instrument with a selected tracking device; and FIGS. 93A and 93B are schematic views of an instrument with a selected tracking device.

DETAILED DESCRIPTION OF VARIOUS EMBODIMENTS

The following description of various embodiments is merely exemplary in nature and is in no way intended to limit the teachings, its application, or uses. As indicated above, the present teachings are directed towards providing improved, non-line-of-site image-guided navigation of an instrument, such as a stylet, probe, suction tube, catheter, balloon catheter, implant, lead, stent, needle, guide wire, insert and/or capsule, that may be used for physiological monitoring, delivering a medical therapy, or guiding the delivery of a medical device, orthopedic implant, or soft tissue implant in an internal body space to any region of the body.

Figure 1:
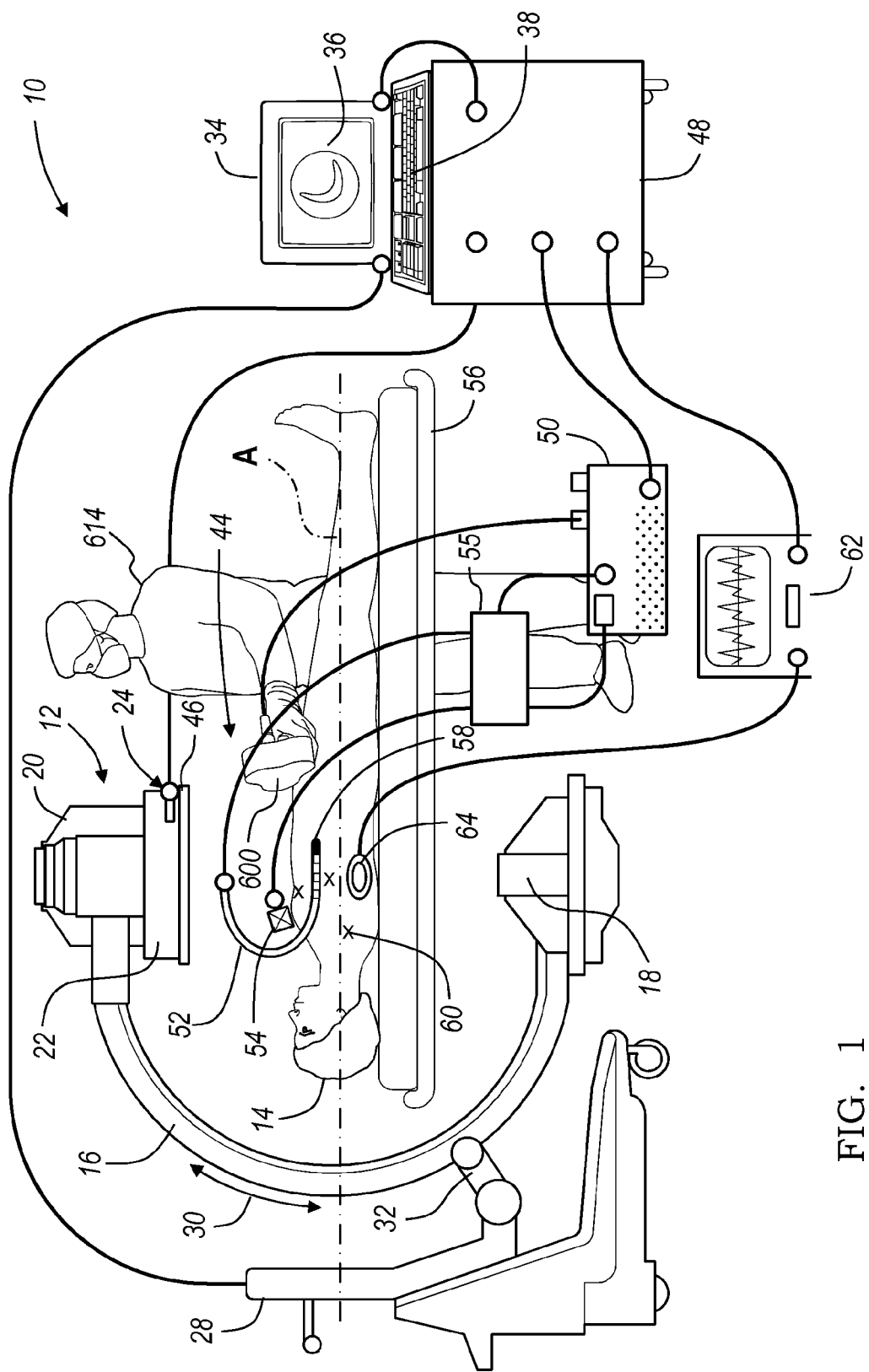
FIG. 1 is a diagram of a navigation system according to various embodiments of the present teachings.

FIG. 1 is a diagram illustrating an overview of an image-guided navigation system 10 for use in non-line-of-site navigating of an instrument. It should further be noted that the navigation system 10 may be used to navigate any type of instrument, implant or delivery system, including guide wires, needles, drug delivery systems, cell delivery systems, gene delivery systems, biopsy systems, arthroscopic systems, etc. Moreover, these instruments may be used to navigate or map any regions of the body.

The navigation system 10 may include an optional imaging device 12 that is used to acquire pre-, intra-, or post-operative or real-time images of a patient 14. The optional imaging device 12 is, for example, a fluoroscopic x-ray imaging device that may include a C-arm 16 having an x-ray source 18, an x-ray receiving section 20, an optional calibration and tracking target 22 and optional radiation sensors 24. The calibration and tracking target 22 includes calibration markers 26 (see FIGS. 2A-2B), further discussed herein. A C-arm, or optional imaging device controller 28 captures the x-ray images received at the receiving section 20 and stores the images for later use. The C-arm controller 28 may also be separate from the C-arm 16 and/or control the rotation of the C-arm 16. For example, the C-arm 16 may move in the direction of arrow 30 or rotates about a longitudinal axis 14a of the patient 14, allowing anterior or lateral views of the patient 14 to be imaged. Each of these movements involve rotation about a mechanical axis 32 of the C-arm 16. In this example, the longitudinal axis 14a of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray that may be used as the optional imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the imaging device 12 generates x-rays from the x-ray source 18 that propagate through the patient 14 and calibration and/or tracking target 22, into the x-ray receiving section 20. The receiving section 20 generates an image representing the intensities of the received x-rays. Typically, the receiving section 20 includes an image intensifier that first converts the x-rays to visible light and a charge coupled device (CCD) video camera that converts the visible light into digital images. Receiving section 20 may also be a digital device that converts x-rays directly to digital images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used at all for cardiac therapies. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images that may be taken by the optional imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg may be appended together to provide a full view or complete set of image data of the leg that can be later used to follow contrast agent, such as Bolus tracking.

These images are then forwarded from the C-arm controller 28 to a navigation computer controller or work station 34 having a display 36 and a user interface 38. It will also be understood that the images are not necessarily first retained in the controller 28, but may also be directly transmitted to the navigation computer 34. The work station 34 provides facilities for displaying on the display 36, saving, digitally manipulating, or printing a hard copy of the received images. The user interface 38, which may be a keyboard, mouse, touch pen, touch screen or other suitable device, allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images.

When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

Figure 2B:
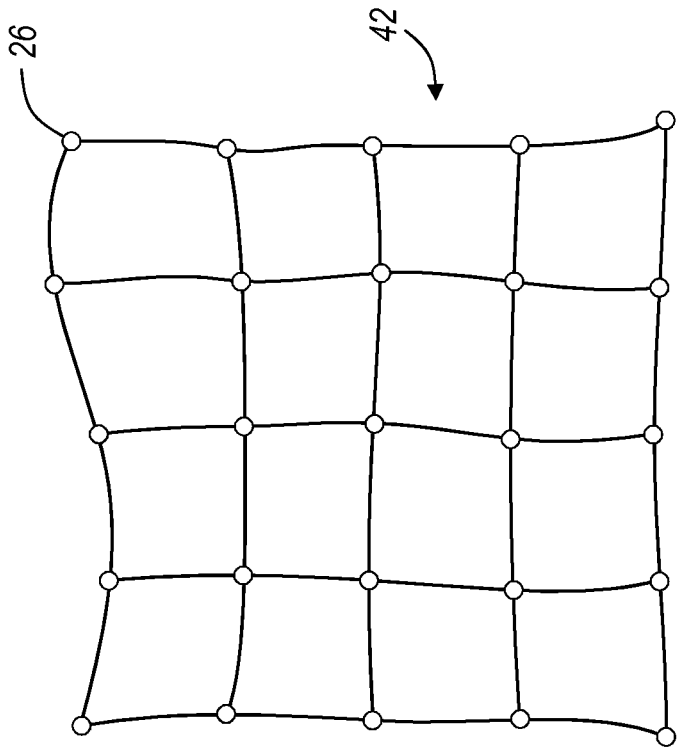
FIGS. 2A and 2B are diagrams representing undistorted and distorted views from a fluoroscopic C-arm imaging device.
Figure 2A:
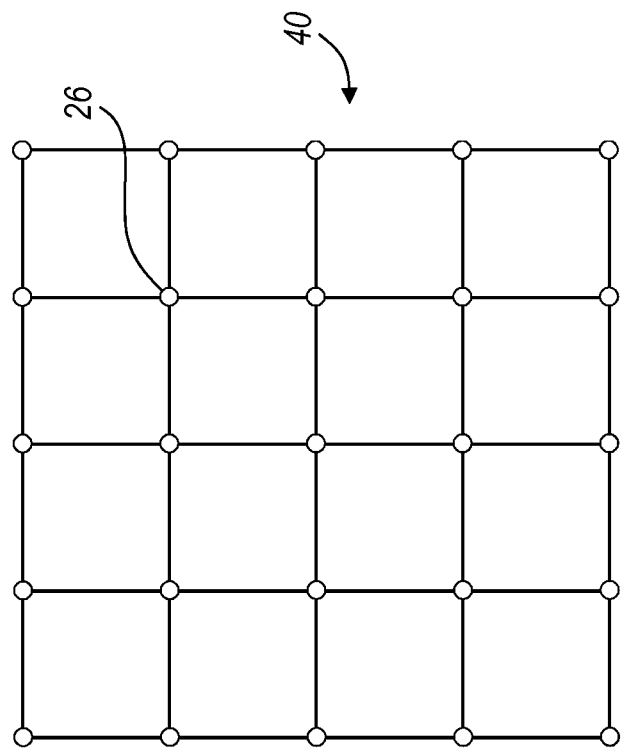

The optional imaging device 12, such as the fluoroscopic C-arm 16, that do not include a digital receiving section 20 generally require the optional calibration and/or tracking target 22. This is because the raw images generated by the receiving section 20 tend to suffer from undesirable distortion caused by a number of factors, including inherent image distortion in the image intensifier and external electromagnetic fields. An empty undistorted or ideal image and an empty distorted image are shown in FIGS. 2A and 2B, respectively. The checkerboard shape, shown in FIG. 2A, represents the ideal image 40 of the checkerboard arranged calibration markers 26. The image taken by the receiving section 20, however, can suffer from distortion, as illustrated by the distorted calibration marker image 42, shown in FIG. 2B.

Intrinsic calibration, which is the process of correcting image distortion in a received image and establishing the projective transformation for that image, involves placing the calibration markers 26 in the path of the x-ray, where the calibration markers 26 are opaque or semi-opaque to the x-rays. The calibration markers 26 are rigidly arranged in pre-determined patterns in one or more planes in the path of the x-rays and are visible in the recorded images. Because the true relative position of the calibration markers 26 in the recorded images are known, the C-arm controller 28 or the work station or computer 34 is able to calculate an amount of distortion at each pixel in the image (where a pixel is a single point in the image). Accordingly, the computer or work station 34 can digitally compensate for the distortion in the image and generate a distortion-free or at least a distortion improved image 40 (see FIG. 2A). A more detailed explanation of exemplary methods for performing intrinsic calibration are described in the references: B. Schedule, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the optional imaging device 12 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT), intra-vascular ultrasound (IVUS), ultrasound, intraoperative CT or MRI may also be used to acquire 2D, 3D or 4D pre- or post-operative and/or real-time images or image data of the patient 14. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 12, as shown in FIG. 1, provides a virtual bi-plane image using a single-head C-arm fluoroscope as the optional imaging device 12 by simply rotating the C-arm 16 about at least two planes, which could be orthogonal planes to generate two-dimensional images that can be converted to three-dimensional volumetric images. By acquiring images in more than one plane, an icon representing the location of a catheter, stylet, suction-probe, or other instrument, introduced and advanced in the patient 14, may be superimposed in more than one view on display 36 allowing simulated bi-plane or even multi-plane views, including two and three-dimensional views.

These types of imaging modalities may provide certain distinct benefits for their use. For example, magnetic resonance imaging (MRI) is generally performed pre-operatively using a non-ionizing field. This type of imaging provides very good tissue visualization in three-dimensional form and also provides anatomy and functional information from the imaging. MRI imaging data is generally registered and compensated for motion correction using dynamic reference frames (DRF) discussed further herein.

Positron emission tomography (PET) imaging is generally a pre-operative imaging procedure that exposes the patient to some level of radiation to provide a 3D image. PET imaging provides functional information and also generally requires registration and motion correction using dynamic reference frames.

Computed tomography (CT) imaging is also generally a pre-operative technique that exposes the patient to a limited level of radiation. CT imaging, however, is a very fast imaging procedure. A multi-slice CT system provides 3D images having good resolution and anatomy information. Again, CT imaging is generally registered and needs to account for motion correction, via dynamic reference frames.

Fluoroscopy imaging is generally an intra-operative imaging procedure that exposes the patient to certain amounts of radiation to provide either two-dimensional or rotational three-dimensional images. Fluoroscopic images generally provide good resolution and anatomy information. Fluoroscopic images can be either manually or automatically registered and also need to account for motion correction using dynamic reference frames.

Ultrasound imaging is also generally intra-operative procedure using a non-ionizing field to provide either 2D, 3D, or 4D imaging, including anatomy and blood flow information. Ultrasound imaging provides automatic registration and does not need to account for any motion correction.

With continuing reference to FIG. 1, the navigation system 10 further includes an electromagnetic navigation or tracking system 44 that includes a localizer, such as a transmitter coil array 46, the coil array controller 48, a navigation probe interface 50, an electromagnetic instrument, such as a stylet or catheter 52 and a dynamic reference frame 54. It will be understood that the localizer may be any appropriate localizer, such as an optical, an acoustic, or other localizer depending upon the system for which the localizer is chosen. Further included in the navigation system 10 is an isolator circuit or box 55. The isolator circuit or box 55 may be included in a transmission line or interrupt a line carrying a signal or a voltage to the navigation probe interface 50. Alternatively, the isolator circuit included in the isolator box 55 may be included in the navigation probe interface 50, the instrument 52, the dynamic reference frame 54, the transmission lines coupling the devices, or any other appropriate location. As discussed herein, the isolator box 55 is operable to isolate any of the instruments or patient coincidence instruments or portions that are in contact with the patient should an undesirable electrical surge or voltage take place, further discussed herein.

It should further be noted that the entire tracking system 44 or parts of the tracking system 44 may be incorporated into the imaging device 12, including the work station 34 and radiation sensors 24. Incorporating the tracking system 44 may provide an integrated imaging and tracking system. Any combination of these components may also be incorporated into the imaging system 12, which again can include a fluoroscopic C-arm imaging device or any other appropriate imaging device.

The transmitter coil array 46 is shown attached to the receiving section 20 of the C-arm 16. It should be noted, however, that the transmitter coil array 46 may also be positioned at any other location as well. For example, the transmitter coil array 46 may be positioned at the x-ray source 18, within or atop the OR table 56 positioned below the patient 14, on siderails associated with the table 56, or positioned on the patient 14 in proximity to the region being navigated, such as on the patient's chest. The transmitter coil array 46 may also be positioned in the items being navigated, further discussed herein. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induce currents in sensors 58 positioned in the instrument 52, such as the catheter, further discussed herein. These induced signals from the instrument 52 are delivered to the navigation probe interface 50 through the isolation circuit 55 and subsequently forwarded to the coil array controller 48. The navigation probe interface 50 may provide all the necessary electrical isolation for the navigation system 10. Alternatively, the electrical isolation may also be provided in the isolator box 55. Nevertheless, as mentioned here, the isolator assembly 55 may be included in the navigation probe interface 50 or may be integrated into the instrument 52, and any other appropriate location. The navigation probe interface 50 also includes amplifiers, filters and buffers required to directly interface with the sensors 58 in the instrument 52. Alternatively, the instrument 52 may employ a wireless communications channel as opposed to being coupled directly to the navigation probe interface 50.

The instrument 52, as will be described in detail below, is equipped with at least one, and generally multiple, localization sensors 58. The instrument 52 can be a steerable catheter that includes a handle at a proximal end and the multiple location sensors 58 fixed to the catheter body and spaced axially from one another along the distal segment of the catheter 52. The catheter 52, as shown in FIG. 1 includes four localization sensors 58. The localization sensors 58 are generally formed as electromagnetic receiver coils, such that the electromagnetic field generated by the transmitter coil array 46 induces current in the electromagnetic receiver coils or sensors 58. The catheter 52 may also be equipped with one or more sensors, which are operable to sense various physiological signals. For example, the catheter 52 may be provided with electrodes for sensing myopotentials or action potentials. An absolute pressure sensor may also be included, as well as other electrode sensors. The catheter 52 may also be provided with an open lumen, further discussed herein, to allow the delivery of a medical device or pharmaceutical/cell/gene agents. For example, the catheter 52 may be used as a guide catheter for deploying a medical lead, such as a cardiac lead for use in cardiac pacing and/or defibrillation or tissue ablation. The open lumen may alternatively be used to locally deliver pharmaceutical agents, cell, or genetic therapies.

In an alternate embodiment, the electromagnetic sources or generators may be located within the instrument 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization sensors or systems may also be used, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. Other types of tracking systems include optical, acoustic, electrical field, RF and accelerometers. Accelerometers enable both dynamic sensing due to motion and static sensing due to gravity. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 is also coupled to the navigation probe interface 50 to forward the information to the coil array controller 48. The dynamic reference frame 54, briefly and discussed in detail according to various embodiments herein, is a small magnetic field detector that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 can be configured as a pair of orthogonally oriented coils, each having the same center or may be configured in any other non-coaxial or co-axial coil configuration. The dynamic reference frame 54 may be affixed externally to the patient 14, adjacent to the region of navigation, such as on the patient's chest, as shown in FIG. 1. The dynamic reference frame 54 can be affixed to the patient's skin, by way of a selected adhesive patch and/or a tensioning system. The dynamic reference frame 54 may also be removably attachable to fiducial markers 60 also positioned on the patient's body and further discussed herein.

Alternatively, the dynamic reference frame 54 may be internally attached, for example, to the wall of the patient's heart or other soft tissue using a temporary lead that is attached directly to the heart. This provides increased accuracy since this lead may track the regional motion of the heart. Gating may also increase the navigational accuracy of the system 10. Gating procedures may be particular important when performing procedures relative to portions of the anatomy that move on a regular basis, such as the heart or the lungs or diaphragm. Although, it is not necessary to provide gating, it may be selected to do so during various procedures. Various gating procedures and techniques are described, such as U.S. patent application Ser. No. 10/619,216 entitled Navigation "System For Cardiac Therapies" filed on Jul. 14, 2003, and incorporated herein by reference. Dynamic reference frame 54 according to various embodiments and a fiducial marker 60, are set forth in U.S. Pat. No. 6,381,485, entitled "Registration of Human Anatomy Integrated for Electromagnetic Localization," issued Apr. 30, 2002, which is hereby incorporated by reference.

It should further be noted that multiple dynamic reference frames 54 may also be employed. For example, an external dynamic reference frame 54 may be attached to the chest of the patient 14, as well as to the back of the patient 14. Since certain regions of the body may move more than others due to motions of the heart or the respiratory system, each dynamic reference frame 54 may be appropriately weighted to increase accuracy even further. In this regard, the dynamic reference frame 54 attached to the back may be weighted higher than the dynamic reference frame 54 attached to the chest, since the dynamic reference frame 54 attached to the back is relatively static in motion.

The navigation system 10 may optionally further include a gating device 62 such as an ECG or electrocardiogram, which is attached to the patient 14, via skin electrodes 64, and in communication with the coil array controller 48. Respiration and cardiac motion can cause movement of cardiac structures relative to the instrument 52, even when the instrument 52 has not been moved. Therefore, localization data may be acquired on a time-gated basis triggered by a physiological signal. For example, the ECG or EGM signal may be acquired from the skin electrodes 64 or from a sensing electrode included on the instrument 52 or from a separate reference probe. A characteristic of this signal, such as an R-wave peak or P-wave peak associated with ventricular or atrial depolarization, respectively, may be used as a triggering event for the coil array controller 48 to drive the coils in the transmitter coil array 46. This triggering event may also be used to gate or trigger image acquisition during the imaging phase with the imaging device 12. By time-gating or event gating at a point in a cycle the image data and/or the navigation data, the icon of the location of the catheter 52 relative to the heart at the same point in the cardiac cycle may be displayed on the display 36, such as disclosed in U.S. patent application Ser. No. 10/619,216, entitled "Navigation System For Cardiac Therapies" filed on Jul. 14, 2003.

Additionally or alternatively, a sensor regarding respiration may be used to trigger data collection at the same point in the respiration cycle. Additional external sensors can also be coupled to the navigation system 10. These could include a capnographic sensor that monitors exhaled $CO_2$ concentration. From this, the end expiration point can be easily determined. The respiration, both ventriculated and spontaneous causes an undesirable elevation or reduction (respectively) in the baseline pressure signal. By measuring systolic and diastolic pressures at the end expiration point, the coupling of respiration noise is minimized. As an alternative to the $CO_2$ sensor, an airway pressure sensor can be used to determine end expiration.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the catheter 52 or a pointing device 66 is used, the work station 34 in combination with the coil array controller 48 and the C-arm controller 28 uses the translation map to identify the corresponding point on the pre-acquired image or atlas model, which is displayed on display 36. This identification is known as navigation or localization. An icon representing the localized point or instruments are shown on the display 36 within several two-dimensional image planes, as well as on three and four dimensional images and models.

To enable navigation, the navigation system 10 must be able to detect both the position of the patient's anatomy and the position of the catheter 52 or other surgical instrument. Knowing the location of these two items allows the navigation system 10 to compute and display the position of the catheter 52 in relation to the patient 14. The tracking system 44 is employed to track the catheter 52 and the anatomy simultaneously.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the catheter 52 by measuring the field strength at the sensor 58 location. The dynamic reference frame 54 is fixed to the patient 14 to identify the location of the patient in the navigation field. The electromagnetic tracking system 44 continuously recomputes the relative position of the dynamic reference frame 54 and the catheter 52 during localization and relates this spatial information to patient registration data to enable image guidance of the catheter 52 within the patient 14.

Patient registration is the process of determining how to correlate the position of the instrument or catheter 52 on the patient 14 to the position on the diagnostic or pre-acquired images. To register the patient 14, the physician or user may use point registration by selecting and storing particular points from the pre-acquired images and then touching the corresponding points on the patient's anatomy with the pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial markers or landmarks 60, such as anatomical landmarks. Again, the landmarks or fiducial points 60 are identifiable on the images and identifiable and accessible on the patient 14. The landmarks 60 can be artificial landmarks 60 that are positioned on the patient 14 or anatomical landmarks that can be easily identified in the image data. The artificial landmarks, such as the fiducial markers 60, can also form part of the dynamic reference frame 54.

The system 10 may also perform registration using anatomic surface information or path information as is known in the art. The system 10 may also perform 2D to 3D registration by utilizing the acquired 2D images to register 3D volume images by use of contour algorithms, point algorithms or density comparison algorithms, as is known in the art. An exemplary 2D to 3D registration procedure, as set forth in U.S. Ser. No. 60/465,615, entitled "Method and Apparatus for Performing 2D to 3D Registration" filed on Apr. 25, 2003, which is hereby incorporated by reference. The registration process may also be synched to an anatomical function, for example, by the use of the ECG device 62.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

The navigation system 10 can be used according to any appropriate method or system. For example, pre-acquired images or atlas or 3D models may be registered relative to the patient and patient space. Various registration regimens and techniques include those described in U.S. patent application Ser. No. 10/619,216 entitled "Navigation System For Cardiac Therapies" filed on Jul. 14, 2003. Generally, the registration system allows the images on the display 36 to be registered and accurately display the real time location of the various instruments, such as the instrument 52, and other appropriate items, such as the pointer 66. In addition, the pointer 66 may be used to register the patient space to the pre-acquired images or the atlas or 3D models. In addition, the dynamic reference frame 54 may be used to ensure that any planned or unplanned movement of the patient or the receiver array 46 is determined and used to correct the image on the display 36.

Figure 3:
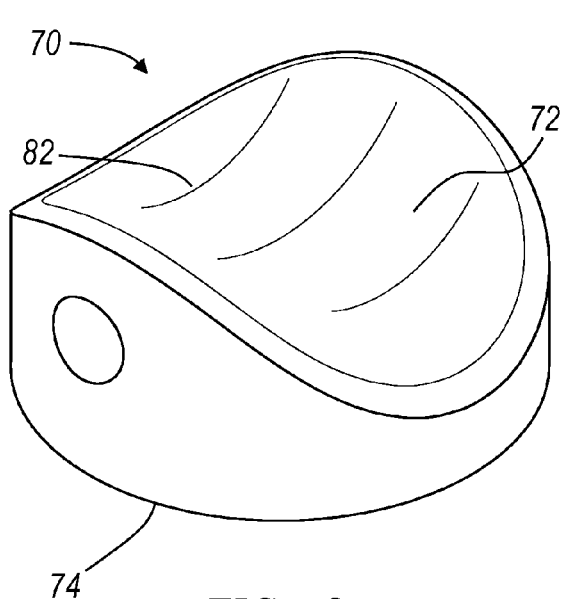
FIG. 3 is a top perspective view of a non-invasive dynamic reference frame according to various embodiments.

As discussed above, the dynamic reference frame 54 may include any appropriate dynamic reference frame, such as the selectively fixable dynamic reference frame 70 illustrated in FIG. 3. The dynamic reference frame 70 generally includes a superior side 72 and an inferior side 74.

Figure 4:
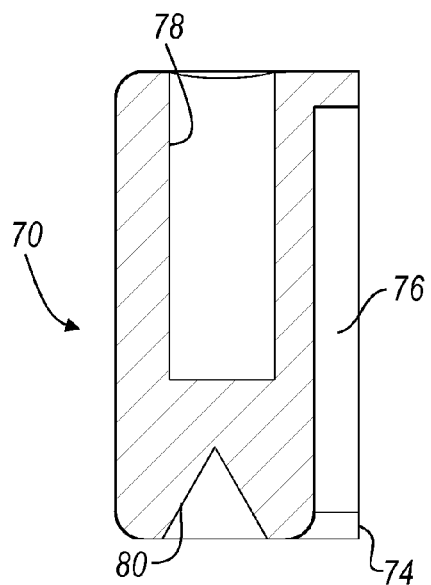
FIG. 4 is a cross-sectional view of the non-invasive dynamic reference frame of FIG. 3.

With continuing reference to FIG. 3 and additional reference to FIG. 4, the dynamic reference frame 70 includes a recess 76 as a portion of the inferior side 74. The recess 76 may be provided for any appropriate purpose, such as receiving a selective adhesive. In addition, as discussed herein, the recess may be used to allow the gathering of soft tissue relative to the dynamic reference frame 70. As described, the dynamic reference frame 70 may be affixed to the patient 14 in any appropriate position.

An adhesive positioned in the adhesive recess 76 generally allows the dynamic reference frame 70 to be fixed to the selected point on the patient 14. As discussed further herein, a tensioning apparatus may also be provided on the dynamic reference frame 70 to further assist holding the dynamic reference frame in a selected position. Further, the dynamic reference frame 70 defines a bore 78 to removably receive a selected sensor or coil. As described herein, the sensor may be fitted into the sensor bore 78 and removed from the sensor bore 78 as selected. For example, should the dynamic reference frame 70 also be used as a fiducial marker 60 it may be radio- or image-opaque, and the sensor bobbin 90 may be removed from the bore 78 during imaging of the patient 14, such as acquiring MRI images. This eliminates any distortion that may be caused by the bobbin 90. Nevertheless, the sensor bobbin 90 may also be permanently provided within the sensor bore 78 for ease of use of the apparatus. It may be desirable to provide the dynamic reference frame 70 as a substantially disposable exterior portion and the sensor may be reusable. In either case, the dynamic reference frame 70 may be formed of a plastic or other non-conductive material.

If the dynamic reference frame 70 is used as a fiducial marker, the dynamic reference frame 70 may define a localization divot 80. The divot or recess 80 allows the pointer 66 or any appropriate mechanism to determine the location of the dynamic reference frame 70 relative to the patient 14 or the patient space. Generally, the pointer 66 is able to engage the divot 80 in a selected manner in patient space, such that the navigation system 44 is able to determine the position of the dynamic reference frame 70 relative to the patient 14. The pointer 66 is also engaged or used to point out the divot 80 in the pre-acquired image to register the image space with the patient space. Therefore, detected movement of the dynamic reference frame 70 may be used to determine movement of the patient 14. It will be understood that the divot 80 may be positioned in any appropriate portion of the dynamic reference frame 70 but is generally provided in an easily accessible and viewable area. moreover, there may be multiple divots 80 or landmarks, as discussed herein. The multiple divots 80 may be used as fiducial markers. There dynamic reference frame 70 may also include a radio-opaque material to be imaged in various imaging techniques.

With further reference to FIG. 3, the dynamic reference frame 70 may include a concave recess 82 defined as a portion of the superior part 72 of the dynamic reference frame 70. The recess 82 may be provided for any appropriate purpose such as engaging a tensioning member 84. The tensioning member 84 may include an adhesive strip that is applied relative to the dynamic reference frame 70 to ensure a substantial selected fixation of the dynamic reference frame 70 relative to the patient 14.

Figure 5:
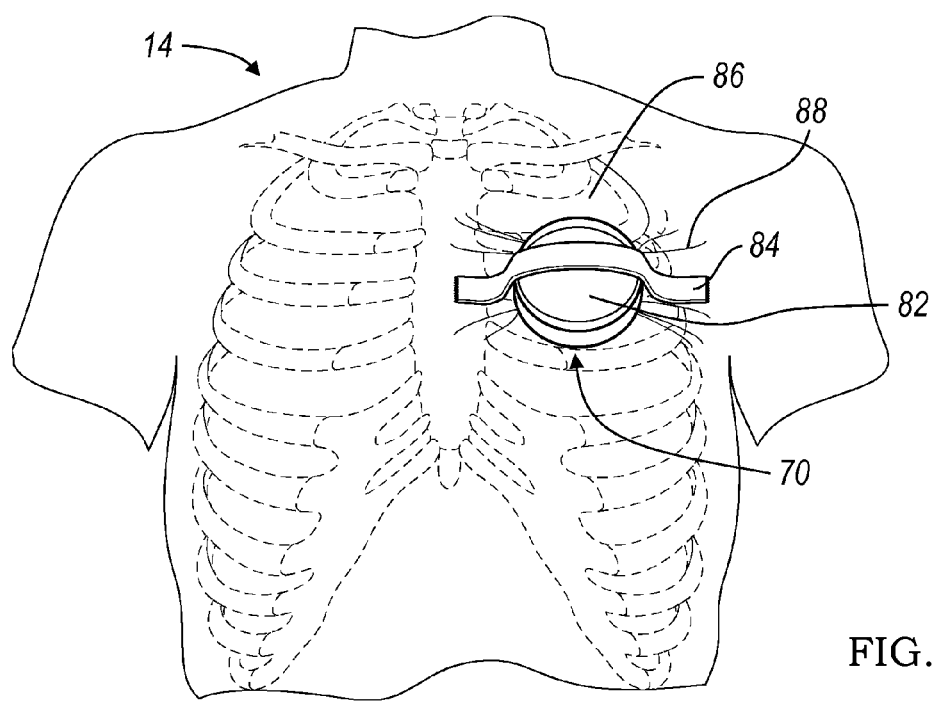
FIG. 5 is an environmental application of the non-invasive dynamic reference frame of FIG. 3.

With reference to FIG. 5, an exemplary use of the dynamic reference frame 70 is illustrated. The dynamic reference frame 70 is affixed to the patient 14 using an adhesive that is included in the adhesive recess 76. In addition, the tensioning strip 84 is placed atop the recess 82 to further hold the dynamic reference frame 70. The tensioning strip 84 helps by tensioning the dermis 86 of the patient 84 relative to the dynamic reference frame 70. Generally, the dermis 86 will form pucker or tension lines 88 to illustrate or ensure that the dynamic reference frame 70 is substantially fixed to the patient 14. In this way, the soft tissue to which the dynamic reference frame 70 is fixed and is not able to move relative to the dynamic reference frame 70, thereby providing a relatively stable and secure attachment to the patient 14.

Although it is illustrated that the dynamic reference frame 70 may be tensioned relative to the skin of the pectoral region of the patient the dynamic reference frame 70 may be tensioned relative to any appropriate portion of the anatomy. For example, the dynamic reference frame 70 may be fixed relative to a posterior portion of the patient 14 relative to the spine, if a spinal procedure is occurring. In addition, the dynamic reference frame 70 may be tensioned to the dermis on the forehead of the patient, if a procedure relative to the cranium is being performed. Nevertheless, the dynamic reference frame 70 may be fixed to the dermis with substantial force using the tensioning device 84.

Although the tensioning device 84 is illustrated to be a separate strip of material having an adhesive, it will be understood that the tensioning device 84 may be integrated into the dynamic reference frame 70. For example, a tensioning system may be fixed to the superior portion 72 of the dynamic reference frame 70 and a backing released to expose an adhesive region to allow the tensioning system to tension the dermis relative to the dynamic reference frame 70. In addition, tensioning strips, that form the tensioning device 84 may be affixed to or formed integrally with any appropriate portion of the dynamic reference frame 70 to allow for easy use during an operative procedure. For example, tape or a belt may be used that may be separate or integral with the dynamic reference frame 70. Therefore, it will be understood that the tensioning device 84 need not be limited according to any selected embodiments and is provided to allow for tensioning the dermis relative to the dynamic reference frame 70.

As is generally known by one skilled in the art, the dermis of an individual is generally not substantially taught over the sub-dermal anatomy. That is, a portion of the anatomy may move relative to the dermis without the dermis moving. Although this may be desired for general anatomical or natural movements, it may be desired to know the precise movements of any portions of the anatomy of the patient 14 during an operative procedure where the navigation system 44 is being used.

The instrument 52, such as the catheter, may be engaged to a subdermal region of the patient 14. Movement of any subdermal portion may be selected to be known during the operative procedure. In addition, the position of the instrument 52 relative to the subdermal anatomical portions may be selected to be substantially known. Therefore, the dynamic reference frame 70 may be fixed to the patient 14 to allow for ensuring that the image on the display 36 substantially correctly illustrates the position of the anatomy of the patient 14. If subdermal portions are allowed to move without the dynamic reference frame 70 moving, however, it may be possible that the display 36 may not correctly display the proper location of the instrument 52 relative to the subdermal anatomy of the patient 14. Therefore, the tensioning strip 84 may allow for more closely tracking the movement of subdermal portions or portions of the anatomy of the patient 14 without using more invasive techniques.

Generally, the dynamic reference frame 70 may be affixed to the dermis or external portions of the patient 14. This allows the dynamic reference frame 70 to be fixed to the patient and used to reference the position of the patient 14 relative to the position of the other elements, such as the instrument 52 and the pointer 66, and to also ensure the appropriate registration of the images on the display 36 in a substantially non-invasive manner. Simply the dynamic reference frame 70 need not penetrate the dermis to be fixed to a rigid portion of the anatomy, such as a bone portion. Therefore, the dynamic reference frame 70 can be easily fixed and removed from the patient 14 as selected.

An electromagnetic bobbin or multiple coil member 90 may be positioned in the recess 78 of the dynamic reference frame 70. The sensor bobbin 90 includes a body 92 that is generally formed from material that is not conductive to allow the coils to operate and sense a position in a field. In addition, the body 92 may be manipulated by a handle or manipulable portion 94 extending from the body 92. In addition, the handle 94 may allow leads or contacts from an external source, such as illustrated in FIG. 1, to be interconnected to the body portion 92 into the coils 96 and 98.

The first coil 96 and the second coil 98 are generally positioned at angles relative to one another. These angles may be any appropriate angle such as a generally orthogonal angle or other appropriate angle. The two coils 96, 98 being positioned at angles relative to one another, allow for six degrees of freedom sensing including translation, angle, pitch, yaw, and rotation. Therefore, the position or movement of the dynamic reference frame 70 can be determined by sensing the electromagnetic field of the coil array 46 with the first coil 96 and the second coil 98

Generally, the body 92 of the bobbin 90 and the exterior or the bodies of the dynamic reference frame 70 are formed of an appropriate material. For example, the material may be a non-metallic and non-conducting material such as an appropriate ceramic, plastic, and the like. The material may be selected from a material that will not interfere with either transmitting or receiving information regarding the magnetic field and not interfere with imaging of the patient 14. Therefore, the material is a substantially non-conducting material, but may also be visible in the image data.

In addition, the dynamic reference frame 70 may be used to address what may be referred to as skin shift. As described above the skin may move relative to the subdermal anatomic portions. Therefore, the dynamic reference frame 70 may be fixed to the patient 14 in a manner to substantially eliminate error that may be introduced by a skin shift. In addition to the tensioning device 84, the tensioning device may be any appropriate portion. For example, the tensioning device 84 may be a band which substantially extends around the selected anatomical portion of the patient. For example, the dynamic reference frame 70 may be fixed to a band that substantially extends around the chest of a patient during a selected procedure. In addition, the dynamic reference frame 70 may be included on or integral with a band that substantially extends around the cranium, the arm, the thigh, or any other appropriate member. In addition, the band may be substantially elastic to engage the selected anatomical portion. The elastic band may be provided to substantially tension the tissue relative to the dynamic reference frame, but not simply in a localized tensioning manner. The dynamic reference frame 70 can, therefore, be fixed to any appropriate portion of the body either with the localized tensioning member 84 or a non-localized tensioning member. The band may form a general tensioning while a tape portion may form a more localized tensioning. The tensioning members allow for tensioning the dermal tissue over the subdermal anatomy to substantially eliminate skin movement relative to the subdermal area.

Figure 7:
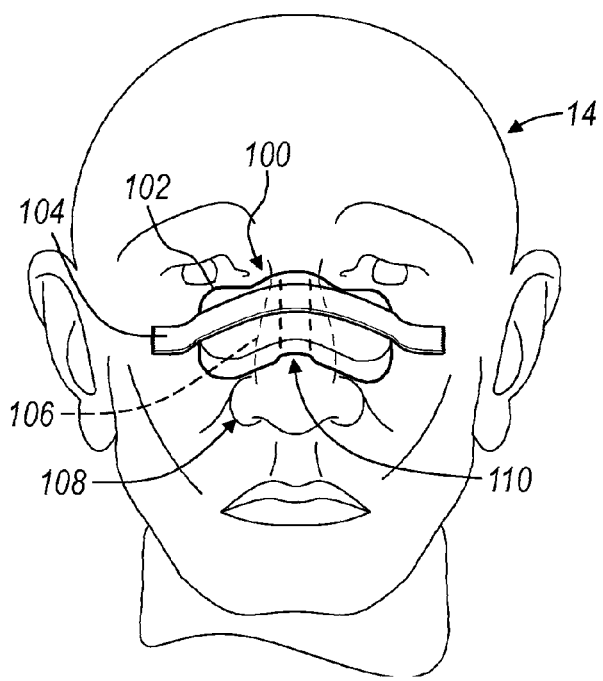
FIG. 7 is an environmental view of another non-invasive dynamic reference frame according to various embodiments.

In addition, the dynamic reference frame 54 may be substantially non-invasively placed near a substantially rigid portion of the anatomy. For example, the dynamic reference frame may include a rhinal dynamic reference frame 100, as illustrated in FIG. 7. The rhinal dynamic reference frame 100 may include a body 102 and an optional tensioning device 104. The rhinal dynamic reference frame 100 is formed to generally fit over a bridge 106 of a nose 108 of the patient 14. Generally, the bridge 106 of the nose 108 is covered with a substantially thin layer of dermal tissue. Therefore, the bridge of the nose 106 is substantially rigid relative to the patient 14. In addition, the tensioning member 104 may be provided to stabilize any portion of the skin that may move relative to the bridge 106 of the nose 108. However, the adhesive portion fixed on the bottom of the dynamic reference frame 100 may simply be the only adhesive necessary to fix the rhinal dynamic reference frame 100 to the bridge 106 of the nose. Nevertheless, the rhinal dynamic reference frame 100 may allow for the dynamic reference 100 to be fixed to the patient 14 in a substantially rigid and repeatable place.

Not only may the rhinal dynamic reference frame 100 be fixed to the bridge 106 of the nose, but the dynamic reference 100 may be substantially molded to a particular portion of the nose 108. Therefore, a molded or moldable inferior portion 110 of the rhinal dynamic reference frame 100 may be fitted to a selected portion of the nose 108. The dynamic reference frame 100 may be positioned and repositioned relative to the bridge 106 of the nose 108 a plurality of times with substantially repeatable placements of the dynamic reference frame 100.

The repeatable substantially precise placement enables the dynamic reference frame 100 to be removed and replaced onto the bridge 106 of the nose 108 without substantially introducing error into the positioning of the dynamic reference frame 100. This allows initial pre-operative images to be taken with the dynamic reference frame 100 in place and used as a fiducial marker. The rhinal dynamic reference frame 100 may then be removed from the patient 14 prior to the operative procedure. Subsequently, during the operative procedure, the rhinal dynamic reference frame 100 may be repositioned on the patient 14. Because the molded portion 110 of the rhinal dynamic reference frame 100 is substantially fitted to a particular portion of the bridge 106 of the nose 108, the rhinal dynamic reference frame 100 can be substantially positioned in the same position as during the pre-operative images. Therefore, the rhinal dynamic reference frame 100 allows for substantially error free referencing of the patient and registration of the patient 14 to the pre-operative images that may be displayed on the display 36. This allows the rhinal dynamic reference frame 100 to be used as both the dynamic reference frame 54 and as a fiducial marker for registering of the pre-operative images.

In addition, it will be understood that the dynamic reference frame 100 may be positioned in any appropriate manner. As illustrated above, the dynamic reference frame 70 may be fixed to a substantially flat portion of the anatomy of the patient 14. Alternatively, the anatomic or rhinal dynamic reference frame 100 may be molded to a substantially uniquely shaped portion of the anatomy of the patient 14. It will be understood that other portions of the anatomy may also be substantially molded to fit a particular portion of the anatomy.

Figure 8:
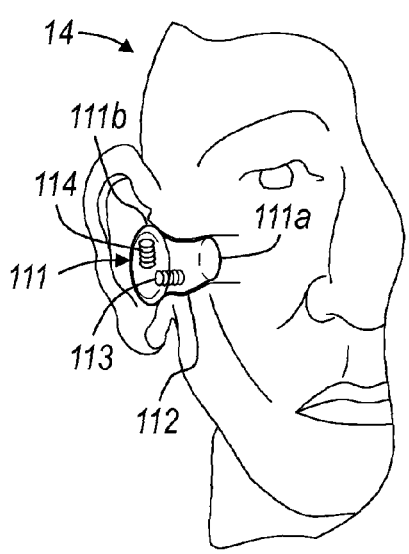
FIG. 8 is an environmental view of another non-invasive dynamic reference frame according to various embodiments

With reference to FIG. 8, a further alternative embodiment of the dynamic reference frame includes an anatomic or inner-cochlear dynamic reference frame 111. The inner cochlear dynamic reference frame 111 is generally molded to fit a portion or the cochlear portion of the ear 112. The cochlear portion of the ear 112 generally includes a substantially unique topography that may be used to fit the dynamic reference frame 111 in substantially only one position. Therefore, as discussed in relationship to the rhinal dynamic reference frame 100 that includes the moldable portion, the inner-cochlear dynamic reference frame 111 may also be formed, at least partially, of a moldable material.

For example, a distal portion 111a of the inter cochlear implant 111 may be formed of a substantially moldable material that may be press fit into the cochlear portion 112 of the ear of the patient 14. After being molded to the cochlear portion 112 of the ear of the patient 14, the moldable material may be cured to substantially maintain the molded shape. An exterior or proximal portion 111B of the inner-cochlear implant 111, may be formed of a moldable or a non-moldable material. Therefore, the inner-cochlear implant 111 may be formed of two materials. Nevertheless the proximal portion 111*b*, or any appropriate portion, may also include a first sensing coil 113 and a second sensing coil 114. The sensing coils 113, 114 may be positioned in any appropriate manner but may be positioned at angles relative to one another. Therefore, the inner-cochlear implant may provide six degrees of freedom information regarding motion of the inner-cochlear dynamic reference frame 111 during use.

The position of the sensors 113, 114 may be referenced and calibrated after molding of the inner-cochlear implant 111. Therefore, the position of the head of the patient 14 may be known based upon the sensed position of the inner-cochlear dynamic reference frame 111. In addition, as discussed in relation to the other dynamic reference frames, the coils 113, 114 may be passive or active. If the coils 113, 114 are active, the inner-cochlear dynamic reference frame 111 may include a power source, such as battery.

The inner-cochlear dynamic reference frame 111 may also be substantially molded as a separate procedure. For example, such as forming an inner-cochlear hearing aid, the inner-cochlear dynamic reference 111 may be molded to the cochlear portion of the ear of the patient 14 and the inner-cochlear dynamic reference frame 111 may be formed separately after the impression is made. Nevertheless, the molding of the inner-cochlear dynamic reference frame 111 relative to the cochlear portion of the ear 112 with the patient 14, allows for a substantially repeatable placement of the inner-cochlear dynamic reference frame 111 relative to the patient 14. Therefore, images displayed on the display 36 may be substantially easily registered relative to the known location and repeatable location of the inner-cochlear dynamic reference frame 111.

It will be understood that the molded portions may be substantially permanently molded or reusably molded. For example, a curable material may be included, in any appropriate dynamic reference frame, such as the inner-cochlear dynamic reference frame 111. The moldable portion of the cochlear implant 111 may be molded to a portion of the ear or press fit into the ear and then cured to substantially maintain the molded shape. Therefore, the dynamic reference frames may be substantially non-invasively positioned relative to the patient to allow for dynamic referencing of the patient 14 during the operative procedure.

In addition, the dynamic reference frame may be formed almost entirely of the substantially molded material. Therefore, the dynamic reference frame may include a molding material that may be molded to a selected portion of the anatomy and then cured to maintain the shape of the anatomy and also may be formed to include an area to receive the sensor bobbin 90. Although it will be understood that any appropriate coils may be used to form the sensor and may include substantially separate coils that can be positioned into the moldable material substantially separately and removably.

It will also be understood that the dynamic reference frame 54 may be fixed to any appropriate portion of the anatomy. As discussed above, the dynamic reference frame may be positioned relative to the nose 108, the chest of the patient 14, the head of the patient 14, also the dynamic reference frame may be formed as a bite block that may be fitted onto selected portions of the oral anatomy. Also, the dynamic reference frame may be fitted onto or in a tooth cap that may be fit over a tooth, an oral bite block that may be held within the teeth or jaws of the patient or any other appropriate location.

Figure 9:
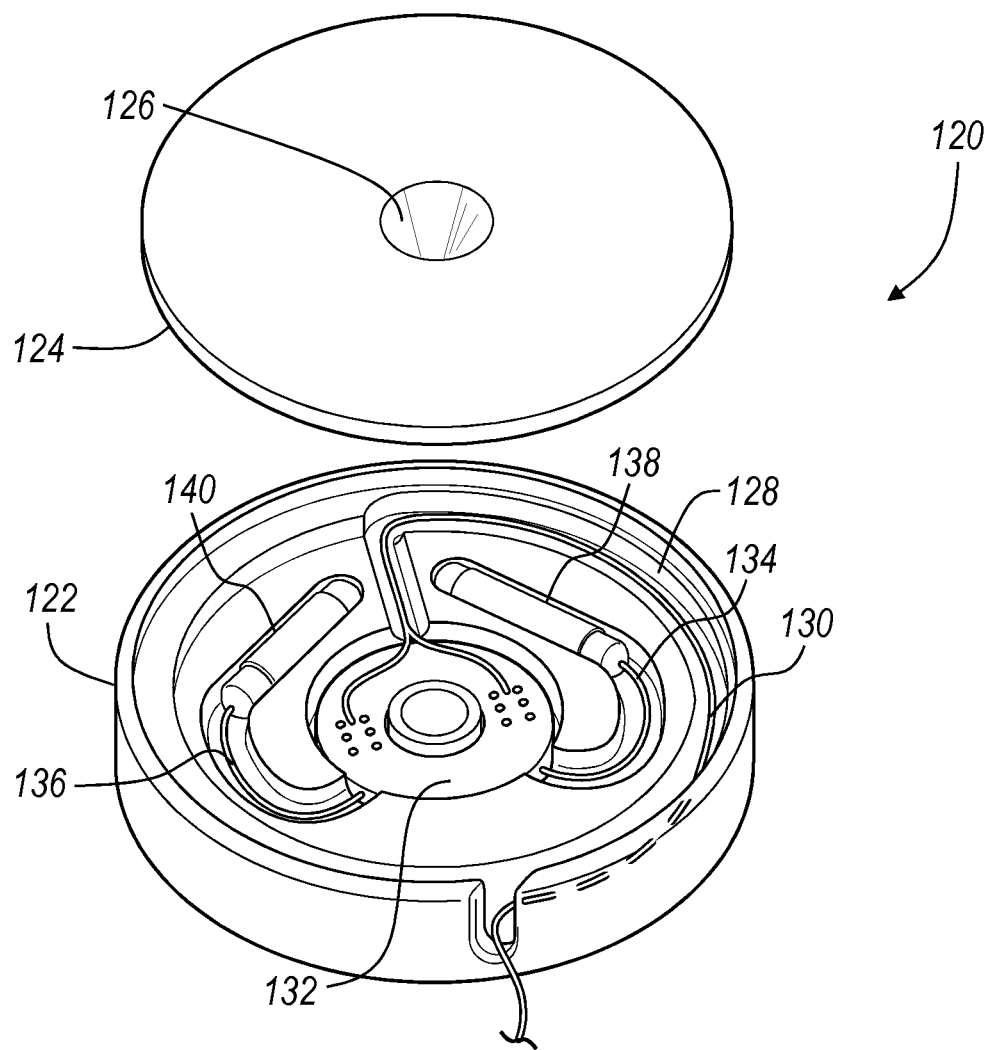
FIG. 9 is an exploded perspective view of another non-invasive dynamic reference frame according to various embodiments.

The dynamic reference frame 54 may either be substantially wireless and powered by an internal power source or may be wired. For example, a hard wire dynamic reference frame 120 is illustrated in FIG. 9. The hard wire dynamic reference frame 120 includes a bottom body portion 122 and a top body portion or cap 124. The cap 124 is generally able to mate with the bottom portion 122 in an appropriate manner and may include a recess 126 to receive the head of a screw to lock the top 124 to the bottom 122. Formed in the bottom portion 122 is a groove 128 that is able to receive a wire such as twisted pair wire 130. The wire 130 may include leads that are soldered to a printed circuit board (PCB) 132. The PCB 132 may include traces that are translated or connected to intermediate wires 134 and 136 that are able to transfer power or a signal to and/or from a first coil 138 and a second coil 140. The coils 138, 140 are generally coils of wire that generate an induced current by an electric field or may transmit an electric field.

The line 130 may operatively interconnect the hard wired dynamic reference frame 120 to the navigation interface 50. Therefore, the hard wire dynamic reference frame 120 may transmit the navigation signals received by the coils through the transmission line 130. Alternatively, as discussed above, an internal power source may be provided such that the information received by the coils 138, 140 may be wirelessly transmitted to the navigation controller 34 using known wireless technology.

The hardwire dynamic reference frame 120 may include any appropriate dimensions. For example the hardwire dynamic reference frame 120 may be about 2 mm to about 10 millimeters in height. Generally, the less the height of the dynamic reference frame the less the possibility for error in transmitting the location of the coils relative to the patient 14. Also, the inferior surface at the base 124 may include a radius to mate with a selected anatomical region, such as a forehead.

The hard wire dynamic reference frame 120 may still be fixed to the dermis of a patient 14 in any appropriate manner. For example, the tensioning member 84 may be provided over the top of the top portion 124 of the hard wire dynamic reference frame 120. In addition, an adhesive may be provided on the inferior portion of the hard wire dynamic reference frame 120.

In addition, the hard wire dynamic reference frame 120, particularly the upper portion 124 and the lower body portion 122, may be formed of an appropriate material. For example, materials may include non-conductive materials such as ceramic or various polymers. In addition, the hard wire dynamic reference frame may be formed of non-conductive carbon fiber materials. In addition, the coils 138, 140 may include conductive carbon fiber materials as the coil component. In addition, the PCB 132 need not be present and the wires may simply be fixed to the coils 138, 140 from the lead 130. Nevertheless, various selections may be chosen to include the PCB 132 or to wire the lead 130 directly to the coils 130, 140.

Therefore, it will be understood that the dynamic reference frame may be formed in any appropriate shape. In addition, the dynamic reference frame 54 may be substantially moldable or non-moldable depending upon the selected shape or position for positioning the dynamic reference frame. Nevertheless, the dynamic reference frame 54 is substantially positioned non-invasively on the patient 14. Therefore, rather than fixing the dynamic reference frame in an invasive manner, such as with bone screws or the like, the dynamic reference frame may be fixed to the patient in a substantially error reducing manner using the tensioning members or a substantially molded portion.

In addition, more than one dynamic reference frame may be provided on the patient 14. More than one dynamic reference frame may be provided for error correction or error detection. Nevertheless, the inclusion of the non-invasive dynamic reference frames may be allowed for substantially simple positioning of the dynamic reference frames during an operative procedure. In addition, the dynamic reference frames 54 may be easily positioned relative to the patient 14 in a substantially quick manner as well. Therefore, the unexpected need for a dynamic reference frame 54 may be solved by simply fixing the dynamic reference frame 54 to the patient 14 using the various constructs. The dynamic reference frame 54 may also be fixed to the patient 14 in any appropriate manner. Such adhesives may be painted on, sprayed on, or include "double-sided" tape. Regardless, the adhesive allows for simple placement of the dynamic reference frame 54 for a selected procedure.

The size, such as the height, the width, etc. of the dynamic reference frame may be selected depending upon selected characteristics. For example, the hard wire dynamic reference frame 120, which may also be substantially wireless dynamic reference frame, may include a select height that is substantially shallow or low to allow for a reduced possibility of movement of the dynamic reference frame 120. In addition, the height or distance of the coils 138, 140 from the anatomy of the patient 14 is small. Therefore, any movement of the hard wire dynamic reference frame 120 is substantially closer to movement of the patient 14 than if the coils were positioned further from the patient 14. Therefore, the size of the dynamic reference frame may also be chosen depending upon the selective amount or error of the system.

In addition, as briefly mentioned above, the coils 138, 140 may be provided in the hard wire dynamic reference 120 or in any appropriate dynamic reference frame. Generally, the coils 138, 140 are substantially similar in functioning to the coils 96 and 98 on the sensor bobbin 90. Simply, the coils are positioned in a slightly different position, but angled relative to one another to provide sensing of six degrees of freedom. Therefore, whether the coils are substantially positioned on the single member, such as in the sensor bobbin 90, or separated such as the coils 138, 140 in the hard wire dynamic reference 120, still provide the required information for sensing the location of the dynamic reference frame.

Any of the dynamic reference frames (which also may be wireless) may be used as the dynamic reference frame 54, such as the dynamic reference frame 70, the intercochealor dynamic reference frame 111, or the hardwire dynamic reference frame 120 may include various selected characteristics. For example, the sensor portion, such as the included respective coils, may be removable for various reasons. If an imaging technique, such as an MRI is used to image the patient and the dynamic reference frame is left as a fiducial marker, the electromagnetic coils may be removed. Therefore, it will be understood that the coils may either be permanently included within the dynamic reference frame or may be removable therefrom, particularly when the dynamic reference frame is used as a fiducial marker.

In addition, the dynamic reference frame may be used as a fiducial marker. For example, the dynamic reference frame may include a region that is substantially matable or molded to mate with a portion of the anatomy in substantially one way. In addition the dynamic reference frame may also include a portion that is inherently contoured to mate with a portion of the anatomy without including a moldable portion. This allows substantially precise replacement and repeatability of placement of the dynamic reference frame to be achieved.

Because of the precise repeatable placement of the dynamic reference frame it may also serve as a fiducial marker that may be used in preoperative imaging to be a fiducial marker for use during registration intra-operatively. Therefore, the dynamic reference frames may include materials that are substantially radio-opaque or opaque to the imaging process. Various materials may be used to form the radio-opaque dynamic reference frames, such as selected metals, selected compounds, and various mixtures.

Moreover, if the dynamic reference frame is used as a fiducial marker, it may be selected to include portions on the dynamic reference frame that may be viewed on the preacquired image and during the procedure. For example, as discussed in relationship to the dynamic reference frame 70, the dynamic reference frame may include the reference dimple or landmark 80. It will be understood that a plurality of the reference dimples may be provided on the dynamic reference frame 70 for use during an operative procedure to reference the patient space to the image space. The number of reference points, which either may be physical portions, such as the dimples, or markings on the dynamic reference frame, are generally viewable and identifiable on the reacquired images, so that each may be matched to a selected portion of the dynamic reference frame during the operative procedure. This allows for multiple degrees of freedom and allows an appropriate and precise registration of the patient space to the image space.

In addition, it will be understood that each of the dynamic reference frames include a portion that allow the dynamic reference frame to be held relative to the patient 14. Therefore, each of the dynamic reference frames includes a selected holding portion. For example, the holding portion may include the adhesive that adheres the dynamic reference frame to a selected portion of the patient 14. In addition, the moldable portion, such as the moldable portion of the intercochealor implant 111*a*, may be a holding portion and no other portion may be provided to hold the intercochealor dynamic reference frame 111 relative to the patient 14. Regardless, each of the dynamic reference frames may include a holding portion that allows the dynamic reference frame to be held relative to a patient. It may be that the holding portion defines a substantially matable and repeatable placement of the dynamic reference frame relative to the patient 14, such that the dynamic reference frame may also be repeatably precisely placed and may be used for various purposes, such as a fiducial marker.

Figure 10A:
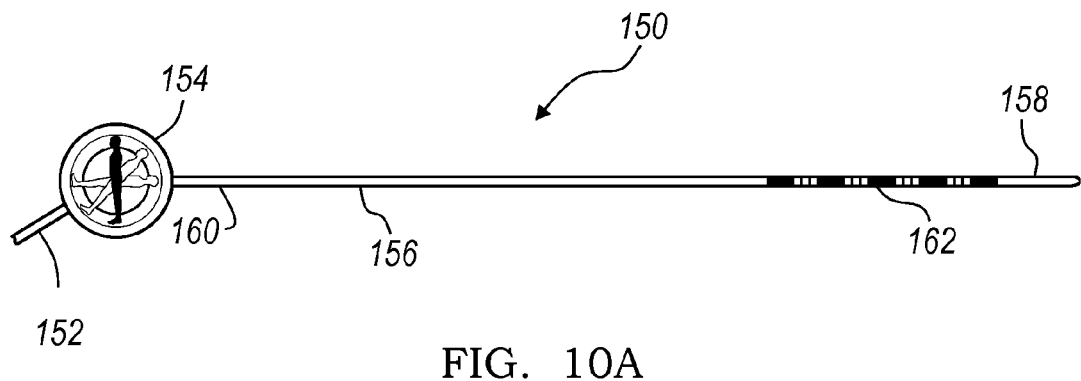
FIG. 10A is a side elevational view of a stylet.
Figure 10B:
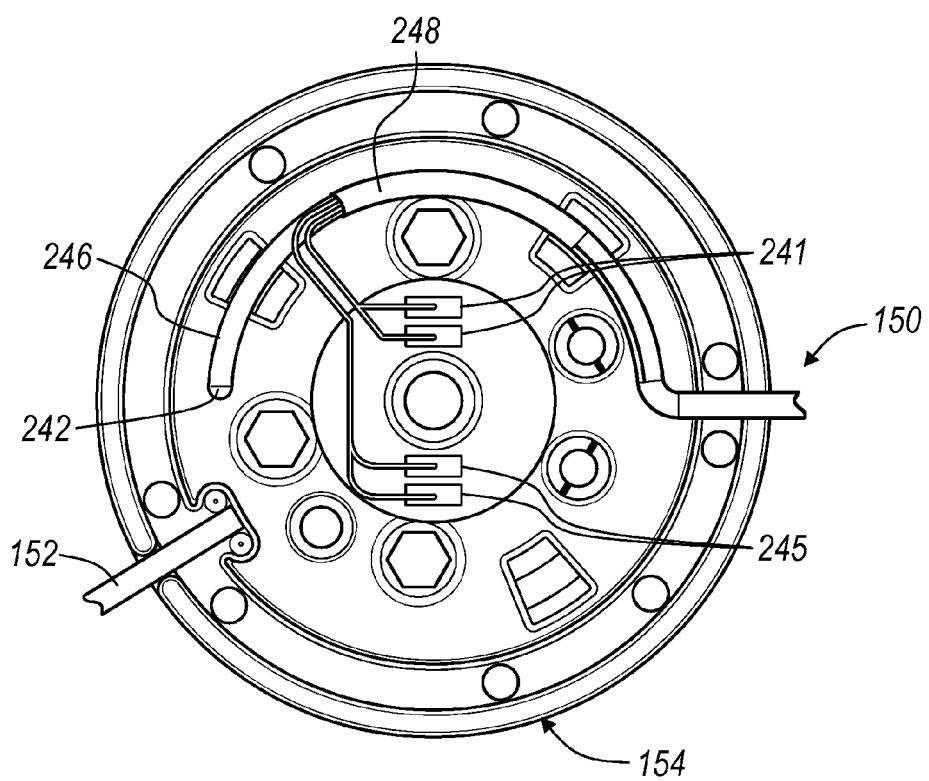
FIG. 10B is a detail interior view of a connection portion of the stylet of FIG. 10A.

Various instruments may be included for use in a selected procedure, such as a stylet 150, with reference to FIGS. 10A and 10B. The stylet 150 generally includes a connection wire or cable 152 and an electronic lead and/or handle 154. Extending from the handle 154 is a stylet portion 156 that is generally moved within the cavity of the patient 14. For example, the stylet 150 may be the instrument 52 rather than the catheter. Therefore, the stylet 150 is an exemplary instrument 52.

Generally, the stylet portion 156 includes a distal or tip end 158 and a proximal end 160. The stylet may be positioned through a cannula and may be used to guide the cannula, though the stylet 150 may be used for any appropriate reason. Positioned near the distal end 158 is a sensor 162. The sensor 162 may be a coil, or multiple coils, to interact with the field transmitted by the transmitter coil array 48. Briefly and described in detail herein, the sensor 162 is generally wrapped around an internal highly electromagnet permeable core insulated with a heat shrink or any appropriate dielectric material. The details of the process and the sensors 162 are described in further detail herein.

With additional reference to FIGS. 10A and 10B, the handle 154 of the stylet 150 may include an area to connect the wires from the coils. A first set of contacts 241 provide an area for contact to each of the leads of the first coil 240. A second pair of contacts 245 is provided for the leads of the second coil 244. In this way, power or sensor leads may be attached to the handle or sensor region 154 for receiving the sensitive information of the sensors or coils 240, 244.

Figure 11:
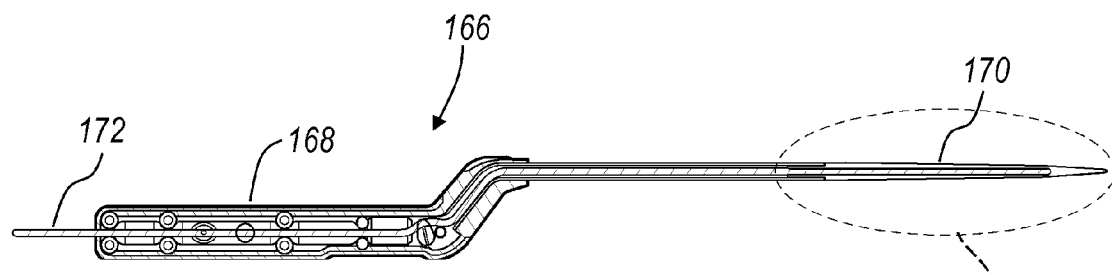
FIG. 11 is a cross-sectional view of a probe including a navigation sensor.

With reference to FIG. 11, a probe 166 is illustrated, as a further alternative for the instrument 52, and generally includes a handle portion 168 and a probe tip 170. The handle 168 is generally formed of a non-metallic material that can be easily grasped and isolated from the electrical lead 172. The electrical lead generally provides a current to a portion of the tip 170.

Figure 12:
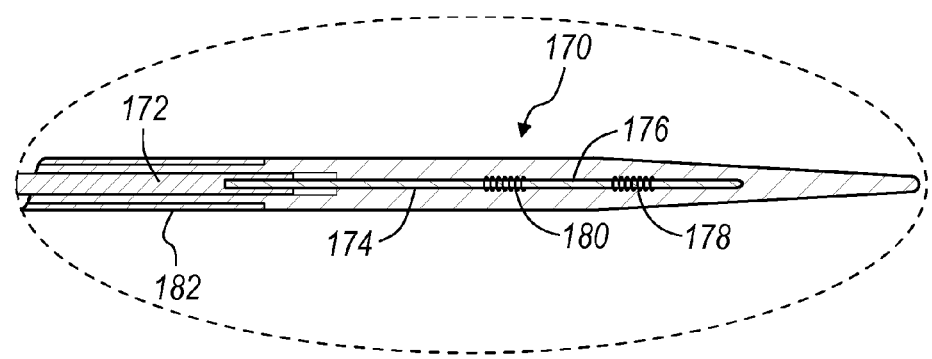
FIG. 12 is an enlarged view of the probe about circle 12 in FIG. 11.

With continuing reference to FIG. 11 and additional reference to FIG. 12, a tip sensor 174 may be positioned in the tip 170 of the probe 166. The tip 170 generally is formed of a non-metallic and/or a non-conductive material. Inside of the tip 170 is a metal shaft 176 that can be formed of an appropriate electromagnetic permeable material. Formed around the metal shaft 176 is a sensor coil 178. A second sensor coil 180 may also be provided. The first and second sensor coils 178, 180 are generally co-axial and formed along the axis of the permeable rod 176. The tip 170 and the rod 176 with the coils 178, 180 are generally positioned within a tube portion 182 of the probe 166. As discussed, the lead 172 provides power to the sensor portion including the coils 178, 180. The sensor portion including the coils 178, 180 may be similar to the sensor portion 162 of the stylet 150 and described in detail herein. Regardless, the sensor portion is generally positioned substantially at the tip or the distal end of the probe 166 to allow for substantially accurate measurement of the position of the tip of the probe.

Figure 13:
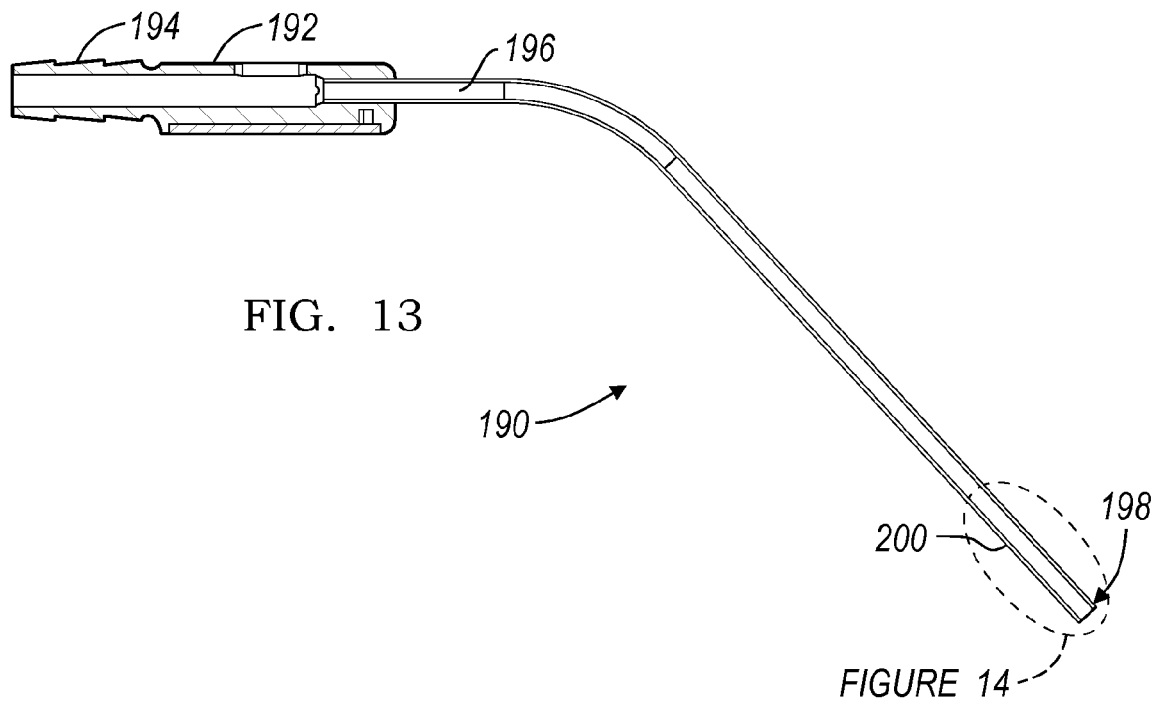
FIG. 13 is a cross-sectional view of a suction instrument according to various embodiments.
Figure 14:
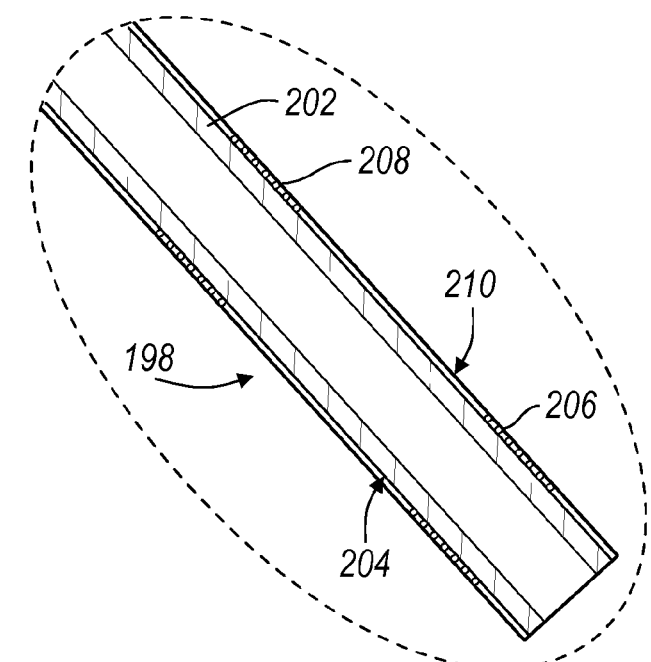
FIG. 14 is an enlarged view about the circle 14 of FIG. 13.

With reference to FIGS. 13 and 14, a suction device 190 is illustrated. Again, the suction device 190 generally includes a handle 192 which includes a connection area 194 to be connected to a suction source. A cannula opening 196 runs the length of the suction portion such that material may be suctioned through a distal tip 198 of the suction instrument 190. Also provided through the handle 192 may be a power source that is able to energize a sensor or sense an electromagnetic field that is acting upon a sensor 200 positioned in the tip 198.

With particular reference to FIG. 14, the suction instrument 190 near the tip 198 generally includes an internal ductile and possibly conductive or nonconductive tube 202. Positioned over the tube is an inner dielectric layer 204. Coils 206 and 208 may also be positioned over the dielectric layer 204. Finally, the sensor 200 may be sealed with an outer dielectric layer 210. Again, the formation of the sensor 200 is described herein including the two coils, 206, 208. Generally, the coils are positioned near the tip 198 of the suction instrument 190 and to provide for substantially accurate position data for the tip 198 of the suction instrument 190. Therefore, the tip 198 of the suction instrument 190 may be moved and the sensor 200 is positioned substantially near the tip 198 so that intended or unintended motion of the tip 198 relative to the handle may be determined.

The sensors, according to any embodiment described above, are generally positioned near a distal end or movable end of an instrument, such as the suction instrument 190, the probe 166, or the stylet 150. Generally, the position of the various instruments, particularly the ends of the instruments, is determined by the known location of a sensor or a transmitting coil and the known size, length, and other physical attribute of the instrument. Therefore, the sensor may be positioned away from or disposed a distance from the extreme end of the instrument. Although a very small and tolerable error may be introduced when the instruments are flexed or move unexpectedly, but this may also cause the exact location of the tip to not be known. This may require many repositioning and attempts to complete a procedure. This error may be detected or substantially eliminated when the sensor is positioned near the distal tip of the instrument, particularly when the instrument is flexible. Therefore, rather than determining or knowing the various physical characteristics of the instrument, the actual sensed portion is the end that may move expectedly or unexpectedly. Therefore, providing the sensor near the distal tip may provide for substantial accurate position data of the instrument.

Generally, the position of the instrument is displayed on the display 36 and is not generally viewable by a user because it is within the cavity of the patient 14. Therefore, the user is generally dependent upon the accuracy of the display 36 to ensure the proper location, orientation and other attributes of the instrument relative to the patient 14. For example, as illustrated in FIG. 1, the instrument 52, such as the catheter, is positioned relative to a specific portion of a heart of the patient 14. Similarly, the stylet 150 may be positioned relative to an extremely particular and precise portion of the brain. Therefore, it may be selected or desirable to substantially eliminate any error when determining the position of the instrument relative to the patient 14.

Although the following description relates generally to the formation of the sensor 162 for the stylet 150, it will be understood that the sensor may be used in any appropriate instrument 52, such as the catheter, the probe 166, the suction instrument 190 or any other appropriate instrument. In addition, the instruments may include any selected tip shape or sizes depending upon a selected use of the instrument. For example, an arthroscope or camera may be provided in the tip for viewing on the display 36 or any other appropriate display. Nevertheless, the sensor may be positioned near the lens portion such that the exact and precise location of the lenses is known.

In addition, various portions of the instrument may be ductile or movable such that the tip is not at a fixed location relative to other portions of the instrument. Therefore, the tip may be movable while the handle is substantially fixed at a known location. Therefore, the sensor positioned at the tip is able to provide the position of the tip even though the handle has not moved.

It will also be understood that various handle calibration and verification points may be included as well as areas for directing wiring within the various instruments and through the handle. It will be understood that these various portions are provided for directing wiring, allowing verification and calibration and are not described in unneeded detail. In addition, the instruments may be substantially disposable or reusable, depending upon the various material specifics being used and the sterilization techniques.

Figure 15:
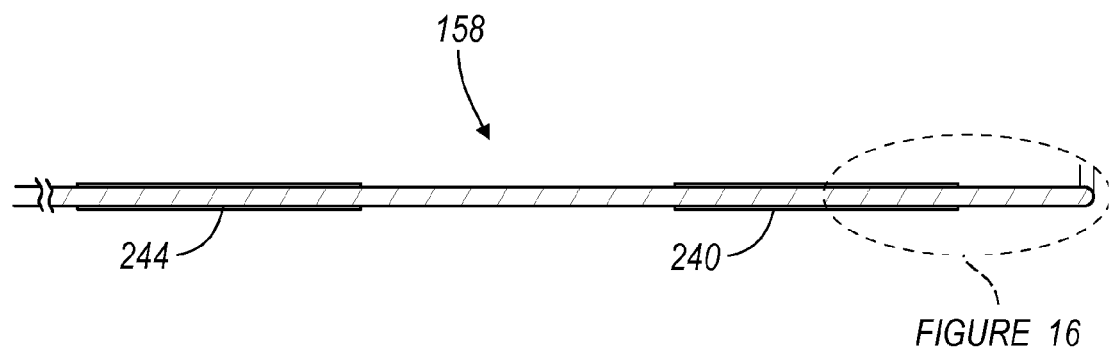
FIG. 15 is a view of a tip of the stylet of FIG. 9A.

According to various embodiments, a method of forming the sensors that can be positioned near the tip in a substantially small volume or space, such as in the stylet tip 158, is described. With reference to FIG. 9 and FIG. 14, the stylet tip 158 is illustrated in detail in FIG. 14. With reference to FIG. 15, a detail of a first sensor coil 240 and an extreme distal tip portion 158A is illustrated. The various coatings or layers around a central rod 242 is illustrated and described herein. Generally, the central rod 242 is a conductive rod and may include various materials such as "302 spring" stainless steel. The material for the rod 242 that is also generally the flexible or steerable portion of the stylet 150 may be any appropriate material. Generally, the material for the rod 242, however, is highly permeable to electromagnetic fields. This generally increases the signal to noise ratio or the gain of the signal of the sent field to a selected amount. Generally, the signal to noise ratio may be increased at least about 5% depending upon the various materials chosen to form the selected construct.

Figure 16:
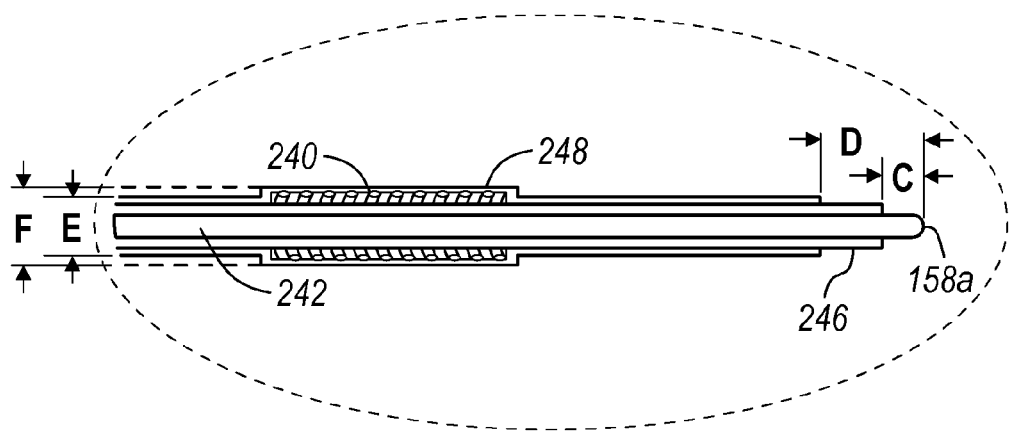
FIG. 16 is a cross-sectional view of the stylet tip of FIG. 15 from circle 16.

With reference to FIGS. 15 and 16 the stylet tip 158 generally includes a first coil and may also include a second coil 244. The first and second coils 240, 244, or any appropriate number of coils may be provided on the tip 158. In addition, the coils 240, 244 may be substantially co-axial or formed at an angle relative to one another. That is, the wire or material used to form the coils 240 and 244 may be wrapped at an angle relative to each other around the rod 242. When the coils are not wrapped at an angle relative to one another, a degree of freedom may not be detected, such as rotation. For various instruments however, such as the uniform stylet tip 158, rotational information may not be necessary and selectively not determined. Nevertheless, for other instruments, such as a suction tube, an ablation tube, or a lens, it may be desired to produce the coils at an angle relative to one another such that rotational direction and location may be determined.

Figure 17:
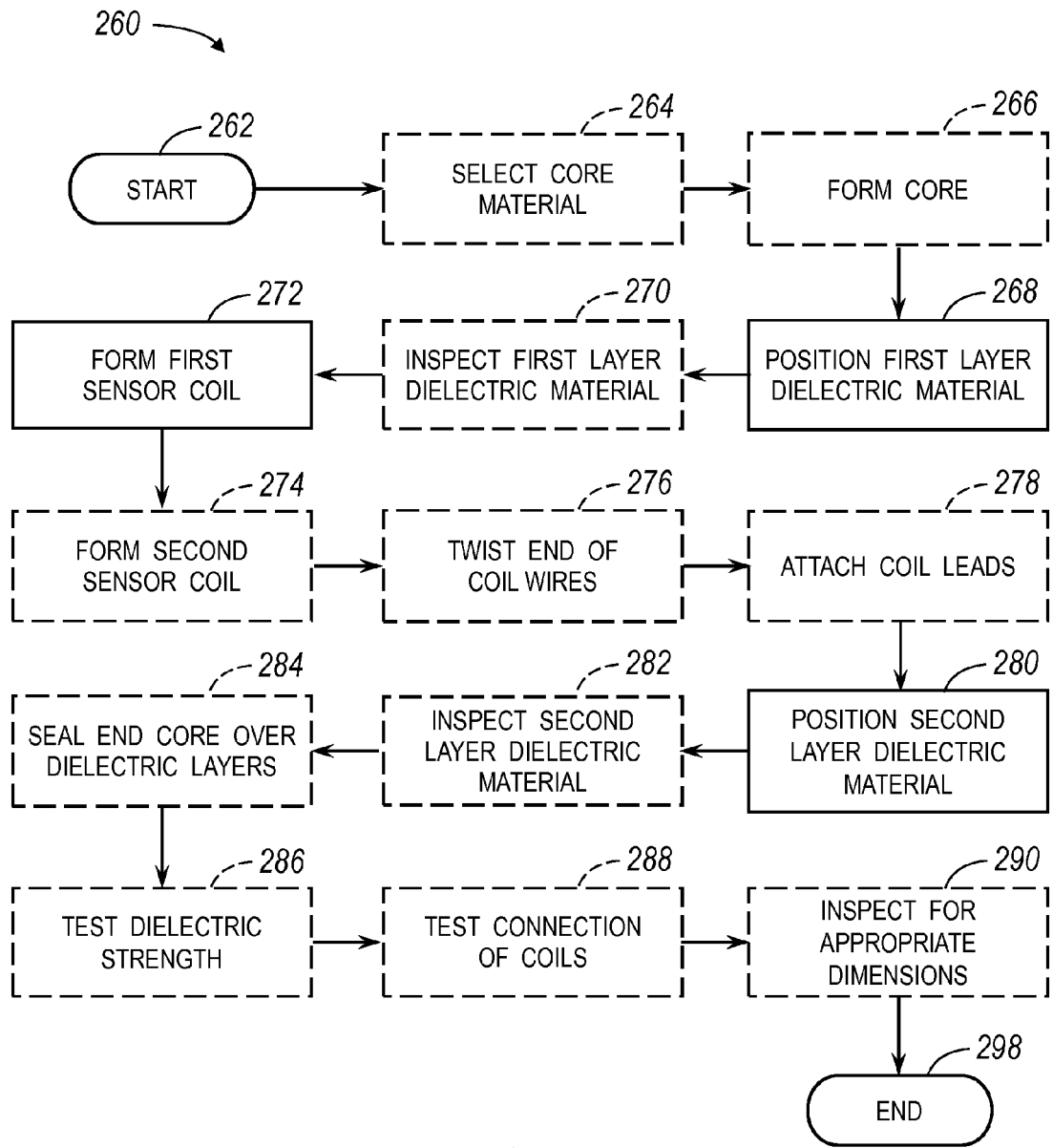
FIG. 17 is a method of forming an electromagnetic sensor according to various embodiments.

As described in detail in flow chart in FIG. 17, prior to forming a coil, a first dielectric barrier or layer 246 may be provided over the rod 242. The first dielectric barrier layer 246 generally is not placed over the extreme end of the tip 158*a* and generally includes a back set or offset distance of about 0.025 mm to about 1.5 mm depending upon the size of the rod 242. For example, the offset distance C may be a selected multiple of a diameter of the rod 242. Not to be limited by the theory, but including the back-set may reduce the possibility of damage to the first dielectric layer 246 during use of the stylet 150. Generally, the extreme tip 159*a* may be used to touch hard surfaces and this may damage the dielectric material. Nevertheless, it will be understood that the first layer of the dielectric material 246 may extend over the extreme tip of the tip 158.

The coils 240, 244 may then wrapped around the first dielectric layer 246. After the coils are positioned over the first dielectric layer 246, a second dielectric layer 248 is provided over the coils 240, 244. Again, the second dielectric layer 248 may be offset a distance D from the extreme end of the tip 158*a*. Nevertheless, it will also be understood that the second dielectric layer 248 may also extend to the end of the tip 158*a*.

It will be understood that the first layer 246 and the second layer 248 need not necessarily be a dielectric material. This is merely exemplary and not intended to limit the scope thereof. For example the material may simply be used to isolate the windings from an exterior environment and the first layer omitted entirely. Alternatively, the wire that forms the coils 240, 244 may be separately or individually coated prior to forming the coils 240, 244. Therefore, the isolation may be achieved without forming a separate layer or coating, such as the first and second layers 246, 248.

Although the apparatus and a very brief process for forming the apparatus is described above, the following description, in addition to the flowchart illustrated in FIG. 17, describes a detailed method of forming the stylet tip including the sensor 162 according to various embodiments.

A method of forming a sensor, such as electromagnetic sensor that may be either passive or active, is described in relationship to the flowchart and a method 260. Generally, the method begins a start block 262.

After the process is started in block 262, a material may be selected for form a core in block 264, such as the core 242. As described above, the selected core material in block 264 may be a highly electromagnetic permeable material. Although it is not necessary that the core be highly permeable to electromagnetic fields or be conductive, it may be desirable to provide a highly permeable core for various applications. For example, when forming the stylet tip 158, it may be selected to provide the stylet tip to have diameter no greater than about 1.25 mm. In addition, it may be selected to include a stylet diameter of less than about 1 mm. It may also be desirable to provide a stylet tip 158 in any appropriate diameter or selected property. Therefore, the stylet 158 may be deflectable or bendable according to selected characteristics. Also, at the small diameter the highly permeable material may increase the gain of the field sensed by the coils. Therefore the location information may be more easily determined and sensed.

After the selected core material is chosen in block 264, the core is formed in block 266. The core may be formed according to any selected specifications, such as those described above. Therefore, the core formed in block 266 may include a length, a cross-section, and other various properties that may be selected for the stylet tip 158. Although the material may be selected for the core in block 264 and the core formed in block 266, it will be understood that these steps are optional as steps for forming the selected sensor. The method 260 is exemplary for forming the stylet tip 158. Although the process 260 is exemplary for forming the stylet tip 158, it will be understood that various portions thereof may be used in any process for forming a sensor according to the below described process and a tip sensor in a substantial small area. Therefore, steps that are substantially optional are positioned in blocks that are outlined with dashed or phantom lines and will be indicated as optional herein. Therefore, it will be understood that various steps, although described, are not required to form the sensor as described herein. Therefore, the process is merely exemplary and various specific details are provided only for clarity and not intended to limit the description or the appended claims.

After the core is optionally formed in block 266, a first layer of material is positioned over the core in block 268. The first layer of material positioned in block 268 may be a dielectric. Though the material for the first layer may be any appropriate material and is merely exemplary a dielectric. The first layer of the dielectric material may be positioned over the core in any appropriate manner. For example, the first layer of the dielectric material may be positioned over the core as a heat shrink or shrink wrap process. This being that a portion of the material may be formed as tube and slide over the core and then shrunk to substantially engage the core along its length. Alternatively, the material may be painted on or sprayed on the core formed in block 266.

For any or all of these processes, a plurality of layers of the material may be positioned on the core to form the first dielectric layer of a selected thickness. The thickness of the dielectric layer may be any appropriate thickness according to selected characteristics. For example, the thickness of the first layer of the dielectric material may be about 0.00025 inches to about 0.03 inches (about 0.00635 mm to about 0.762 mm). Generally, however, the first layer of the dielectric material may be about 0.001 inches (about 0.0254 mm) in thickness.

The dielectric material may also be any appropriate dielectric material to achieve selected results. For example, it may be selected to have dielectric breakdown strength of about at least about 4,000 volts per about 0.001 inches (mil) (about 0.0254 mm) in thickness. Although any appropriate dielectric break down strength may be selected. Also, it may be selected to choose other properties for the first dielectric layer placed in block 268. Various materials may be used such as polyester shrink tubing or ULTRATHIN WALL POLYESTER (PET) shrink tubing provided by Advanced Polymers Inc. of Salem, N.H. Although any appropriate material may be used, it may be selected to include the dielectric breakdown strength of at least about 1000 volts per mil.

After the first layer of dielectric material is positioned on the core, the layer may be inspected in block 270. The inspection may be any appropriate inspection such as a visual inspection, magnification inspection, or various electrical tests to ensure that the selected installation is achieved. Also, the first layer of dielectric material may be inspected to ensure that it has been positioned on the core in a selected manner. As described above, it may be selected to only cover a selected portion of the core and not extend the first layer of dielectric material substantially to the tip of the core. As illustrated in FIG. 15, it may be selected to position the first layer of dielectric material 246, the distance C from the extreme end 158*a* of the tip 158.

After the optional inspection of block 270, a first sensor coil is formed in block 272. The sensor coil, such as the coil 240 illustrated in FIG. 15, may be formed using any appropriate materials. For example, a 48 gauge magnetic wire that is coated with a single built polyurethane with butyl bonds may be wrapped around the core including the first layer of dielectric material to form the first sensor coil.

The wire may be wrapped around the first layer of the dielectric material in any appropriate manner. For example, the coils may be wrapped substantially co-axially with a longitudinal axis of the core. Alternatively, the wire may be wrapped substantially at an angle to the core for selected reason, such as sensing rotation of the core during use. As an example, a first sensor coil may include a first layer of coils including approximating 300 turns and a second layer positioned over top of the first layer also having approximately 300 turns. Therefore, the first coil formed in block 272 may include approximately 600 turns. Nevertheless, it will be understood that only a single layer or any number of layers may be used and that any appropriate number of turns may be used to form the first sensor coil in block 272.

The first coil formed in block 272 is exemplary wound around the first layer positioned in block 268. It will be understood that the wire used to form the coil in block 272 may first be coated or may be a coated wire. When the wire is coated or covered positioning the first layer of material in block 268 may be omitted. The coating on the wire may provide all of the properties, such as electrical, environmental and the like, that the material in the first layer formed in block 268 may otherwise provide.

An optional second coil, which may also be formed of coated or covered wire, may be formed in block 274. Therefore, it will be understood that any appropriate number of coils may be formed for reasons discussed herein but may include a first coil formed in block 272 and a second coil formed in block 274. If there are two coils, the second coil may be positioned a selected distance from the first coil. For example, the first coil may have an edge that is about 0.25 mm to about 10 mm from an end of the second coil. Nevertheless, it will be understood that the coils may be positioned at any appropriate position on the tip 158 and relative to one another.

After the first sensor coil is formed in block 272 and optionally the second sensor coil in block 274, the ends of the wires forming the sensor coils may optionally be twisted in block 276. The ends of the wires that form the coils formed in blocks 272 and optionally in block 274 may be twisted in any appropriate manner. For example, the wires may be twisted in about 10 to about 30 twist per inch and may be uniformly twisted rather than twisting one around the other. Although it will be understood that the wires may be formed in any appropriate manner and that twisting the wires in block 276 is merely optional.

After the wires are optionally twisted in block 276, the ends of the coils are attached to locations on the stylet handle in block 278. Generally, the leads of the coil are attached to selected positions, such as to a printed circuit board or to other wire leads, that allow for interconnection to various components, such as the navigation interface 50 (FIG. 1). The coil leads that are attached from block 278 may be attached to any appropriate portion and may be from either the first sensor coil formed in block 272 or the optional second sensor coil formed in block 278.

After the leads from the coils are attached in block 278, or at any appropriate time, a second layer of material may be positioned in block 280. The second layer of material positioned in block 280 may be any appropriate material and is only exemplary a dielectric. The second layer of dielectric material may be positioned over both of the first layer of dielectric material, that was positioned in block 268, and over the sensor coil formed in block 272, and optionally in block 274. The material that is used to form the second layer of the dielectric material may be the same or different than the material chosen to form the first layer of the dielectric material in block 268. In addition, the method of positioning the second layer of the dielectric material in block 280 may also be the same or different that the method used to position the first layer of dielectric material in block 268. For example, the first layer of the dielectric material positioned in block 268 may be a substantially heat shrink or shrink tubing that is positioned over the core formed in block 266 and then shrunk according to any selected method, such as heating. Alternatively, the second layer of dielectric material positioned in block 280 may be sprayed or painted on over. In addition, the material may be the same, such as the Ultra Thin Wall polyester (PET) heat shrink tubing produced by Advanced Polymers Incorporated or may be any other appropriate material.

Nevertheless, the second layer of the dielectric material may include the same or different dielectric break down strength in the first layer. For example, the dielectric breakdown strength of the second layer of the dielectric material may be at least 4000 volts per mil or may be any other appropriate amount.

Briefly, as an example, the first layer of the dielectric material may provide insulation between the sensor coil formed in block 272 and the core formed in block 266. Therefore, the sensor coil formed in block 272 is electrically isolated from the core formed in 266. This allows the core formed in 266 to also be a conductive material and may also act as a core and a gain amplifier for the sensor coil, as described further herein. In addition, the second layer of the dielectric material may act as an electrical insulator relative to a patient or a portion exterior to the core and as an environmental seal to the sensors formed in block 272 and optionally in block 274.

It will also be understood that the second layer of the material positioned in block 280 may also be omitted. It may be omitted for any reason, such as the wires that form the coil formed in block 272 are previously coated. Therefore, the second layer of material formed in block 280 may be omitted. Regardless, the second layer of material may be any appropriate material and need not be a dielectric. The second layer of material in block 280 may be positioned for any appropriate reason, such as a liquid seal, an electrical isolation, etc.

After positioning the second layer of the dielectric material in block 280 the second layer of dielectric material may be optionally inspected in block 282. As in block 270, the material may be inspected according to any appropriate method, such as visual inspection, magnification inspection, and electrical testing.

After the second layer of the dielectric material is optionally inspected in block 282 the ends over the core may be sealed. As illustrated in FIG. 16, the first layer of dielectric material 246 and the second layer of dielectric material 248 may not extend over the extreme tip 158a of the core 242. Therefore, it may be selected to seal the extreme end 158a over the dielectric layers 246, 248 to achieve a substantially water tight or other material tight seal.

The seal formed optionally in block 284 may be formed in any appropriate manner. For example, the extreme tip 158a and any selected length along the tip 158 may be dipped into a selected material, such as Loctite® 4014 produced by Henkel Corporation of Rocky Hill, Conn. The material may substantially seal the interior so that no fluid can be wicked or drawn towards the coil 240 through capillary action. Therefore, the coating of the dielectric layers, blocks 268 and 280 may be sealed in any appropriate manner to ensure that no fluid is allowed to destroy or short the coils formed on the tip 158.

In addition to the steps described above, various other steps such as testing the dielectric strength in block 286, testing the connection of the coil after attaching the coil leads in 278, testing the coils in block 288, and inspecting the construct for achieving the appropriate dimensions in block 290 may be performed. Then the process ends in block 292.

Although various optional steps may have been performed in the method 260 it will be understood that the sensors generally formed by positioning on a first layer over dielectric material over a core, forming a sensor coil around the first layer of the dielectric material in block 272, and positioning a second layer of dielectric material in block 280 over the coil may be performed. In addition, the dielectric materials may be any appropriate materials and are generally provided only for safety considerations. Therefore, simply forming the coil around the core may be performed for any appropriate purpose. Providing the dielectric layers are able to protect the user and the patient from any possible surges and insure that the instrument is not corrupted by environmental degradation.

Furthermore, additional assembly steps may be performed depending upon the selected instrument. As illustrated in FIG. 10, the cable 152 may be interconnected with the connection area 154 and interconnected with the navigation probe interface 50. Alternatively, if the other instruments, such as the probe 166 or the suction tube 190 are formed, the relative handles may be provided and affixed thereto and various other connections may also be performed. Nevertheless, it will be understood that these steps are not necessary for forming the sensor near the tip of the construct.

With reference to FIG. 16 the exterior dimension or diameter E of the tip 158 and of the stylet portion 156 of the stylet 150 may be any appropriate dimension and may be about 0.09 mm to about 1.5 mm in diameter. It will be understood that the dimension may be any appropriate exterior dimension as the stylet portion 160 may be formed in any shape, but may be a cylinder. The diameter E generally includes the dimension of the core 242 the first dielectric layer 246 and the second dielectric layer 248. In addition, a diameter F that includes the diameter or size of the coil 240 may be about 0.9 mm to about 1.50 mm in diameter. Therefore, the diameter F may be greater than the diameter E depending upon whether the space between the coils is selected to be equal to the size as around the coils 240.

Regardless of the actual size, it is desired to include a diameter of the stylet portion 156 that is substantially small for use in various purposes. For example, the stylet portion 156 may generally be provided with a cannula that is positioned in various portions of the anatomy, such as the brain. Therefore, it may be desirable to provide the stylet portion 156 and a plurality of other instruments through the cannula without moving the cannula. Therefore, the stylet may be of a selected diameter that will substantially freely move within the cannula.

Although it may be selected to keep the maximum diameter F under a selected size, it will be understood that any appropriate or selected size of diameter may be used. Simply having a substantially small diameter may provide various selected properties, as having it selected for various instruments and purposes. Again, as described above, various portions of the instrument and the method may be optional and not necessary. Although the core 242 may be formed of a substantially conductive material that is surrounded by the first layer of dielectric material 246, that is able to isolate the coil 240 from the conductive material of the core 242, and the second layer of dielectric material 248 provided to enclose the coil 240 from an exterior environment; it will be understood that various other portions, such as providing the core 242 as the core 176 in the probe 166 or the metal tube 202 on the suction instrument 190 may also be provided.

The core 242 may be formed of any appropriate material, but may be formed of the permeable material that may include ferrous materials such as ferrites like those provided by Fair-Rite Products Corp. of Wallkill, N.Y. The permeable material may provide a gain to the signal of the coils, such as the first coil 240 and the second coil 244 in the stylet 150. The material may provide a gain that is relative to its permeability, especially above the permeability of air. Therefore, the gain experienced may be dependent upon the type of material chosen for the core 242, or any core about which the coils are formed in various embodiments.

In addition, it will be understood that any appropriate number of coils may be provided. For example, the stylet 150 may include the first coil 240 and the second coil 244. As described above, the windings of the coils 240, 244 may be substantially co-axial so that only five degrees of freedom are determined. Nevertheless, the windings of the coils may also be formed at an angle relative to one another so that rotational orientation of the stylet 150 may also be determined. In addition, any appropriate number of coils may be provided along the length of the instrument for various purposes.

For example, two coils that are coaxial may be provided for error detection. The first coil may be provided at a known distance from a second coil. Therefore, the sensed position of the first coil 240 relative to the second coil 244 may be used to detect errors between the positions of the two to determine the exact location of the tip 158 of the stylet 150. In addition, a compensation circuit may be provided to compensate for the sensed signal from the first coil 240 relative to the second coil 244. Therefore, providing two coils in the stylet 150 may be provided for any number of reasons or for all appropriate reasons. In addition, it will be understood that the number and types of coils may be provided in each of the instruments described above and any other appropriate instrument. Nevertheless, a substantially small or narrow sensor coil may be provided according to the steps described above and may also be provided according to the various optional steps described above.

Figure 18:
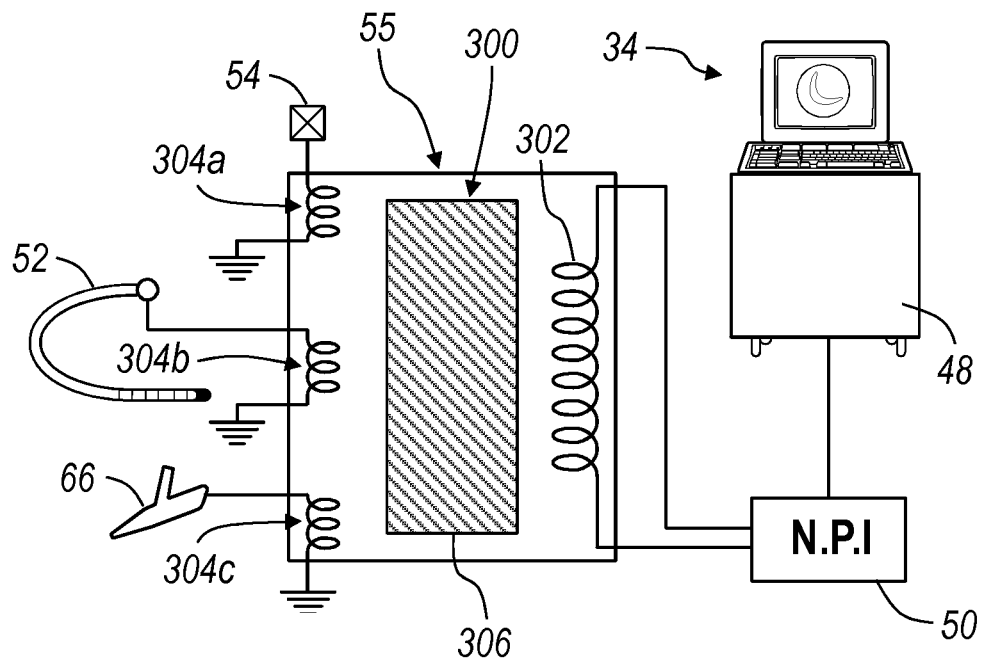
FIG. 18 is a schematic view of an isolator circuit according to various embodiments.

With reference to FIGS. 1 and 18 the isolator circuit 55 may be provided to isolate any portion of the instrument 52 that may engage the patient 14 from the electrical source, such as the work station 34. As illustrated in FIG. 1, the instrument 52, which may include the stylet 150, the probe 166, the suction instrument 190, and/or any other appropriate instrument, is inserted into the patient 14. Each of the instruments may include the sensor 58, as disclosed herein and above, to which an electrical current has provided. In addition, the dynamic reference frame 54, according to any of the embodiments or various other embodiments, as described herein or understood to be included within the scope of the present disclosure, may also include an electrical lead from the navigation probe interface 50. In addition, any other systems such as the probe 66 may each have an electrical current provided thereto. The isolator circuit 55 may be positioned anywhere to isolate any of these instruments from the electrical source.

The isolator circuit 55 may include any appropriate isolation transformer 300. The transformer 300 may include a first coil 302 that is operable to transmit or receive a signal. The first coil 302 may generally be on an output side that receives a signal and transmits it through the navigation probe interface 50 and to the workstation 34 or the coil array controller 48.

The first coil 302 may be separated from a plurality of second coils 304a, 304b, and 304c by a dielectric or appropriate medium 306. As described herein each of the coils 304a-304c may be in-line with a selected instrument or device. It will be understood, however, that a single second coil may be provided with a plurality of taps connected thereto. The dielectric medium 306 eliminates a current that may attempt to transfer from the first coil 302 to the second coils 304a, 304b, and 304c or vice versa. Nevertheless, an electromotive force may be provided into either of the first coil 302 or the second coils 304a, 304b, and 304c that may couple across the dielectric material 306. In this way, the second coils 304a, 304b, and 304c is electrically isolated from the first coil 302, such that only a potential is able to transfer across the dielectric medium 306.

The second coil 304 may include leads to the dynamic reference frame 54, the instrument 52, such as a catheter, and the probe 66. As discussed above the instrument 52 may also be the stylet 150, the probe 166, and/or the suction tube 190, or any appropriate instrument. Both the first coil 302 and the second coils 304a, 304b, and 304c may also include a ground lead. Generally, the first coil 302 is operably connected to the work station 34 through the navigation probe interface 50. The navigation probe interface may include appropriate power sources and amplifiers as necessary. Therefore, the navigation probe interface 50 may be electronically isolated from the various portions of the assembly 10 that may engage the patient 14. In this way, a current may not be transferred through the electrical isolator 55 to any of the instruments, sensors, or portions that touch the patient, such as the instrument 52 and the dynamic reference frame 54.

In addition, as discussed briefly below, the first coil 302 may include a different number of windings than the second coils 304a, 304b, and 304c. For example, if it is desired to include a stronger signal going back to the navigation probe interface 50, a number of windings in the first coil 302 may be greater than the number in the second coil 304. Therefore, the electrical isolator 55 may also act as an amplification circuit for receiving a signal from the various components, such as the dynamic reference frame 54 and the instrument 52.

As illustrated in FIG. 1, the isolator circuit 55 may be provided on any of the lines from the navigation probe interface 50. Therefore, any electrical surge may be immediately stopped before engaging the patient 14 or instrument 52. Thus, the isolator circuit 55 may be positioned on each of the lines leading to each of the instruments, the probe 66 or the dynamic reference frame 54. Furthermore, the isolator circuit 55 may be incorporated into the navigation probe interface 50 or into any of the instruments 52, the dynamic reference frame 54, or the probe 66. The isolator circuit 55 may be positioned anywhere to eliminate the current that may be unintentionally provided to the patient 14.

For example, with reference to FIG. 9B, the isolator circuit may be included within the circuit capsule 154 of the stylet 150. Therefore, the power provided to the stylet 150 may be interrupted when a selected voltage or current is reached. The isolator circuit may allow stopping a voltage before it is able to pass through the circuit to reach the sensors. The isolator circuit 55 in addition to the dielectric layers positioned over the coils 240, 244, may assist in protecting the patient 14 from undesired electrical shock. In addition, the isolator circuit 55 may be incorporated into any other appropriate portion of the other instruments with a dynamic reference frame.

In addition to isolating the patient 14 from undesired electrical current or shock, the isolator circuit 55 may also act as an amplifier to increase the signal to noise ratio. For example, the isolator circuit 55 may be a step up transformer that is designed to increase the signal to noise ratio a selected amount. For example, a selected side, such as the signal output side, of the circuit may include a number of windings that is greater than the signal input side such that the signal is stepped up and the signal to noise ratio is increased. Therefore, the isolator circuit 55 may not only electrically isolate the patient 14 from an undesirable surge, but may also increase the signal to noise ratio to increase the efficiency of the navigation system 10.

Therefore, the navigation system 10 may be provided to include a dynamic reference frame 54 that is substantially non-invasive such that the patient 14 does not endure further trauma than required from the operative procedure. Generally, the navigation system 10 is able to provide a less invasive or minimally invasive procedure to achieve less trauma to the patient 14. Therefore, providing a substantially non-invasive dynamic reference frame may assist in decreasing the overall trauma or invasiveness of the procedure.

In addition, the sensor coils may further reduce the size of the instrument for various purposes. In addition, the size of the coils may allow the coils to be positioned near the distal end of the instrument to more precisely determine the position of the instrument. Therefore, the position determination of the instrument can be more accurate. For example positional accuracy can be increased by at least about 5% over placing the sensors away from the tip. The procedure may then be performed with fewer attempts thereby again further reducing the possible trauma of the procedure.

Also, the isolator circuit 55 may increase the signal to noise ratio to better determine the position of the various sensors and therefore determine the position of the instrument. In addition, the isolator circuit 55 may assist in isolating the patient 14 from any electrical sources of the navigation system 10. Therefore, the navigation system 10 may increase the efficacy.

According to various embodiments dynamic reference frames (DRFs) may be provided. DRFs may include a tracking sensor. The tracking sensor may be tracked by a tracking system. The DRF may be used by the system to register or maintain registration of patient space to image space.

Various DRFs may be fixed or inserted in various portions of the anatomy, such as those described above and herein. Various DRFs may be fixed in bores in hard or boney portions. Various DRFs may be fixed in at least one orientation relative to selected portions of the anatomy. It will be further understood that although a DRF is discussed in particular herein, any appropriate sensor may be provided. The sensor may be a portion of a tool, a probe, or any other instrument. Also the DRF, according to various embodiments may include coils for use in an electromagnetic tracking system, but may also include or alternatively include optical sensors, acoustic sensors, or any appropriate sensor portion. The DRF may be also referred to as a DRF assembly. The sensor in the DRF may generally be referred to as a tracking sensor for us in a DRF or a DRF sensor. Thus, it will be understood, that a DRF may include a DRF sensor that includes a tracking sensor used as a DRF.

Further, as described above and herein, a plurality of the DRFs may be used to assist in maintaining registration of the patient space to the image space. As described above, the registration allows for the tracking system to track an instrument relative to the patient and ensure that the display shows an accurate position and orientation representation of the instrument relative to the patient. The DRFs, as described above, assist in maintaining the registration of the patient space to the image space during a selected procedure regardless of movement of the patient. It will be understood, however, that any appropriate number of DRFs may be provided on the patient or in a selected position for maintaining the registration of the patient space to the image space.

For example, a single DRF that provides six degrees of freedom information may be used. The single six degree of freedom DRF (6 DOF DRF) tracks six types of movements in space that may be identified with the single DRF and maintained relative to the patient. Generally, the 6 DOF DRF is substantially fixed both rotationally and translationally relative to a portion of the patient. For example, an anti-rotation DRF may be positioned relative to the patient, such as in a bony portion, that includes a selected number of tracking sensors or coils to ensure the 6 DOF DRF. In this regard, three coils, positioned for example, orthogonal to one another will provide 6 degrees of freedom information.

Nevertheless, more than one DRF may be provided if a selected type of motion is not fixed or trackable. For example, a rotational movement may not be fixed and therefore at least one degree of freedom, or one type of motion may not be tracked by the tracking system. Therefore, it may be selected to include more than one DRF to allow for determination of the type of movement not detectable by the single DRF but may be compared between a plurality of the DRFs to determine the last type of motion. Alternatively, the single DRF may only include two orthogonal coils and still be rotationally fixed to the patient. However, use of the two coils generally will not provide 6 degrees of freedom information.

In this regard, generally in an electromagnetic tracking system, three coils substantially unaligned with one another, such as orthogonal to one another, are required to provide six degrees of freedom information. These coils or tracking sensors may be located in a single DRF. Alternatively, three DRFs, where each DRF includes a single coil, where each coil is again not positioned coaxial or linear relative to the other coils. This combination will also provide six degrees of freedom information. By providing less than three coils within a single DRF enables the DRFs to be smaller due to requiring less coils and hence, overall smaller size. Therefore, a single six degree of freedom DRF would generally be larger than individual DRFs each providing only a single coil and three degrees of freedom information. The size of the DRFs may assist in positioning the smaller DRFs relative to a selected portion of the anatomy. This may be useful when positioning the smaller DRFs in substantially tight or small areas, such as under a small tissue portion relative to the cranium or any selected portion of the anatomy, such as cervical vertebrae. Nevertheless, the smaller DRFs would be used for any appropriate purpose.

Figure 19:
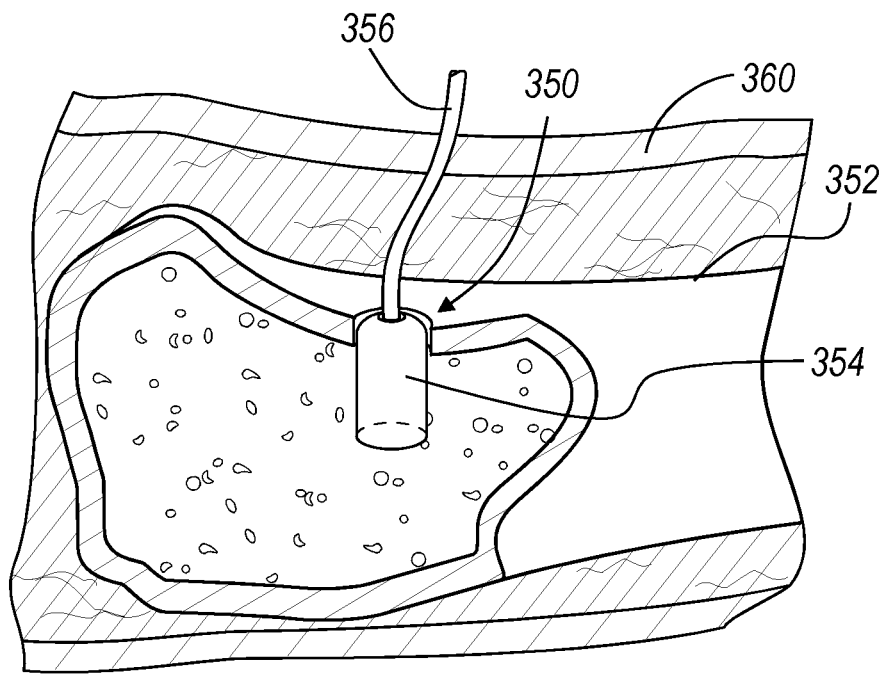
FIG. 19 is a detailed partial cross-sectional view of a portion of the patient including a recessed DRF.

With reference to FIG. 19, a tracking sensor that can also operate as a DRF 350 is illustrated. The DRF 350 generally includes a tracking sensor that can be tracked with a tracking system. The DRF 350 may be positioned relative to a bone or anatomical portion 352. The bone may be any appropriate bone, such as a femur, humerus, etc. For example, a bore 354 may be formed in the bone 352 to receive at least a portion of the DRF 350. The DRF 350 may include a wired portion 356, which may provide power to the DRF 350 or transmit a signal from the DRF 350. It will be understood, however, that the DRF 350, or any appropriate DRF discussed above or herein may be substantially wireless. For example various wireless channels may be used to transmit or receive information. Various internal power sources may be provided, such as an internal battery. A power signal may be used to apply remote power to the DRF, and an LC Tank circuit may be used to transmit a signal. Various exemplary wireless DRFs are described in U.S. patent application Ser. No. 10/245,843, entitled, "SURGICAL COMMUNICATION AND POWER SYSTEM", filed Sep. 22, 2002; and U.S. patent application Ser. No. 10/837,997, filed May 3, 5004, entitled, "METHOD AND APPARATUS FOR IMPLANTATION BETWEEN TWO VERTEBRAL BODIES", each of which is incorporated herein by reference. The DRF 350 may be any appropriate sensor, such as an acoustic sensor, an optical sensor, an electromagnetic sensor, or a combination thereof. Regardless, the DRF 350 may be positioned in the bore 354 to substantially receive the DRF 350, such that it can be fixed relative to the bone 352.

Positioning the DRF 350 in the bore 354 may eliminate or reduce the need for other attachment mechanisms to provide for a fixed position of the DRF 350 relative to the bone 352. For example, various pins, interference portions, and the like may be used to interconnect the DRF 350 with the bone 352. For example, various screws, pins, interference portions, and the like, may be provided and connect the DRF 350 with the bone 352. Also, in addition to or alternatively to the pins, the DRF 350 itself may be formed in an interference shape such as a square, polyhedron, etc. The various geometries may interact with the bore 354 to resist or eliminate rotation of the DRF 350. Nevertheless, the use of the bore 354 may assist in assuring the DRF 350 does not move relative to the bone 352, whether or not various other interconnection portions are used. It will be understood, however, that the bore 354 may both fix and reduce an exposed profile of the DRF 350.

Further, it will be understood that the DRF 350 need not include the wire 356. For example, the DRF 350 may be substantially self powered or powered by an external source or signal. Therefore, the wire 356 may not be necessary and the DRF 350 may be provided in the bore 354 alone.

In addition, the bore 354 may allow the DRF 350 to be positioned relative to the bone 352 and be provided below or underneath a surface of soft tissue 360. Therefore, the DRF 350 may be a substantially sub-dermal or sub-soft tissue DRF. This may allow the DRF 350 to be positioned in the bone 352 and remain in the bone 352 while not affecting a soft tissue 360 that may be positioned next to the bone 352. This may also assist in providing a substantially normal operation, such as a range of motion, of the bone 352 with the soft tissue 360 in place. in this case the profile or shape of the DRF 350 may be made to reduce or eliminate any sharp edges or surfaces to prevent the DRF 350 from interfering with the soft tissue 360.

Nevertheless, as discussed above, the DRF 350 may be tracked according to various procedures to allow for a determined position of the DRF 350. Therefore, movement of the bone 352 may be tracked with the DRF 350 even while soft tissue portions, such as the soft tissue 360, surrounds or is positioned relative to the bone 352. Keeping or positioning the soft tissue 360 near the bone, in a generally natural orientation, may allow for obtaining a substantially natural motion of the bone 352.

With reference to FIGS. 20-24, various DRFs according to various embodiments, may include mechanisms to reduce rotation or other unselected movement of the DRF relative to a selected portion, such as a portion of the anatomy. Further, it will be understood that the DRF sensor, as a part of the DRF, may be positioned at any appropriate position relative to the anatomy or any other portion to which it is fixed. Therefore, it will be understood that DRFs, according to the various embodiments may include mechanisms or apparatuses that fix the DRF in a selected orientation or position relative to an anatomy, or other appropriate portion.

Various DRFs according to various embodiments, may include the DRF or DRF assembly 370, illustrated in FIG. 20. The DRF 370 may include a DRF sensor portion 372 that may be a substantially optical DRF, an electromagnetic DRF, and acoustic DRF or the like. Nevertheless, the DRF sensor 372 may be provided with the DRF 370 in a substantially anti- or reduced rotation mechanism. The DRF sensor 372 may include a wired portion 374, as discussed above. Nevertheless, also as discussed above, the DRF sensor 372 may be substantially wireless and include a power signal or be internally powered, such as those discussed above.

The DRF sensor 372 may be attached to a connection portion 376 that includes a first arm or leg 378 that is hingedly or movably interconnected with a second arm or leg portion 380. The first leg portion 378 may be movable relative to the second leg portion 380 with a movement mechanism 382. The movement mechanism 382 may be any appropriate mechanism, such as a screw that interconnects a boss 384 extending from the first leg 378 with the second leg 380. Therefore, movement of the screw 382 may move the first leg 378 relative to the second leg 380. In this way, the two legs 378, 380 may be moved and locked or fixed relative to one another to form an engagement relative to a selected surface, such as a spinous process of a vertebra of the spine. In addition, the legs 378, 380 may include further engagement portions 386 that assist in holding the DRF 370 relative to a selected position. For example teeth or spikes may be included as the engagement portions 386 to bite into or fixedly engage the anatomy, such as a spinous process S. In addition, the screw 382 may be operated with any appropriate mechanism, such as with a tool, substantially manually operated, or the like.

Nevertheless, the DRF 370 may be positioned relative to a selected portion of the anatomy, substantially in a manner that reduces or eliminates rotation of the DRF 370. As discussed above, various degrees of freedom of the DRF 370 such as six degrees of freedom (6 DOF), to assist in determining its location, may be determined using various techniques. The accuracy or efficacy of the determined locations may be reduced if the DRF 370 is allowed to rotate relative to a selected portion. Therefore, various mechanisms, such as the first leg 378 and the second leg 380 that may be positioned relative to one another, may assist in reducing or eliminating the rotation of the DRF 370. Fixing rotation of the DRF 370 may assist in assuring that substantially any movement of the DRF 370, such as the DRF sensor 372, may be due to the portion to which the DRF 370 is attached and not to motion of the DRF 370 itself.

With reference to FIG. 21, a DRF or DRF assembly 400 is illustrated. The DRF assembly 400 may include a DRF sensor 402, a DRF connection portion or anti-rotation portion 404 and an interconnection portion or member 406. Generally, the DRF sensor 402 may include a casing that surrounds the sensor portions of the DRF sensor 402. Nevertheless, the interconnection portion 406 may include a shaft 408 defining a thread 410. The thread may engage a portion of the connection member 404 as to substantially fix the DRF sensor 402 relative to the connection portion 404. The connection portion 404 may also include a first leg 412 and a second leg 414. The two legs 412, 414 may engage two sides of a selected structure, such as a spinous process S of the spine (FIG. 21A). In the case of engaging a spinous process, the threaded portion 410 may both engage one or both of the spinous process and the connection member 404.

Regardless, the interconnection with the connection member 406 may assist in holding the connection member 404 relative to the selected portion of the anatomy. The two legs 412, 414 may allow for at least two points of contact to resist movement of the DRF sensor 402, such as rotational movement thereof, relative to a structure of the anatomy. Therefore, the DRF 400 may be positioned relative to a portion of the anatomy while substantially reducing a selected motion of the DRF 400 relative to the anatomy. As discussed above, position information of the DRF 400 may be used to determine a location of a selected portion of the anatomy, such as a spinous process or a vertebra.

As exemplary illustrated in FIG. 21A, each of the legs 414, 412 may engage or contact a selected side of the spinous process S. The legs may further include engagement portions to bite into or fixedly engage the spinous process S. Further, the screw may be screwed into the spinous process to lock or fixedly engage the DRF 400 together. The screw may engage the sensor portion 402 relative to the member 404 to hold the sensor 402 in a selected position. Also the sensor 402 may be keyed, such as with the member 404, such that it may not rotate relative to the legs 412, 414.

Figure 22:
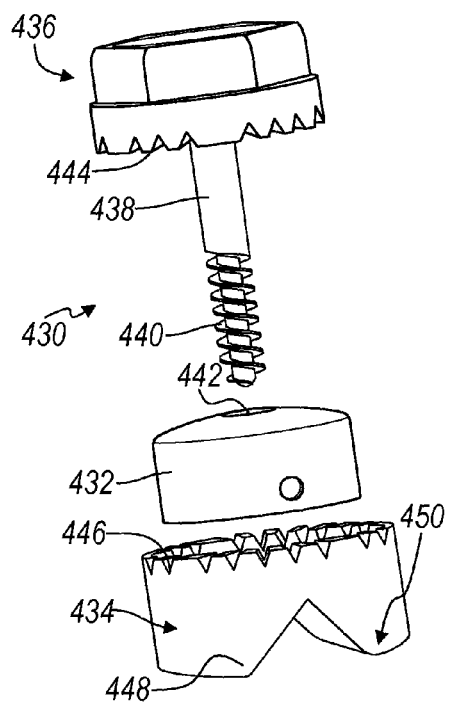
FIG. 22 is an exploded perspective view of a DRF including an anti-rotation mechanism according to various embodiments.

With reference to FIG. 22, according to various embodiments, a DRF or DRF assembly 430 is illustrated. The DRF assembly 430 may include a DRF sensor portion 432, which may include or provide a DRF sensor. The DRF sensor may be any appropriate tracking sensor, such as an optical sensor, an acoustic sensor, an electromagnetic sensor, or any appropriate sensor. The DRF assembly 430 further includes an engagement portion or member 434, such as a member to engage a selected portion of the anatomy. A further connection portion 436 is provided to interconnect the DRF sensor 432 with the connection member 434.

The interconnection portion 436 may include a shaft 438 that defines a thread 440. The shaft 438 may pass through a bore 442 formed in the sensor portion 432 to engage or pass through the attachment member 434 and engage a selected portion of the anatomy, such as a bone. In addition, the connection portion 436 includes a surface or structure 444 that may interconnect or mate with a second surface or structure 436 defined by the connection portion 434. Therefore, the DRF sensor 432 may be held fixed relative to the connection portion 434 in a selected manner and/or orientation. Further DRF sensor 432 may be keyed or include portions to engage the member 434 to resist or eliminate rotation relative to the member 434.

In addition, the connection member 434 may include a first leg portion 448 and a second leg portion 450 that may allow for at least two points of contact with a selected portion. For example, the two portions 448, 450 may engage either side of a spinous process to assist in holding the DRF assembly 430 relative to the spinous process, for example similar to the legs 412, 414 in FIG. 21A. The portions 448, 450 may assist in reducing or eliminating rotation of the DRF assembly 430, including the DRF sensor 432, relative to the anatomy or other structure. Therefore, the threaded portion 440 may engage a portion of the anatomy compressing the connection portion 436 to interconnect the first structure 444 with the second structure 446. In addition, the first portion 448 and the second portion 450 may engage two sides or two points relative to a selected portion of the anatomy for assisting and holding the DRF assembly 430 relative thereto in a substantially immovable manner.

As discussed above, the DRF assembly 430, including the DRF sensor 432, may assist in determining a position of the DRF assembly 430 and a portion to which it is interconnected. Therefore, reducing a motion of the DRF sensor 432 relative to a selected member may increase the accuracy, the efficacy and the degrees of freedom of the sensed movement or position of the member to which the DRF assembly 430 is attached.

Figure 23:
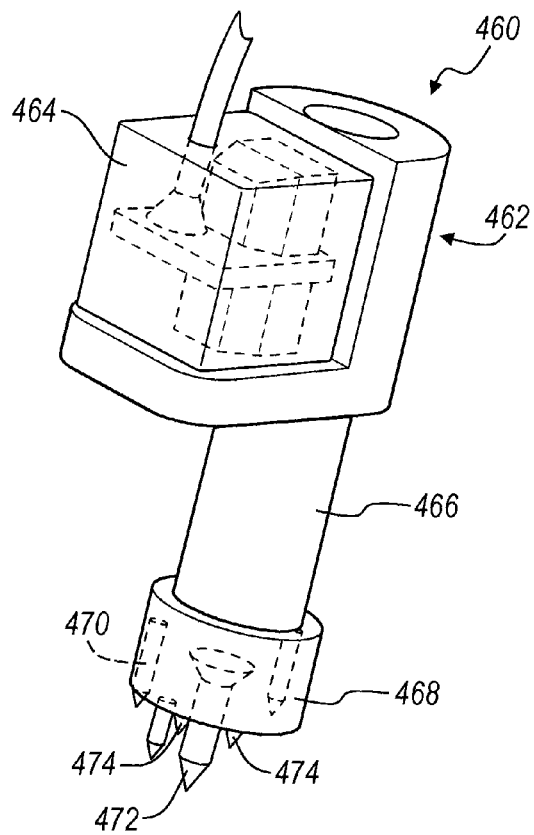
FIG. 23 is a perspective view of a DRF including an anti-rotation mechanism according to various embodiments.

With reference to FIG. 23, a DRF assembly 460 is illustrated. The DRF assembly 460 may include a first portion 462 that may define or include a DRF sensor 464. As discussed above, the DRF sensor 464 may be any appropriate sensor, such as an optical sensor, an acoustic sensor, an electromagnetic sensor, or combinations thereof. Similarly, as discussed above, the DRF sensor 464 may be substantially wired or wireless according to various embodiments.

The first portion 462 may extend or be interconnected with a second portion or shaft portion 466. The first portion 464 may be substantially fixedly attached to the shaft portion 466 or may be removable therefrom. The shaft portion 466 may extend from a base portion 468 that is operable to interconnect with a selected member, such as a portion of the anatomy including a cranial or spinal region. Therefore, the shaft member 466 and/or the base member 468 may be implanted at a selected time and the first portion 462 may be interconnected with the shaft 466 at a selected later time. Further, it will be understood that the shaft 466 and/or the base 468 may be provided as fiducial markers. These portions may be inserted as markers for use in pre-operative imaging and used as fiducial markers for registering the images before or after the DRF 462 is attached.

The base portion may include one or a plurality of anti- or reduced rotation members 470. The anti-rotation members 470 may engage a member, such as an anatomical structure, including a bone, off center from a central axis defined by an attachment mechanism 472, such as a screw. The screw 472 may interconnect the base 468 with a selected portion of the anatomy, while the anti-rotation pins 470 interconnect the base 468 with the anatomy at a different axis. Therefore, rotation around the axis of the screw 472 may be substantially reduced or eliminated. It will be understood that a plurality of the anti-rotation pins 470 may be provided according to various embodiments.

Also, the shaft 466 may be provided in a plurality of lengths depending upon various applications. For example, the shaft may include a length of one centimeter or less for various low profile or percutaneous applications. Other applications may use a longer shaft, such as a shaft greater than about one or two centimeters for various applications, such as connection to a spinous process or a cranial portion. Regardless, the anti-rotation pins 470 may assist in eliminating rotation of the first portion 462, including the DRF sensor 464 relative to a selected portion of the anatomy, such as a bony portion.

In addition to the anti-rotation pins 470, or alternatively thereto, the base 468 may also define a spike or projection 474. The spike 474 may engage the member, such as a bony structure at an axis different from the axis of the screw 472. The may also assist in reducing rotation or rotational tendencies of the DRF assembly 460.

The spikes 474 may be molded into the base 468 to first engage a selected portion, such as a bony portion. After preliminary engagement, the separate of modular anti-rotation pins 470 may be passed through the base 468 to further assist in reducing rotation of the DRF assembly 460. Therefore, it will be understood that the DRF assembly 460, or any appropriate DRF assembly, may include one or a plurality of anti-rotation mechanisms.

Figure 24:
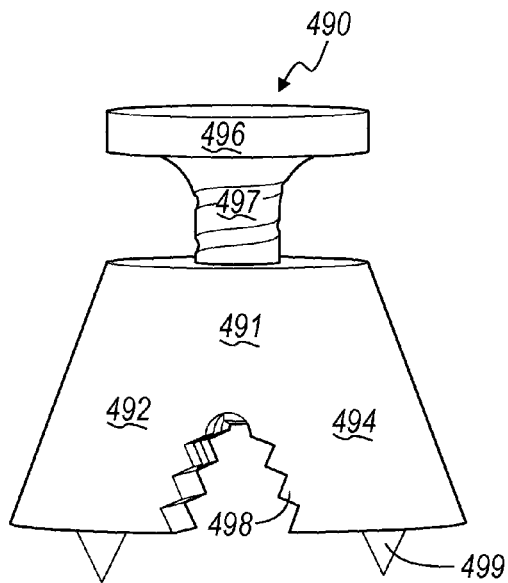
FIG. 24 is a DRF including an anti-rotation mechanism according to various embodiments.

With reference to FIG. 24, a DRF assembly 490 according to various embodiments is illustrated. The DRF 490 may include a body portion 491 defining a first leg 492 and a second leg 494. A connection mechanism 496 is provided to interconnect the DRF 490 with a selected portion, such as a portion of an anatomy.

The connection mechanism 496 may define a thread 497. The thread 497 may engage threads defined by the body 491. The connection mechanism may further engage the anatomy. Also, the legs 492, 494 may include a structure 498 operable to engage a portion of the anatomy. A spike or further fixing member 499 may extend from the legs 492, 494 to engage the anatomy.

The connection mechanism 496 may be used to connect the body 491 to the anatomy. As discussed above, according to various embodiments, each of the legs 492, 494 may engage a different portion of the anatomy to resist rotation or other movement of the DRF 490. This may hold a DRF sensor portion in a selected position relative to the anatomy. The DRF sensor portion may be included in the body 491, the connection mechanism 496, or connected to either. For example, after positioning the DRF assembly 490, a DRF sensor may be fit to the connection mechanism 496.

It will be further understood that a DRF or other instrument may include one or a plurality of anti-rotation mechanisms according to various embodiments. Therefore, the DRF need not include only a single or small combination of anti-rotation mechanisms, but may include a plurality of more than one anti-rotation mechanism. Further, as briefly discussed above, various anti-rotation mechanisms may be selected based upon various applications. For example, a DRF to be interconnected with a spinal portion, such as a spinous process, may include various anti-rotation mechanisms, while various other DRFs may include different anti-rotation mechanisms.

Figure 25A:
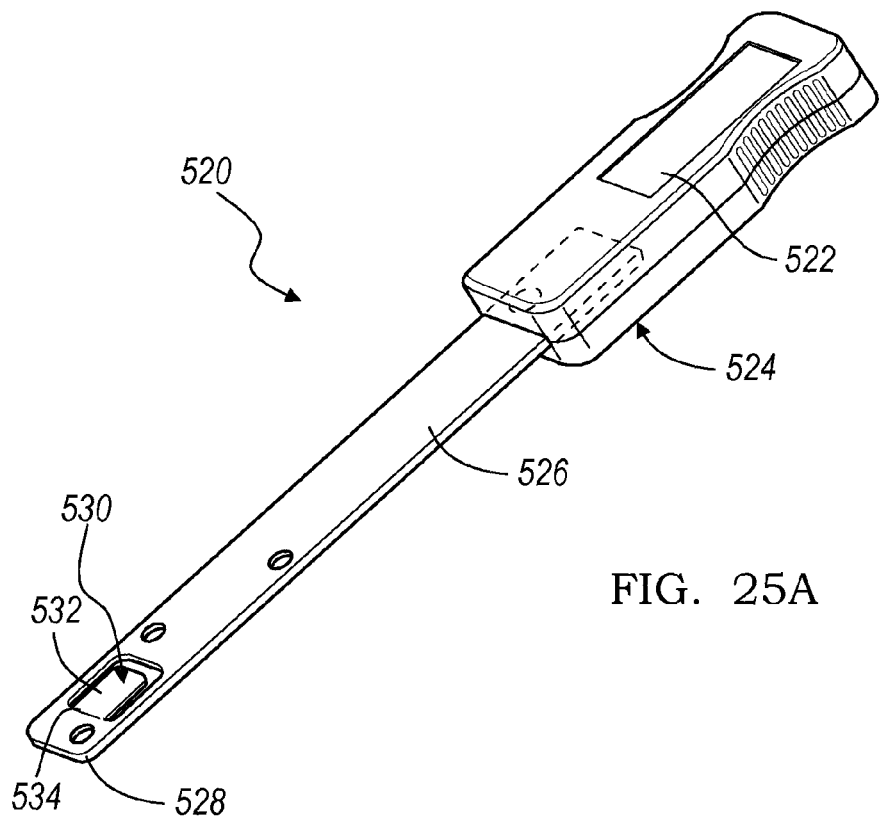
FIG. 25A is a perspective view of an instrument including a tracking sensor according to various embodiments.

With reference to FIG. 25A, an instrument 520 that may include a tracking sensor 522 is illustrated. The tracking sensor 522 may be positioned in any appropriate position, such as in a handle portion 524. The tracking sensor 522 allows the instrument 520 to be tracked such that a location of the instrument 520 or a member to which is connected can be tracked. The tracking sensor 522 may be any appropriate tracking sensor, such as an electromagnetic sensor, an optical sensor, an acoustic sensor, or the like. Nevertheless, the tracking sensor 522 may be positioned in the handle 524 or any appropriate portion relative to a shaft or extension portion 526.

The shaft 526 may include a fitting or connection end 528. The connection end 528 may include a locking or spring paddle portion 530. The attachment portion 530 may include a flexible or deformable member 532 that may flex or move relative to the shaft 526 through a flexing or hinge area 534. The inner connection portion 530 may allow the instrument 520 to be interconnected with a selected instrument or tool, such as a cutting block 540 (FIG. 26), in a desired orientation.

The tracking sensor 522 interconnected in the instrument 520 may be used to sense a position of the instrument 520 relative to the tool 540. For example, the length of the shaft 526 or an orientation of the shaft 526, may be known relative to a selected portion of the shaft, such as the interconnection portion 530. Thus the location and orientation of the tracking sensor 522 relative to the tool 540 is known. This known orientation and location can be used to assist a user, such as a surgeon, in a procedure, such as an orthopedic procedure. For example, the tool 540 may be a cutting block to be oriented for a selected resection.

Figure 25B:
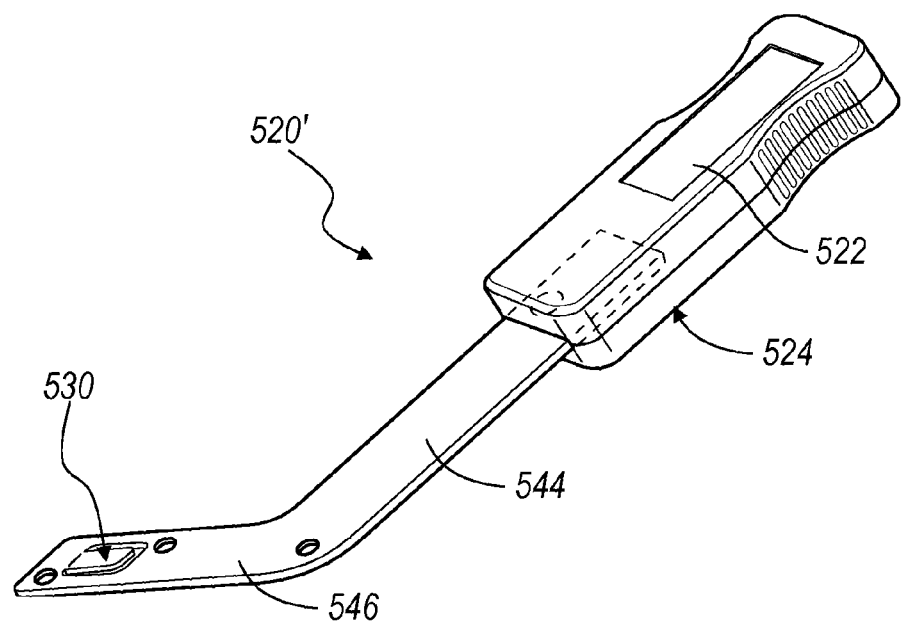
FIG. 25B is a perspective view of an instrument including a tracking sensor according to various embodiments.

With reference to FIG. 25B, an instrument 520' may include a shaft 544 that includes a bent or angled portion 546. The instrument 520' may still include the tracking sensor 522 in the handle or operable portion 524 for positioning or operating the instrument 520'. Further, the instrument 520' may include an attachment region 530 similar to the attachment region 530 of the instrument 520'. The bent portion 546, however, may allow for positioning of the instrument 520' in a selected position that may not allow for a substantially straight shaft. In addition, the bent shaft 544 may allow for an efficient use of the instrument 520', such as easy viewing of a surgical area or movement of selected instruments, such as a minimally or less invasive surgical procedure.

Figure 26:
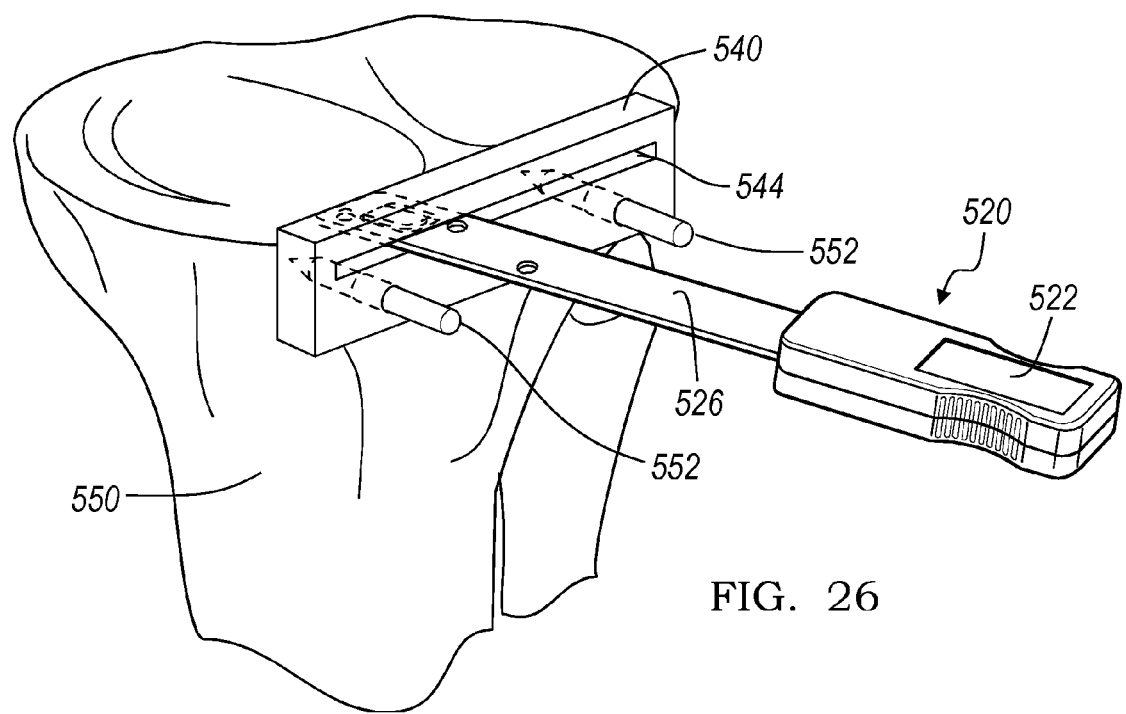
FIG. 26 is an environmental view of the instrument including a tracking sensor of FIG. 25A in use.

Regardless of the configuration selected for the shaft 526 or any appropriate shaft portion, such as the shaft 544, the instrument 520 may be fit relative to the tool 540 that may be a cutting block, as illustrated in FIG. 26. For example, to resect a selected portion of anatomy, such as a tibia 550, the cutting block 540 may be positioned relative to the tibia 550. The cutting block 540 may be held relative to the tibia 550 in any appropriate manner. For example, a pin 552 or a plurality of pins 552 may be provided to fix the cutting block 540 in a position relative to the tibia 550.

In a surgical navigation system, such as the system described above, it may be desirable to assure that the cutting block 540 is positioned at a selected position, orientation, etc. The instrument 520, including the interconnection portion 530, may be positioned relative to the cutting block 540. For example, the cutting block 540 may include a guide or cutting slot or surface 554 defined by the cutting block 540. The interconnection portion 530 of the shaft 526 may be fit into the guide slot 554 to hold the instrument 520 relative to the cutting block 540. It will be understood that the interconnection region 530 may be any appropriate interconnection region and is not limited to a spring member 532. For example, various deformable legs, quick-release screws, and the like may be used to efficiently interconnect the instrument 520 with a selected member.

Once the instrument 520 has been fit in the cutting block 540 the tracking sensor 522 may be used to determine a location and orientation of the guide slot 554 of the cutting block 540. This may assist in insuring that the cutting slot or guide surface 554 is positioned relative to the tibia 550 in a selected position, such as a pre-selected or planned position.

Therefore, the instrument 520 may assist in positioning or determining a position of the cutting block 540 relative to a selected portion of the anatomy. This may also allow a user to determine a cutting plane and the cutting plane may be displayed for use by a user. The instrument 520 may be used without pre-selecting or knowing the position or type of cutting block 540. Thus any appropriate cutting block 540, or other tool, may be used with the instrument 520 to ensure a proper or planned location, orientation, angle, etc. is obtained without including the tracking sensor 522 on the tool 540.

The instrument 520 may be inserted into the tool 540 before fixing the tool relative to the patient, as well. This may allow a representation of the tool 540 to be displayed relative to the patient 14 on the display. This may allow the tool 540 to be positioned in a substantially planned or selected position, for example in a less or minimally invasive procedure. The user may use the display with the represented tool 540 to ensure that the selected location, orientation, etc. is achieved before or while fixing the tool to the patient or using the tool 540. Also, the plane of the cut may be displayed on the display 36 prior to the cut being formed.

It will be understood that the instrument 520 may be used with any appropriate tool, such as a cutting block for cutting various other portions of the anatomy, other than the tibia 550. For example, the interconnection region 530 may be interconnected with the cutting block for selecting a cut in a spinal area. In addition to determining the position of the cutting slot 554, or any appropriate cutting slot, the instrument 520 may be used to determine an orientation of the cutting guide 554 relative to a selected surface. For example, as discussed above, the tracking sensor 522, may be used to determine an angle of a selected portion, such as the cutting guide 554, relative to the anatomy. Further, the instrument 520 may be used to determine a depth or length to be formed with the guide 540.

In addition, the interconnection region 530 allows for a substantially efficient connection of the instrument 520 to a selected portion, such as the cutting block 540. As discussed, the connection portion 530 may be any appropriate interconnection region 530. For example a screw, a pin, or the like may be used. Regardless, the instrument 520 may allow for the navigation of the tool 540 without including a sensor on the tool 540. Thus, the tool 540 need not include the bulk of the sensor or be specially made to include the sensor for use with the tracking system 44.

The interconnection portion 530 may allow for a hands-free or single hand operation of the instrument 520. Once positioned, the instrument 520 may be held relative to the cutting block 540 with no additional need for intervention by a user. Therefore, the instrument 520, including the tracking sensor 522, may be positioned in a selected cutting block and held in the selected cutting block with the interconnection region 530 for various procedures. Also, the position of the cutting block 540 can be determined with the instrument 520 by positioning the instrument 520 and using the navigation system 10.

Regardless, the instrument 520 may be efficiently connected with an instrument or tool for determining a location of the tool. A user need not hold or continually hold a probe relative to a tool when the instrument 520 may be interconnected with the instrument for a selected period of time. Therefore, the cutting block 540 need not permanently include a separate or its own tracking sensor, but may use the tracking sensor 522 interconnected with the instrument 520 for locating and tracking purposes.

Further, as discussed above, the instrument 520 may include the angled shaft 544 or straight shaft 526. It will be further understood that a plurality of shafts, including various angles, lengths various configurations or geometries, or the like, may be provided. Each of the plurality of shafts, including a selected feature, may be interconnected with a single handle portion 524, which may include the tracking sensor 522. Therefore, an inventory or kit may be maintained of the plurality of the shafts 526, 544 without providing a plurality of the tracking sensors 522. Further, various or all portions of the instrument 520 may be reusable or disposable. For example the shaft 526 may be substantially disposable and the handle 524 may be reusable and or can be sterilized. It will be understood, that this is merely exemplary and any portions maybe disposable or reusable. Moreover, the sensor 522 may be wired or be wireless, such as that described above.

Although the instrument 522, which may include the tracking sensor 522, may be provided to be interconnected with the tool 540, it will be understood that the tool 540 may also include integrated tracking sensors. Therefore, although the instrument 520 may be interconnected with the tool 540 to assist in planning or tracking the position of the tool 540 relative to a selected portion, such as the tibia 550, the tracking sensor 522 may not be provided in the instrument 520, but may be included in the tool 540.

Including the tracking sensor 522, or any appropriate tracking sensor in the tool 540, may assist in minimizing the size of the tool 540 or the portion required to track the tool 540. Therefore, a position, orientation, or the like of the guide surface 544 of the tool 540 may be determined relative to the anatomy, such as the tibia 550. This may allow for tracking a tool or a position of the tool 540 relative to the anatomy for a selected procedure. Further, the tool 540, if it includes the tracking sensor, or is used with the instrument 520, may be used to achieve a planned procedure. Therefore, it will be understood that the tool 540 or any appropriate tool may include integral tracking sensors rather than providing the instrument 520 separate or interconnectable with the tool 540.

Figure 27A:
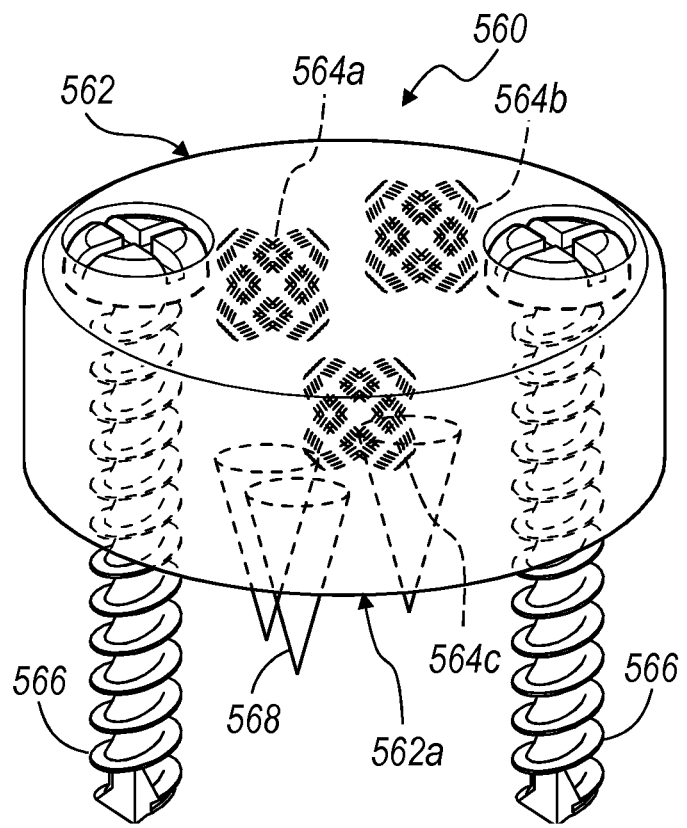
FIG. 27A is a perspective view of a DRF according to various embodiments.

With reference to FIG. 27A, a DRF or a low profile DRF assembly 560 is illustrated. The DRF 560 may include a case or assembly housing 562 that surrounds one or more DRF sensors or coils 564a, 564b, 564c, for various purposes, such as those described herein. As discussed above, the DRF 560 may be any appropriate DRF, such as an acoustic DRF, an electromagnetic DRF, or an optical DRF. Nevertheless, as discussed above, the DRF sensors 564 may include electromagnetic coils or coils that may sense a position in electromagnetic field, such that a direct line of sight between the DRF sensor 564 and a receiver or localizer is not necessary. Therefore, the housing 562 may include a size that allows it to be positioned within a selected portion of the anatomy, as discussed herein.

For example, the DRF housing 562 may include a height that is less than about two centimeter or a height that is less than about one centimeter. It will be understood that the height of the DRF case 562 may be any appropriate height to allow it to be positioned relative to a selected portion of the anatomy. The case 562 may also include a shape or geometry that allows a substantially smooth movement relative to soft tissue of an anatomy, such as when the DRF 560 is positioned subdermally. Thus the size and geometry of the case 562 may provide for a subcutaneous placement and movement of the DRF 560. The shape allowing for the subcutaneous placement may be substantially short, such as less than about 2 cm. Also the shape may be substantially smooth to allow the soft tissue to move over a surface of the DRF 560. This allows the DRF 560 to be positioned and allow soft tissue to move relative to the DRF 560 without the DRF 560 substantially interfering with the movement of the soft tissue.

The DRF 560 may be positioned relative to a portion of the anatomy, such as a soft tissue portion or bone portion with a connection mechanism, which may include a screw 566 or a plurality of screws 566. In addition, as discussed above, the DRF 560 may include anti-rotation or fixation portions 568. The anti-rotation or anti-movement portions 568 may extend from a surface, such as a bottom surface 562a of the DRF case 562. The anti-rotation portions 568 may engage any appropriate portion, such as a bony surface, a soft tissue portion, or the like to assist in holding the DRF 560 or the DRF sensors 564 in a selected location.

In addition, the DRF sensor 560 may be provided, such that it may be moved relative to the soft tissue and then held in a selected position. Therefore, the DRF case 562 may include substantially soft or smooth sides that do not include sharp edges, such as would be found in a square or other angular geometry. Nevertheless, it will be understood, that the DRF case 562 may be provided in any appropriate shape or size.

Figure 27B:
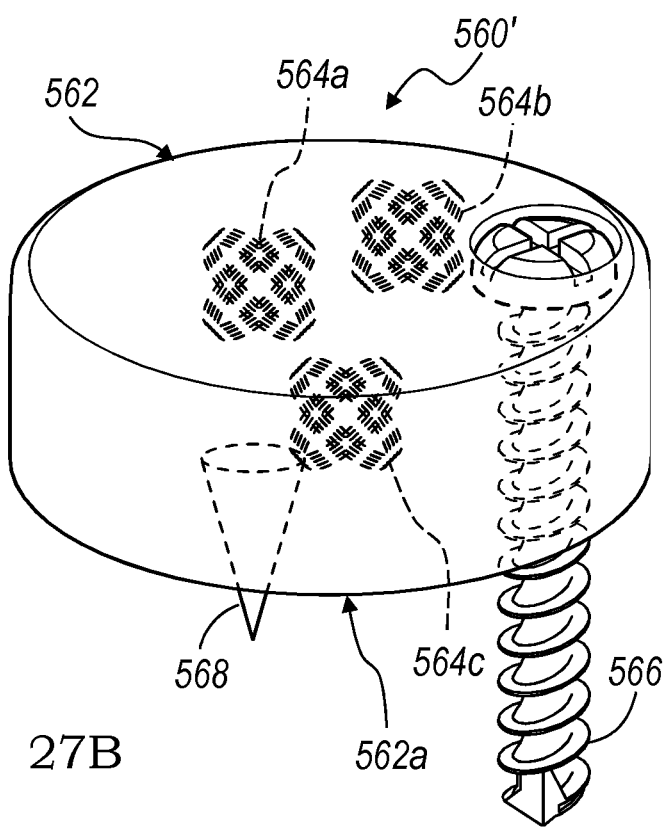
FIG. 27B is a perspective view of a DRF according to various embodiments.

With reference to FIG. 27B, a low profile DRF 560' is illustrated. The low profile DRF 560 may be similar to the low profile DRF 560 illustrated in FIG. 27A. The low profile DRF 560', however, may include only a single or a plurality of the screws 566 or a single or plurality of the spikes 568. The spike 568 may act as an anti-rotation device such that the low profile DRF 560' does not move or rotation relative to an axis thereof. It will be understood that the low profile DRF 560' or any DRF according to various embodiments, generally may include at least two points of contact with a selected anatomical portion to substantially reduce or resist rotation of the DRF. Therefore, the low profile DRF 560' or a DRF according to any appropriate embodiment may be interconnected with a portion of the anatomy for assisting in obtaining and maintaining registration of image space to patient space and the DRF may maintain the registration by reducing or eliminating error due to rotation. Therefore, the DRFs according to various embodiments, such as the low profile DRF 560', may include a mechanism to create two points of contact with the selected portion of the anatomy rather than a plurality more than two contacts.

The DRF 560, according to various embodiments, may be provided with various types of screws 566. For example, the screws 566 may be substantially self tapping, drill tapping or any appropriate type of screw Therefore, the screw 566 may be positioned in a portion of the anatomy, such as bone, in a preformed hole or a hole that is tapped by the screw 566.

Further, the screw 566 may be inserted in any appropriate manner. For example, the screw 566 may be captured in or held relative to any driver to assist in driving the screw 566 relative to the DRF 560. The screw may be captured relative to the driver using a tapered fit or other type of interference fit between the screw and the driver. Therefore, the screw may be held relative to the driver, such that a generally one handed driving may occur. The driver may be interconnected with a power drill or may be hand driven for inserting the screw relative to the anatomy through the DRF 560. Further, the screws 566 may be captured in the DRF 560, such as in the body 562. For example, the bores or holes, through which the screws 566 pass, may include a locking or capturing tab to allow the screw 566 to be held relative to the DRF for a selected period of time.

Further, it will be understood that the screws 566 may include any appropriate driving form. The driving head of the screw 566 may be include a cruciform driving mechanism, a box, or square driving mechanism, a hex driving mechanism, or any appropriate type of mechanism. Further, the driving head may assist in holding or aligning the screw relative to the driver to assist in positioning the screw relative to the DRF 560.

Further, the DRF 560 or DRF according to any appropriate embodiment, may include a body 562 that is substantially deformable or conformable. For example, the body 562 may include a substantially flexible body or material that allows the body 562 to conform to the surface onto which it is placed. For example, such as the DRF described above in FIG. 3, the DRF may include a portion that is flexible that engages the anatomy. Therefore, the DRF may substantially conform to the anatomical structure to assist in holding the DRF in a selected position. The body 562 may be deformed with exterior pressure or when positioning the screws 566, or any appropriate holding mechanism, relative to the anatomy.

Although the body 562 may be flexible to assist in positioning the DRF 560 relative to the anatomy. The tracking sensors 564A-564C of the DRF 560 may be tracked by the tracking system in any appropriate manner. For example, the tracking sensors 564A-564C may be positioned within a substantially rigid portion of the body with the body 562 being deformable relative to the rigid portion holding the tracking sensors 564A-564C. In this way, the tracking sensors 564A-564C are held fixed relative to one another to maintain registration of the DRF 560 relative to a portion of the anatomy. Alternatively, or in addition thereto, the body 562 may be substantially completely flexible such that the tracking sensors 564A-564C of the DRF 560 are able to move relative one to another during the deformation of confirmation of the body 562. In this case, registration is performed after the DRF 560 is securely fixed to the patient in its conformed condition.

Regardless, the DRF 560, or a DRF according to any appropriate embodiment, may include a body or structure that is able to conform to a selected portion of the anatomy. The deformation or confirmation of the body 562 or any appropriate body may assist in holding the DRF relative to the selected portion of the anatomy during a selected period of time. For example, although the DRF may be provided with a substantially planar bottom 562A, it may be positioned relative to a non-planar surface and deformation of the body 562 to conform to the non-planar surface may assist in positioning or holding the DRF 560 relative to the selected portion of the anatomy.

According to various embodiments DRFs, such as the DRF 560 may be used to position relative to soft tissue. As discussed above and herein a DRF may be positioned relative to or in soft tissue and not obstruct movement of the soft tissue or other anatomical portions. With reference to FIGS. 28A-28C an exemplary method is illustrated.

With initial reference to FIG. 28A an exemplary incision 574 may be made through a selected portion of soft tissue, such as dermis, skin, fascia, muscle, or any appropriate portion. The incision 574 may be used for performing a selected procedure, such as those discussed above and herein. Nevertheless, it may be selected to position the DRF 560 at a location M not at the location of the procedure. Thus the incision 574 may be moved in direction of arrow N towards the selected location M.

Once at the selected location M, illustrated in FIG. 28B, the DRF 560, or any appropriate DRF, may be positioned. The DRF 560 may be fixed to bone, soft tissue, or any appropriate portion. Once the DRF 560 is positioned at the selected location M the incision 574 may be moved back to its initial position, near where the procedure is to be performed, FIG. 28C. As discussed above this may allow a transdermal or sub-dermal placement of the low-profile DRF 560, or any appropriate DRF. The DRF 560 may be provided with a selected size or shape, such as a low profile (such as less than or equal to about 2 cm in height), to allow for movement of the incision after placing the DRF 560.

Thus the single incision 574 may be used to both position the DRF 560 and perform a selected procedure. This may reduce incisions to be formed and decrease recovery time for the patient 14. Thus, the incision 574 may be formed at a first location, the DRF 560 positioned, through the incision 574, at a second location, and the incision returned to a third location, which may be the first location. The sub-dermal placement may assist in performing minimally or less invasive procedures, such as minimally invasive orthopedic procedures.

According to various embodiments, with additional reference to FIG. 28D, a portion of an anatomy, such as a leg 572 may exemplary have a procedure performed relative thereto. For example, an incision 574 in a soft tissue 576, such as skin or muscle surrounding a selected portion, such as a femur 578, may be provided. The DRF 560 may be positioned relative to a portion of the anatomy, such as the femur 578. The DRF 560 including a selected size, such as less than about one centimeter in height, may be positioned or fixed relative to the femur 578.

After positioning the DRF 560 relative to the femur, the incision 574 may be unretracted or placed over the DRF 560. For example, a retractor 580 may be used to move a portion of the soft tissue or expand the incision 574 for positioning of the DRF 560 on a particular portion of the femur 578. After positioning the DRF 560 relative to the femur 578, the retractor 580 may be removed and the soft tissue allowed to be replaced or moved back over the DRF 560.

Once the soft tissue is positioned over the DRF 560, various tracking or localization procedures may be used to determine a position of the DRF 560 and further determine a position of the femur 578 relative to other portions. For example, a second DRF 582 may be positioned relative to a tibia 584. Therefore, the DRF 560 may be used to determine a location of the femur 578 relative to the second DRF 582 and the tibia 584. The size, shape, orientation, and other features of the DRF 560 may allow the DRF 560 to move relative to the soft tissue 576 surrounding the DRF 560, after the soft tissue is replaced, and the femur 578. This may be useful in determining a range of motion of the femur 578 relative to the tibia 584. It will be understood that a range of motion of any two bones relative to a joint may be determined using the DRF 560 and any other appropriate DRF portions, such as the second DRF 582 or a second of the DRFs 560.

A range of motion may be determined after resurfacing a bone surface or positioning an implant relative to a bone. The range of motion may assist in determining a proper placement of a prosthesis or an appropriate resection or resurfacing of a bony portion. Therefore, allowing the DRF 560 to move with a bone portion, such as the femur 578, with the soft tissue in a substantially natural position, may assist in determining a proper conclusion of a procedure.

Further, it will be understood that the DRF 560 need not be fixed directly to a bony portion. For example, the DRF 560 may be interconnected with a selected portion of soft tissue, such as a muscle, a tendon, a ligament, or any other appropriate soft tissue portion. The DRF fixed to a selected soft tissue portion may move with the soft tissue portion relative to other portions of the anatomy or other instruments. Regardless, movement of the soft tissue may be determined by use of sensing the location of the DRF 560, as discussed above.

Again, the DRF 560 may be provided in an appropriate size, geometry, location and the like to allow it to move relative to soft portions of the anatomy. The features of the DRF 560 may allow it to not obstruct the movement of the soft tissue to which the DRF 560 is attached or the soft tissue relative to which the DRF 560 is moving. Thus, the DRF 560 may be positioned and used to determine a movement of a bony portion, a soft tissue portion, and the like, where the DRF is moving and touching the soft tissue portions without interrupting the movement of the various selected portions. It will be understood that the DRF 560 may be any appropriate size, or any appropriate DRF. The DRF 560, or any appropriate DRF, according to various embodiments, may include selected sizes, shapes, and/or configurations to assist in movement relative to various selected locations. For example, the percutaneous or subcutaneous placement of the DRF may be performed without requiring an external positioning or fixation of the DRF. Further, the DRF 560 may be substantially wired or wireless to allow for various configurations and purposes.

Figure 29:
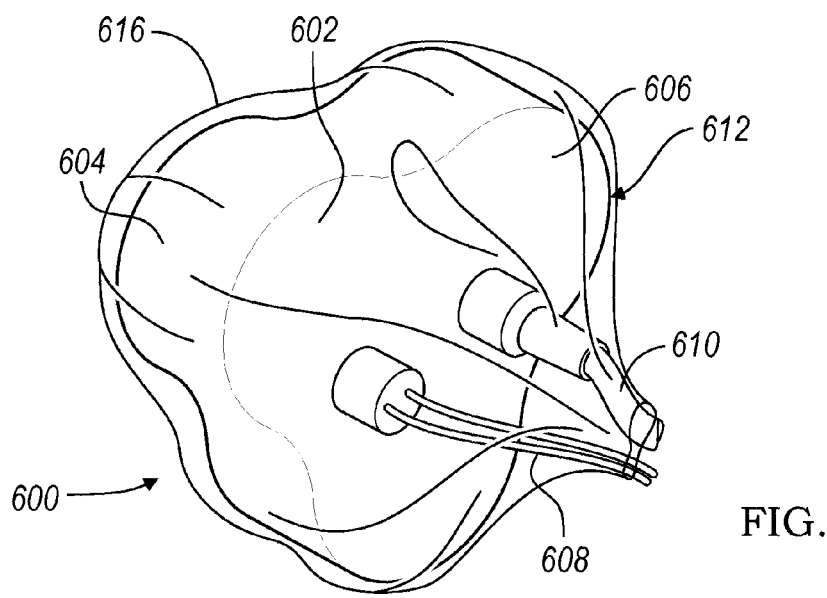
FIG. 29 is a detail perspective view of a mobile localizer.
Figure 30:
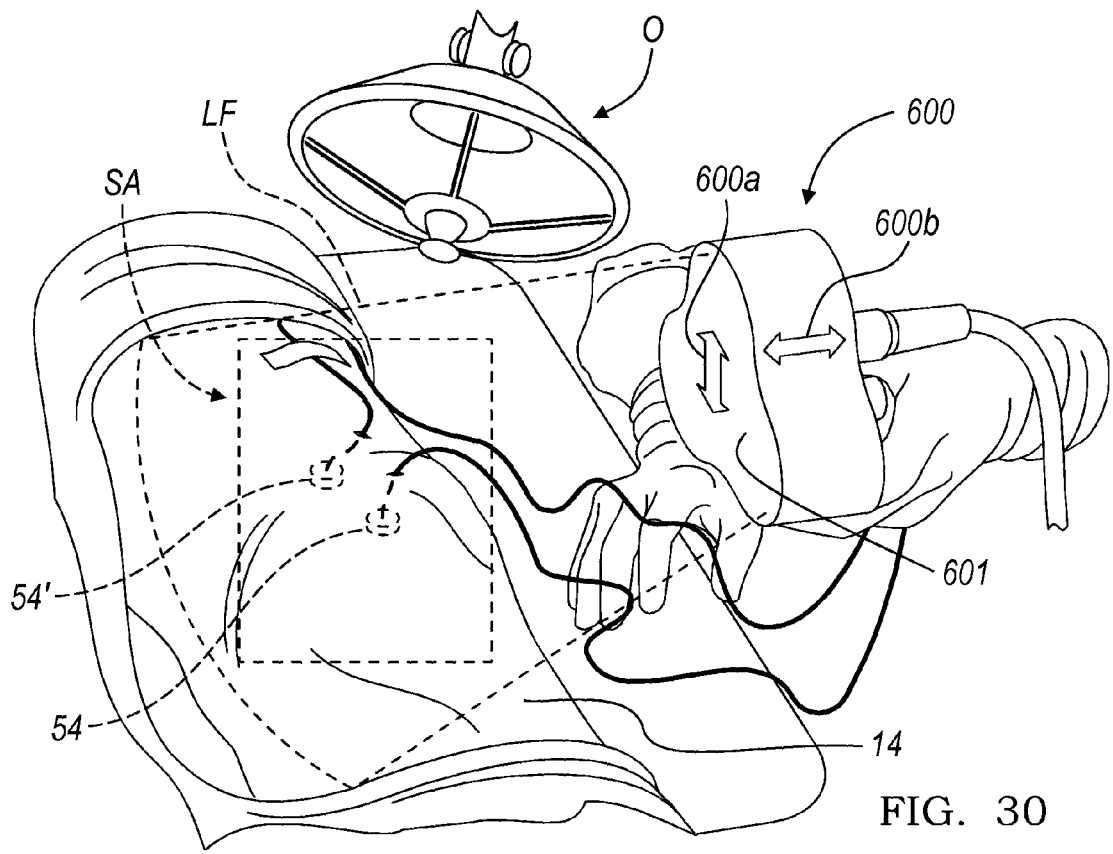
FIG. 30 is an environmental view of the mobile localizer of FIG. 29 in use.

With reference to FIGS. 29 and 30, a mobile localizer 600, according to various embodiments, is illustrated. The handheld or mobile localizer 600 may be similar to the transmitter coil array 46 and may be part of the electromagnetic navigation or tracking system 44. The mobile localizer 600 may be used in conjunction with or in addition to the coil array 46. The coil array 46 may be used to form a field until an obstruction is positioned that distorts the field and then the mobile localizer 600 may be used. Alternatively, both may be used together to assist in determining a location of the tracking sensor.

It will, nevertheless, be understood that the mobile localizer 600 may be an instrument separate from the tracking system 44, but may include portions or control systems similar to the tracking system 44. The handheld localizer 600 may include portions similar to the transmitter coil array that allows for localization, registration, and the like of various portions, such as the DRF 54, any appropriate DRFs, such as those discussed above, the probe or pointing device 66, or any appropriate member.

The mobile localizer 600 may include any appropriate shape, size, geometry, and the like according to various purposes. For example, the mobile localizer may include a first lobe or portion 602, a second lobe 604, and the third lobe 606. Each of the lobes 602, 604, 606 may house or define a transmitter coil positioned or included in the mobile localizer 600. It will be understood that the mobile localizer 600 may include a substantially round, square, rectangle, or any appropriate shape. The lobe shape is merely exemplary and not limiting.

Further, the mobile localizer 600 may include a power and/or transmission cable 608 interconnected with a selected power source and/or tracking system. For example, the cable 608 may interconnect the mobile localizer 600 with the coil array controller 48 for transmission and/or reception of a tracking signal. The mobile localizer 600, therefore, may be used to communicate or be operated by the system 44 to assist in tracking or locating a selected sensor, such as the DRF 54. It will be understood, however, that the mobile localizer 600 may also be internally power or powered with a power signal. The mobile localizer may also include a wireless transmitter or receiver. This may allow the mobile localizer to be substantially wireless.

Further, a handle or graspable portion 610 may extend from a housing 612 defining the selected instrument. The graspable portion 610 may be used to orientate or move the mobile localizer 600 relative to a selected portion, such as the patient 14. It will be understood, however, that the mobile localizer 600 need not include a graspable portion 610. A user, such as a physician may grasp the mobile localizer 600 directly. Also the mobile localizer 600 may be substantially wireless.

The mobile localizer 600 may include the casing 612 that is easily removable from the various coils held within the lobes 602, 604, 606. The casing 612 may be substantially sealable relative to a selected external environment, such that a casing 12 may be easily sterilized and replaced over the coils. The case 612 may also be disposable and discarded after a use. Alternatively, or in addition to the casing 12, a sterile bag 616 may be provided to selectively surround a portion of the mobile localizer 600. Therefore, the mobile localizer 600 may be used in a sterile environment through a plurality of applications without contaminating the sterile environment. It will be understood that any appropriate sterilization technique or portions may be used to insure a sterile environment for the mobile localizer 600.

The mobile localizer 600 may include any appropriate selected dimensions. For example, the mobile localizer 600 may include external dimensions of about 50 $cm^2$. It will be understood, however, that the mobile localizer 600 may include any appropriate dimensions, such as less or more than about 50 $cm^2$. Regardless, the mobile localizer 600 may be moved by the physician or user 614 to any appropriate location relative to the patient 14.

With reference to FIG. 30, the mobile localizer 600 may produce a field LF that can be selectively directed over a selected area, such as a surgical area SA. The field LF, as discussed herein may be tuned or shaped for various reasons using various components and coil orientations. Further size of the field may be selected depending upon a size of the mobile localizer 600 and may be any appropriate size. Also the coils included in the mobile localizer 600 may be of a selected size to assist in selecting a size or strength of the field LF. Thus the mobile localizer 600 may include various dimensions, such as a selected area or face 601 or volume (such as a three dimensional size). The area 601 may be an area through which the field LF is focused or directed while a volume may be a three dimensional size of the mobile localizer 600. The mobile localizer 600 may also include a mass of less than about 2 kg, and may even be smaller than about 1 kg.

The mobile localizer 600 may include coils of any selected size. The coils, however, may be larger, and may be similar in size to coils used in the coil array 46. Nevertheless, the coils in the mobile localizer 600 may be positioned in an area, such as the area of the face, that is within a circle having a diameter of no more than about 16 cm (about 6 in) or any appropriate dimension that may allow ease of movement by a user. Thus the area of the face 601, which may be equivalent to the area of the coils, may be about 200 $cm^2$ or less. The size of the mobile localizer 600 may, however, be selected based upon an ergonomic consideration for ease of use by a user, such as a one handed use by a user. Thus, the area of the face 601 may be less than 200 $cm^2$. The mobile localizer 600 may also include a volume that is about 1200 $cm^3$ or less.

Nevertheless, the mobile localizer 600 may be moved such that the field LF is not obstructed or interfered with by an object O. The mobile localizer 600 may be moved by a user in any appropriate direction, such as arrows 600a, 600b. It will also be understood that the mobile localizer may be moved to a new location to ensure that no or little obstructions interfere with the field LF. Also, even if the field LF is less than the surgical area SA, the mobile localizer may be moved to ensure that the entire area SA is covered by the field LF at a time. Thus the small mobile localizer 600 and the field LF may be used to cover a large area without requiring a large static or acquired localizer. Nevertheless, both may be used together or separate. For example, the coil array 46 may be used until the object O creates interference, then the mobile localizer could be used. Thus the tracking system 44 may switch between the coil array 46 and the mobile localizer 600 or the two may be used together.

Moving the field LF may increase the accuracy or assist in determining the position of the DRF 54 or a coil in a sensor. For example, although the surgical area SA may be an area including one or more of the DRFs the object O may affect the field LF more in a first position than a second position. The mobile localizer 600 may be moved to assist in reducing the affects of the obstruction O. Further, as discussed herein, various techniques may be used to determine a least affected coil or sensor. The mobile localizer 600 may be moved to assist in decreasing the interference and increase the number of accurate coils or sensors.

It will be understood that the mobile localizer may be held by a hand or on a moveable portion for use. For example, the mobile localizer 600 may be clamped or held relative to the bed 56. Also the mobile localizer may be held by a user not performing the procedure.

The mobile localizer 600 may be positioned relatively close to a selected portion of the patient 14 for determining a location of a portion, such as a DRF 54 or an instrument. For example, the DRF 54 may be positioned relative to the patient 14, such as subcutaneously using the subcutaneous DRF 560. The mobile localizer 600 may be positioned at a small distance, such as less than about one meter from the patient 14, to localize the DRF 54. It will be understood, however, that the mobile localizer 600 may be positioned at any distance from the patient 14, such as less than about twenty centimeters or less than about fifty centimeters. Regardless, the mobile localizer 600 may be positioned substantially near the patient 14 for various purposes.

For example, the mobile localizer 600 may be easily or efficiently moved relative to the patient 14 to substantially reduce metal effects on the field produced by the mobile localizer. As discussed above, the mobile localizer 600 may produce an electromagnetic field that is used by the system 44 to determine a location of the DRF 54 relative to the mobile localizer 600. Therefore, the navigation system 44 may be used to determine the position of the DRF on the patient or a selected position of the DRF 54 relative to a second DRF 54'.

Further, the mobile localizer 600 may be used to reduce interference from various portions or materials that may be present near the patient 14. For example, the operative bed 56, the imaging device 12, or other portions in a selected theater, such as an operating theater, may produce interference that may otherwise need to be accounted for in the tracking system 44 to determine an accurate position of the DRF 54, or other trackable portion. Positioning the mobile localizer 600 substantially near the DRFs 54, 54', however, may be used to substantially remove various interferences that may otherwise need to be accounted for. The removal of interferences may allow for simplifying various portions of the tracking system 44 or eliminating various algorithms that would need to be used to account for the interferences.

The mobile localizer 600 may be used, as discussed above to determine a location of a tracking sensor. The tracking system may determine a position of the sensor, such as one included in a DRF or the instrument 52, relative to the patient 14 in the image space. As the mobile localizer 600 is moved relative to the patient 14 and the various tracking sensors, the position of each can be determined with reference to the fixed DRF 54, or DRF 54'. The position of the DRFs 54, 54' may be known or registered to the image space so that they may also be displayed on the display 36.

Further, the mobile localizer 600 may also be fixed to the patient 14. The mobile localizer 600, as fixed to the patient, may then produce the field LF relative to the patient 14 from the fixed point on the patient 14. In this instance the position of the various tracking sensors may be determined to the fixed position of the mobile localizer 600 on the patient. Thus, it will be understood, that the mobile localizer may be held by a used or fixed directly to the patient 14.

In either instance, whether held by a user or fixed to the patient 14, the affect of various interferences may be reduced or eliminated. The filed LF may be formed at and directed closer to the surgical area SA or area of interest with a lower instance of interfering objects O. Also, the mobile localizer 600 may be positioned and aimed or directed toward the surgical area SA in a manner to eliminate obstructions O from the filed LF.

In addition, the mobile localizer 600 may be easily used to perform localization and verification purposes, such as various optimization or verification steps may occur. For example, the field strength produced by the mobile localizer 600 may be substantially tuned, depending upon the position of the localizer 600 relative to the patient 14 or the DRFs 54, 54'. The field strength, or other feature, may be tuned or changed depending upon a selected local environment. The tuning may be used to increase the efficiency of the mobile localizer 600 and increase its accuracy. Regardless, the field strength need not be tuned for the mobile localizer 600 and it may be used to perform the localization according to various methods.

Further, the mobile localizer 600 may be integrated into any appropriate instrument. For example, the mobile localizer may be integrated into various instruments, such as the probe 66 or the stylet 52. The mobile localizer 600 may be integrated into the instruments to reduce the number of instruments or portions in a selected operating theater and/or for simplifying the performance of selected procedures. Therefore, the mobile localizer 600 may be moved with the various instruments to assure that the localizer is positioned near the DRF or the selected tracking sensor for determining a position of the tracking sensor. Also, as discussed above, the mobile localizer 600 may be incorporated into an instrument fixed relative to the patient 14, thus possibly eliminating the DRF.

For example, the mobile localizer 600 may be integrated into the probe 66, such that the field generated relative to the probe 66 may be substantially tuned to provide a precise location of the probe 66 for the navigation system 44. As discussed above, the field strength may be substantially tuned for various applications to achieve selected results. In addition, providing the mobile localizer 600 near to a selected sensor, as discussed above, may substantially reduce metal interference and improve metal immunity.

Therefore, it will be understood, that the mobile localizer 600 may be used to increase efficacy of the tracking system 44 according to various embodiments. Although the mobile localizer 600 may not be required in various applications, the mobile localizer 600 may be used to improve metal immunity and reduce interference that may otherwise need to be accounted for. Further, the mobile localizer may be positioned in various orientations relative to the patient 14 or the localizer sensors, such as the DRFs 54, 54' for achieving a more precise signal.

Various systems, algorithms, and the like may be provided to further assist in increasing accuracy and efficacy of the navigation system 44. For example, a plurality of coils, such as greater than about two coils for an electromagnetic system, may be positioned in a sensor, such as a DRF. For example, any appropriate number of coils may be positioned in a DRF to be localized with the coil array 46 or the mobile localizer 600. The various coils may be used to provide an accurate determined position of the sensor, according to various embodiments. For example, various averaging methods, weighting methods, or selection methods may be used to determine a most precise sensed or determined location.

Various methods, according to various embodiments, may be used to determine a location of a sensor, such as the DRFs 54, the probe 44, the instrument 52, or any other appropriate portion. As discussed above, the various elements may include electromagnetic portions or coils that allow for sensing and determining a location of the sensor. The determined position of the sensor can assist in determining or interpreting a location of a portion attached to the sensor, such as the instrument, a portion of the patient, and the like. For example, each of the electromagnetic sensors may include one or more of conductors or inductive coils in which a magnetic field may be induced or sensed. As one generally skilled in the art will understand, a magnetic field may be produced with various elements, or a field or current may be induced in the sensor. Therefore, it will be understood that any appropriate portion may be used to form an electromagnetic field or induce an electromagnetic field in the sensor for various purposes.

Further, one skilled in the art will understand that a magnetic field produced or induced in a selected portion may include both a determinable position and orientation. Therefore, these sensed or determined positions and orientations may be used to determine a position of a sensor, such as the DRF 54. Nevertheless, for various reasons, a plurality of sensors or coils may be positioned in a sensor, such as the DRF 54. For example, various redundancies and increased accuracy may be achieved by providing a plurality of coils or sets of coils within the DRF 54, or any appropriate portion, for determining a location and orientation of the DRF 54. It will be understood that the discussion herein, though directed to the DRF 54, may be used in any appropriate sensor for various portions, such as the instrument 52, the probe 44, or any other portion. The DRF in the discussion of the following methods and apparatuses is merely exemplary.

With reference to FIG. 31, a selected algorithm or method of averaging signals 620 is illustrated. The averaging method 620 may generally allow for averaging a plurality of sensed positions or points, such as a position and orientation of a magnetic field, for determining a location of the DRF 54. Generally, the averaging method 620 may make use of a plurality of sensed locations and averaging methods to provide a precise position of the sensor including the plurality of coils.

The averaging method 620 generally starts at start block 622. In the start block 622, the DRF 54 may be positioned on the patient 14 (with reference to FIG. 1) or any other appropriate location. It will also be understood that various other steps may occur, such as registering the position of the DRF 54 relative to the patient 14 and image space, if so required. It will be further understood that the navigation system 10 may include the monitor 34 that may provide an image 36 of image space of the patient 14 and the position of the DRF 54 relative to the image space may be used. As discussed above, the DRF 54 may be used to insure that the patient space is registered and matched to the image space for performing a selected procedure.

After the procedure is initiated or started in block 622, magnetic field information may be received from the coils in block 624. It will be understood that the magnetic information collected from the various coils may include the position and orientation of the magnetic fields produced or induced in the coils or any other appropriate information. Further, it will be understood that the DRF 54 may include any appropriate number of coils, such as one, two, three, four or any appropriate number. Further, any appropriate number of sets of coils may be provided. For example, two sets of two coils may be provided in the DRF 54 at a known or selected geometry for various purposes, such as those discussed herein. Nevertheless, each of the coils may be allowed to produce magnetic field information that may be collected in block 624. Also, more than one of the DRFs 54 may be used together, such as discussed above. The localizer or tracking array may be used with any appropriate number of the DRFs.

Figure 6:
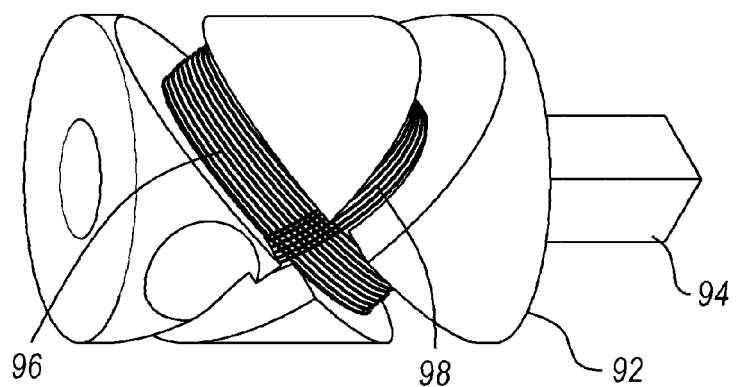
FIG. 6 is a sensor bobbin that may be used in the non-invasive dynamic reference frame of FIG. 3.

Briefly, as discussed above the sensor or DRF 90 may include the first coil 96 and the second coil 98 (FIG. 6). As illustrated the coils 96, 98 may be placed in a selected geometry, such as an angle, relative to one another, such as an orthogonal angle. Although both coils 96, 98 may be formed about a single axis or origin. It will be understood that any appropriate number of coils may be formed in the DRF 90, or any appropriate DRF. Thus three or more coils may also be formed generally orthogonal to one another about the single axis.

In addition to the DRF, such as the DRF 90, including more than one coil, the DRF could include a plurality of sets of coils. With reference to FIG. 27 the DRF 560 may include the first coil sensor set 564a, the second coil sensor set 564b, and the third coil sensor set 564c. Though any appropriate number of sensor coil sets may be provided, three are exemplary illustrated. The coil sets 564a, 564b, 564c may be arranged in the DRF 560 in a selected geometry, such as shape, orientation, separating distance and the like. The geometry of the coil sets 564a, 564b, 564c, may be known and used in various techniques to determine the position of the DRF 560. It will be understood that any appropriate sensor, DRF, or member may include the coil sets, coils, and the like to assist in determining a position of the member.

The magnetic field information collected in block 624 of the coils and/or sets of coils may be transferred to the work station 48 or any appropriate processor, such as a microprocessor. As discussed above, the information may be transferred through various wired portions or may be transferred substantially wirelessly. Therefore, it will be understood that the DRF 54 using the method 620 may be a substantially wireless or wired instrument.

The positions of the coils may be computed in block 626 according to various methods, such as those described above or described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference. It will be understood that any appropriate methods may be used to compute the positions of the received coils or the magnetic field information received from the coils. Further, as discussed above, the position of various portions, such as the patient 14 in the image space or of the instrument 52 relative to the DRF 54 may be also determined. Therefore, the computation of the position of the coils in block 626 may be any appropriate computation and further may include various other relational computations.

After the position of the coils is computed in block 626, an averaging or combination technique in block 628 may be used to average the computed position. In block 628, the various computed positions of the coils from block 626 may be geometrically combined using various methods. For example, a Single Value Decomposition (SVD), as is known in the art, may be used to average the various computed positions of the coils in block 626. Further, it will be understood that other averaging methods may be used to average the computed positions of the coils from block 626. For example, averaging the positions, using other known least squares fit computation or any other appropriate averaging method may be used. Regardless, the various or plurality of computed positions of the coils from block 626 may be averaged or combined in block 628.

The combined or averaged positions in block 628 may be used to determine a final position of the DRF 54. The various positions computed in block 626 may each be a coil positioned within the DRF 52. Therefore, each of the coils may provide a position of the DRF 54. Nevertheless, to assist in assuring accuracy or reduce the effects of interference, such as metal, space, etc., the plurality of coils, for which positions are determined or computed in block 626, may be averaged in block 628 to possibly increase the accuracy of determining the position of the DRF 54. In other words, only a number of the coils, generally less than all of the coils or coil sets would be affected by interference, or the signals received by them. Thus averaging the interfered and non-interfered coil signals reduces, to an acceptable level, or eliminates error that may be created by the interference.

Further, in block 628 the various degrees of freedom, such as a six degree of freedom (6 DOF) transform may be determined. Thus, the combination of the various computed positions of block 628 may provide information regarding the position and orientation of the DRF 54 in a substantially precise manner. As discussed above, averaging the position of the plurality of coils in block 628 may provide for a plurality of position information for the DRF 54.

Finally, the navigated position may be displayed in block 630. The position of the DRF 54, the instrument 52, or any appropriate portion may be displayed on the monitor 34. As discussed above, the image space may be registered to the patient space or a position of the instrument may be displayed on the image space relative to the patient 14. Therefore, the navigated position determined using the method 620 may be displayed in any appropriate manner. As discussed above, the display may include the monitor 34, may be a heads up display for the physician 614, or any appropriate display.

With reference to FIG. 32, a selection method for determining a position of the DRF 54 is illustrated. It will be understood that although the selection method 640 may be discussed in relation to the DRF 54 that the selection method 640 may be applied to any appropriate portion. For example, the selection method 640 may be applied to determining and displaying a position of the instrument 52, the probe 44, or any appropriate portion. Therefore, the discussion herein related to the DRF 54 is understood to not be limited to the DRF 54 alone.

The selection method 640 generally starts in block 642. As discussed above, various procedures may occur prior to the start block 642. For example, registering the image space to the patient space may be performed or positioning of the DRF 54 on the patient 14 may be performed. Further, various images may be obtained preoperatively of the patient 14 for use in the selection method 640. Regardless, the selection method may generally begin at block 642 and allow for determination of the position of the DRF 54.

Similar to the averaging method 620, information regarding the magnetic field may be collected in block 644. Further, the position of the each of the coils may be computed in block 646. As discussed above, each of the DRFs 54 may include a plurality of coils, such as any appropriate number for use in the method 640. Each of the plurality of the coils may include unique magnetic field information, such as orientation and position. Further, a plurality of sets of the coils may be provided in the DRF 54, such as those described above in relation to FIGS. 6 and 27. Each of the coils and/or each of the sets of coils may be positioned at a known or selected orientations or geometry relative to one another. The known respective or relative positions or geometry may be generally fixed relative to each of the coils or sets of coils for use in the selection method 640.

Once the position of the each of the coils or sets of coils is computed in block 646, the six degrees of freedom transform may be computed in block 648. It will be understood that the 6 DOF transform may be computed for each of the coils or the coil combinations according to various generally known methods, such as those described above or in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference. The 6 DOF transform may be computed to determine the geometry or position of the coils or sets of coils relative to one another.

In block 650, the computed geometry of the coils in block 648 may be compared to a known geometry in block 650. As discussed above, the coils or sets of coils may be positioned in the DRF 54 or any appropriate portion at generally known or specifically known geometry. The computed geometry in block 648 may therefore be compared relative to the known geometry in block 650.

For example, three coil sets may be positioned in the DRF 54. Each of the coil sets may include or be computed to have a sensed geometry or position in block 646 and 648. The computed positions of the three coil sets may then be compared to the known positions of the three coil sets in block 650. For example, if the first coil set is known to be at a known position relative to the second and third coil set, while the second coil set is known to be at a selected and known position, relative to the first and third coil sets, and finally the third coil set is at a selected and known position relative to the first and second known coil sets, those known positions may be compared to the determined or calculated positions in block 648. Therefore, each of the coil sets may be compared to the known positions of the coil set to the other coil sets. This comparison may be used to determine which coil set is least affected by various interferences.

The coil sets or coils least affected by interferences may be used to determine the position of the DRF 54. As is known various items may interfere with a magnetic field produced or induced in the coils. Nevertheless, a position of the coils may be sensed and a sensed geometry may be compared to the known and/or saved geometry of the coils. As discussed above, the coils are generally fixed relative to one another. Therefore, in block 654 the coil set that gives the closest match to the known geometry may be selected. The coil set that most closely matches the known geometry is most likely the coil set least affected by interferences. The coil set least affected by interferences may provide the most accurate position of the DRF 54 for determining a location of the DRF 54 relative to the patient 14 and for determining a position of the patient relative to the image space.

Once the coil set is selected that is closest to the known geometry, a position of the DRF 54 or the instrument 52, or any appropriate portion may be displayed on block 656. The position displayed on block 656 may be the position of one or more of the coil sets. As discussed above, the plurality of coil sets included for the selection method 640 may be used to select a single coil set to determine a position of the DRF 54. Therefore, only one or more of the coil sets may be used to determine the position and display the navigated position in block 656.

It will be understood that the selection method 640 may be combined with the averaging method 620 to determine or display a position of the DRF 54. For example, a plurality of coil sets such as the three, may be included for the selection method 640. More than one coil set may be selected in block 654 as being close or equally close to the known geometry. Therefore, the averaging method 620 may be used to average the two or more selected coil sets to provide further refinement for determining a position of the DRF 54. Therefore, after block 654, selecting the coil sets closest to the known geometry, the method may proceed to block 628 of the averaging method 620 or may proceed directly to block 656. That is the selected coil sets may be geometrically combined or averaged in block 628. After combining or averaging the coil set in block 628, the position of the DRF may then be displayed in block 656. Therefore, it will be understood, that any method may be used in combination with any other method or methods to determine a position of the DRF 54.

Figure 33:
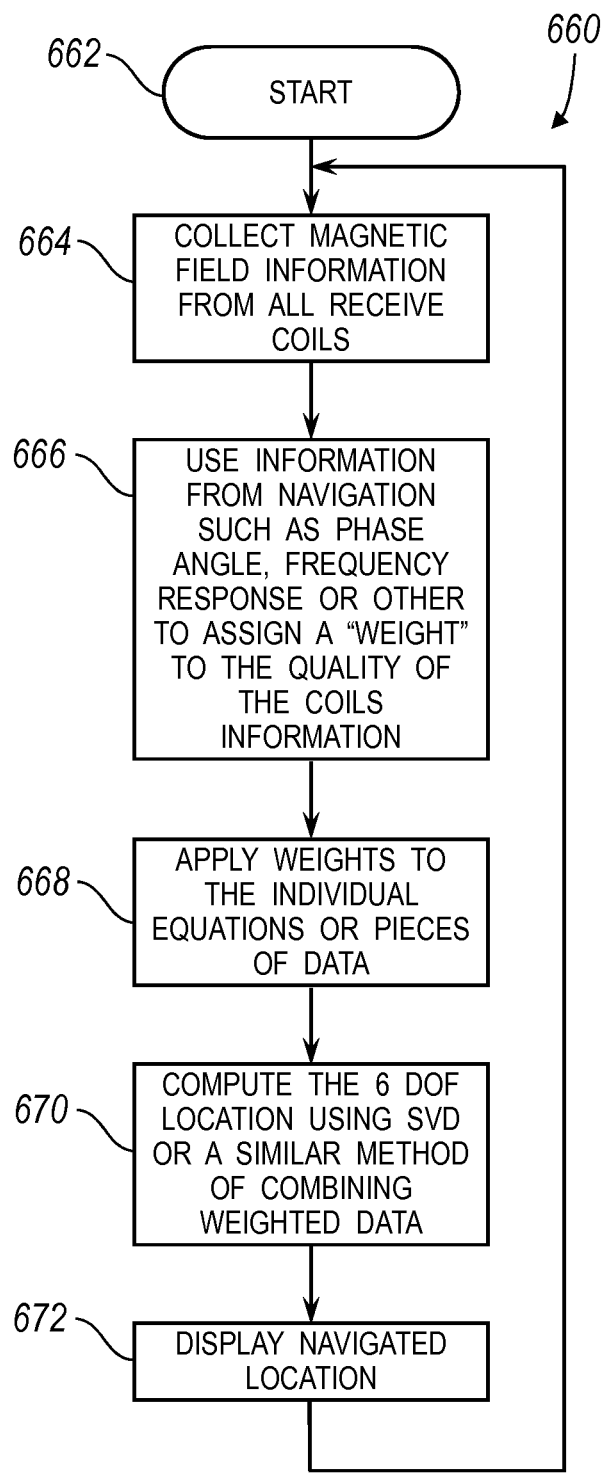

With reference to FIG. 33, various methods may be used to determine a position of the DRF 54. For example, a weighting method 660 may be used to determine a position of the DRF 54. It will be understood, as discussed above, that a position of the DRF 54 is merely exemplary and not limited. Therefore, the weighting method 660 may be used to determine the position of the instrument 52, the probe 44, or any appropriate portion, such as an implant, to the patient 14 for displaying the image space 36. Therefore, the discussion below related to the DRF 54 is intended to be exemplary and not limiting.

The weighting method 660 may generally begin at block 662. As discussed above, the start block 662 may include any appropriate preparation or steps, such as positioning the DRF 54, obtaining images of the patient 14 or any appropriate steps. Merely starting at block 652 is exemplary and it will be understood to include any appropriate portions.

Further, as discussed above, magnetic field information may be collected from the various coils in block 664. The collection of magnetic field information may be collected from any appropriate number of coils, such as two coils, three coils, or any appropriate number of coils. Further, various magnetic field information may be collected from the sets of coils, rather than individual coils.

Magnetic field information collected from the coils may also include information other than position and orientation of the field. For example, as one will understand, various other information, such as phase angle, frequency response, and other information regarding the navigation of the instrument or the DRF 54 or information collected from the sensors in the DRF 54 may be collected in block 660. These various pieces of information may be collected when the field information regarding the coils is collected or at any appropriate time.

The various data or information collected in block 664 may be used to weight the information collected in block 666. Weighting the information in block 666 may be used to determine or assist in determining the integrity of the information collected in block 664. Various portions or materials, such as metal immunity, and the like, as discussed above, may affect the information collected in block 664. The various materials may also affect the additional information. Thus the various additional data may be used to determine a relative affect of the various portions on the field information being collected in block 664.

The additional information that may be collected in block 664, besides position and orientation of the magnetic field, may be used to weight the information collected in block 664 to assist in determining the position of the various coils and the DRF 54. The weights may be applied in block 668 to the various pieces of data or to the equations regarding determining or evaluating the positions of the coils or the DRF 54. Once the weights are applied in block 668, the 6 DOF or position and orientation of the coils or the DRF 54 may be computed in block 670. For example, coils or coil sets that appear or are being affected more by interference may be weighted less than those that are less affected. Thus, all information may be used according to its known or determined weight, which can increase the accuracy of the tracking system.

Various methods may be used to compute the position or geometry of the coil or coil sets, such as those discussed above, or generally known in the art. Various methods may be used to compute the position of the coils where the DRF 54 using the weighted data to determine a position in orientation of the DRF 54 relative to the patient 14 and for navigation.

Once the position and orientation is computed in block 670 with the weighted data or equations, the navigated position may be displayed in block 672. As discussed above, the navigated position may be displayed at any appropriate display for various applications.

Therefore, it will be understood that according to various embodiments, more than one coil may be used to determine a position of an instrument, such as the instrument 52, the DRF 54, an implant (such as those discussed above), the probe 56 or any appropriate portion. The positions of the coils may be used to register the image space to the patient space, real-time register the image space to the patient space, or determine a position of the instrument, relative to the patient 14. Regardless, the plurality of methods, or any appropriate method, may be used to collect data from a plurality of coils. As discussed above the plurality of coils may be positioned in a single portion, such as a single DRF, a single instrument, or the like, to assist in precisely determining the position of the instrument, the DRF, or the like. Thus, any appropriate portion or method may be used to assist or determine a position of the DRF.

According to various embodiments, including those discussed above, various methods may be used to determine a position or axis of a portion of the patient 14. Various anatomical landmarks or geometries, such as an axis of a femur, humerus, or the like may be determined. For example, a transepicondylar axis may be determined by determining or finding a position of a first epicondyle, such as a medial epicondyle, and a second epicondyle, such as a lateral epicondyle.

Figure 34A:
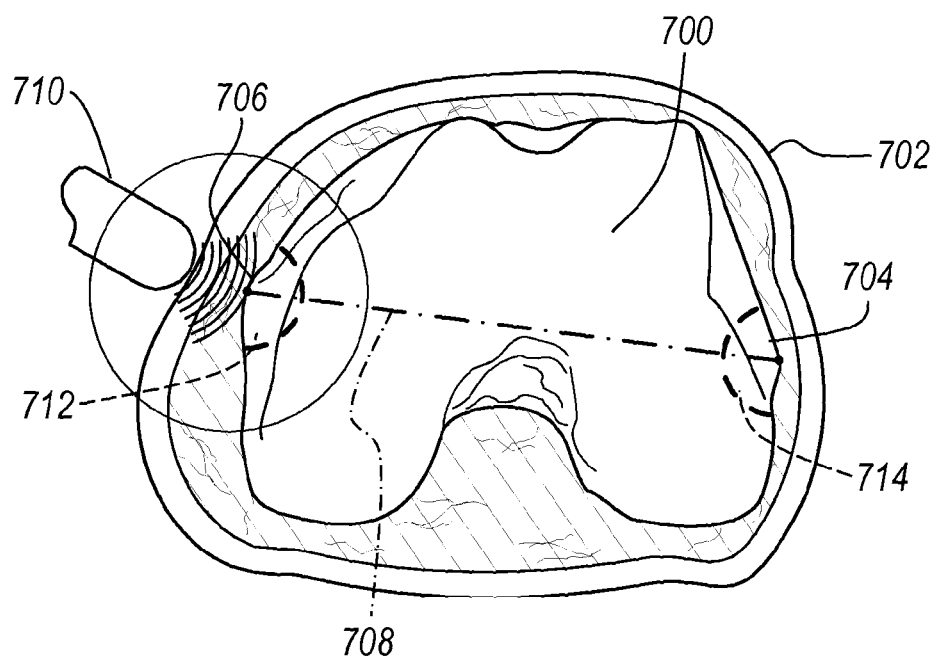
FIG. 34A is a detail partial cross-sectional view of a portion of anatomy including a scanning element.
Figure 34B:
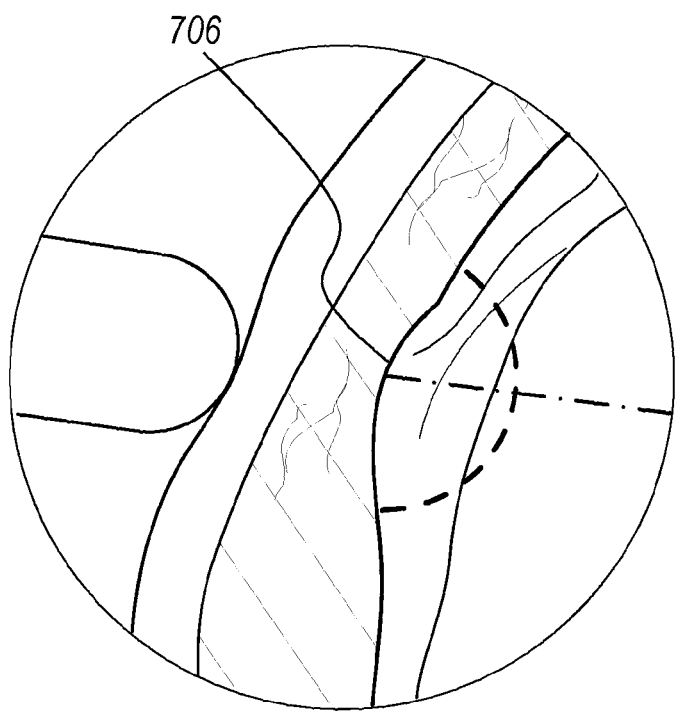
FIG. 34B is a detail from circle in FIG. 34A.

With reference to FIGS. 34A and 34B, a distal end of a femur 700 may be provided as a portion of the patient 14. It will be understood that the femur 700 is generally surrounded by a portion of soft tissue 702, including skin, fascia, muscle, and the like. It will be understood that the FIGS. 34A and 34B are diagrammatic for ease of the following discussion and are not detailed for clarity. The distal end of the femur 700 may include a plurality of landmarks, including a first epicondyle 704, and a second epicondyle 706. It will be understood that the epicondyles 704, 706 may be any appropriate epicondyle of the femur 700. For example, the femur 700 may be a left or right femur and thus the epicondyle 704, 706 may be medial or lateral condyles, depending upon the femur selected.

Regardless, the epicondyles 704, 706 may define a transepicondylar axis 708. The transepicondylar axis 708 is generally an axis or a line between the epicondyles 704, 706 drawn across or through the femur 700.

The transepicondylar axis 708 may be used for any appropriate procedure, such as a total knee arthroplasty (TKA). The transepicondylar axis 708 may be used for positioning an implant, forming a resection of a distal portion of the femur 700, or any appropriate reason. Nevertheless, determining the transepicondylar axis 708 may be performed using an ultrasound probe 710 and generally associated ultrasound equipment.

The ultrasound probe 710 may produce a cloud of points or information, such as the area 712 relative to the epicondyle 706 or area 714 relative to the epicondyle 704. As discussed herein, this mosaic method may be used to determine a selected point. The ultrasound may be any appropriate ultrasound, such as a mode A or a mode B. Regardless, the ultrasound probe 710 may be moved across the soft tissue 702 relative to the femur 700 for determining the epicondyle 704, 706. Various systems for using ultra-sound systems for registration are disclosed in U.S. Pat. Nos. 6,106,464 and 5,398,875. It will be understood that the ultrasound probe 710 may also include a tracking sensor, similar to the DRF sensor, to allow the tracking system to track the position of the ultrasound probe relative to the patient for use in the tracking system 44. The various images and displayed images of the position of the ultrasound probe 710 may be displayed on the display 34.

As is understood by one skilled in the art, the ultrasound may produce ultrasonic waves that may be used to determine a position of a selected anatomical portion through the soft tissue 702. Therefore, the ultrasound probe 710 may be used to determine various anatomical points, such as the epicondyle 704, 706 without invading or passing through the soft tissue 702. In addition, the ultrasound probe 710 may be used to determine various anatomical landmarks or points using a substantially minimally or less invasive procedure when exposing the entire or distal end of the femur 700 is not generally performed.

As discussed above, the area of information 712, 714 generally near the epicondyle 704, 706 may be used to determine or compute the position of the epicondyle 704, 706. For example, the most medial or lateral points in the information areas 712, 714 may be used to determine the position of the epicondyles 704, 706. These points maybe determined to be "high" points in the areas 712,714 and may be determined to be the epicondyles 704,706 of the femur 700. It will be understood that various methods may be used to determine the positions of the epicondyle 704, 706 according to various embodiments.

The determined points of the epicondyle 704, 706 may be displayed relative to a patient image, such as a pre-acquired or preoperative CT scan, MRI scan, x-ray, or the like. Therefore, the determined epicondyle axis 708 may be displayed on a display or image space of the patient 14 without piercing the soft tissue to expose the femur 700. This may allow for intra-operative planning and determining of the procedure without producing further incision in the patient 14.

Further, the ultrasound probe 710 may be used to determine various other anatomical axes or points. For example, a posterior condylar axis, anterior cortex point, tibial tubercle, anterior-posterior femoral axis, and the like may be determined with the ultrasound probe 710 and various navigation displays. For example, the navigation system 10 may be used with the ultrasound probe 710 to assist in displaying on the display 34 an image of the patient 14 and the determined transepicondylar axis 708. Therefore, the display 34 may display a non-invasively determined anatomical axis for use by a user, such as a physician for planning or performing a selected procedure.

Figure 35:
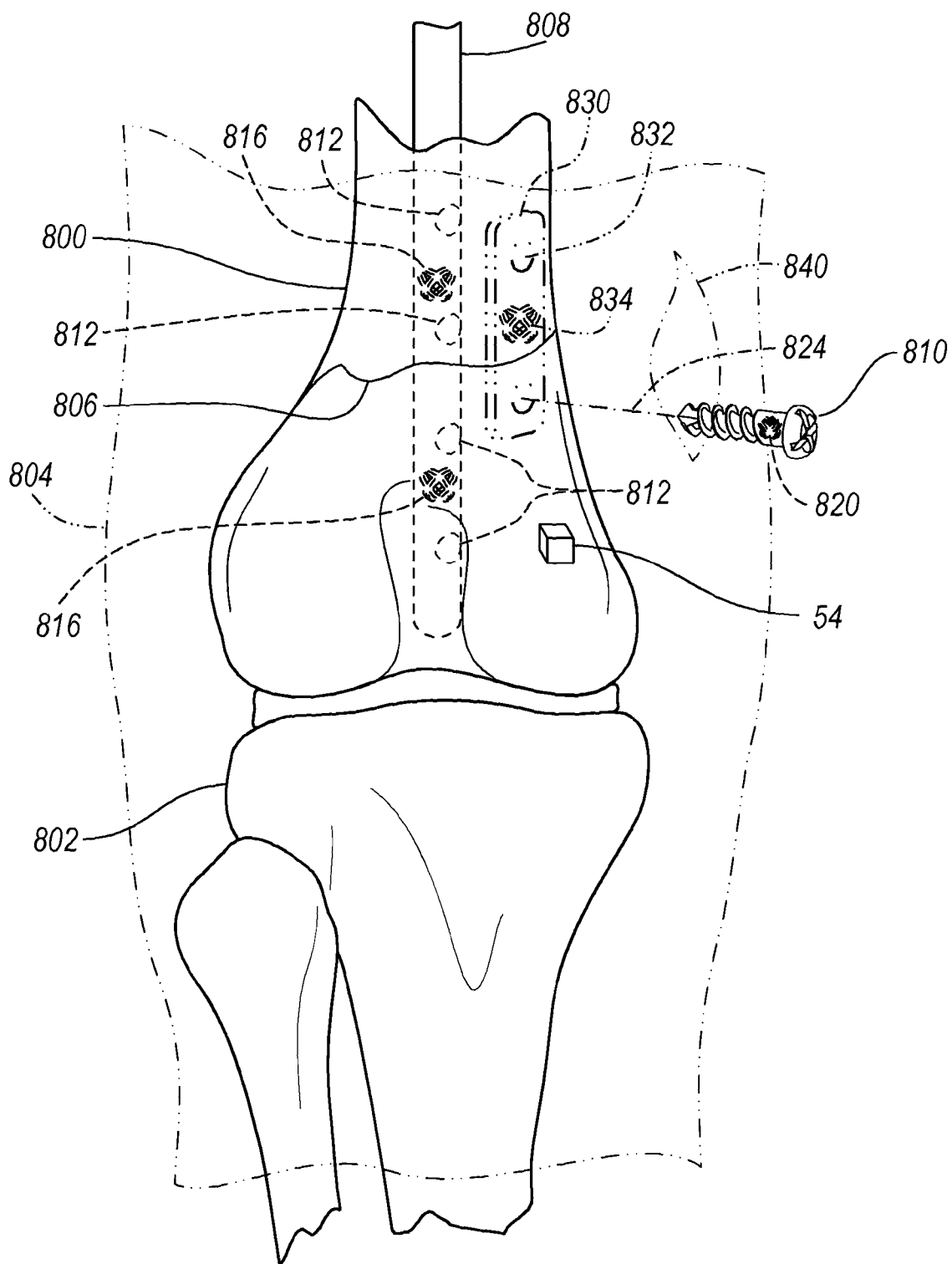
FIG. 35 is an environmental view of implants with tracking sensors according to various embodiments.

With reference to FIG. 35, the patient 14 may include a bone, such a femur 800 relative to a tibia 802. The bones, such as the femur 800 and the tibia 802, may be surrounded by various portions of soft tissue 804, including skin, muscle, etc. The bones, such as the femur 800 are generally substantially contiguous and integral but may become damaged due to disease, injury, or the like. For example, a fracture 806 may form in the femur 800. The fracture 806 may be repaired or held together such that the femur 800 may again act as an integral bone with the various portions. For example, an intramedullary (IM) rod 808 may be provided through an intramedullary canal of the femur 800. The IM rod 808 may span the fracture 806 such that two or more portions of the femur 800, or any appropriate bone portion, may be held relative to one another for use. The IM rod 800 may be positioned to allow for healing of the fracture 806 or for permanently holding the portions of the femur 800 relative to one another. It will be understood, that although the following discussion relates generally to the IM rod 808 and its use in a femur 800, that any appropriate bone portion or implant may be used to achieve a similar result.

Regardless, the IM rod 808 may be positioned through the intramedullary canal of the femur 800 to span the fracture 806. It may be desired, however, to further fix the IM rod 808 relative to the femur 800 to ensure that the various portions on the other side of the fracture 806 are held relative to each other. Therefore, a fixation screw or pin 810 may be provided that is operable to pass through a portion of the femur 800 and a portion of the IM rod 808, such as a bore 812 formed in the IM rod 808. It will be understood that a plurality of screws may be used to fix the IM rod 808 relative to the femur 800 in a plurality of positions or a plurality of points. Regardless, the screw 810 is generally positioned such that it is operable to pass transversely through the bore 812 and not another portion of the IM rod 808.

The IM rod 808 may further include one or more of a tracking sensor 816. The IM tracking sensor 816 may be used to track a position of the IM rod 808 with the tracking system 10, according to various embodiments. Further, the tracking sensor 816 may be any appropriate tracking sensor, such as those described above. Nevertheless, the tracking sensor 816 may include an electromagnetic tracking sensor, an acoustic tracking sensor, a radiation tracking sensor, an optical tracking sensor, or any appropriate tracking sensor. The tracking sensor 816 may be tracked using the array 46 or the mobile localizer 600 according to various embodiments. This may allow for determining a position of the IM rod 808 and a bore 812 in the IM rod 808. The IM rod 808 may be used in an image or imageless system for tracking the position of the IM rod 808. Regardless, the position of the IM rod 808 is tracked relative to the screw 810, or vice versa.

The screw 810 may also include a tracking sensor 820 that is operable to be tracked with the tracking system similar to tracking the tracking sensor 816 in the IM rod 808. Therefore, the screw 810 may be tracked relative to the bore 812 in the IM rod 808. The tracking system may then be used to determine whether the screw 810 is positioned or will be inserted on a selected path to allow it to intersect to the bore 812 after insertion into the bone 800.

The bone 800 may also include a DRF thereon, which may be any appropriate DRF, such as those described above. Therefore, the image space of the system may be registered relative to the patient space and the DRF 54 is used to maintain the registration should movement of the femur occur. Further, the IM tracking sensor 810 may be used to track a position of the IM rod 808 and the bore 812 in the IM rod 808 relative to the screw 810. This may allow the screw 810 to be passed along a selected path, such as a path 824, to ensure that the screw 810 engages and will pass through the bore 812 in the IM rod 808. Thus, the tracking sensors 816, 820 may be used by the tracking system in lieu of other instrumentation to ensure proper alignment of the screw 810 relative to the bore 812.

Further, it will be understood that any appropriate implant may be positioned relative to the anatomy. For example, rather than providing the IM rod 808, the implant may be a bone plate 830 implant that is operable to span the fracture 806.

With continued reference to FIG. 35, the bone plate 830 may also be provided, or as an alternative to the IM rod 808, to span the fracture 806. The bone plate may also include a bore 832 through which the screw 810 or any appropriate screw may pass. In addition, the bone plate 830 may include a tracking sensor 834 such that a position of the bone plate 830 may be tracked. Therefore, as with the IM rod 808, the screw 810 may be tracked relative to the bone plate 830 such that the screw will pass through the bore 832 to allow for fixation of the bone plate 830 relative to the bone 800 with the screw 810.

The various tracking sensors 816, 820, 832 may be used to allow for alignment of the screw 810 relative to the selected portion through a substantially small or minor incision 840. in this way the incision may remain small, but the positioning of the incision and the screw 810 relative to the portion through which the screw will pass may be substantially precisely determined, planned, and tracked with the tracking system. Therefore, a substantially open procedure or one requiring various other external mechanisms, such as alignment guides generally known in the art, may be reduced by using the tracking system. The tracking system is operable to allow for precise alignment of the screw 810 relative to the portion through which it must pass to allow for proper positioning of the implant relative to the bone 800 may be maintained.

Further, the various tracking sensors may be any appropriate tracking sensors. For example, the tracking sensor may be integrated into the implant such as the IM rod 800, the screw 810 or the bone plate 830. However, the tracking sensor may also be rigidly attached with selected portion, such as the implant or an instrument positioning or holding the implant relative to the anatomy. Various connectable or engageable tracking sensors include those disclosed in U.S. Pat. No. 6,499,488 issued Dec. 31, 2002 entitled "Surgical Sensors", incorporated herein by reference. Therefore, it will be understood that the tracking sensor may be any appropriate tracking sensor and may be either integrated into the implant or instrument or selectively attachable thereto.

Further, the DRF 54 or any appropriate tracking sensor positioned relative to the femur 800 or the tibia 802 may be used by the tracking system to determine motion of the bones relative to one another. The motion or articulation of the bones, such as the femur 800 relative to the tibia 802, may be used to determine an anatomical plan, a range of motion, a joint line, a distance between various bones, or any other appropriate measurement. The tracking sensors may be tracked by the system to display motion of the various portions of the anatomy on a display or for determining measurements of the anatomy. For example, this may be used to determine a position of the implant, such as the IM rod 808 or the bone plate 830 relative to the bone or any appropriate implant, such as an articulated implant or the like.

The various portions of the anatomy may be measured to ensure that an appropriate distance, pre- and post-operatively is achieved or any other appropriate measurement. For example, when repairing the fracture 806, a length of the femur 800 may be selected. Various tracking sensors, including the DRF 54, may be used to assure that the selected length is achieved post-operatively or intra-operatively, or if further adjustment is necessary. Various types of joint measurements are disclosed in U.S. Pat. No. 5,772,594 to Barrick, issued Jun. 30, 1998, incorporated herein by reference. Regardless, the tracking sensors used may include the tracking sensors discussed above and may be used by the tracking system to ensure or assist in planning or determining the achievement of a selected surgical plan.

Various instruments can be used to perform the various procedures, such as positioning implants, performing resections, positioning implants, and the like. The various instruments can be tracked to display a position of the instrument during the operative procedure. The tracking can be done with tracking sensors that can be positioned near or at a distal or working end of the instrument, or at any appropriate position on the instrument.

Figure 36:
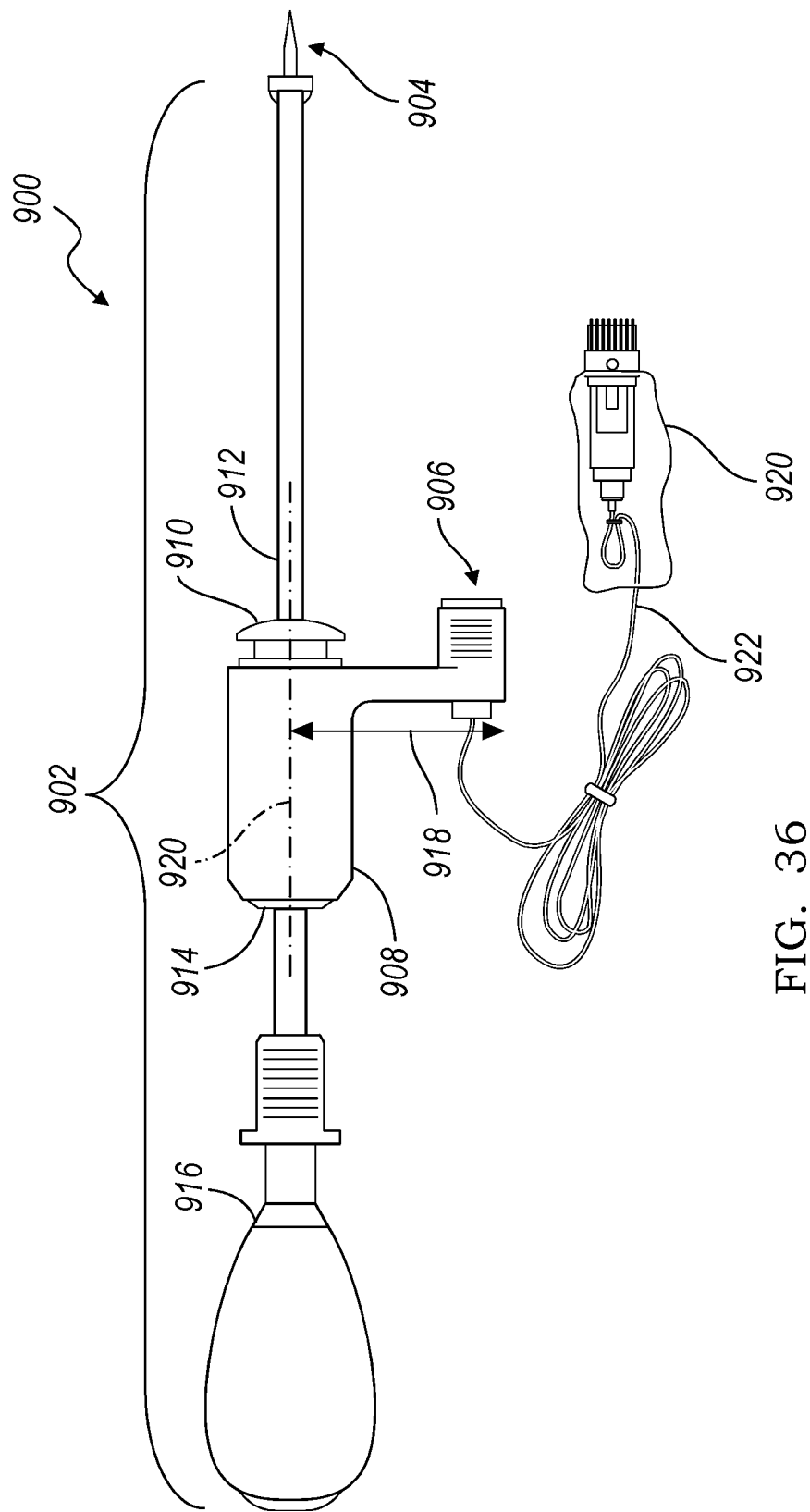
FIG. 36 is a plan view of an instrument with a tracking sensors according to various embodiments.

As discussed above, various instruments can be used during a surgical procedure. For example, an instrument 900 can be an awl, probe, tap (APT) instrument, as illustrated in FIG. 36, according to various embodiments. The instrument 900 can include a general or universal tool portion 902 and an interchangeable portion 904. The interchangeable portion 904 can be any appropriate portion such as a screw tap, a probe, or an awl. It will be understood that the interchangeable portion 904 can also be any other appropriate member, such as a screw, a nail, a fixation pin or the like. The interchangeable member 904 can be any appropriate member that is operable to interchange with the standard portion 902 in an operable manner. The interchangeable member 904 may include a quick connect portion, a tool engagement portion, and a thread portion, or the like, to connect with the tool portion 902.

The tool portion 902 and the interchangeable portion 904 can be formed of any appropriate materials. As discussed herein, the instrument 900 can be tracked using an electromagnetic tracking system or any other appropriate tracking system. If an electromagnetic tracking system is used, it may be selected to form the instrument 900 of a non-ferrous material such that it is not likely to interfere with the electromagnetic tracking system. Therefore, the instrument 900 can be formed of titanium, other non-magnetic alloys, non-magnetic synthetic materials, or any appropriate materials. It will be understood that the various instruments described herein that are used with the electromagnetic tracking system may all be formed of non-magnetic materials or any other appropriate materials.

The instrument 900 can be used with the navigation system 10. The navigation system 10 can be an image or an imageless navigation system. That is, as discussed above, images can be acquired of the patient 14 and displayed on the display 34. Further representations of various instruments, such as the instrument 900, can also be displayed on the display 34. Alternatively, the navigation system 10 can be substantially imageless such that the instrument 900 is illustrated relative to a selected point.

The navigation system 10 can be any appropriate navigation system, such as an electromagnetic navigation system as discussed above. The instrument 900, therefore, can include a tracking sensor 906. The tracking sensor 906 can be positioned at any appropriate position relative to the instrument 900. The tracking sensor 906 can generally be interconnected with a bobbin or interchangeable member 908. The interchangeable member 908 can include a tool engaging end 910 that can include a quick connect portion that can interconnect with a tool engaging shaft 912. The interconnecting portion 908 can further include a handle engaging end 914 that is operable to engage a handle 916. The connections can be any appropriate connections such as quick connections, permanent connections, threaded connections, or the like.

The tracking sensor 906 can be positioned at any appropriate position, but can be interconnected with the interchangeable member 908 such that the tracking sensor 906 is present in the various handles 916 and shafts 912 can be interconnected with the interconnecting member 908. The tracking sensor 906 can be positioned at a distance 918 from an axis 920 of the instrument 900. The distance 918 can be any appropriate distance. For example, the distance 918 can be selected for operation by a user to minimize interference of the tracking sensor 906 with use of the instrument 900. Nevertheless, the distance 918 can be known and unchangeable so that the position of the tracking sensor 906 relative to the other parts of the instrument 900 can be known for determining a location of any portion of the instrument 900.

The tracking sensor 906 can be any appropriate sensor or transmitter, such as an electromagnetic sensor including those described above. It will be understood that the tracking sensor 906 can include a plurality of coils, such as three coils, that can be positioned relative to one another in a substantially selected manner. Further, the tracking sensor 906 can be any appropriate EM sensor, such as a Hall Effect sensor. Thus, the use of coils is not required, but is merely exemplary. For example, the three coils can be positioned substantially orthogonal to one another and in a substantially fixed orientation to allow for up to six degrees of freedom of tracking. The various types of the tracking sensors can include those described above or any appropriate tracking sensor.

The tracking sensor 906 can be wired or hard wired to the tracking system that is interconnected with a connector 920 and a wire 922. It will be understood that the tracking sensor 906 can also be a wireless sensor. The connector 920 can be interconnected with the navigation probe interface 50, the isolator circuit 55, or any combination thereof. It will be understood that the instrument 900 can be interconnected in a manner substantially similar to the probe 52 discussed above. Therefore, the tracking sensor 906 can be used to track the instrument 900 in any appropriate manner. Further, the connector 920 can be any appropriate connector for connection with the navigation system 10. The illustrated connector 920 is merely exemplary of any appropriate connector.

As discussed above, the instrument 900, including the distance 918, the connector portion 908, the shaft 912, and the interchangeable member 904 can have positions and orientations substantially known relative to one another. Therefore, the position of the tracking sensor 906 can be known substantially relative to any other portion that is interconnected or interacting with the tracking sensor 906. Thus, the instrument 900 can be tracked, including any portion, thereof by determining the position of the tracking sensor 906 and calculating a position of any of the other portions of the instrument 900 relative to the tracking sensor 906.

The instrument 900 can be used for any appropriate procedure. For example, the interchangeable member 904 can include an awl for creating a pilot bore or divot at a location, such as in a spinal portion. A tap can be interconnected as the interconnectable member 904 to form a tapped bore for receipt of a selected screw member. All of these may be used for performing a spinal procedure, such as for fixing a spinal implant relative to a spine or any other appropriate procedure.

With reference to FIGS. 37 and 38, an instrument 940 is illustrated that can be similar to the instrument 900. The instrument 940 can include a generally fixed or handled portion 942 and an interchangeable portion 944. The interchangeable portion 944 can be similar to the interchangeable portion 904 of the instrument 900. The handle portion 942 can be similar to the handle portion 902 of the instrument 900. The instrument 940, however, can selectively not include the interchangeable portion 908, but simply include the rod engaging or tool engaging portion 946 and an operable handle 948.

Defined through the instrument 940 is a cannula 950. The cannula 950 can extend through the handle 948, the shaft 946 and the interchangeable portion 944. The cannula 950 can be formed in any appropriate dimension and for any selected instrument, such as those described herein. The cannula 950 can be operable to interact with the stylet 150. The stylet 150, including the tracking sensor 162, as described above according to various embodiments, can be positioned through or in the cannula 950 defined by the instrument 940. The stylet 150 can include the portions described above and illustrated in FIGS. 10A and 10B. Generally, however, the stylet 150 can be positioned in the cannula 950. As discussed above, the tracking sensor 162 defined by a portion of the stylet 150 can be used to track a portion of the instrument 940. As discussed above, positioning the stylet 150 within the cannula 950, as illustrated in FIG. 38, can allow for tracking any appropriate portion of the instrument 940 by tracking a position of the tracking sensor 162 defined by the stylet 150.

It will be understood that the tracking sensor 162 defined by the stylet 150 can be positioned at any appropriate position within the instrument 940. That is the tracking sensor 162 can be positioned substantially near the interconnectable member 944, within the interconnectable member 944, or within the fixed portion 942. If the tracking sensor 162 is positioned substantially near a distal end of the instrument 940, such as in the interconnectable member 944 or near the interconnectable member 944, the tracking sensor 162 can be tracked to determine a substantially precise location of the interconnectable member 944 or the distal end of the instrument 940.

The stylet 150 can be interconnected with the handle 948, the shaft 946, or any appropriate portion of the instrument 940. Nevertheless, the stylet 150 can be provided in any appropriate dimension such that it is nonbinding inside of the cannula 950. Therefore, the instrument 940 can move, or at least portions thereof can move, relative to the stylet 150, in particular the tracking sensor 162. Therefore, as the interchangeable member 944 is moved relative to a selected portion of the patient 14 it can be deformed or deflected, but its position can be substantially known due to the positioning of the tracking sensor 162 on the stylet 150.

As discussed above, the interconnectable member 944 can be an awl. Therefore, as the awl is being used a tip of it may deform or deflect, but the position of the interconnectable portion 944 is substantially known. Similarly, if the tracking sensor 162 is positioned substantially near the interchangeable member 944, the shaft portion 946, which can be any appropriate length and formed of any appropriate material, can also change its dimensions while the position of the interchangeable member 944 is still known. For example, the shaft 946 can be formed of a deformable material that allows it to flex under a selected load. Although the shaft 946 can flex under a selected load, the positioning of the tracking sensor 162 near or in the interchangeable member 944 can allow for tracking the position of the interchangeable member 944 due to the fact that the tracking sensor 162 formed on the stylet 150 is near the distal end of the instrument 940.

It will be understood that the tracking sensor, such as the tracking sensor 162, can be formed in any appropriate manner, for example, the tracking sensor 162 can be formed on the stylet 150 according to any appropriate method such as those described above according to various embodiments. Therefore, the stylet 150 can be formed of any appropriate materials. Nevertheless, it will be understood, that the tracking sensor 162 can be formed on the shaft 946 or on the interchangeable member 944, itself. Although the selection of the material for the various portions can be chosen to allow for formation of the tracking sensor on the instrument 940 itself rather than the stylet 150, it will be understood that the stylet 150 can be used interchangeability.

Further, the stylet 150 can be used with any non-unique instrument 940. That is the stylet 150 can be positioned in any cannulated instrument to allow for tracking of a selected portion of the cannulated instrument. Therefore, the tracking sensor 162 is substantially portable and can be used with any appropriate instrument, such as those already existing in the operating theater. But the stylet 150 still allows for tracking a portion of any appropriate instrument at a working or distal end thereof.

The stylet 150 can be wired including the wire 152, such as that illustrated in FIG. 10A. Alternatively, the stylet 150 may include substantially wireless sensors, thus as generally known in the art including those disclosed in U.S. Pat. No. 6,474,341 to Hunter et al., issued Nov. 5, 2002, incorporated herein by reference. Therefore, it will be understood that the tracking sensors 162 can be any appropriate tracking sensors. The stylet 150 can be interconnected with the navigation probe interface 50, the isolator circuit 55, or any appropriate portion of the navigation system 10. Therefore, the stylet 150 can be used to track the position of the instrument 940 or a selected portion of the instrument 940 even though the instrument 940 may become deformed during an operative procedure. In addition, the instrument 940 can be formed of any appropriate materials, including those that are appropriate for the instrument 900. For example, it may be selected to the instrument 940 of substantially non-magnetic or non-ferrous materials which may include various metal alloys or synthetic materials.

Figure 39:
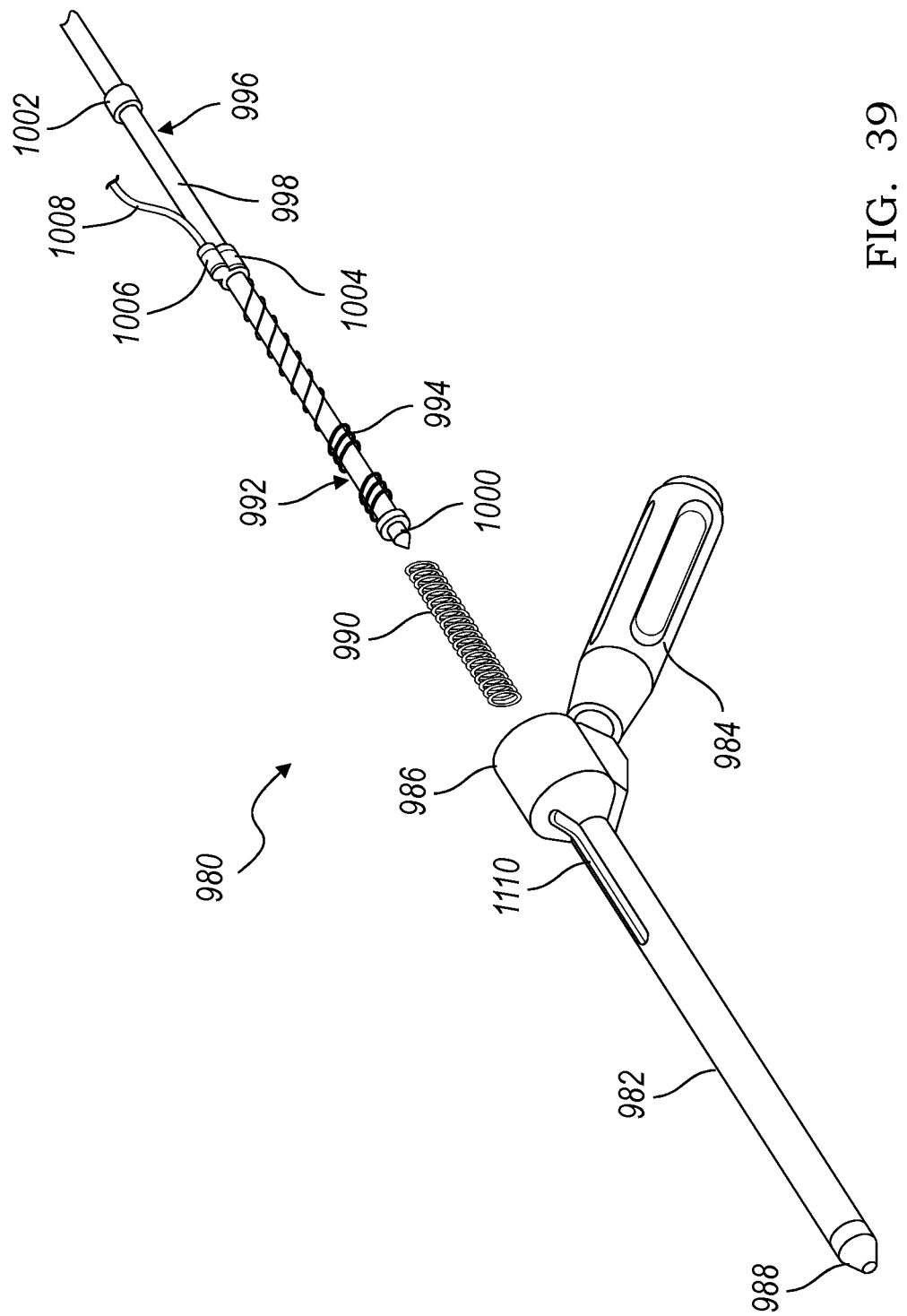
FIG. 39 is an exploded view of a guide with a tracking sensor according to various embodiments.
Figure 40:
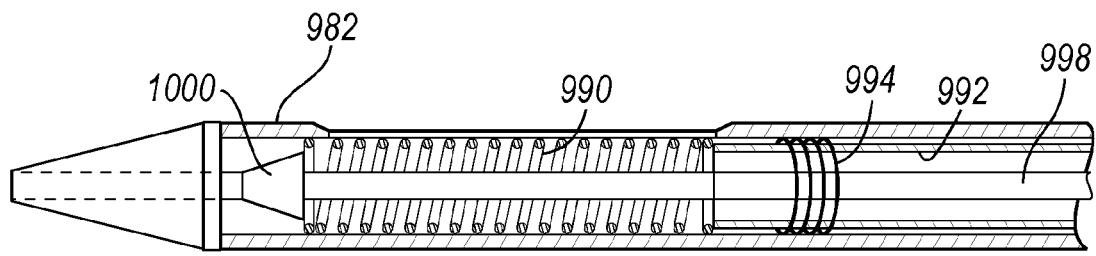
FIG. 40 is a detail cross-sectional view of the guide of FIG. 39 according to various embodiments.

With reference to FIG. 39, a guide instrument 980 is illustrated. The guide instrument 980 can include various portions such as an external tube 982, a handle 984, and a connection or collar portion 986. The external tube 982 can be substantially hollow and define a cannula and can also include a working end 988. The working end can allow for operation of any appropriate portion, such as a drill bit relative to the working end 988. The working end 988 may be interconnected or formed as one-piece with the tube 982 or formed substantially as a single member therewith.

The collar 986 can further define a cannula bore that interconnects with the cannula bore defined by the tube 982. Positionable within the tube 982 can be a spring 990, a sleeve 992 that can include a tracking sensor 994 or any appropriate number of the tracking sensors 994. Positionable within the sleeve 992 is a drill bit 996. The drill bit 996 can include an extended shaft 998 and a drill tip 1000. The drill tip 1000 can be any appropriate drill tip. Further, the drill bit 996 can include a stop collar or stop member 1002 for interacting with an appropriate portion such as with a proximal end 1004 of the tube 992. The collar 1004, or any appropriate portion, can also allow for a fixed connection of the sleeve to the drill bit 996. It will be understood that the drill bits 996 may also include a tool engaging portion, such as a proximal end of the drill bit 996. The tool engaging portion can engage any appropriate tool such as a hand crank drill, a power drill motor, or any other appropriate member. Nevertheless, the drill bit 996 can be positioned within the sleeve 992 to be positioned within the tube 982.

As discussed above, a substantially hollow cannula such as the suction tube 190 illustrated in FIG. 13 can include the tracking sensors 206, 208. It will be understood that the tube 992 can be similar to the tube portion of the suction tube 190 illustrated in FIGS. 13 and 14. Further, the tracking sensor 994 can be substantially similar to the tracking sensors 206, 208 described and illustrated above. Therefore, detailed description thereof is not necessary herein.

Nevertheless, the tube 992 can be positioned within the exterior tube 982 to offer tracking by the tracking sensor 994 once the tube 992 is positioned within the exterior tube 982. As discussed above, the tracking sensors, such as the tracking sensor 994 can be tracked with the navigation system 10. The tracking sensor 994 positioned on the tube 992 is operable with the drill bit 996 and can allow for tracking of a selected portion of the drill bit 996, such as a portion substantially near the drill tip 1000. Therefore, it will be understood that the tracking sensor 994 can be positioned on any appropriate portion of the tube 992 where the tube 992 can be formed relative to the drill bit 996.

During an operative procedure, the spring 990 may be positioned in the external tube 992 which can be followed with the sleeve 992 and the drill bit 996. The drill bit 996 can be positioned within the tracking sleeve 992 and the unit can be positioned within the outer tube 992. It will be understood, however, that the assembly can be interconnected in any appropriate manner.

During operation, the drill tip 1000 can be advanced towards or out of the working end 998. As the drill at 1000 is operated, the tracking sensor 994 is able to be used to determine a position of a portion of the sleeve 992 substantially near the drill tip 1000. The spring 990 can also be used to assist in determining a positioning of the drill tip 1000. The spring 990 compresses a selected distance during operation of the drill bit 996. The compression of the spring 990 can be used to determine an exact location of the drill bit 1000 even if the tracking sensor 994 is not substantially on or adjacent the drill tip 1000. Therefore, the instrument 980 can be used to determine a substantially precise location of the drill tip 1000 during an operative procedure even if the drill bit 996 becomes deformed during an operative procedure.

Further, the sleeve 992 allows for free rotation of the drill bit 996 during an operative procedure, while still allowing for the tracking sensor 994 to be positioned substantially near the drill tip 1000. As discussed above, the tracking sensor 994 can be formed on the tube 992 substantially similar to the tracking sensors 206, 208 formed on the tube and the suction tube 190.

The sleeve can be substantially wired or wireless. For example, a connector 1006 can be interconnected with the tracking sensor 994 and further connected with a wire 1008 to be interconnected with the probe interface 50 or the isolator circuit 55. The tube 998 may include a recess or slot 1010 that is operable to allow for reveal of the sensor connection 1006. It will understood, however, that the tracking sensor 994 can be substantially wireless, as is known in the art.

Further, it will be understood that various portions of the instrument 980 can be formed of selected materials, including those discussed above. The instrument 980 can be formed of substantially non-magnetic materials, including non-magnetic alloys, synthetic materials, or the like. Nevertheless, the instrument 980 can be formed of materials to allow for the tracking sensor 994 to operate effectively to allow for determination of the position of the tracking sensor 994 and position of the various portions of the instrument 980 relative thereto.

As discussed above, positioning the tracking sensor substantially near the working end, such as the drill tip 1000, can allow for a precise determination of a position of the drill tip 1000 even if the drill tip 1000 moves or is deformed relative to the shaft 998 of the drill bit 996. Therefore, during an operation, such as during a spinal procedure, a cranial or neurological procedure, or the like, the position of the drill tip 1000 can be substantially precisely known due to its proximity to the tracking sensor 994.

It will be understood that the tracking sensors, such as the tracking sensor 994 on the instrument 980 or the tracking sensors 162 on the stylet 150 can be provided as a plurality for tracking verification. For example, if two or more of the tracking sensors are provided, then the spatial position, including distance and orientation, between the two or many should be substantially constant due to the materials rigidly relative to the tracking sensors. Therefore, the tracked location of the two tracking sensors on the same instrument can be used to determine accuracy of the tracked system.

Further, as discussed above, the navigation system 10 using the tracking sensors near a working end or a distal end of the instrument can allow for reduced calibration of the system. For example, the position of the tracking sensor is known to be near the working end of the instrument. Therefore, a calibration of a length of the instrument is not necessary between the working end of the instrument and the tracking sensor. By positioning the tracking sensor substantially near the working end, the tracking sensor is able to very accurately determine that position of the working end of the instrument, such as a drill tip or an awl.

Figure 41:
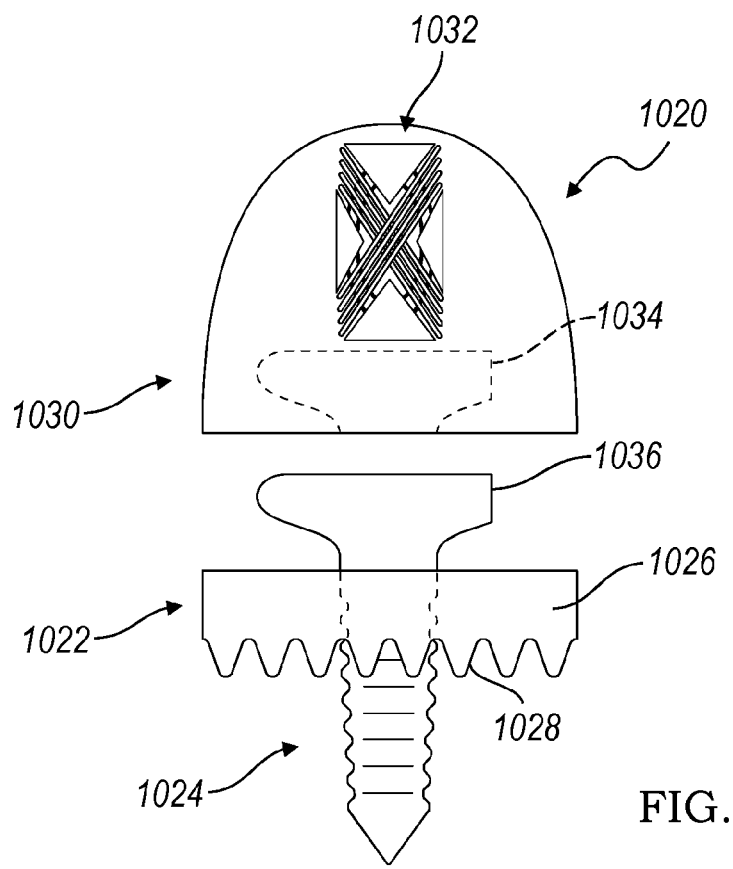
FIG. 41 is an exploded view of a tracking sensor assembly according to various embodiments.

With reference to FIG. 41, a tracking sensor 1020 is illustrated. The tracking sensor can be any appropriate tracking sensor and may exemplary be used as a dynamic reference frame, such as the dynamic reference frame 54. The tracking sensor 1020 can be used as a dynamic reference frame and can include a fixation base 1022 for fixation to a selected anatomical portion, such as a boney portion including a spinal process, a femur or any other appropriate boney portion. The fixation base can include a bone engaging screw portion 1024 and a fixation platform 1026. The fixation platform can include teeth or projecting members 1028. The projecting members 1028 can engage the bone to assist in reducing rotation of the base 1026 relative to the portion to which it is fixed. Therefore, rotation of the tracking sensor 1020 can be substantially reduced or eliminated to allow for greater degrees of freedom of tracking.

The tracking sensor 1020 further includes a tracking head 1030. The tracking head 1030 can include the tracking sensor coils 1032. The tracking sensor coils 1032 can be any appropriate coils such as the coil 90 illustrated in FIG. 6, according to various embodiments. Nevertheless, as discussed above, the tracking head 1030 can use any appropriate sensor, rather than only coils. It will be understood that the sensor may be any appropriate sensor, such as any appropriate EM sensor including Hall Effect sensors. Although the tracking coils 1032 can be fitted inside of the cap 1030, such as through molding or casting, the tracking coils 1032 can be fitted to the cap 1030 according to any appropriate manner.

The cap 1030 further includes a base engaging portion 1034. The base engaging portion 1034 can engage a portion of the screw 1024 such as a proximal or cap engaging portion 1036. The interconnection between the cap 1030 and the cap engaging portion 1036 can be substantially firm and resist rotation of the cap, including the tracking coils 1032 relative to the base 1022, and therefore, relative to the anatomy to which the base 1022 is connected. The cap engaging portion 1036 can include a portion that binds or engages the base 1026 to drive the engaging members 1028 into a selected portion of the anatomy to assist in resisting rotation of the base 1026. Further, the base engaging portion 1034 can be keyed relative to the cap engaging portion 1036 to resist rotation or ensure a selected orientation of the cap 1030 relative to the base 1022. The keyed portion or the anti-rotation feature can be the engaging portion is substantially non-cylindrical and includes a selected geometry.

Further, the base portion 1022 can be used as a fiducial marker. For example, the base 1022 can be fixed to a selected portion of the anatomy of the patient 14 during an imaging process to produce image data. The images can include the image of the base 1022 and the base can be maintained in place prior to and during an operative procedure. Therefore, the base 1022, such as the cap engaging portion 1036, can include a divot or a marking portion that can be used to calibrate the image space to the patient space.

Although the tracking sensor 1022 can be any appropriate tracking sensor, such as that disclosed in U.S. Pat. No. 6,499,488 to Hunter et al. issued Dec. 31, 2002 or U.S. Pat. No. 6,381,485 to Hunter et al. issued Apr. 30, 2002, each of which is incorporated herein by reference, the tracking sensor 1020 can be any appropriate tracking sensor. For example, the tracking 1030 can be substantially a single use member and can snap onto the base 1022. Further, the cap 1030 can be formed in any appropriate shape for use in the operative procedure. Also, the sensor coils 1032 can be substantially integrally formed to form as a single piece with the cap 1030, such as molding the coils 1032 within the cap 1030. Further, the coils 1032 can be substantially wireless or wired. Therefore, it will understood that a wire may extend from the cap 1030 to interconnect the coils 1032 with the probe sensor 50. Nevertheless, the cap 1030 can be formed in such a manner to allow it to be only destructively removal from the base 1022. Therefore, the cap 1030 can be substantially a single use cap for various purposes, such as insuring sterility, insuring operability, and the like.

Figure 42:
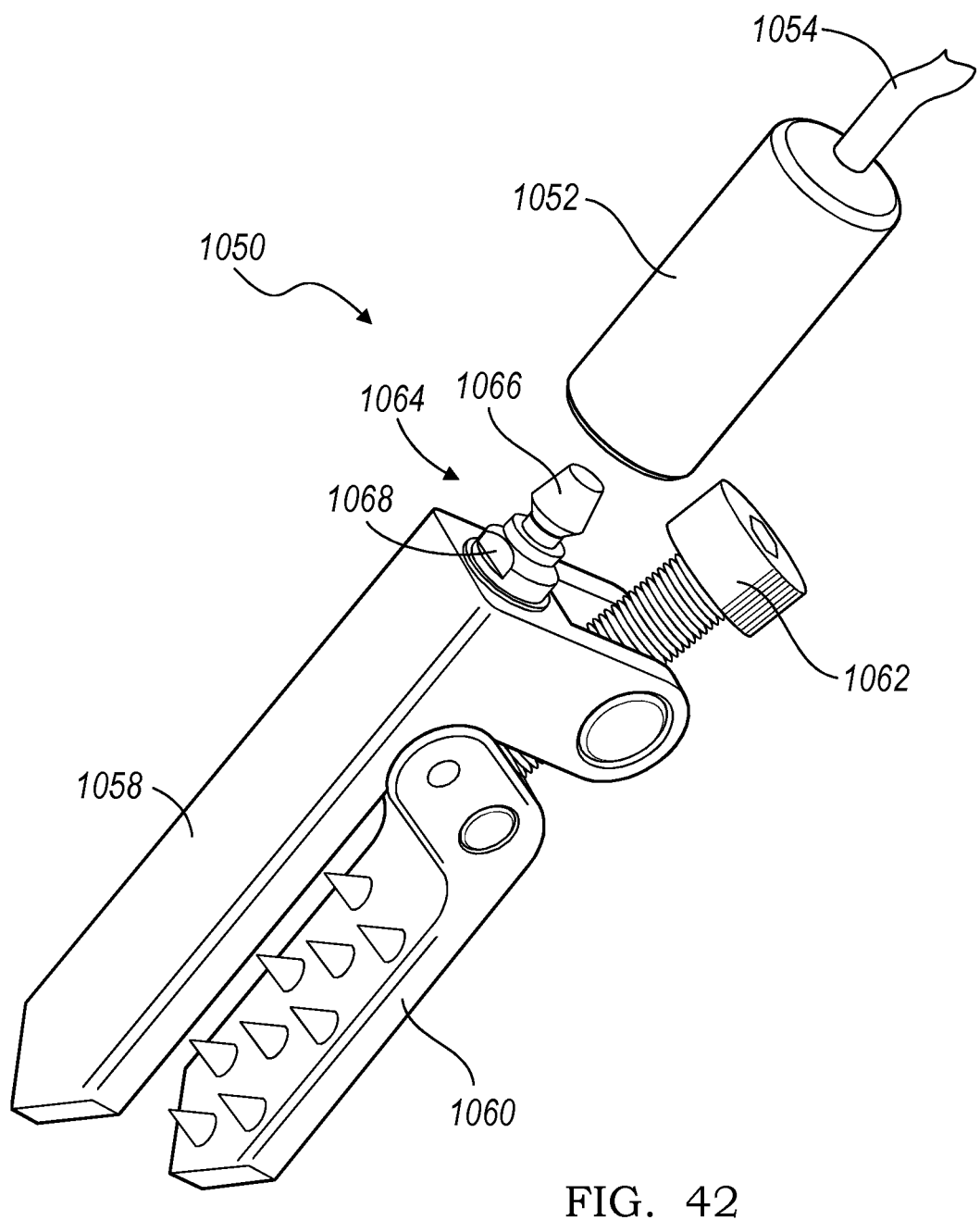
FIG. 42 is an exploded view of a tracking sensor assembly according to various embodiments.

With reference to FIG. 42, a tracking sensor assembly 1050 is illustrated, according to various embodiments. The assembly 1050 can include a tracking sensor cap 1052 that can be similar to the cap 1030 in the tracking sensor assembly 1020. The cap 1052 can include sensor coils (not illustrated) or any other appropriate sensor, such as those discussed above, and can be wired with a wire 1054 or wireless, according to various embodiments. The assembly 1050 can include a connection portion 1056 similar to the connection portion 370 described above. It can, briefly, include a first leg 1058 and a second leg 1060 that can be moved relative to one another with the fixation screw 1062.

The connection member 1056 can further include a connection post 1064. The connection post 1064 can include a sensor engaging portion 1066 and an anti-rotation or keyed portion 1068. The sensor engaging portion 1066 can engage a complimentary portion of the sensor body 1052. The connection can be a snap engagement such that no other tools are required to interconnect the body 1052 and the post 1064.

The anti-rotation portion 1068 can also fit or engage with a complimentary portion of the body 1052. The anti-rotation portion can assist in reducing or eliminating rotation of the body 1052, and thus the sensors, relative to the connector 1056. This can assist in increasing the degrees of freedom of tracking that is possible if the sensor and the second body 1052 are fixed relative to the connector 1056. It will be understood, however, that the anti-rotation portion 1068 can be any appropriate portion. For example, any appropriate geometry, such as a polygon or square, can be used to resist rotation with connection to the body 1052.

Figure 43:
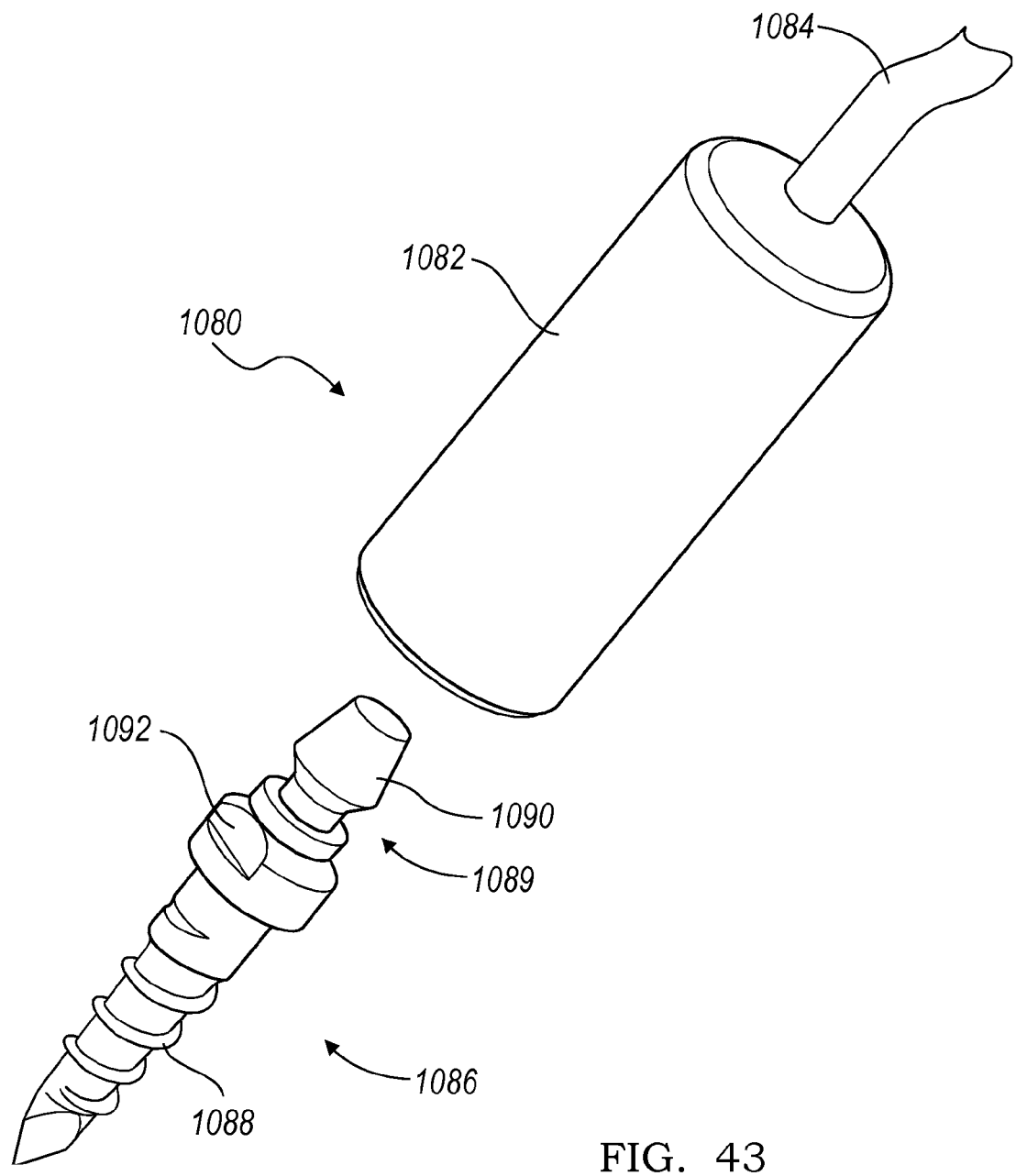
FIG. 43 is an exploded view of a tracking sensor assembly according to various embodiments.
Figure 44:
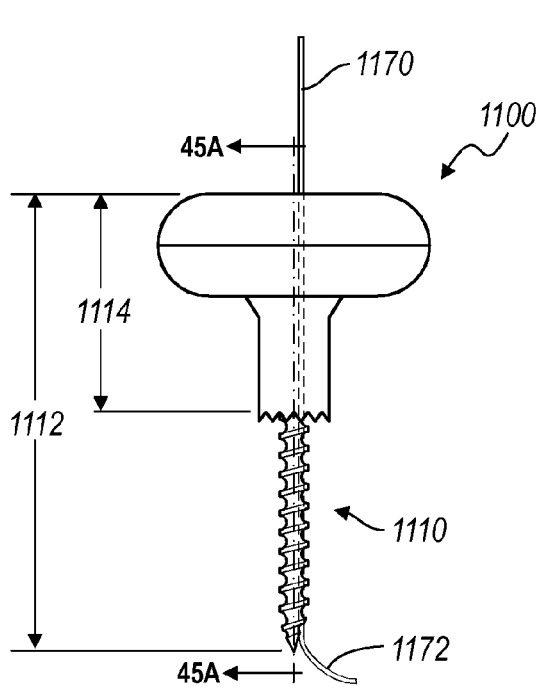
FIG. 44 is a plan view of a dynamic reference frame according to various embodiments.
Figure 45A:
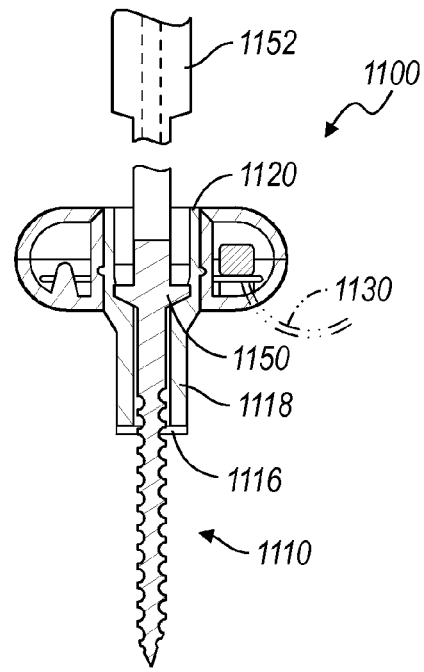
FIG. 45A is a cross-sectional view taken along line 45 of FIG. 44.
Figure 45B:
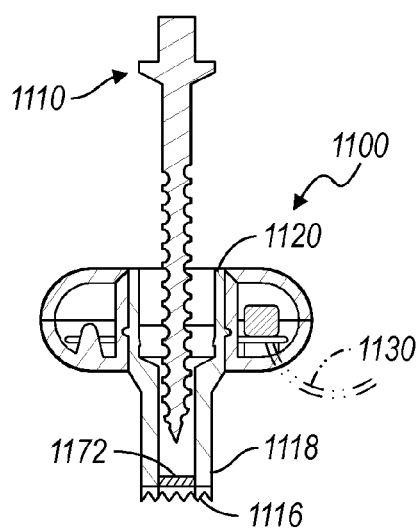
FIG. 45B is a cross-sectional view taken along line 45 of FIG. 44 including a protective element according to various embodiments.
Figure 46:
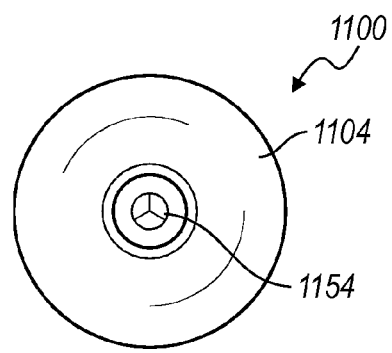
FIG. 46 is a bottom plan view of the DRF illustrated in FIG. 44.
Figure 52:
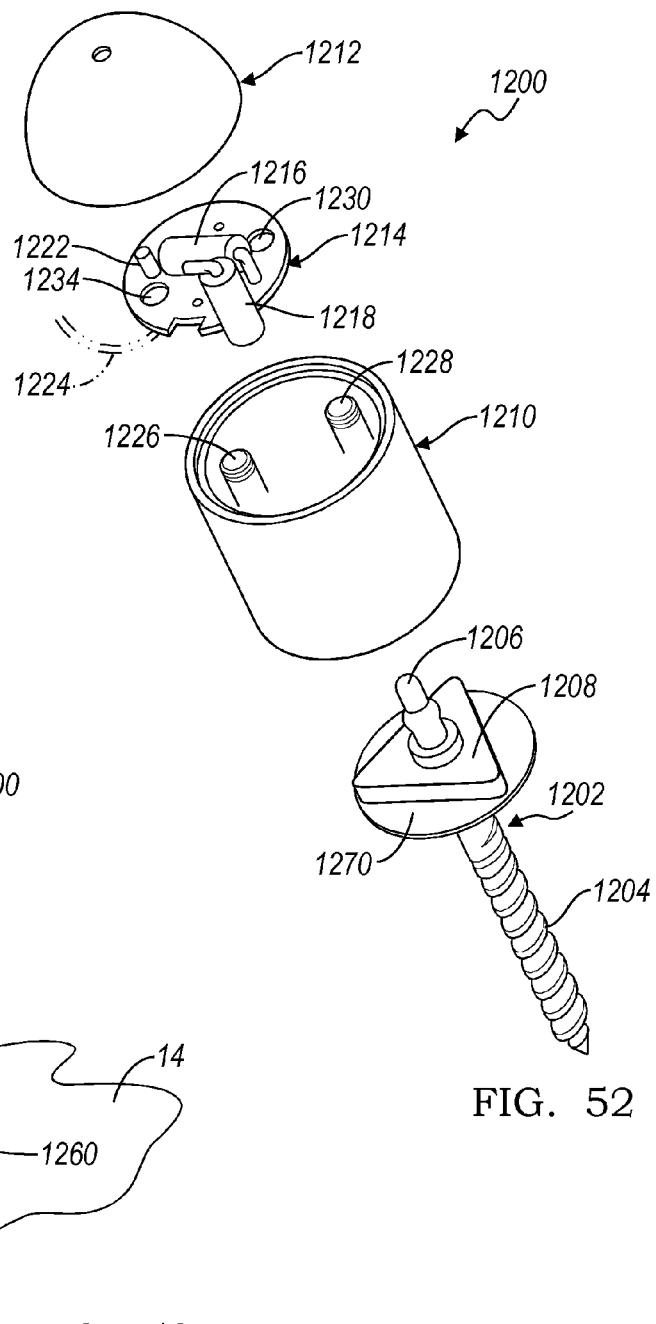
FIG. 52 is a top perspective exploded view of a DRF according to various embodiments.
Figure 53:
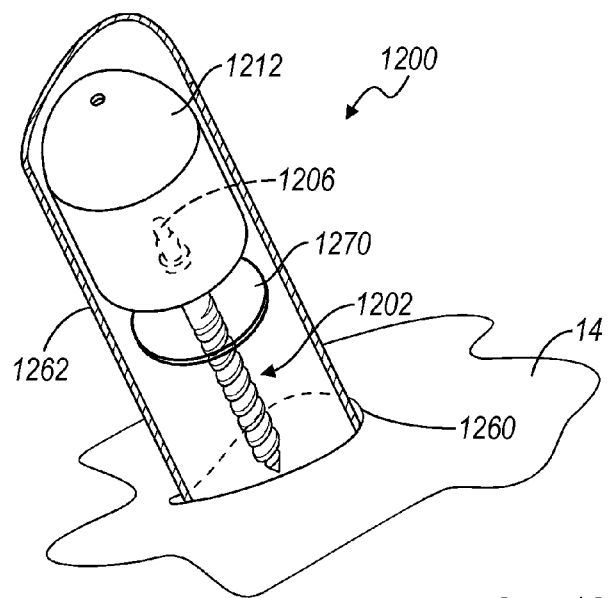
FIG. 53 is a detailed environmental view of a DRF according to various embodiments being positioned relative to a patient.
Figure 54:
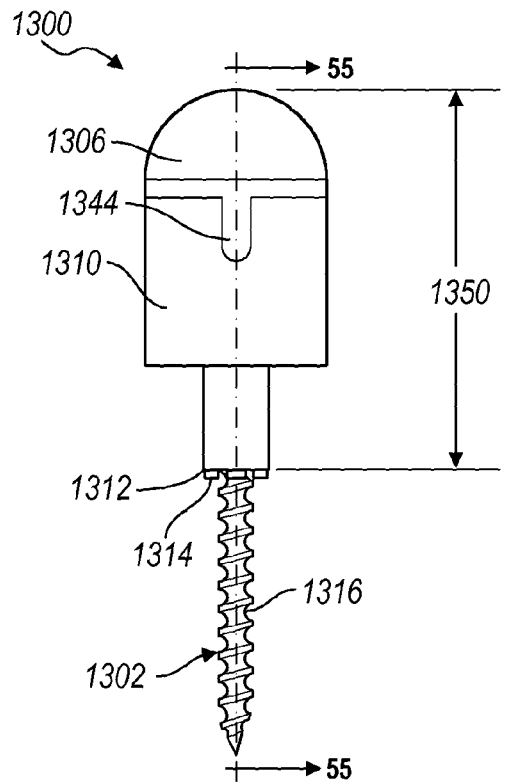
FIG. 54 is a side plan view of a DRF according to various embodiments.
Figure 55:
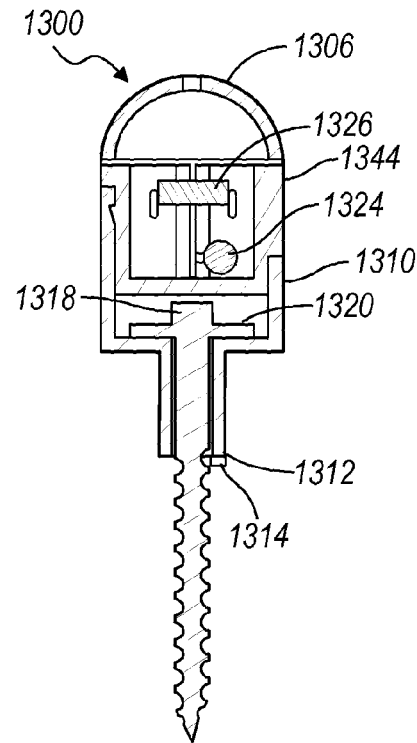
FIG. 55 is a cross-sectional view of a DRF, according to various embodiments, taken along line 55-55 of FIG. 54.
Figure 56:
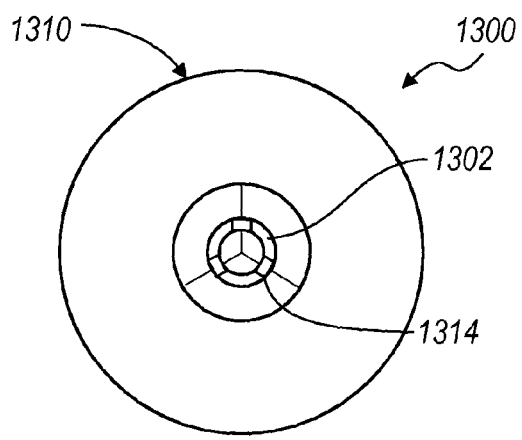
FIG. 56 is a bottom plan view of a DRF according to various embodiments.
Figures 57, 58:
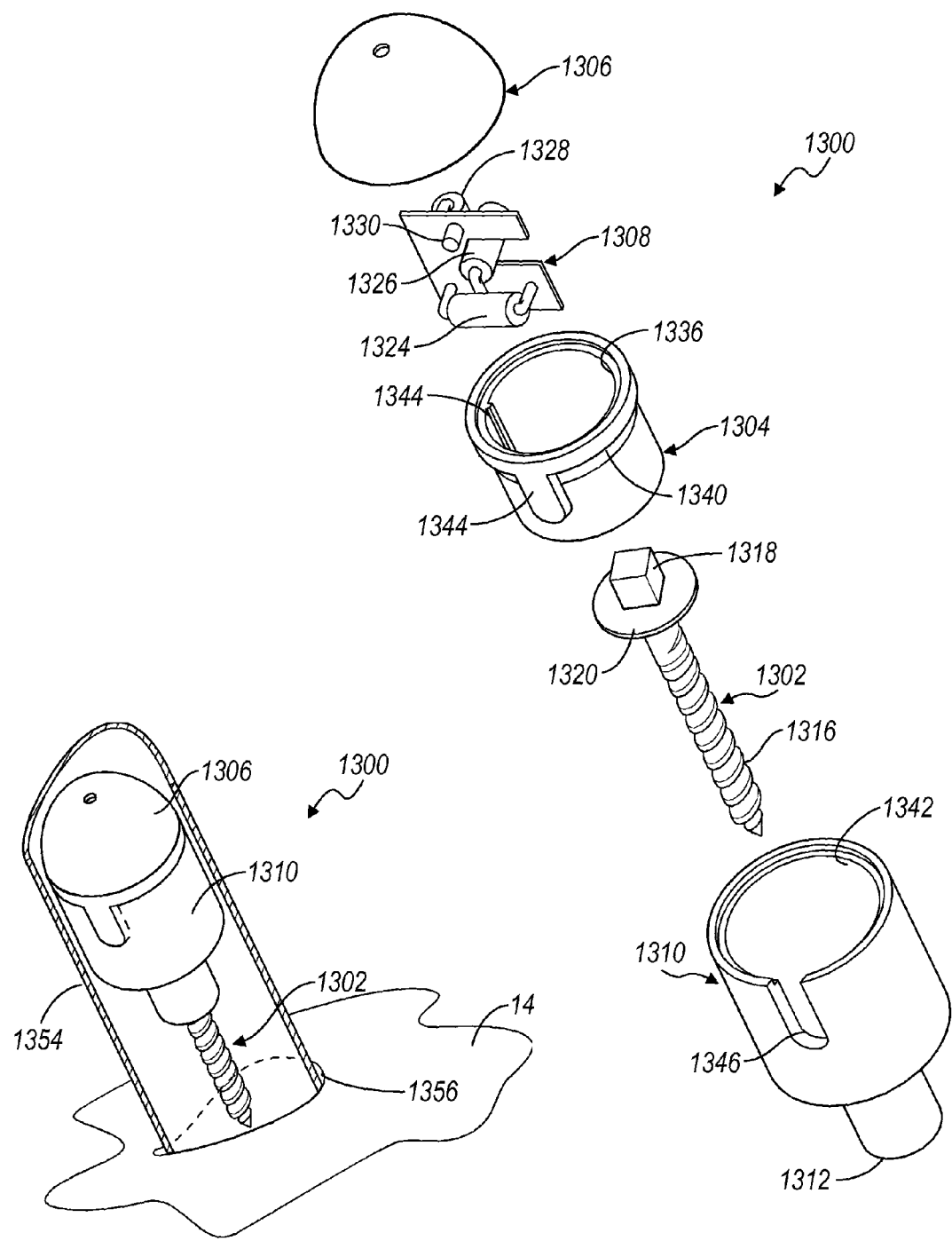
FIG. 57 is a top perspective exploded view of a DRF according to various embodiments.
FIG. 58 is a partial detail environmental view of a DRF being positioned relative to a patient.
Figure 59:
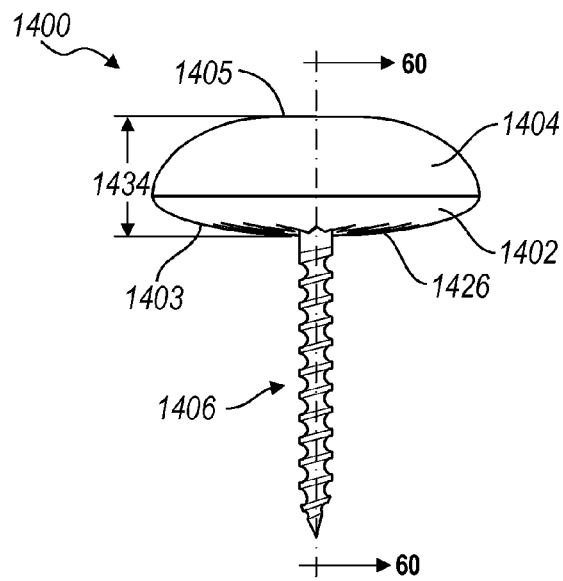
FIG. 59 is a side plan view of a DRF according to various embodiments.
Figure 60:
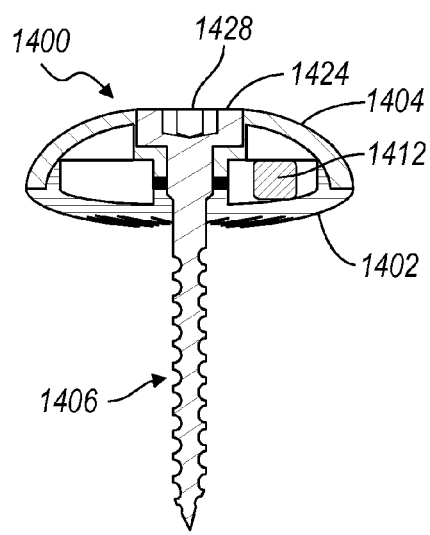
FIG. 60 is a cross-sectional view of a DRF, according to various embodiments, taken along line 60-60.
Figure 61:
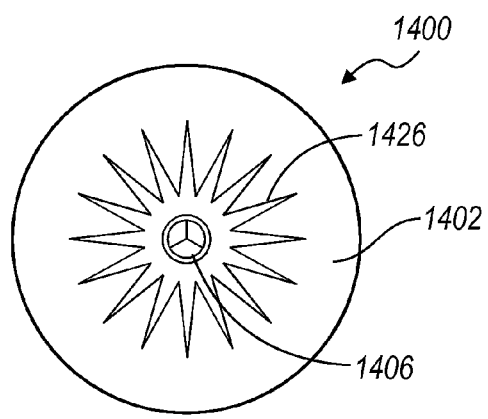
FIG. 61 is a bottom plan view of a DRF according to various embodiments.
Figures 62, 63:
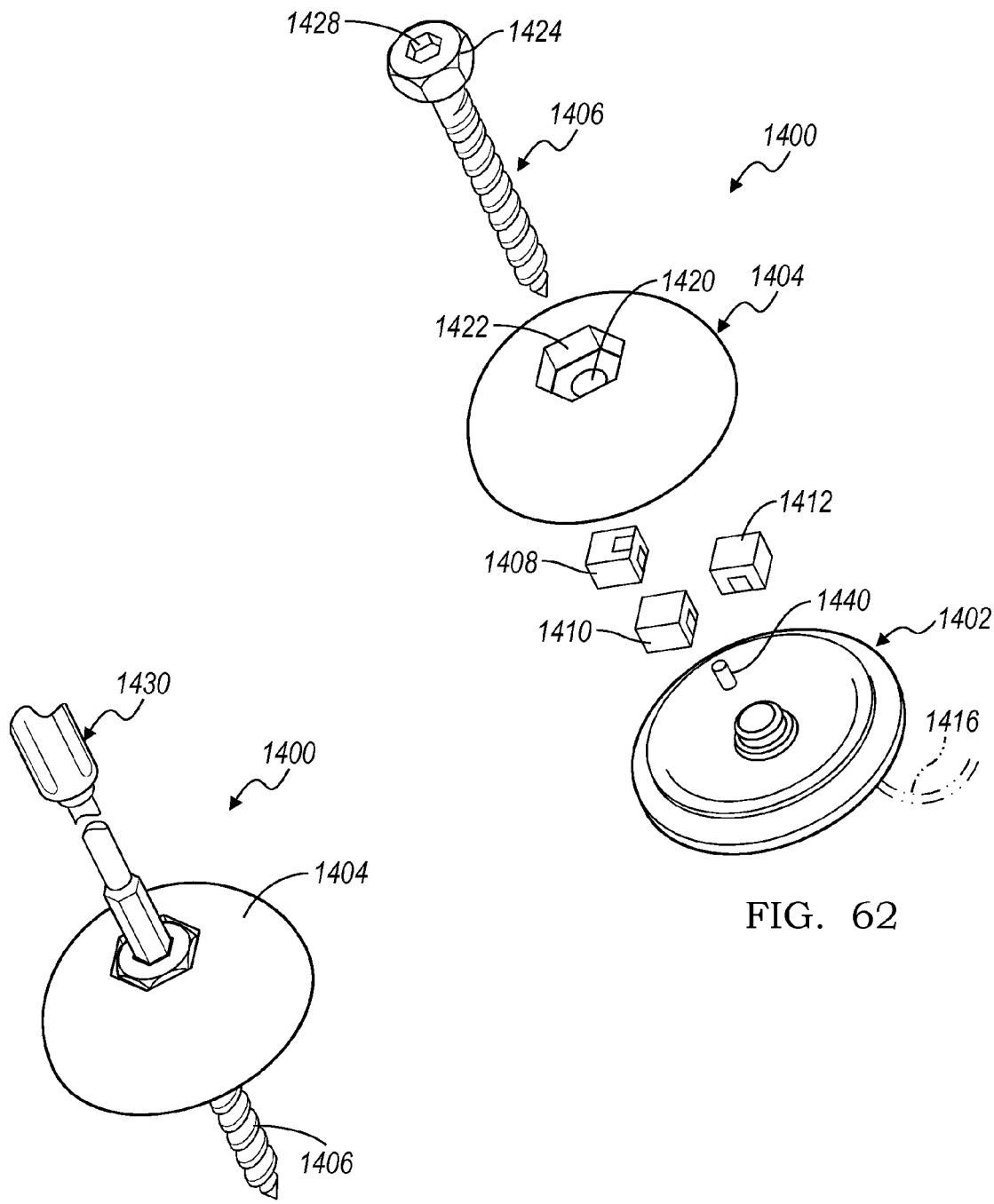
FIG. 62 is a top perspective exploded view of a DRF according to various embodiments.
FIG. 63 is an assembly view of a DRF and a tool according to various embodiments.

With reference to FIG. 43 a tracking sensor assembly 1080 is illustrated. The assembly 1080 can include a sensor cap 1082 that includes tracking sensors that can be wired with the wire 1084 or wireless, such as those discussed above according to various embodiments. The sensor cap 1082 can be connected to a connector 1086. The connector can include a threaded body 1088 that can be threaded into bone or any other appropriate portion. The connector 1086 can, therefore, connect the cap 1082 and the sensor (not illustrated) included therein to a selected portion.

The connector 1086 can further include a cap connector portion 1089 that extends from the body. The cap connector 1089 can be similar to the connector 1064 described above. The cap connector can include a cap fixing portion 1090 that is able to engage and hold a complimentary portion of the cap 1082, such as that discussed above according to various embodiments. This connection can be a snap connection such that no additional tools are necessary for the connection to be made. Further an anti-rotation portion 1092 can be provided. The anti-rotation portion 1092 can also engage a complimentary portion in the cap 1082. As discussed above the anti-rotation portion 1092 can be the depression or any other appropriate mechanism or geometry.

Further, it will be understood that the various portions of the tracking sensors according to various embodiments can be formed of selected materials, such as non-magnetic materials including various synthetic materials or non-magnetic alloys. Further the cap or body portions, which can also be referred to as sensor body portions according to various embodiments, can be formed in a manner such that they are single use sensors and are destroyed upon removal from the connecting portions. Moreover, as described above, the snap connections can ease the use of the devices and increase operative efficiency.

This can also allow for of interchangeability. The same sensor body can be moved from instrument to instrument in a selected procedure or from base to base. For example, a sensor body can first be used as a DRF in a selected location on the patient 14 and then moved to a second location. For example, the DRF 50 can be moved from a femur to a pelvis, one vertebrae to another, or from the anatomy to an instrument, etc. The DRF 50, or appropriate sensors, can also be attached to any portion that can move relative to another. For example, fractured portions of bone can be tracked relative to one another for repairing the bone or placing an implant relative to one another. Also, the sensor body can be moved from a DRF location to an instrument or vice versa. This can decrease cost, inventory, and the number of items in an operating theatre.

Also, in the surgical navigation system, such as the surgical navigation system 10 illustrated in FIG. 1, the dynamic reference frame 50 can be used to maintain a registration between the patient space and the image space. That is, the dynamic reference frame 50 can be used to insure that the displayed image or coordinates of the patient and the instruments and the relative positions between the two, in image space, are in fact, substantially similar to what is actually occurring between the real instruments and the actual patient, in patient space.

Not only can a registration be formed and maintained between image space and patient space, it can also be formed between the image space and a coordinate system. Alternatively, or in addition thereto, a registration may also be between the coordinate of the patient and a coordinate system. For example, an instrument can be tracked relative to a coordinate system and illustrated on a display, such as the display 34. The coordinate system can simply be a system that shows a representation of a position of the instrument relative to a position of the dynamic reference frame 50, or any appropriate reference frame. Therefore, the instrument can be tracked only to a coordinate system, such as an XYZ coordinate system, rather than to a specific image. This can be used for efficiency, positioning of elements in space, and the like. Further, the instrument or the dynamic reference frame 50 can be used to track or localize morphed atlas models, atlas models, to an imageless system, such as one including a coordinate system, or any appropriate system. Therefore, it will be understood that the registration and localization can be done between the patient space and any appropriate system such as an image, an imaging system, a coordinate system, an atlas model, or the like.

Nevertheless, the dynamic reference frame 50 can be designed according to a selected configuration, geometry, and other considerations for achieving a selected result. Including the various embodiments discussed above and herein. For example, the size and geometry of the dynamic reference frame can be selected to allow for a percutaneous or subcutaneous positioning of tissue over the dynamic reference frame, as discussed briefly above. Various design aspects can also be selected for partial placement through a skin while a portion of the DRF extends above the skin. Nevertheless, the dynamic reference frame can be provided according to various embodiments, including those described further herein. It will be understood, that although reference can be made to a dynamic reference frame (DRF) herein, that the DRF can also be used for any appropriate tracking portion to track any appropriate member, or any portion thereof.

With reference to FIGS. 44-48, a tracking sensor assembly 1100 is illustrated. The tracking sensor assembly 1100 can be used for any appropriate purpose, such as a dynamic reference frame that is selectively interconnected with a portion of an anatomy, such as a portion of the patient 14. The tracking sensor assembly 1100 or DRF 1100 generally includes a tracking sensor or coil holding board 1102, a housing assembly, including a housing lid or upper portion 1104, and a housing base or lower portion 1106 that is able to surround and hold the board 1102 in a selected position. The housing 1104,1106 can be interconnected with a sleeve 1108 and an anchor or holding member, such as a bone screw 1110, can be used to hold the housing 1104, 1106 and the sleeve 1108 relative to the patient 14, when positioned relative thereto. The anchor can also be any appropriate anchor or attachment member, such as, but not limited to, a staple, a rivet, a pin, barb, screw, clamp, crimping onto the bone, combinations thereof, etc.

The dynamic reference frame 1100 can include any appropriate dimensions. For example, from a distal end of the screw to a top of the housing 1104, when assembled, the DRF 1100 can have a dimension 1112. The dimension 1112 can be any appropriate size, such as about 10 mm to about 100 mm. Further, the sleeve 1108 can extend from a first end and the assembly 1100 can terminate at a top of the housing 1104 and have a dimension of 1114. The dimension 1114 can be any appropriate dimension, such as about 1 mm to about 50 mm.

The sleeve 1108, at a distal end thereof, can include a plurality of attachment portions 1116. The attachment portions 1116 can be any appropriate portion such as a tooth, plurality of teeth, thread turn or partial turn, an anchor (e.g. the anchors discussed herein), or the like. It will be understood, however, that the attachment portion 1116 can be any appropriate attachment or engagement portion according to various embodiments. The projections 1116 can extend from a second end 1118 of the sleeve 1108, while a first end 1120 of the sleeve 1108 can be near an exterior of the anatomy of the patient 14 when positioned relative to the patient 14. The teeth 1116, or any appropriate projection, can engage a portion of the anatomy, such as a bony portion of the patient 14 to assist in holding the dynamic reference frame 1100 in a selected position. For example, the projections can be used to prevent rotation of the sensor 1100, as well as to hold and secure the sensor in the X, Y, and Z as well as pitch, yaw, and roll (i.e. six degrees of freedom). Therefore, the dimension 1114 can be the dimension that is substantially equivalent to the distance between the first end 1118 and a second end 1120 of the sleeve 1108.

The housing including the lower portion 1106 and the upper portion 1104 can surround the board 1102. The board 1102 can include a plurality of coils, such as inductor portions, conductive portions, or the like. It will be understood that the coils discussed according to various embodiments can be inductive, conductive, combinations thereof or any appropriate coil type. Further the coils can be distinct cold, surface mount coils, or formed in any appropriate manner according to various embodiments.

The coils can, however, include three coils 1122, 1124, and 1126. Each of the coils 1122, 1124, 1126, can be positioned on the board 1102 substantially orthogonal to one another or at any appropriate angle relative to one another. The various angles of the sensor coils 1122, 1124, 1126 can be used in various navigation systems to determine a precise location of the DRF 1100. It will be understood that the board 1102 can also include a battery 1128, so that the board 1102 is self-powered. Alternatively, or in addition thereto, a power signal can be sent to a component in the board 1102 to provide power to the DRF 1100. For example an LC tank circuit can be provided or any circuit that can be charged and discharged on the board. It will be understood, however, that according to various embodiments the DRF, such as the DRF 1100, can be wireless. Further, the various portions of the board 1102 can be substantially hard-wired for both power and a transmission of a signal from or to the DRF 1100. The wire 1130 can be interconnected with the surgical navigation system, somewhere to the DRF 54 (FIG. 1).

Although the three coils 1122, 1124, 1126 are illustrated it will be understood that any appropriate number or sets of coils can be used, according to various embodiments described herein, and discussion of coils herein is not limited to a single coil at any location. For example, the DRF can include three sets of two coils, or any appropriate number. Having three coils is not a requirement or a limitation. Also, the coils or sets of coils can be provided at any appropriate angle relative to one another. For example, the coils can be set at about 60 degrees to one another or in any appropriate triangle.

Also, the coils could be any appropriate type of sensor. For example, the coils can also be positioned near a flux gate or the flux gate can be positioned with the coils. Thus, either an AC or DC source can be used to drive the sensor portions, such as the coils or flux gate sensors. It will be understood that the various types of coils, the orientation thereof, the groupings thereof, and the like, can be used in various embodiments described herein. Therefore, reference to the coils herein will also be understood to relate to the various types of coils and orientations thereof described above.

The DRF 1100, according to various embodiments, including those described herein, can be completely or partially reusable or disposable. For example the anchor can be formed of a material that can be cleaned and/or sterilized for use on multiple different patients. While the housing or body can be formed of a material that is made for a single use and is disposed after the single use.

The board 1102 can be positioned within the housing defined by the upper portion 1104 and a lower portion 1106 in any appropriate manner. For example, the board 1102 can include one or more positioning points, such as an aperture or bore 1132*a*, 1132*b* and 1132*c*. A member of either or both of the housing portions 1104, 1106 can engage the apertures 1132*a*-1132*c* in the board 1102. For example, a projection or a plurality of projections 1134*a*, 1134*b*, and 1134*c* can project from the lower housing 1106. The projections 1134a-1134c can engage the apertures 1132a-1132c to hold the board 1102 in a fixed position relative to the lower housing portion 1106 and the upper housing portion 1104 to enable precise tracking.

The upper and lower housing portions 1104, 1106 can be interconnected in any appropriate manner. For example, a snap fit or friction fit can be formed by engaging a projection on one of the portions into a recess of the other portion. Further, or alternatively thereto, the housing portions may define complimentary threads. Nevertheless, the upper housing portion 1104 can be positioned relative to the lower housing portion 1106 to be fixed thereto.

Further, either or both of the housing portions can define a plurality of splines 1136 that can engage a plurality of splines 1138 defined by the sleeve 1108. The splines 1138 on the sleeve 1108 can engage the splines 1136 on the lower housing portion 1106 to substantially eliminate or resist rotation of the lower housing portion 1106 relative to the sleeve 1108. This can help insure that the board 1102 also does not rotate relative to the sleeve 1108 and, as discussed briefly above, and described further herein, this can help insure that the board 1102 does not rotate relative to the patient 14 due to the positioning of the screw 1110 through the housing and the sleeve 1108 and the projections 1116, which can engage the anatomy.

The upper housing portion 1104 can define a bore 1140 through which the screw 1110 can pass. When assembled, the bone screw 1110 can pass through the bore 1140 defined by the housing, a bore 1142 defined by the board 1102, a bore 1144 defined by the lower housing, and a bore 1146 defined by the sleeve 1108. It will be understood that each of the bores can cause the respective portions to define a cannula or that the bore is throughbore.

As illustrated in the various drawings, particularly when the screw is positioned and the housing is assembled, the screw 1110 can include an upper washer or abutment portion 1148 that can engage an internal bearing surface 1150 of the sleeve 1108. This can provide a force onto the sleeve 1108 that can help push or force the projections 1116 into the anatomy. Also, as discussed herein, the screw 1110 can include various other portions or be interconnected with other members to assist in holding it relative to the patient 14 and resist movement once it has been positioned relative to the patient 14.

The DRF 1100 can be positioned relative to the patient 14 in any appropriate manner. For example, a tool 1152 can be interconnected with a screw head 1154 of the screw 1110. The tool 1152 can engage the screw head 1154 in any appropriate manner, such as with attracting magnets, a friction fit, an interference fit, or the like. Examples of interference fit screws and tools include the TiMesh™ system sold by Medtronic, Inc. This can allow the screw 1110 to be driven into the patient 14 with a substantially single hand of a user, such as the physician 614. This can also allow a first user to assemble the tool 1152 and the screw 1110 and pass it to a second user, such as the physician 614. Such an assembly or assemblance of the portions can be used for various portions, such as passing it from a non-sterile to sterile field, between sterile fields, from a sterilization system to a sterile field, or the like.

The tool 1152 can engage the screw 1110 once it has passed through the housing 1104, 1106 and the sleeve 1108. The entire assembly can then be positioned relative to the patient 14 to drive the DRF 1100 into the patient 14. According to various embodiments, however, the screw 1110 alone can be engaged by the tool 1152 for insertion or it can be inserted through the sleeve 1108 positioned on a portion of the screw 1110 during the insertion.

The DRF 1100 can be positioned into the patient 14 in any appropriate manner. For example, with particular reference to FIG. 48, an incision 1160 can be formed in the patient 14. The incision 1160 can be formed relative to any appropriate portion of the anatomy, such as the pelvis, a femoral head, a tibia, or any other appropriate portion. A passing tube or cannula 1162 can be positioned through the incision 1160 in any appropriate manner, such is known to one skilled in the art. Further, the incision 1160 can include a stab wound formed by the passing cannula 1160 with a trocar (not illustrated) or any other appropriate portion. Regardless, the passing tube or cannula 1162 can allow the DRF 1110 to be passed through the soft tissue of the patient 14 without substantially engaging or touching the soft tissue of the patient 14. For example, the passing cannula 1162 may allow for positioning of the DRF 1100 and performing a procedure without requiring suturing the incision 1160. Further, the tool 1152 that can be interconnected with the screw head 1154 can ease the insertion of the DRF 1100 by allowing a substantially single handed implantation of the DRF 1100 into the patient 14. The tool 1152 can also, or alternatively, be interconnected with any portion of the DRF 1100 for a substantially single handed positioning thereof.

As discussed above, driving the DRF 1100 into the patient 14 with the screw 1110 can assist in driving the projections 1116 into the patient to assist in reducing rotation of the housing 1104, 1106. Further, or alternatively, or in addition thereto, the screw 1110 can define a cannula or through-bore and a wire, such as K-wire, can be passed through the cannula defined by the screw 1110. The wire 1170 can exit the screw 1110 in any appropriate position to assist in reducing rotation of the screw 1110 or any portion of the DRF 1100. The wire 1170 can be keyed relative to the cannula defined by the screw 1110, such as including a substantially non-circular external circumference. For example, the wire 1170 can be square, octagon, oblong, or the like to substantially assist in reducing or resisting rotation of the screw 1110. The wire 1170 can also be used to assist in positioning the DRF 1100 relative to the patient 14, similar to a generally known guide wire, but can also exit the screw or define a barb 1172 that can further engage the anatomy, such as a bony portion to assist in reducing rotation of the screw 1110.

Further the sleeve 1108 can define a thread at a distal end thereof, such as a partial turn of a thread 1174 to further assist in engaging the bone portion. For example, the turn of thread 1174 can engage the bone during a final rotation or tightening of the screw 1110 into the anatomy of the patient 14. Thus, the thread 1174 can engage the sleeve 1108 substantially into the bone to assist in reducing rotation of the DRF 1100.

During insertion of the DRF 1100, it will be understood that various protective or covering portions can be provided. For example, with reference to FIG. 48, a protective sleeve or covering 1170 can be provided to cover a portion of the screw 1110. The covering 1170 can be any appropriate covering, such as a polymer coating, a foil, or the like. The covering 1170 can cover a portion of the screw 1110, such as a distal end of the screw which may be sharp. The covering 1170 can assist in protecting various soft tissues of the patient 14, such as skin, muscle, and the like. The covering 1170 can work in cooperation with the cannula 1162 or can be provided when the cannula 1162 is not used. The covering 1170 can be deformable, destructable or the like. For example the covering 1170 can be punctured by the screw 1110 when it is engaged near a hard surface, such as a bone of the patient 14. As the screw 1110 is driven into the patient 14, the screw 1110 can push through the covering 1170 to engage the bone.

Further, a covering or plug can 1172 can be provided near a portion of the sleeve 1108. The plug or protective portion 1172 can be positioned near an end of the sleeve 1108 while the screw 1110 is positioned more proximally rather than through the sleeve 1108. The DRF 1100 can then be positioned relative to the patient 14, similar to that illustrated in FIG. 45B. However, as the sleeve 1108 engages the bone, the screw 1110 can push through the plug 1172 to engage the bone to assist in holding or fixing the DRF 1100 relative to the bone. Therefore, the plug 1172 can assist in protecting various portions of the patient 14, such as the skin, the muscle, and other soft tissues from portions of the screw 1110 that may be sharp. The plug 1172 can be used with or separate from the cannula 1162 for various purposes. It will be understood that various other protective portions can be provided, such as having the plug 1172 extend over the projections 1116. Therefore, the various portions of the DRF 1100 that can be sharp can be covered during positioning of the DR 1100 relative to the patient 14 until the DRF 1100 engages a hard part of the patient, such as a bone.

It will be understood that various portions of the DRF 1100 can be formed of different materials. It may be selected that the various portions of the DRF 1100 are formed of non-ferrous or non-magnetic materials to assist in resolution of the coils 1122, 1124, 1126. Nevertheless, the various portions of the DRF 1100 can be formed of biologically acceptable metals or metal alloys or polymers. For example, the housing 1104, 1106 can be formed of polymer materials, so that they are easy to form, can be flexible, if selected, or other selected considerations. For example, the housing portions 1104, 1106 can be injection molded in any selected shape, size, design or the like. Nevertheless, the substantially radiused edges of the housing 1104, 1106 can be provided for various reasons, such as aesthetic considerations, reduced friction or engagement of the soft tissue during or after implantation, reduced engagement of the various tools or surgical instruments, or the like. The substantially uniform and radiused geometry can assist in reducing friction or engagement between the housing 1104, 1106 and the soft tissue, the instruments, or the like to assist in reducing rotation of the DRF 1100. Further, the aesthetic appeal of the design and the tactile smoothness can also be considerations.

Nevertheless, various portions, such as the screw 1110 can be formed, either completely or partially, of bioabsorbable or resorbable materials. Also, the screw 1110 can include a coating or other portion than can allow for a delivery of a biological active agent, such as a pharmaceutical. For example, during positioning of the DRF 1100 relative to the patient 14, the DRF 1100 can be fixed relative to the patient 14. For a removal of the DRF 1100, however, it can be selected to allow a selected portion of the DRF 1100 to remain in the patient to be resorbed. For example, the retaining washer or abutment washer portion 1148 can be formed to break away at a selected stress, such that the sleeve 1108 and the housing 1104, 1106 can simply be pulled off of or pulled away from the patient 14 so that the abutment washer 1148 breaks away and the housing 1104, 1106 and the sleeve 1108 can simply be pulled away from the patient 14. If the screw 1110 is formed of a resorbable material, it will resorb over a selected period of time and will not cause any discomfort or ill effects to the patient 14. It will be understood, however, that various other attachment portions may also be used to affix the DRF 1100 to the patient 14 and they may also be formed of bioabsorbable or resorbable materials. For example, surgical staples, spikes, or the like can be used to affix the DRF 1100 to the patient 14.

The sleeve 1108, including the projections 1116 can be positioned relative to a portion of the patient 14, while allowing for a substantially minimal amount or no amount of preparation of the portion of the anatomy. For example, the sleeve 1108 includes geometry or construction and the projections 1116 that allow the sleeve 1108 to engage a substantially unprepared portion of bone. The sleeve 1108 can easily and efficiently be positioned relative to a bony portion and driven in with a selected amount of force to cause the projections 1116 to engage the bone of the patient 14, regardless of the underlying geometry of the bone of the patient 14. Therefore, the bone of the patient 14 need not necessarily be prepared, such as by flattening a bone portion, for engagement by the sleeve 1108. It will be understood that the various users may select that the bone be prepared or a selected amount of preparation may be selected for various procedures, (e.g. forming a flat surface on the bone) but the sleeve 1108 need not necessarily be used with a prepared bone surface.

Further, as discussed above, the board 1102 can provide or include a selected number of sensor coils. Nevertheless, various other portions of the DRF 1100 can also define or include a plurality of coils. For example, a coil 1180 can be defined on the portion of the screw 1110, such as on a shank portion of the screw 1110. The coil 1180 can be provided in addition or supplementary to the coils 1122, 1124, 1126 on the board 1102. Alternatively, the coil 1180 defined on the screw 1110 can replace one or more of the coils on the board 1102.

The various portions of the DRF 1100 described above with reference to FIGS. 44-48 can be provided according to any of a plurality of various embodiments described below and above, such as the sensor 1020 illustrated in FIG. 41. Further, the various portions of the dynamic reference frame 1100 can be included in any of the various embodiments of the reference sensors, tracking sensors or the like, described herein, even if they are not specifically described with relation to various embodiments. The omission is not meant to limit the various embodiments, but simply for efficiency of the description and teachings included herein.

With reference to FIGS. 49-53, a sensor assembly 1200 is illustrated. The sensor assembly 1200 can be used for any appropriate purpose, such as a dynamic reference frame (DRF) for use with the patient 14. The dynamic reference frame 1200 can be used for any purpose, such as the dynamic reference frames described above according to various embodiments. The dynamic reference frame 1200, however, can include an attachment member, such as a bone screw 1202. The bone screw 1202 can include a distal threaded portion 1204, a proximal sensor body engagement portion 1206, and an anti-rotation collar 1208. The anti-rotation collar 1208 can engage a selected portion of a lower housing member 1210, as discussed further herein.

The lower housing portion 1210 can interconnect with an upper housing portion 1212 to hold a board 1214 in a selected position. The board 1214 can be similar to the board 1102 discussed above. The board 1214 can include one or more coils, such as inductor coils, electromagnetic coils, or the like. The coils 1216, 1218, and 1220, can be positioned relative to each other in any appropriate manner. For example, the coils can be formed around axes that are substantially orthogonal to one another. The board 1214 can also include a battery 1222 to power the board 1214.

Alternatively, or in addition thereto, the dynamic reference frame 1200 can be wired, such that it includes a hard-wire 1224 for various purposes, such as providing power, transmitting a signal, receiving a signal, or the like. Alternatively, or in addition thereto, a power signal can be provided to various components 1214 for operation of the DRF 1200.

The lower housing 1210 can include projections 1226, 1228 that can engage or project through bores 1230, 1232 defined by the board 1214. This can allow the board 1214 to be held relative to the lower housing portion 1210 to insure that the board 1214 does not move or has limited movement relative to the base 1210. The upper housing portion 1212 can engage the lower housing portion 1210 in any appropriate manner. For example, the upper housing portion 1212 and the lower housing portion 1210 can include mating or complimentary threads, a snap fit can be formed between the upper housing portion 1212 and the lower housing portion 1210, or any other appropriate interconnection can be used. The snap fit can include a groove formed in one of the two housing portions and a complimentary projection formed in the other for a mating engagement.

The lower housing portion 1210 can define a plurality of portions for interconnection with a portion of the screw 1212. For example, a female receiving port 1238 can be defined by the lower housing portion 1210 to engage the male connection portion 1206 of the screw 1202. The interconnection can be a snap fit, a threaded fit, or the like to allow for interconnection of the lower housing portion 1210 into the screw 1202.

The lower housing portion 1210 can also include an anti-rotation recess or female portion 1240. The anti-rotation recess 1240 can engage the anti-rotation collar 1208 of the screw 1202. The anti-rotation collar 1208 of the screw 1202 can include any appropriate geometry that can mate with the geometry of the anti-rotation recess 1240 to resist rotation of the lower housing portion 1210 relative to the screw 1202. For example, as illustrated, the anti-rotation collar 1208 can be substantially triangular. The anti-rotation collar 1208 can then engage a portion of the recess 1240, such as a depression 1242. It will be understood that a plurality of the portions of the anti-rotation collar 1208 can engage a plurality of the depressions 1242 defined by the anti-rotation recess 1240.

As discussed above, the various portions of the DRF 1200 can be formed of selected materials. For example, the lower housing portion 1210 and the upper housing portion 1212 can be formed of a polymer material or any other appropriate material. This may allow the housing 1212, 1210 to be deformable for various purposes. Further, the screw 1202 can be formed of various metals or metal alloys for interconnection with a selected portion of the patient 14. Alternatively, the screw 1202 can include various polymer materials that can resorb over a period of time. Thus, the screw 1202 can be left in the anatomy without causing adverse reaction within the anatomy of the patient 14, due to the fact that it is able to resorb over time.

The DRF 1200 can also include any appropriate dimensions. For example, the screw 1202 can include a dimension 1250 that allows for interconnection of the screw 1202 into a selected portion of the anatomy. However, the housing 1210, 1212 can include a dimension 1252. The dimension 1252 can be any appropriate dimension that allows for positioning of the DRF 1200 relative to a selected portion of the anatomy. The DRF, according to various embodiments, therefore, can be low profile to allow soft tissue to pass over the DRF.

It will be understood that a lower portion of the housing 1211 can engage a selected portion of the anatomy, such as the surface of a bone. Therefore, the dimension 1250 of the screw 1202 can be substantially buried in a portion of the anatomy, such as a bone, while the bottom 1211 of the lower housing portion 1210 contacts the bone surface. Therefore, the dimension 1252 of the housing 1210, 1212 can be any appropriate dimension that is selected to extend beyond a surface of the bone. For example, the dimension 1252 can be about 1 mm to about 50 mm. The dimension 1252 can be selected for various purposes, such as for subcutaneous movement, percutaneous positioning, or the like.

Further, it will be understood that various portions of the housing 1210, 1212 can be substantially rounded or radiused for various purposes. For example, the radiused edges can help minimize tissue disturbance during positioning of the DRF 1200, movement of the DRF 1200 relative to soft tissue during a movement of the anatomy, or any other appropriate reason. Further, a top 1213 of the upper housing portion 1212 can include a selected radius for minimization of contact or disturbance of the soft tissue or contact with various surgical instruments.

It can be selected that the dimensions and geometry of the housing 1212, 1210 can be selected for movement about soft tissue. For example, the DRF 1200 can be positioned below soft tissue and relative to a bone portion. Then, when the bone is moved the DRF 1200 can move relative to the soft tissue without substantially damaging the soft tissue, hindering movement of the bone portion relative to the soft tissue, or the like.

Although discussed in detail above, the DRF 1200 can include features substantially similar to the DRF 1100 discussed above. For example, the screw 1202 can be cannulated, as can the portion of the housing 1210, 1212 for positioning of a guide wire or wire therethrough. As discussed above, the wire can include a portion that is keyed relative to the screw 1202 and/or the housing 1210, 1212 to resist rotation relative thereto and can include a barb to engage the anatomy.

Further, the DRF 1200 can be passed through an incision 1260 in the patient 14. However, the DRF 1200 can be implanted in any appropriate manner. For example, a tool can interconnect with any portion of the screw 1202, such as the anti-rotation collar 1208 and the housing can engage portion 1206 to pass the screw 1202 through a cannula 1262 that can be positioned through the incision 1260. The tool can engage the housing engagement portion 1206 substantially similar to the housing 1210. Therefore, the screw 1206 can be efficiently held relative to a tool for manipulating the screw 1202.

The screw 1202 can be inserted into the anatomy, such as a bone portion, to any appropriate depth. Once the screw 1202 is inserted a selected length, such as by twisting the screw 1202, the tool can be disengaged by removing it from the engagement portion 1206, due to the resistance by the threads engaging the bone. It is optional to position relative to the anti-rotation flange a protective washer or sleeve 1270. The protective washer or sleeve can be formed of any appropriate material, such as a bioresorbable or resorbable material. The tissue protective washer 1270 can assist in reducing interaction between the various portions of the screw, such as the anti-rotation flange 1208, and the soft tissue of the patient 14. This can assist in minimizing the trauma during a surgical procedure.

The housing 1210, 1212, that can be pre-assembled or assembled during its positioning relative the screw 1202 can also be passed through the cannula 1262 to engage the engaging portion 1206. Thus, it will be understood that the DRF 1200 can be implanted in any appropriate manner. It can allow for positioning of the screw 1202 relative to a selected portion of the anatomy and then engaging the engagement portion 1206 with the housing 1210. As discussed above, the various portions can resist rotation of the housing 1210 and the board 1214 relative thereto, due to the interconnection therewith. Therefore, the housing 1210, 1212 can be held in a relative orientation to the screw 1202.

It will be understood that the various features described above and herein can be applied to the DRF 1200 even though not specifically described. Further, the DRF 1200 can be positioned relative to any appropriate portion of the anatomy, such as a femur (e.g. greater trochanter), a pelvis (e.g. the iliac crest), the tibia, the humerus, or the like. It will be understood that the DRF 1200 can be positioned relative to any appropriate portion of the anatomy for use of the DRF 1200.

With reference to FIGS. 54-58, a sensor assembly 1300 is illustrated. The sensor assembly 1300 can be used for any appropriate purpose, such as a DRF, similar to the DRF 54. The dynamic reference frame 1300 can include any appropriate portions, such as an anchor portion, which can include a screw 1302. A lower housing portion 1304 and an upper housing portion 1306 can surround and enclose a board 1308. The housing portions 1304, 1306 can be positioned through or into a sleeve 1310.

The sleeve 1310 can include a lower portion 1312 and a projection 1314 that extends from the lower portion 1312. The projection 1314 can be similar to the projection 1116 described above. The projection 1314 can engage a selected portion of the anatomy, such as a bony portion for resisting rotation of the sleeve 1310 relative to the anatomy.

The screw 1302 can include a lower portion defining a thread 1316. According to various embodiments, the screw 1302 can be completely or partially resorbable or formed of any appropriate material. An upper portion can include a tool engaging portion 1318 and a washer or flange 1320. During insertion of the screw 1302 through the sleeve 1310, the flange 1320 can engage the sleeve 1310 in any appropriate manner to allow for a force to be transferred from the screw 1302 to the sleeve 1310. Further, the flange 1320 can act as a lock washer to resist rotation between the sleeve 1310 and the screw 1302 during and after positioning of the screw 1302 through the sleeve 1310.

Further, the sleeve 1310 can be formed as a single member with the screw 1302. Also, the screw 1302 can be any appropriate anchor portion (e.g. a staple, a pin, a wire, a rivet, etc.), which allows for anchoring the sleeve or the DRF 1300 relative to a selected portion of the anatomy. Nevertheless, the screw 1302 and the sleeve 1310 can be formed as a single member for efficiency or positioning of the DRF 1300 relative to the patient 14 or for other appropriate purposes.

The board 1308 can include a portion similar to the board 1214 or other boards described herein. For example, the board 1308 can include a sensing coil or a plurality of sensing coils 1324, 1326 and 1328. The coils can be formed in any appropriate manner and can be formed substantially orthogonally to one another or define axes that are orthogonal to one another. The sensing coils can be electromagnetic coils or induction coils. Further, a battery 1330 can be included for powering the board 1308. Alternatively, or in addition thereto, a wire 1332 can be provided to provide power, transfer a signal or the like between the board 1308 and other portions of the assembly. Further, as discussed above, a power signal can be provided to the board 1308.

The board 1308 can be positioned within the lower housing portion 1304 in any appropriate manner. For example, the lower housing portion can define a first track or passage 1334 and a second track or passage 1336 into which the board 1308 can be positioned. The board 1308 can be positioned between the two tracks 1334, 1336 to assist in holding the board 1308 relative to the lower housing portion 1304. The two tracks 1334, 1336 can assist in holding the board 1308 in a selected position within the lower housing position 1304.

The lower housing portion can also define a connection portion, which allows it to interconnect with the upper housing portion 1306. For example, complimentary threads can be defined on the lower housing portion 1304 and the upper housing portion 1306, a snap interconnection can be formed between the two, or any other appropriate interconnection can be formed, including those discussed herein according to various embodiments.

The lower housing portion 1304 can also define an engagement region 1340, which can engage an engagement region 1342 of the sleeve 1310. The lower housing portion 1304 can snap into the sleeve 1310, include a complimentary thread, or any other appropriate connection portion, such as an adhesive. Further, the lower housing portion can define a projection 1344 that can interconnect or interact with a passage or recess 1346 defined in the sleeve 1310. The interconnection of the projection 1344 of the lower housing portion 1304 and the recess 1346 of the sleeve 1310 can assist in reducing or resisting rotation between the lower housing portion 1304 and the sleeve 1310 and also the board 1308 relative to other portions of the DRF 1300.

The DRF 1300 can include appropriate dimensions, such as those discussed above. Nevertheless, the lower portion 1312 is generally able to connect or touch a selected portion of the anatomy, such as a surface of the bone. Therefore, a top 1307 of the DRF 1300 can extend the dimension 1350. The dimension 1350 can be any appropriate dimension, such as the dimensions described above, or those understood by one skilled in the art. Further, it will be understood that the various portions of the DRF 1300 can include any appropriate geometries. For example, many of the portions of the DRF 1300 can be provided with substantially radiused edges to reduce interference contact with the soft tissue. Also, the dimension 1350 can be used to position the selected portion of the DRF 1300 at a selected position relative to the patient 14.

The DRF 1300 can be positioned relative to the patient 14 in a manner similar to those methods described herein. For example, a cannula 1354 can be used to pass each of the portions of the DRF 1300 through an incision 1356 formed in the patient 14. It will be understood, however, that the sleeve 1310 and the screw 1302 can be first positioned relative to a portion of the patient 14.

As discussed above, the screw 1302, or any other appropriate anchor portion, and the sleeve 1310 can be formed as a single member for efficiency of positioning relative to the patient 14. Nevertheless, even as separate members, a tool can interconnect with a tool engaging portion 1318 of the screw 1302 to be positioned relative to the patient 14. As discussed above, a friction fit or other appropriate interconnection can allow for the screw 1302 to be held relative to the tool for manipulation of the screw 1302 with a single hand. Further, the sleeve 1310 can be positioned relative to the screw 1302 prior to positioning the screw in the patient 14. Therefore, the interconnection between the tool and the screw 1302 can allow for manipulation of the sleeve 1310 as well.

Nevertheless, the screw 1302 can be inserted a selected depth into the patient 14 and can allow for connection or interaction of the projection 1314 with a selected portion of the anatomy, such as a surface of the bone. Nevertheless, the bone can be either prepared or unprepared in any appropriate manner for receipt of the DRF 1300. For example the bon surface can be flattened or left in a natural state.

Once the screw 1302 and the sleeve 1310 have been positioned, the housing assembly, including a lower housing portion 1304, the upper housing portion 1306, and the board 1308 can be fit into the sleeve 1310, such as with a snap fit, a friction fit, or other connection. This can allow the DRF 1300 to be positioned relative to the anatomy of the patient 14 in any appropriate manner and as a separate or plurality of portions, or as a less number of portions, such as if the sleeve 1310 and the screw 1302 are formed as a single member.

It will be understood that the portions described herein, such as the positioning techniques, the interconnection, or the like can be applied to the DRF 1300 even though not specifically described here. Nevertheless, one skilled in the art will understand that the DRF 1300 can be used with a plurality of instruments or positioning techniques.

With reference to FIGS. 59-69, a sensor assembly 1400 is illustrated. The sensor assembly 1400 can be a DRF 1400, for uses similar to the DRF 54. The DRF 1400 can include any appropriate portions, such as a lower housing portion or base 1402, an upper housing portion or top 1404, an anchor, such as a screw 1406, and a sensor or a plurality of sensor coils 1408, 1410, 1412. The coils 1408, 1410, 1412 can be positioned on the base 1402 or on the top 1404 in any appropriate manner. For example, the coils 1408-1412 can be positioned, such that they include axes that are substantially orthogonal to one another. Further, a battery or power cell 1414 can be included in the DRF 1400, to provide power to the sensors 1408-1412. Alternatively, or in addition thereto, the DRF 1400 can include a wire 1416, such that it is hard-wired to a selected portion of the navigation system. Further, the DRF 1400 can include or be used with a power signal that is operable to provide a power signal that is operable to provide power to the DRF 1400 for receiving a signal, sending a signal, and the like.

The housing top 1404 can engage the housing base 1402 in any appropriate manner. For example, a snap fit, a friction fit, or complimentary threads can be formed between the housing top 1404 and the housing base 1402. This can allow for the housing 1402, 1404 to be formed relative to the portions that are positioned within the housing 1402, 1404, such as the battery 1414 and the sensors 1408-1412.

The screw 1406 can pass through a bore 1418 defined by the lower housing portion and a bore 1420 defined by the upper housing portion 1404. The upper housing portion 1404 can further define a recess 1422 that can complement a portion of the screw 1406, such as a head 1424 of the screw. The complimentary geometry can include a key geometry, such that the upper housing portion 1404 resists rotation relative to the screw 1406. Because the housing lid 1404 engages the housing base 1402, the resisting of rotation between the screw 1406 and the housing lid 1404 can also resist rotation of the lower housing portion 1402.

Further, projecting from a portion of the lower housing portion 1402 can be a projection or a plurality of projections 1426. The projections 1426 can be bone engaging projections that engage or project into a selected portion of bone once the DRF 1400 is positioned in the patient 14. Therefore, the screw 1406 can be passed through the housing portions 1404, 1402 and provide a force to push the projections 1426 into a portion of the bone to allow for the resisting of rotation between the lower housing portion 1402 and the bone, which can also, because of the interconnection of the screw 1406 and the upper housing portion 1404, resist rotation of the entire DRF 1400.

The screw 1406 can include a tool engaging portion 1428. The tool engaging recess 1428 of the screw 1406 can allow a tool 1430 to engage the screw 1406. The tool 1430 can interact, such as with a friction interaction, with the tool engaging recess of the screw 1406 so that the DRF 1400 can be implanted with a single hand of a user, such as a physician.

As described above according to various embodiments, the DRF 1400 can be passed through an incision in any appropriate manner, such as with a cannula, tube, or the like. Further, due to the interconnection of the tool 1430 with the screw 1406, the DRF 1400 can be manipulated with a single hand. Alternatively, the DRF 1400, or DRF of any of the various embodiments can be manipulated and/or implanted with a robot arm or appendage. A friction fit can be formed between the recess 1422 and the upper housing portion 1404 in the head of the screw 1424 so that the entire DRF assembly 1400 is held together for manipulation with the tool 1430.

Further, as discussed above, the screw 1406 can be cannulated for use with a guide wire or a keyed wire to further resist rotation of the screw 1406, and therefore the DRF 1400, after implantation of the DRF 1400.

The DRF 1400 can include a selected dimension 1434. The dimension 1434 can extend from an upper portion 1405 of the housing top 1404 to a lower portion 1403 of the housing base 1402. The dimension 1434 can be any appropriate dimension, for example, about 1 mm to about 50 mm. The dimension 1434 can be any appropriate dimension that can be similar to the dimensions above or any other appropriate dimension. Nevertheless, the dimension 1434 can allow for positioning of the DRF 1400 relative to a selected portion of the anatomy, such as a pelvis, a femur, a vertebrae, humerus, tibia, or the like. Further, dimension 1434 can allow for minimal contact or interaction with soft tissue during positioning of the DRF 1400, movement of soft tissue relative to the DRF 1400, or any other appropriate reason. Further, the housing 1402, 1404 can include a selected geometry to allow for reduced interaction with the soft tissue, reduce interaction between the DRF 1400 and various instruments, and for other reasons.

With reference to FIGS. 64-68, a DRF 1500 is illustrated. The DRF 1500 can include a plurality of portions, such as an anchor member, which can be a screw 1502, an upper housing portion 1504, and a lower housing portion 1506 can be connected to form a housing member. The housing member can house a plurality of sensor coils, such as a sensor coil 1508, and sensing coil 1510, and a sensing coil 1512. Also, a battery 1514 can be provided to provide power to the DRF 1500, such as for receiving and transmitting a signal. Further, alternatively, or in addition to the battery 1514, a wire 1516 can be provided to transmit or receive a signal, provide power to the DRF 1500, or any other appropriate reasons. Further, as discussed above, a power signal can be provided to the DRF 1500.

The housing base 1506 can define one or a plurality of tooth bores 1520. The tooth bores 1520 can receive one or a plurality of teeth 1522. The teeth 1522 can engage a portion of the patient 14, similar to the projections as described according to various embodiments. The teeth 1522, however, can be formed as members separate from the base housing 1506. It will be understood that the teeth 1522 may also be formed as a single member with the lower housing 1506. Nevertheless, the teeth 1522 can be interconnected with the base housing 1506 through an appropriate connection in the bores 1520. For example, complimentary threads can be formed on the teeth 1522 and in the bores 1520, a friction fit (e.g. a taper), or other appropriate interconnections can be provided. Further, the teeth 1522 can be provided in different sizes and interconnected by a user during an operative procedure. Therefore, the size, the number, the geometry, and other considerations of the teeth 1522 can be selected by a user during an operative procedure.

The base 1506 can further define an anchor bore 1524 that can be aligned with an anchor bore 1526 defined by the upper housing 1504. The respective bores 1524, 1526 can be aligned when the upper housing 1504 is fit to the lower housing 1506. The housing 1504, 1506 can interconnect in any appropriate manner, such as with a friction fit, including a snap fit, a respective thread or the like. Further tabs and/or projections can be defined by either portion of the housing, 1504, 1506 and engage respective slots, or recesses, or the like in the other housing portion (i.e. a snap fit).

The anchor, including the screw 1502, can include a threaded region 1528 and a tool engaging head 1530. The tool engaging head 1530 can be used to engage the screw 1502 by a tool for positioning the DRF 1500 relative to the patient 14. The tool can frictionally engage the head 1530 in a manner that allows a user to manipulate the DRF 1500 with a single hand. Therefore, the DRF 1500 can be implanted with the tool 1532 in an efficient manner.

Further, the DRF 1500 can be positioned through a cannula, an incision, or the like relative to the patient, according to various embodiments, including those described herein. Further, the screw 1502 can be cannulated to allow for passing a wire, such as a keyed guide wire, through the screw 1502 to assist in positioning the DRF 1500 and reducing or resisting rotation of the screw 1502 within the patient 14 after implanting the DRF 1500 therein.

With reference to 65B, a protective element or member can include the spike 1522 initially provided substantially above a surface of the lower housing 1506. It will be understood that a biasing member, such as a spring, including a metal coil, a polymer coil, a rubber sleeve, or the like, can be provided to assist in biasing the spike 1522 within the housing assembly. Nevertheless, the spike 1522 can be provided so that substantially no selected portion of the spike 1522 extends below the lower housing 1506 to engage a portion, such as selected soft tissue portions, of the patient 14 until selected. For example, the screw 1502 can include a flange or collar 1560 that can engage the spike 1522 at a selected time. The flange 1560 can engage a top portion of the spike 1522 as the DRF 1500 is driven into the patient 14 as the lower housing 1506 abuts a selected portion of the patient 14, such as a bone thereof, the screw 1502 can be further driven into the patient 14 therefore allowing the flange 1560 to engage the spike 1522 and drive the spike 1522 into the patient. Therefore, the spike 1522 can be limited in its contact with selected portions of the patient 14 during positioning of the DRF 1500 relative to the patient 14. Because the spike 1522 is positioned substantially within the housing during the initial positioning of the DRF 1500 relative to the patient 14, the spike 1522 can be limited in its contact with other portions of the patient 14, such as selected soft tissues. Further, it will be understood that the various protective elements described herein can be used with any various embodiments of the DRF. Therefore, even if a particular protective element is not described with it, it can be understood that it can be used for the various embodiments.

Figure 64:
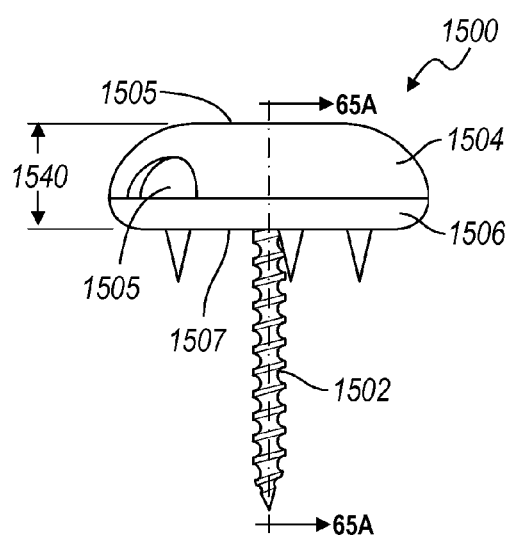
FIG. 64 is a side plan view of a DRF according to various embodiments.
Figure 65A:
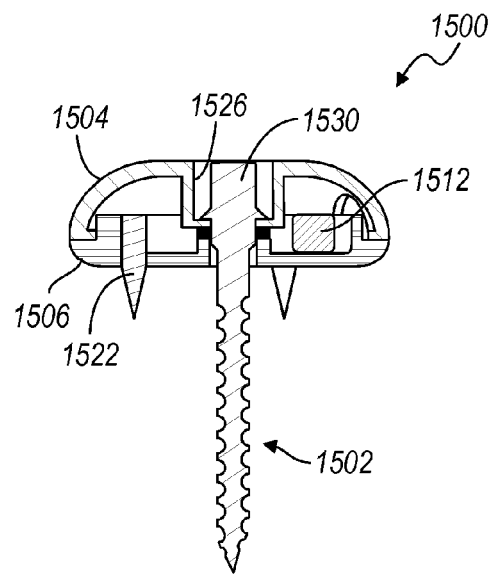
FIG. 65A is a cross-sectional view taken along line 65-65 of FIG. 64.
Figure 65B:
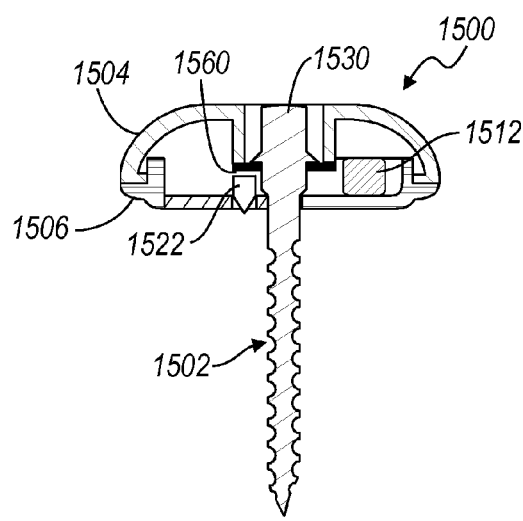
FIG. 65B is a cross-sectional view taken along line 65-65 of FIG. 64 including a protective element, according to various embodiments.
Figure 66:
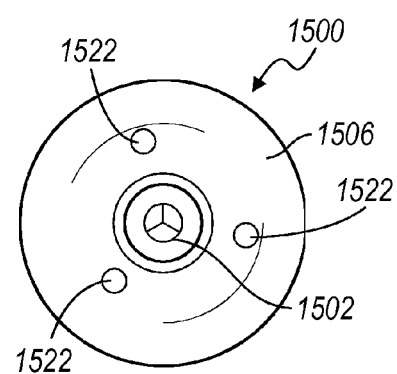
FIG. 66 is a bottom plan view of a DRF according to various embodiments.
Figures 67, 68:
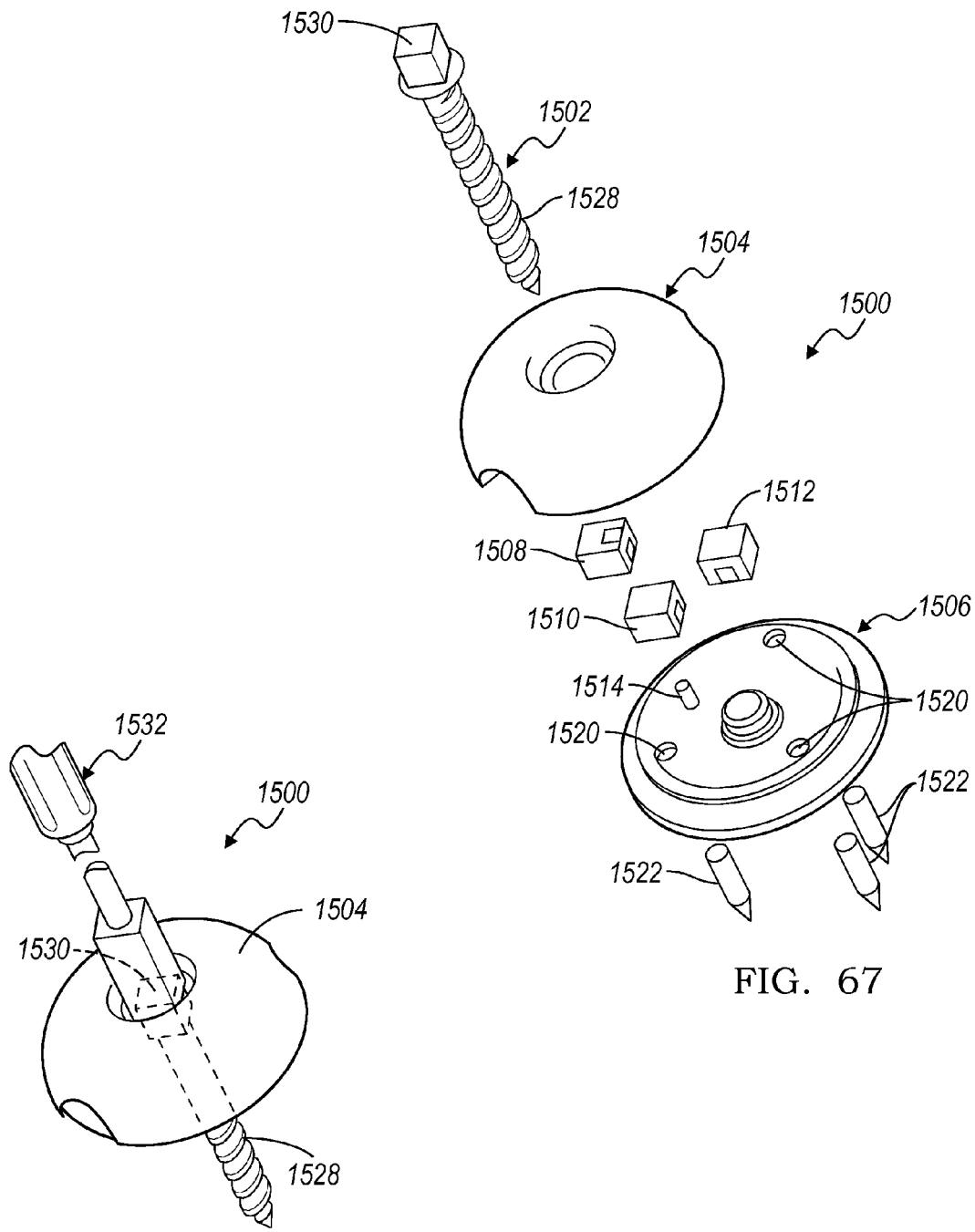
FIG. 67 is a top perspective exploded view of a DRF according to various embodiments.
FIG. 68 is an assembled view of a DRF and a tool according to various embodiments.
Figures 72, 73:
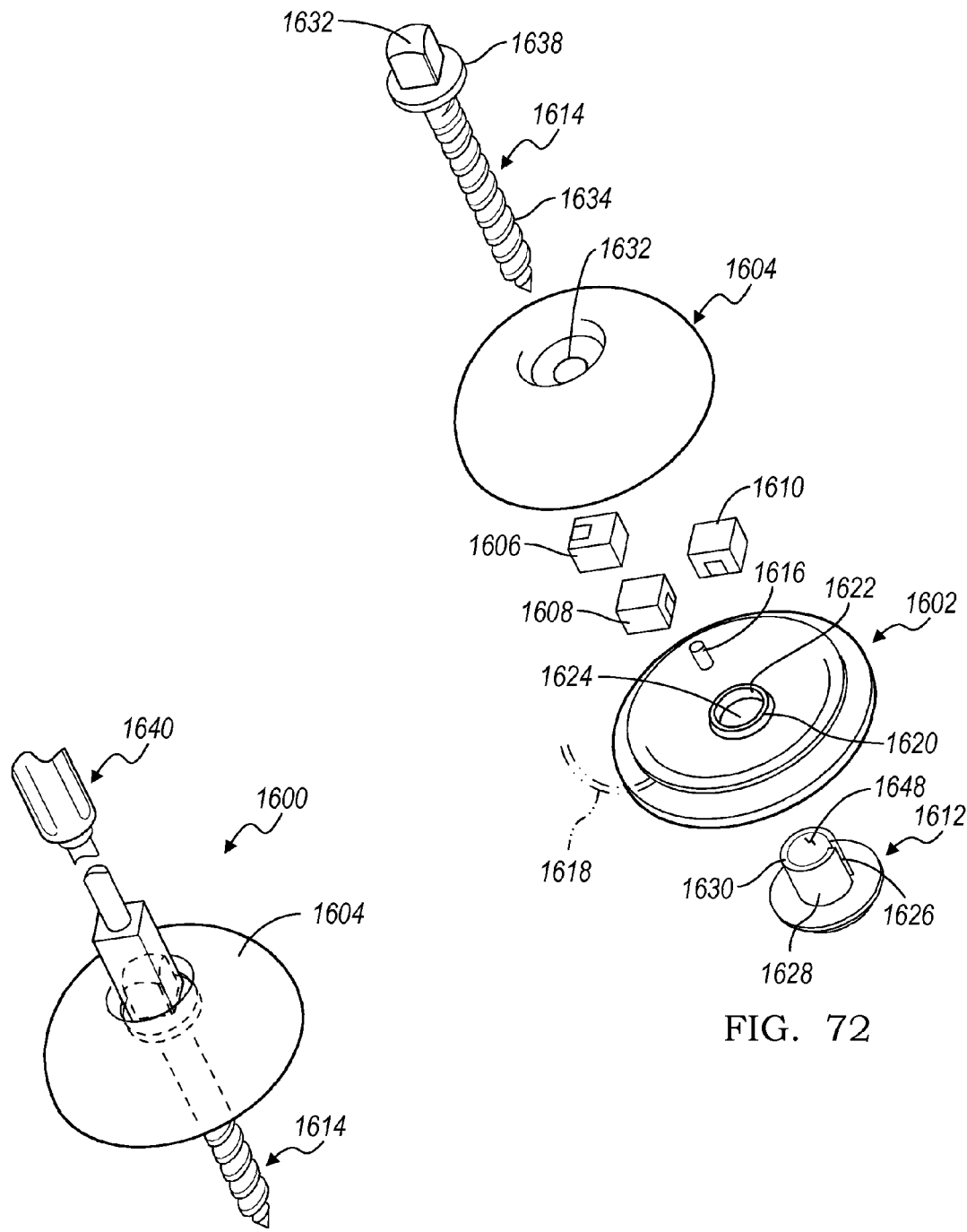
FIG. 72 is a top perspective exploded view of a DRF according to various embodiments.
FIG. 73 is an assembled view of a DRF and a tool according to various embodiments.
Figure 74:
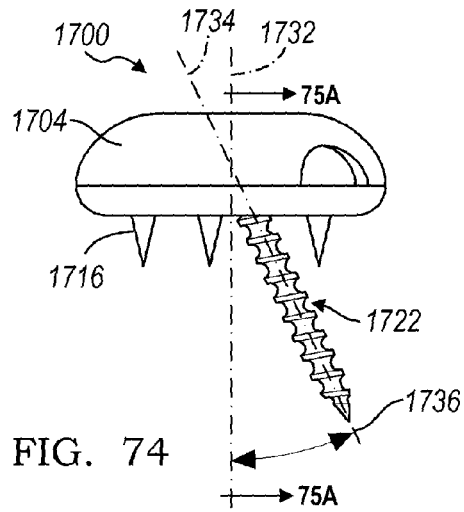
FIG. 74 is a side plan view of a DRF according to various embodiments.

According to various embodiments, such as exemplarily illustrated in FIG. 64, a positioning element 1505 can be provided with a DRF 1500, or any DRF according to various embodiments. The positioning element 1505 can be any appropriate portion, such as a depression defined by the housing, a projection defined by the housing, a surface structure defined by the housing, or the like. It will be understood that the positioning element 1505, according to various embodiments, can be formed integrally with the DRF, can be formed as a single member with a portion of the DRF, or in any appropriate manner. However, the positioning element 1505 can assist in positioning, such as implanting or removal, of the DRF. The positioning element 1505 can be engaged by selected tools, a hand of the user, or in any appropriate manner to assist in positioning the removal of the DRF 1500. Further, the positioning element 1505 can be used in concert with the tool that engages the head 1530 or in any other appropriate manner. It will be understood, however, that the positioning element can be used with any appropriate of the various embodiments and can be any appropriate portion to assist in implanting, removal, or the like of the DRF according to various embodiments.

The DRF 1500 can include any appropriate geometry, such as a substantially radiused or annular geometry. The radiused geometry can assist in reducing interaction with soft tissue, other instruments, or the like during a procedure. Therefore, rotation of the DRF 1500 can be further reduced by reducing contact or interaction of the DRF 1500 with other anatomical or instrument portions.

Further, the housing 1504, 1506 can define a dimension 1540 that is any appropriate dimension. The dimension 1540 can extend between a top 1505 of the upper housing portion and a bottom 1507 of the lower housing portion 1506. The bottom 1507 of the lower housing portion 1506 can contact a selected portion of the anatomy, such as a surface of the bone. The dimension 1540, however, can be any appropriate dimension for various purposes, such as reducing interaction with soft tissue, allowing movement of a bony portion relative to soft tissue without or reducing trauma to the soft tissue or any other appropriate purpose. Therefore, the dimension 1540 can be any appropriate dimension, for example, about 1 mm to about 50 mm.

Further, as discussed above, the DRF 1500 can be formed of any appropriate materials. For example, the screw 1502 can be formed of a substantially bioresorbable or resorbable material for allowing resorbtion of the screw 1502 at a selected rate. Therefore, the DRF 1500 can be implanted, according to various embodiments and the housing 1504, 1506 can be removed by breaking away a portion of the screw 1502, while the remaining portion of the screw 1502 remains in the patient 14 to be resorbed at the selected rate. The screw may also be formed of other materials, such as metals, metal alloys, or other appropriate materials.

Further, the housing 1504, 1506 can be formed of any appropriate material. For example, the housing 1504, 1506 can be formed of selected polymer or other resiliently deformable materials. The housing 1504, 1506 can be formed of a deformable material so that it can mate or conform with a selected portion of the patient, such as a surface of a bone, without the surface of the bone being substantially prepared. Further, the teeth 1522 can include a dimension that allows the housing base 1506 to not be positioned on a substantially flat or non-flat portion of the bone and the teeth 1522 are able to engage the bone in a manner that substantially resists rotation of the housing 1504, 1506 after positioning of the anchor in the bone.

With reference to FIGS. 69-73, a sensor assembly 1600 is illustrated. The sensor assembly 1600 can be used as a DRF, such as the DRF 54 for various purposes. The DRF 1600 can include various portions, that may be formed as a plurality of modular portions or as a single portion, based upon various considerations. Nevertheless, the DRF 1600 can generally include a lower housing portion 1602, an upper housing portion 1604, one or a plurality of coils, such as sensor coils 1606, 1608, 1610, an insert 1612, and an anchor, such as a screw 1614. The DRF 1600 can also include a battery or other power cell 1616. Alternatively, or in addition thereto, a wire 1618 can be provided to provide power to the DRF 1600, transfer a signal to or from the DRF 1600, or for various other purposes. In addition, or alternatively thereto, a power signal can be provided to the DRF 1600 as is understood by one skilled in the art.

The sensor coils 1606-1610 can be interconnected with the DRF 1600 in any appropriate manner. For example, the coils 1606-1610 can be fixed to the housing portions 1602, 1604 in any appropriate manner. Also, the coils 1606-1610 can be formed in the housing or as a single member with the housing. Also, according to various embodiments the one or more of the coils 1606-1610 can be formed on or as part of the screw 1614.

The inserts 1612 can interconnect with a portion of the housing 1602, 1604, such as a sidewall 1620 defining a bore 1622. The sidewall 1620 can also define a key portion 1624 that can interconnect with a complimentary key portion 1626 on the insert 1612. The insert 1612 can also define a sidewall 1628 that defines the key portion 1626. The sidewall 1628 can define a bore 1630 that can complement or allow for passage of the anchor 1614 therethrough. The upper housing portion 1604 can also define a bore 1632 for passage of the anchor 1614.

The anchor 1614 can include a threaded portion 1634, a tool engaging portion 1636, and a flange 1638. The tool engaging portion 1636 can engage a selected tool to allow for insertion of the anchor 1614 and the DRF 1600 relative to a portion of the patient 14. According to various embodiments, the tool can engage the tool engaging portion 1636 in any appropriate manner. For example, the tool can form a friction fit or the like to allow for interconnection or efficiency of implantation of the DRF 1600. The tool 1640 can allow for substantially single-handed implantation or positioning of the DRF 1600 relative to the patient 14.

Extending from a bottom 1642 of the insert 1612 can be one or a plurality of projections 1644. The projection 1644 can engage a portion of the patient 14, such as a bony portion. The projection 1644 can extend into or engage a portion of the patient 14 to assist in resisting rotation of the insert 1612 relative to the patient 14. As illustrated, the flange 1638 of the screw 1614 can press against a flange 1646 of the upper housing 1604 and a top portion 1648 of the insert 1612 defined by the sidewall 1628. The force of the flange 1642 of the screw 1614 on the various portions can assist in holding the housing 1604, 1602 relative to the insert 1612, which can engage the bone through the projection 1644 to assist in resisting rotation of the DRF 1600 relative to the patient 14. Therefore, the DRF 1600 can be held relative to the patient 14 in a selected manner and in an appropriate orientation and position.

Further, the housing 1604, 1602 can include any appropriate dimension 1650, such as those described above. The dimension 1650, however, can be any appropriate dimension that extends from a top 1605 of the upper housing portion 1604 to a bottom 1603 of the bottom housing portion 1602. The dimension 1650, although it can be any appropriate dimension, can be, for example, about 1 mm to about 50 mm.

The dimension 1650 of the DRF 1600 can be selected for various appropriate reasons, such as ease of positioning the DRF 1600 relative to the patient 14, reducing interaction with the soft tissue of the patient 14, allowing the DRF 1600 to move subcutaneously or percutaneously on the patient 14, or other appropriate reasons.

It will be understood, however, that the various portions of the DRF 1600 can be formed as single portions. Although the insert 1612 is shown separate from the housing 1602, it will be understood that the portions can be formed as a single member. Nevertheless, the insert 1612 being separate from the housing 1602 can allow for selection of the insert 1612 for various purposes. For example, the size of the projection 1644, the material of the insert 1612, and other considerations can be chosen, for example, intraoperatively, for various purposes.

Further, as discussed above, the portions of the DRF 1600 can be formed of any appropriate materials, for example, the screw 1614 can be formed of any appropriate materials, such as metal alloys, polymers, or the like. According to various embodiments, the screw 1614 can be formed of a resorbable material, such that the housing 1602, 1614 can be removed by a breaking away portion of the screw 1614 while the remaining portion of the screw 1614 resorbs into the patient 14 at a selected rate. Further, as discussed above, the screws 1614 can be any appropriate anchor and a screw, as illustrated here, is merely exemplary.

With reference to FIGS. 74-78, a tracking sensor assembly 1700 according to various embodiments is illustrated. The tracking sensor 1700 can be used for any appropriate purpose, such as a DRF, similar to the DRF 54. The DRF 1700 can include a plurality of portions, such as a base or lower housing portion 1702, an upper housing portion 1704, and a plurality of sensor coils 1706, 1708, 1710. As described above, the sensor coils 1706-1710 can be interconnected with the housing portions 1702, 1714 in any appropriate manner. Further, the sensor coils 1706-1710 can be inductor coils or can be any appropriate type of coils that are oriented in a selected manner. For example, the plurality of coils 1706-1710 can define axes that can be positioned substantially orthogonally to one another in the DRF 1700. Further, a battery or power cell 1712 can be provided to provide power to the DRF 1700. Alternatively, or in addition thereto, a wire 1714 can be provided to provide power to the DRF 1700. As discussed above, however, the DRF 1700 can be powered by a power signal.

The DRF 1700 can further include a plurality of teeth or spikes 1716. The teeth 1716 can be similar to the teeth 1622 described above. The teeth 1716 can be received or interconnected with a bore 1718 defined by the lower housing portion 1702. The teeth 1716 can interconnect with the bore 1718 in any appropriate manner, such as those described above and, as such, will not be described in detail here.

The lower housing 1702 defines a bore 1720 that can allow an anchor, such as a screw 1722 to pass therethrough. The upper housing portion 1704 can also define a bore 1724 for the anchor 1722 to pass through. The bore 1724 can be defined by a sidewall 1726 of the upper housing portion 1704 that can interact with an arcuate or otherwise radiused head portion 1728 of the screw 1722. The screw can also include a thread 1730 and a tool engaging portion 1732.

The arcuate head portion 1728, however, can interact with the sidewall 1726 defined by the upper housing portion 1704 in a selected manner to allow the screw 1728 to be positioned at an angle relative to a central axis defined by the housing 1704. The central axis 1732 of the upper housing 1704 can be a central axis thereof. The screw 1722, although it can be positioned at any appropriate angle relative to the central axis 1732, it can define a central axis 1734 that can be positioned at an angle 1736 relative to the central axis 1732 of the upper housing portion 1704. The angle 1736 can be any appropriate angle, for example it can range from about 0° to about 90°.

The screw 1722 can be angled relative to the housing 1704 for any appropriate reason. For example, it may be selected to interconnect to the DRF 1700 with a selected portion of the anatomy, but not allow the screw 1722 to intersect or pass through a selected portion of the anatomy. For example, if the DRF 1700 is positioned relative to a long bone, it can be selected to angle the screw 1722, such that the screw does not pass the cortical bone portion and intersect the intramedullary canal of the long bone. It will be understood, however, that the screw 1722 can be angled relative to the housing 1704 for any appropriate purpose.

Further, the housing 1702, 1704 can be interconnected in any appropriate manner, including those described above. For example, the housing portion 1702, 1704 can define complimentary threads, friction fit portions (e.g. snap fit), or any other appropriate interconnection. It will be understood that the housing portions can be interconnected either pre-operatively or intraoperatively.

Further, as discussed above, the teeth 1716 can be selected intraoperatively for various reasons. For example, the teeth 1716 can be selected for a length, a diameter, or the like for interconnecting with a selected portion of the anatomy.

Further, the DRF 1700 can be positioned relative to the anatomy as a single unit due to interconnection of the screw 1722 with the housing portion 1704, 1702. Further, a tool 1740 can engage and frictionally or otherwise hold the screw 1722 for positioning the DRF 1700 with a single hand of a user. Further, as discussed above, the DRF 1700 can be passed through a cannula 1742, passed through an incision, or otherwise positioned in the anatomy of the patient 14.

Figure 75A:
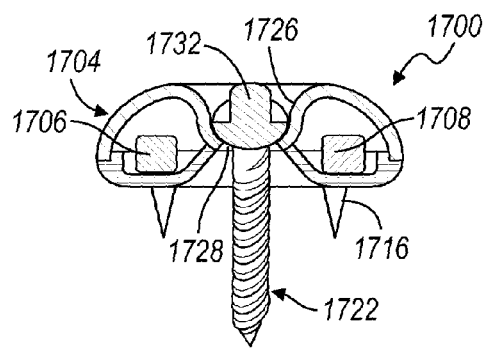
FIG. 75A is a cross-sectional view taken along line 75-75 of FIG. 74.
Figure 75B:
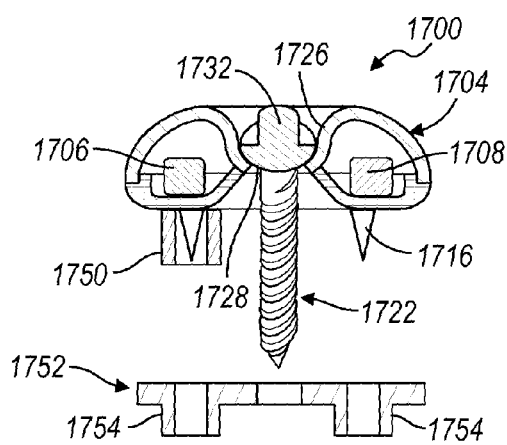
FIG. 75B is a cross-sectional view taken along line 75-75 of FIG. 74 including a protective element according to various embodiments.

With reference to FIG. 75B, a protective element according to various embodiments can be provided around the projections for spikes 1716. The protective element can include a compressible or crushable sleeve 1750. The crushable sleeve 1750 can be formed of any appropriate material such as a metal foil, a polymer material, or the like. The compressible sleeve 1750, however, can crush or deform when the screw 1722 is driven into a selected portion, such as a bone of the patient 14, and the protective sleeve 1750 engages the bone. As the screw 1722 is further driven into the bone, the protective sleeve 1750 can compress, if selected, and the spike 1716, however, will not compress. Therefore, as the screw 1722 is driven further into the bone, the compressible sleeve 1750 is pushed up while the spike 1716 is driven further into the bone. Therefore, as discussed above, the spike 1716 can be protected from contacting various portions of the patient 14, such as soft tissues, or other instruments. It will be understood that the screw 1722, can also include a selected protective element.

Further, the crushable sleeve 1750 can include a portion that covers each of the plurality of the spike 1716, as illustrated in FIG. 75B. It will be understood that the crushable sleeve 1750 can be formed as a single portion with the lower housing 1702, formed as a separate member thereof, or the like. Further, the crushable sleeve 1750 can include a bottom portion or extend past the end of the spike 1716.

Further, a single piece protective member 1752 can include a plurality of protective portions 1754 to protect each of the spikes 1716 defined by the DRF 1700. The separate protective elements 1752 can also be formed as a separate member to be fit over the screw 1722 and the projection 1716 or can be formed integrally with the housing 1702, or as a single piece with the bottom housing 1702. The protective member 1752, however, can include substantially similar characteristics to the protective sleeve 1750. That is, each of the protective elements 1754 can be crushed or deformed as the DRF 1700 is driven into the bone. Nevertheless, the protective elements 1752 can be provided for various purposes, such as manufacturing efficiency, assembly efficiently, or the like.

Figure 75C:
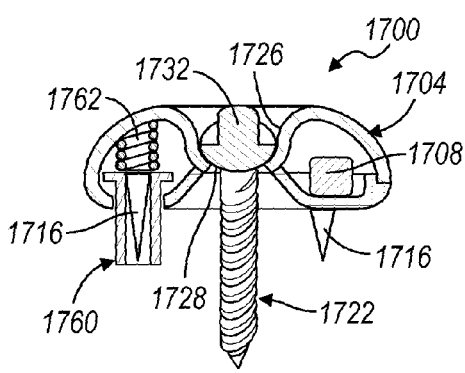
FIG. 75C is a cross-sectional view taken along line 75-75 of FIG. 74 including a protective element according to various embodiments.
Figure 76:
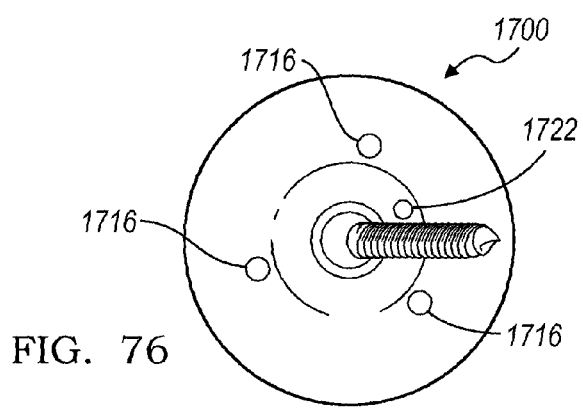
FIG. 76 is a bottom plan view of a DRF according to various embodiments.
Figure 77:
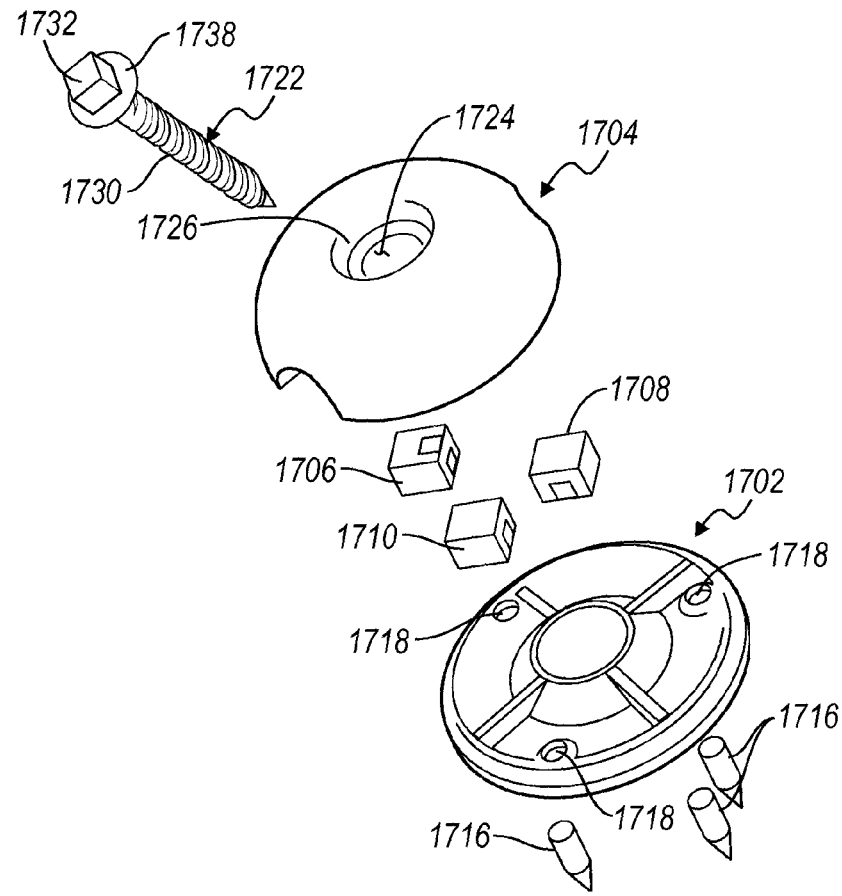
FIG. 77 is a top perspective exploded view of a DRF according to various embodiments.
Figure 78:
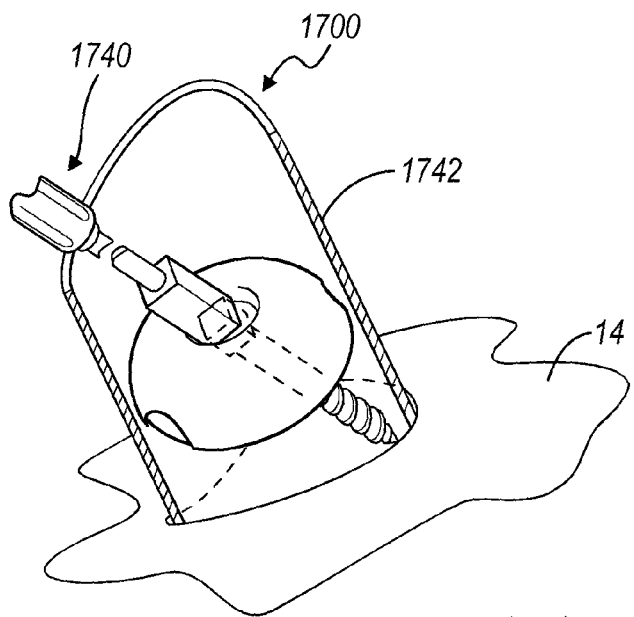
FIG. 78 is an assembled view of a DRF and a tool according to various embodiments.
Figure 79:
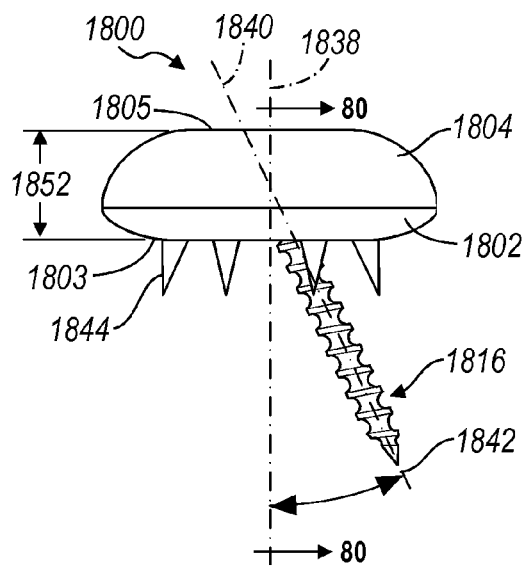
FIG. 79 is a side plan view of a DRF according to various embodiments.
Figure 80:
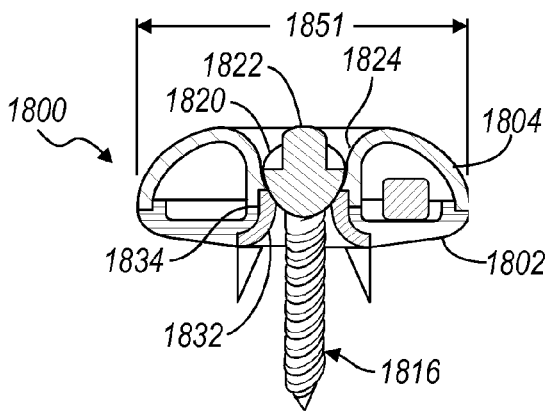
FIG. 80 is a cross-sectional view taken along line 80-80 of FIG. 79.
Figure 81:
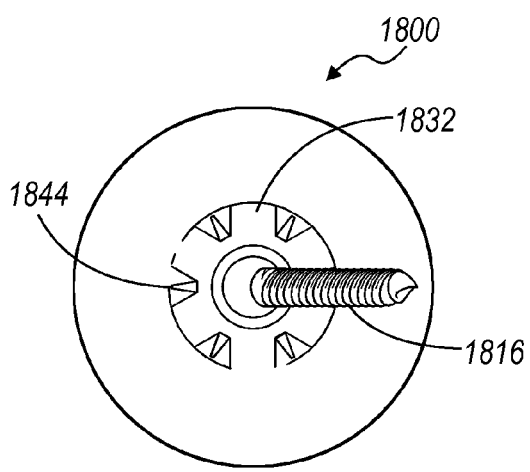
FIG. 81 is a bottom plan view of a DRF according to various embodiments.
Figures 82, 83:
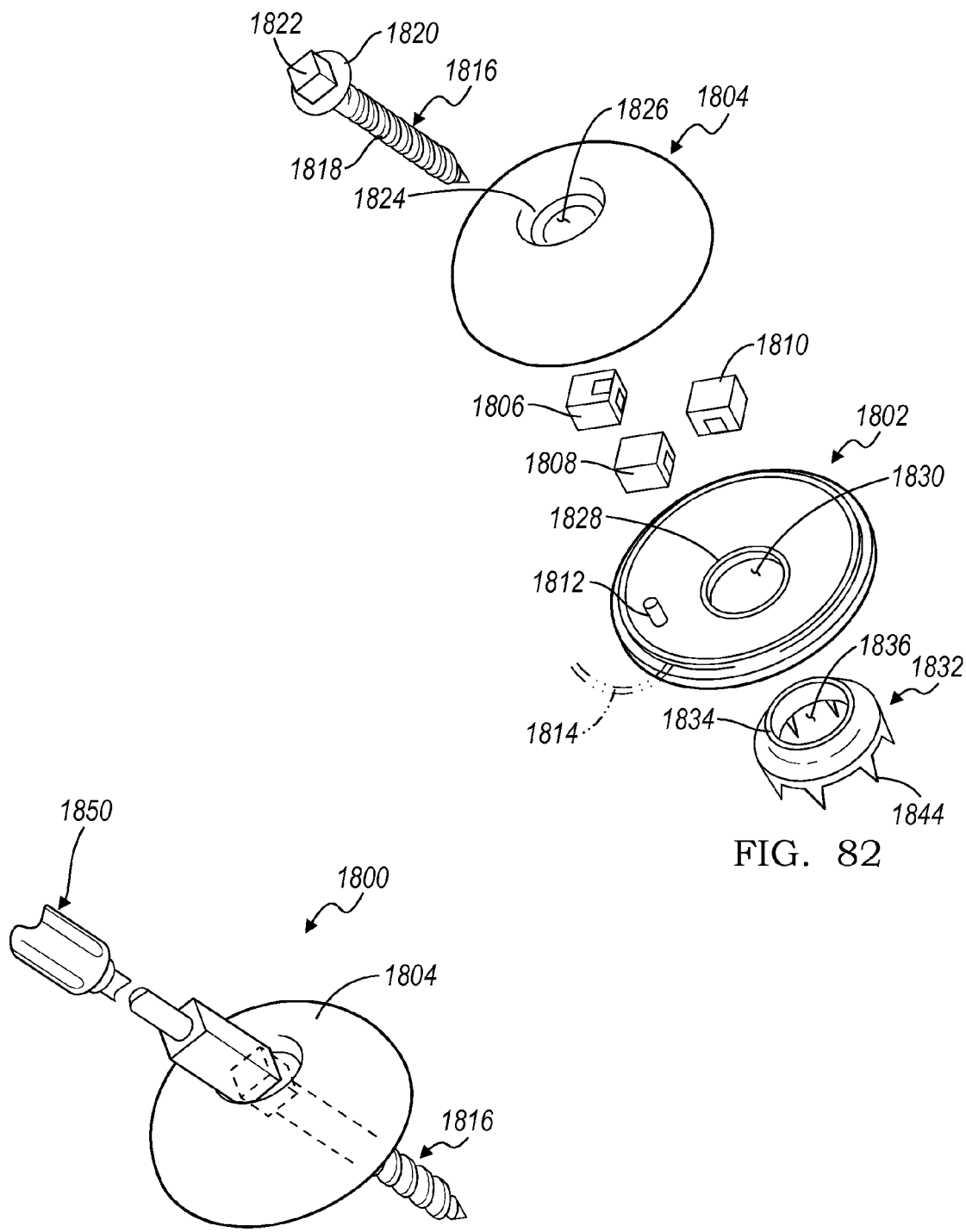
FIG. 82 is a top perspective exploded view of a DRF according to various embodiments.
FIG. 83 is an assembled view of a DRF and a tool according to various embodiments.

Further, a protective element or member can include a retractable sleeve 1760, as illustrated in FIG. 75C. The retractable sleeve 1760 can be formed of any appropriate material, such as a metal alloy, a polymer, or the like. The protective sleeve 1760, however, is generally rigid. A deformable member or a biasing member, such as a spring 1762 is provided to bias the protective sleeve 1760 in a direction, such as a direction that would cover the spike or tooth 1716. Again, as the DRF 1700 is driven into the patient 14, the protective sleeve 1760 can engage the bone and as the sleeve DRF 1700 is further driven into the patient 14, the sleeve 1760 can push against the biasing member 1762 and expose the spike 1716. Therefore, the spike 1716 would be substantially covered by the protective sleeve 1760 until such time as the spike 1716 is driven into the bone. It will be understood, however, that the biasing member 1762 can be any appropriate member and is not necessarily limited to a spring. For example, a rubber spring, a resilient member, or the like, can be provided to bias the protective sleeve 1760 in a selected direction.

It will be understood that the various protective members, can be used in the various embodiments whether particularly described or not. The protective elements such as the crushable sleeve, the biased sleeve, the crushable member, or the like, can be provided in the various embodiments to reduce the contact between various portions of the DRF, according to various embodiments, and selected portions of the patient 14.

Further, the DRF 1700 can include a dimension 1750 that is any appropriate dimension, including those described above. The dimension 1750 can extend from a bottom 1701 of the lower housing portion 1702 to a top 1705 of the upper housing portion 1704. Although the dimension 1750 can be any appropriate dimension, it can for example, be about 1 mm to about 50 mm.

As discussed above, the DRF 1700 can be formed of various materials, including polymers, metals, metal alloys, or the like. Further, various portions of the DRF 1700 can be formed of various different materials. According to various embodiments, the screw 1722 can be formed of a resorbable material to allow the housing 1704, 1702 to be broken away from the screw 1722 after a procedure so that the screw 1722 can resorb into the patient 14.

It will also be understood that various other specific features can be included in the DRF 1700, that are not specifically described here. For example, the screw 1722 can be cannulated, such that a guide wire can be passed therethrough to assist in reducing rotation of the screw 1722.

Further, the housing 1702, 1704 can be formed of selected materials that allow it to deform or conform to selected portions of the anatomy. Therefore, the DRF 1700 can be positioned relative to a bone surface without substantially preparing the bone surface prior to positioning the DRF 1700 relative thereto. Further, the teeth 1716 can assist in engaging the patient 14 without providing a substantially prepared or flat surface of the bone.

With reference to FIGS. 79-84, a tracking sensor assembly 1800 is illustrated. The tracking sensor 1800 can be used for any appropriate purpose, such as a DRF, similar to the DRF 54 described above and for various purposes, including those described above. The DRF 1800 can include any appropriate portions, such as a lower housing portion 1802, an upper housing portion 1804, and one or a plurality of sensor coils 1806, 1808, 1810. The sensor coils 1806-1810 can be positioned relative to the housing portions 1802, 1804 in any appropriate manner. For example, the sensor coils 1806-1810 can define axes that are positioned substantially orthogonally to one another within the housing portions 1802, 1804. The tracking sensor 1800 can further include a battery or power cell 1812 to provide power to the DRF 1800. Also, as discussed above, a wire 1814 can provide power, signal transmission, or other purposes to the DRF 1800. In addition, or alternatively thereto, a power signal can provide power to the DRF 1800 for various purposes.

The DRF 1800 can further include an anchor 1816 that can be a screw that includes a thread 1818, a radiused or polyaxial head 1820 and a tool engaging portion 1822. The polyaxial head 1820 can allow for the screw 1816 to be positioned at a plurality of angles relative to the upper housing portion 1804, similar to the screw 1722 in relation to the DRF illustrated and according to various embodiments at 1700.

The upper housing portion 1804, therefore, can define a sidewall 1824 that further defines a bore 1826 so that the screw 1816 can pass therethrough. Further, the lower housing portion 1812 defines a sidewall 1828 and a bore 1830. The bore 1830 defined by the lower housing portion 1802, however, allows for positioning an insert 1832 relative thereto. The insert 1832 can define an upper wall 1834 that defines a portion of a bore 1836. The upper wall 1834 can interact with the polyaxial head 1820 to allow for the screw 1820 to be positioned at an angle relative to a central axis 1838 of the upper housing 1804. The screw 1816 can define a central axis 1840 that can be positioned at an angle 1842 relative to the central axis 1838 of the upper housing 1804. The angle 1842 can be any appropriate angle, for various reasons, including those discussed above, but can be about 0° to 90°.

The insert 1832 can further define a singular projection 1844 or a plurality thereof. The projections 1844 can engage a selected portion of the patient, such as a surface of a bone for various reasons. For example, the projections 1844 can engage the bone to resist rotation of the insert 1832, and therefore, rotation of the DRF 1800. The screw 1816 can provide a force to the upper wall 1834 of the insert into the sidewall 1824 of the upper housing 1804 to assist in resisting rotation of the DRF 1800. Further, because the upper housing 1804 and the lower housing portion 1802 can be interconnected the rotation of the DRF 1800 can be substantially reduced or eliminated.

Further, the insert 1832 can be formed as a separate member or as a single member with the lower housing portion 1802. If the insert 1832 is provided as a separate member, it can be selected either intraoperatively or preoperatively for various purposes. For example, the size, the number, the geometry or the like of the projections 1844 can be selected. Further, the overall size of the insert 1832 can also be selected. The selection of the insert 1832 can be provided for various reasons, such as positioning of the DRF 1800, the size of the patient 14, or other reasons. Regardless, the insert 1832 can allow for intraoperative selection and specification of the DRF 1800 for various purposes.

The DRF 1800 can be positioned relative to the patient according to any appropriate procedure. For example, as according to various embodiments, a tool 1850 can engage the tool engaging portion 1822 of the screw and be held relative thereto for various reasons. The DRF 1800, either as an assembly or separately, can then be passed through a cannula, an incision, or the like to be positioned relative to the patient 14.

The DRF 1800 can be positioned relative to any portion of the anatomy, including those described above. The DRF 1800 can be positioned relative to a pelvis, an iliac crest of a pelvis, a femur, a tibia, a humerus, a vertebra, or the like. The DRF 1800, however, can include a geometry of the housing portions 1804, 1802 for various purposes, such as subcutaneous movements, percutaneous placements, reduction of interaction with the soft tissue, or any other appropriate reason.

The DRF 1800 can include a dimension 1852 that is defined by a top 1805 of the upper housing portion 1804 and a bottom 1803 of the lower housing portion 1802. The dimension 1852 can be any appropriate dimension, such as those described above, and for example, about 1 mm to about 50 mm. Regardless, the DRF 1800 can include any appropriate dimension for various purposes, including a selected position on the anatomy, a size of a patient, or the like. Also, the DRF 1800, according to various embodiments discussed herein, can include a dimension 1851 that is a dimension that can define a width or diameter of the DRF 1800. The dimension 1851 can be any appropriate size, such as about 1 mm to about 50 mm. The dimension 1851 can also assist with percutaneous and/or subcutaneous positioning and or movement of the DRF 1800.

The DRF 1800 can be formed of any appropriate materials. For example, various polymers, metals, metal alloys, and the like can be selected. The housing portion 1802, 1804 can be formed of a selected material, such that it can deform or conform to a selected portion of the anatomy. For example, the housing portion 1802 can be formed to conform to a portion of the anatomy, such that the anatomy, including a bone surface, need not be substantially flattened or position the DRF 1800 relative thereto. Further, the screw 1816, can be formed of a resorbable material, such that the housing 1802, 1804 can be broken away from the screw 1816 for ease of removal of the housing 1802, 1804 at the screw 1860 will resorb at a selected rate.

It will be understood, that various embodiments of the various DRFs described above. It will be understood, however, that the various adaptations can be formed and still be within the scope of various embodiments and the teachings herein. For example, any appropriate anchor portion can be used to anchor the DRF according to various embodiments relative to the patient 14. For example, a staple, a pin, a rivet, or the like can be used to fix the DRF relative to the anatomy. Further, the DRF can be anchored for anti-rotation or other purposes using portions other than projections extending from a portion of the DRF. For example, an auxiliary pin, screw, rivet, or the like can be positioned through the DRF to assist in reducing or resisting rotation of the DRF relative to the patient 14.

Figure 84:
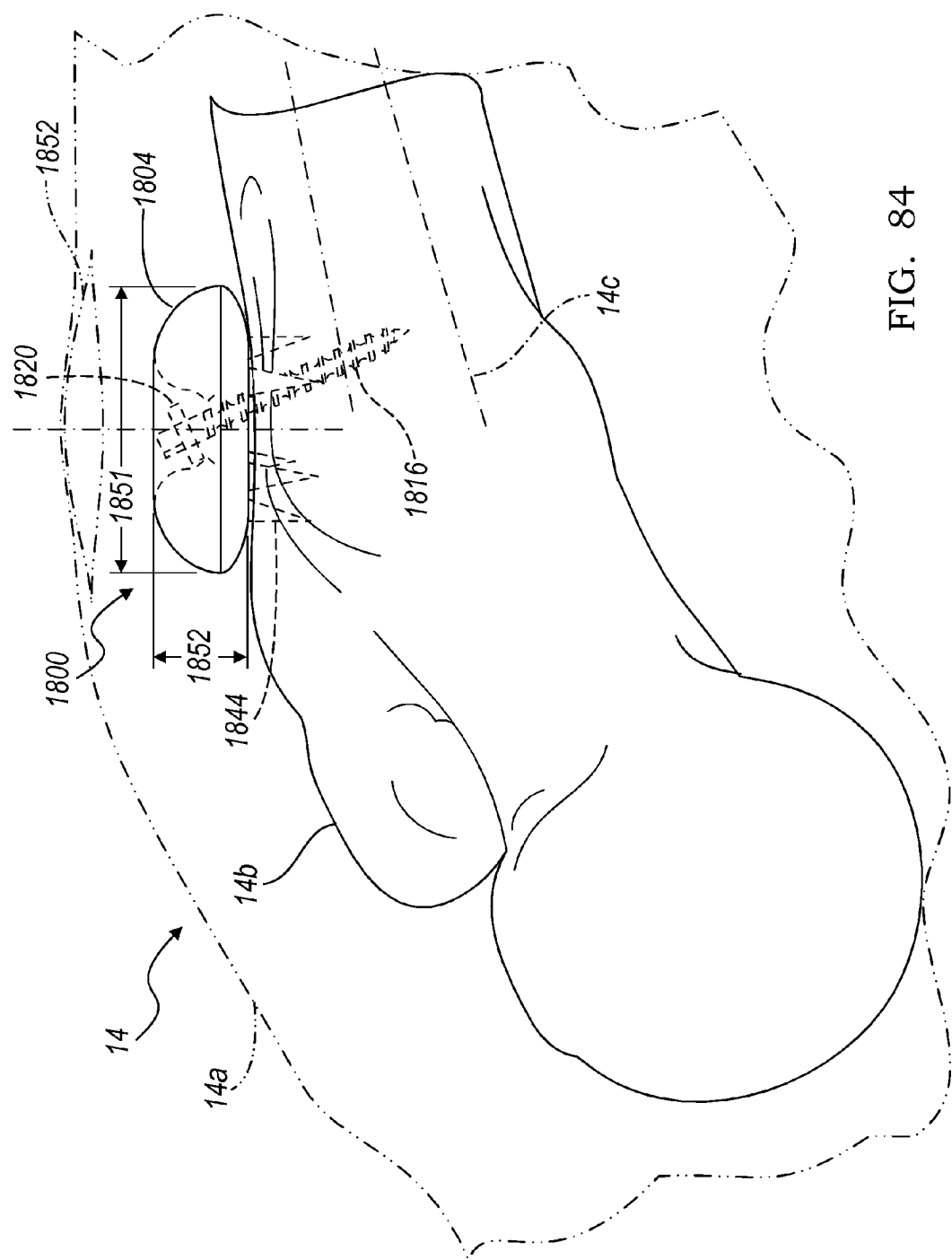
FIG. 84 is an environmental view of a tracking sensor assembly, according to various embodiments, positioned in a patient.

With particular reference to FIG. 84, the DRF 1800, or any DRF according to various embodiments can be positioned in a patient 14 through soft tissue 14a (e.g. skin, dermis, muscle, adipose tissue, or the like) and positioned relative to a bone 14b, such as a femur. As discussed above the bone 14b can be prepared or unprepared as selected by a user or the various embodiments.

The incision 1852 can be any appropriate incision and include any appropriate dimension. Generally the dimension of the incision 1852 need not be much greater than any dimension of the DRF 1800. Such an incision can allow for a percutaneous positioning of the DRF 1800. Further, the soft tissue 14a can remain above the DRF 1800, cover, or rencapsulate the DRF 1800 after the DRF 1800 is positioned on the bone 14b. This can allow the bone 14b to move relative to the soft tissue 14a, or vice versa, without much interaction or disturbance of the soft tissue 14a.

Also, the poly-axial anchor 1816 can be positioned at an angle relative to the housing or body 1804, 1806. The angle can allow the DRF 1800, according to various embodiments, to be fixed to the bone 14b without engaging a portion thereof, such as the intramedullary canal 14c. The attachment portions, such as the projections 1844, however, can engage the bone 14b to assist in resisting rotation of the DRF 1800, fixation of the DRF 1800 or other appropriate purposes. Also, as discussed herein, the bone 14b can remain substantially unprepared or natural, if selected, and the DRF can still be mounted thereto.

Initially, it will be understood although various embodiments are not necessarily illustrated to include each of the discussed portions, such as protective sleeves and the like, that each will be available and can be included with the various embodiments. Further, the protective elements, such as the crushable or moving member, can be used to protect various portions. For example the protective elements can protect the patient or the anatomy of the patient into which they are placed. Also, the protective elements can protect the user or the person placing the DRF as the sharp portion is generally covered or not substantially revealed until it engages the bone of the patient. Therefore, it will be understood that the protective element can protect many portions, be it the patient, user, instrument, or any appropriate portion or person.

As discussed above, the DRF, according to various embodiments, can be attached to any selected portion of the anatomy or multiple DRFs can be attached to a plurality of anatomic portions or regions. Also, the DRF according to the various embodiments can be used for any selected use. For example, a first DRF can be positioned on a first bone and a second DRF can be positioned on a second bone for determining a position of the DRFs, and therefore the bones, relative to one another. For example, as illustrated above, a first DRF can be positioned on a selected portion of a femur and a second DRF can be positioned on a portion of a pelvis.

Various DRFs can also be positioned on various portions of a single bone or what naturally was a single bone. For example, during a fracture, a single bone may be divided into more than one piece. The fracture may either be complete or partial, but the various portions of the bone may move relative to one another in a non-rigid manner. Therefore, a first DRF and a second DRF can be attached to a first portion of the bone and a second portion of the bone, respectively, to determine a position of the various portions of the bone relative to one another. This can assisting in tracking the bone portions to assist in setting bones, positioning various portions of a fractured bone relative to one another and for various other purposes. It will be understood, however, that the various uses described herein are merely exemplary and not intended to limit the scope of the present teachings.

Instruments can be moved relative to the patient 14 and the tracking devices on the instrument can be used to illustrate the position of the instrument on a display device. The display device can also display image data that is registered to the patient space. The various DRFs can be used to maintain registration even if the patient 14 moves. Alternatively, the patient 14 can be fixed in space during a procedure, thus not requiring any DRFs.

Figure 85:
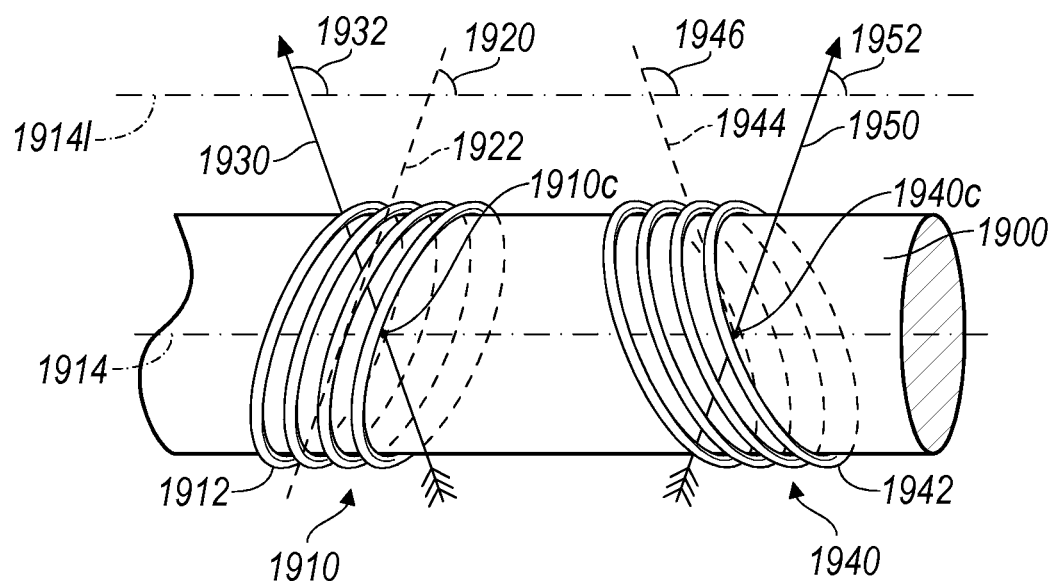
FIG. 85 is a plan view of an instrument with a selected tracking device.

An instrument 1900 is illustrated in FIG. 85. The instrument 1900 can be any appropriate instrument including those discussed and illustrated above. For example, instrument 1900 can be the stylet portion 156, suction device 190, probe device 166, or any other appropriate instruments. The instrument 1900 can also include other instruments including cranial stylets, biopsy needles, ear nose and throat instruments (e.g. drill guides, shavers, etc.), small diameter dynamic reference frames, transveinous catheters, other catheters, dynamic reference frames or other patient attached devices, and other selected devices. Generally, the selected instrument 1900 can include a long thin configuration, such as that of the stylet 150. It will be understood, however, that the instrument 1900 can be any appropriate instrument and discussion herein of the stylet 1900 is merely exemplarily.

The instrument 1900, as the stylet 1900, can be positioned in selected instruments or can be incorporated with selected instruments. The stylet 1900, if positioned in another secondary instrument, can be rotationally fixed relative to the secondary instrument along a longitudinal axis. The position of the stylet 1900 can be determined by tracking the location of a tracking device 1910. The tracking device can include multiple windings or turns of a wire 1912 into a coil, to form the tracking device 1910. The tracking device 1910 can be wrapped around a long axis 1914 of the instrument 1900. The tracking device 1910 can include a long axis that is substantially co-axial with the long axis 1914 of the instrument 1900. It will be further understood, that multiple coils can be used to define a single tracking device, thus each tracking device can be used to identify more than one navigation vector, as discussed herein. Thus, discussion of the tracking device as including only a single coil is for illustration and ease of discussion only.

The long axis 1914 of the instrument 1900 is illustrated in FIG. 85 as being parallel to a line 1914I that is external to the instrument 1900 for illustration purposes of the following discussion. It will be understood that because the long axis 1914 and the line 1914I are parallel that any angle relative to the line 1914I is identical to an angle relative to the long axis 1914 of the instrument 1900. The windings of the wire 1912 can be wound at an angle 1920 relative to the line 1914I. The angle 1920 can be defined as an angle between the line 1914I and a line that is defined by one of the windings of the wire 1912 or a plane generally through the instrument 1900 defined by a single winding of the wire 1912. For illustration, the line 1922 can define a line or plane extending from one of the windings of the wire 1912. As illustrated in FIG. 85, the angle 1920 is generally non-perpendicular to the line 1914I. The angle 1920 is an acute angle relative to the line 1914I. A supplementary angle will be formed on the reverse side of the line 1922 relative to the line 1914I.

The angle 1920 can be selected in a range of about 10 degrees to about less than 90 degrees, including about 40 degrees to about 50 degrees, and including about 45 degrees. The angle 1920 can be referred to as a winding or coil angle. As discussed herein the winding angle is an angle of the windings of the various coils relative to the long axis around which the coils are wound which can also be a long axis of an instrument around which the coil is wound. The winding angle is substantially an angle that is greater than an angle formed when a wire is wound tightly in a single layer on an instrument, which can generally form a helix due to the thickness of the wire being wound. The winding angle can be defined relative to the long axis of the coil by two points opposed to one another one a single turn or by a plane through a single turn, as illustrated in FIG. 85.

The tracking device 1910 can be part of an electromagnetic tracking system, as discussed above. In such a system, the wire 1912 can be acted upon by an electromagnetic field or can generate an electromagnetic field. In the example discussed herein, the wire 1912 of the tracking device 1910 can be acted upon by an external magnetic field to generate a current in the wire 1912 or set up the voltage within the wire 1912 of the tracking device 1910.

Because the wire 1912 of the tracking device 1910 is wound at the angle 1920 to the line 1914I, a navigation vector 1930 is defined through the tracking device 1910 at an angle 1932. The navigation vector 1930 is generated and based on the tracking system localizer 600. In other words, the angle of the windings 1920 is based on the physical turns of the wire 1912, but the navigation vector 1930 is based on the induced voltage from the localizer 600 and is generally perpendicular to the coils of the wire 1912,1942. The voltage induced in the wire 1912 is proportional to the strength of the magnetic field generated by the localizer 600 multiplied by the cosine of the angle between the vector magnetic field and a line or vector normal to a winding of the wire 1912. Thus, when all other variables of location are known, such as position in space and a field strength of the magnetic field generated by the localizer 600, the angle (e.g. the navigation vector 1930) between the coil's normal and the vector magnetic field can be determined. The determination can be performed by executing instructions with a processor. In other words, the navigation vector can be computed by comparing the measured strength of the magnetic field to the theoretical value at a specific location. It will also be understood that the tracking devices discussed herein can generate a field that is sensed by the localizer for navigation purposes.

The angle 1932 when added to the angle 1920, as illustrated in FIG. 85, can equal substantially 180 degrees. Accordingly, the angle of the navigation vector 1932 and the angle of the coil winding 1920 can be substantially supplementary angles.

The external field that can induce a current in the wire 1912 due to generally understood and accepted electromagnetic properties. Accordingly, the operation of the tracking device 1910 will not be discussed in detail here, however, it is discussed above. The position of the navigation vector 1930 can be used to identify the location of the instrument 1900 and to determine the orientation of the tracking device 1910 in space (e.g. patient space). The orientation of the navigation vector 1930 relative to the long axis 1940 of the instrument allows for multiple tracking devices to be positioned on the instrument including navigation vectors that are all non-perpendicular to the long axis 1914 of the instrument 1900. For example, a second tracking device 1940 can include a wire 1942 that is wound around the instrument 1900 to form a coil that has a coil axis 1944 at an angle 1946 relative to the line 1914I. The second tracking device 1940 therefore defines a navigation vector 1950 that has a second navigation vector angle 1952. The second navigation vector angle 1952 is also supplementary to the angle 1946 of the tracking device 1940. The navigation vector angle 1932 of the first tracking device 1910 can be different than the navigation vector angle 1952 of the second tracking device. With the two tracking devices 1910, 1940 six-degree of freedom information (6DOF), including x, y, and z positions and three degree of orientation can be determined. Though more than two tracking devices can be included, they are not necessary to determine the 6DOF location information regarding the instrument 1900.

Figure 86A:
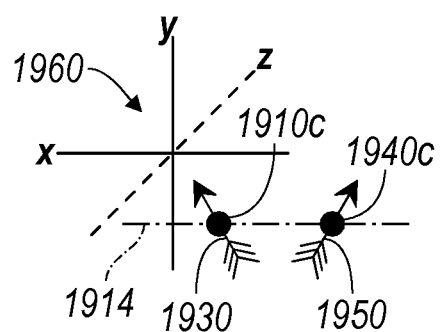
FIGS. 86A and 86B illustrate a representation of navigation vectors.
Figure 86B:
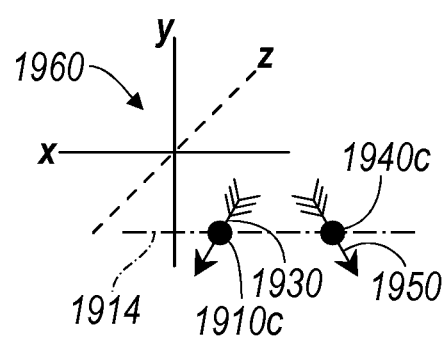

As illustrated in FIGS. 86A and 86B, the vectors 1930, 1950 can provide orientation information regarding the two tracking devices 1910, 1940 positioned on the instrument 1900 relative to a coordinate system 1960. The coordinate system 1960 can be a three dimensional coordinate system having three orthogonal axes 1960x, 1960y, and 1960z. Within the coordinate system 1960 the vectors 1930, 1950 can be used to identify locations of the tracking devices 1910, 1940 in the three dimensional coordinate system 1960. The navigation system can be used to determine the location information by executing instructions based on the signal received about the tracking devices 1910, 1940.

The vectors 1930, 1950 regarding the orientation of the respective tracking devices 1910, 1940 relative to the centers 1910c, 1940c can be used to determine location information, including position and orientation information, regarding the two tracking devices 1910, 1940. Although the single position and orientation information for any one of the tracking devices 1910, 1940 may not be enough information to identify all location information for the instrument 1900, the information regarding both of the tracking devices 1910, 1940 can be used to identify six degree of freedom information regarding the instrument 1900.

The vectors 1930, 1950 both extend through respective centers 1910c, 1940c of the respective tracking devices 1910, 1940. Accordingly, the direction of the vectors 1930, 1950 in combination with the three dimensional coordinate positions of the center of the respective tracking devices 1910c, 1940c can be used to identify the location information of the instrument 1900. As illustrated in FIGS. 86A and 86B as the instrument 1900 is rotated in space the vectors will change direction. Because the vectors are non-normal to the instrument 1900 a rotation of the instrument 1900 can be efficiently determined, including the amount of rotation and orientation in all three of roll, pitch, and yaw. As illustrated between FIGS. 86A and 86B the orientation of the two vectors 1930, 1950 are substantially different relative to the long axis 1914 of the instrument 1900. Again, location information includes both x, y, and z axis position information and roll, pitch, and yaw orientation.

Figure 87A:
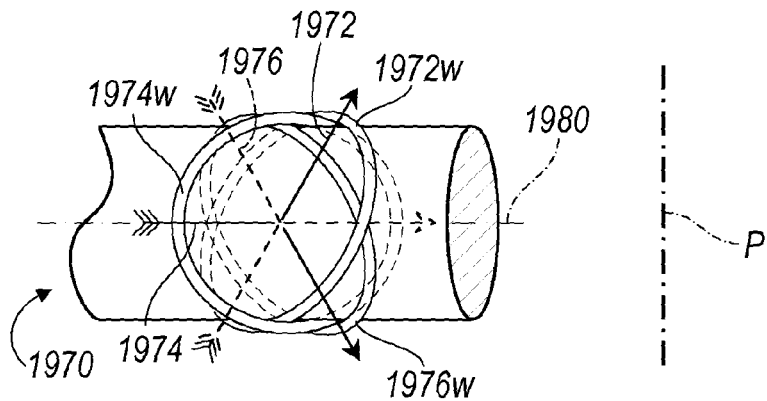
FIG. 87A is a perspective view of an instrument with a selected tracking device.
Figure 87B:
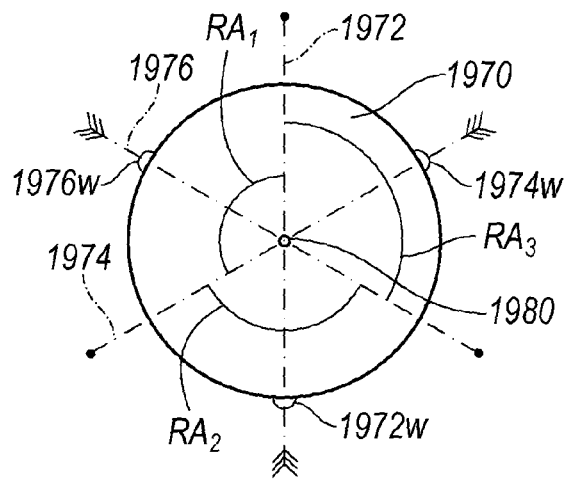
FIG. 87B is a cross-section view of an instrument with a selected tracking device.

With reference to FIGS. 87A and 87B, an instrument 1970, which can be similar to the instrument 1900, can include at least three tracking devices 1972w, 1974w, and 1976w. Each of the tracking devices can be formed around the instrument 1970 similar to the tracking devices 1910, 1940 discussed above. Each of the tracking devices 1972w, 1974w, and 1976w positioned on the instrument 1970 can include a navigation vector 1972, 1974, 1976. Therefore, a first navigation vector 1972 can be formed by a first tracking device 1972w, a second navigation vector 1974 can be formed by a second tracking device 1974w, and a third navigation vector 1976 can be formed by a third tracking device 1976w relative to the instrument 1970. Each of the navigation vectors 1972-1976 can be formed relative to the instrument 1970 due to the positioning of the windings of material of the respective tracking devices 1972w, 1974w, and 1976w at the winding angle relative to the instrument 1970.

FIG. 87A attempts to illustrate on a two-dimensional plane of a page a three-dimensional rotation of angles of the three different windings 1972w, 1974w, and 1976w. As discussed above, in relation to FIG. 85, each of the windings can be wound at the winding angle relative to a long axis 1914 of the instrument 1900. As illustrated in FIGS. 87A and 87B, however, rather than having the windings formed at various and different winding angles relative to the long axis 1980 of the instrument 1970 (as the windings are illustrated in FIG. 85), each of the windings can be formed at substantially a single winding angle, including those winding angles discussed above and such as about 20 degrees to about 70 degrees, relative to the long axis 1980 of the instrument 1970.

Because each of the coils of the tracking device windings 1972w, 1974w, and 1976w are at the same winding angle, to resolve the six degrees of freedom a top 1972 wt, 1974 wt, and 1976 wt of each of the coil windings 1972w, 1974w, and 1976w are rotated a rotation angle, such as about 120 degrees relative to one another around the long axis 1980 of the instrument 1970. As discussed above, however, three windings are not required and an appropriate number of windings can be used with an appropriate number of localizer coils. The rotation angle RA can be selected to be 120 degrees to place each of the tops 1972 wt, 1974 wt, 1976 wt substantially equidistant apart around the long and central axis 1980 of the instrument 1970. It will be understood, however, that the rotation angle RA can be about 90 degrees to about 180 degrees, including about 120 degrees. Also, a rotational distance between each top or winding 1972w-1976w can be different, such as $RA_1$, $RA_2$, and $RA_3$.

As illustrated in FIG. 87B, the front or top end of the windings 1972 wt-1976 wt are all in substantially the same direction, such as towards a distal end of the instrument 1970. Each of the windings 1972w-1976w rotationally spaced apart around the center long axis 1980 of the instrument 1970. In this way, the navigation vectors 1972-1976 for each of the windings 1972w-1976w can be formed at the same winding angle relative to the long axis 1980 of the instrument 1970. The navigation vectors 1972-1976 are also, due to the rotational spacing of the coil windings tops 1972 wt-1976 wt, rotationally spaced around the long axis 1980.

The different navigation vectors 1972-1976 are defined relative to a center 1980 of the instrument 1970. Each of the vectors 1972-1976 can point towards a plane P, as illustrated in FIG. 87A, which can is illustrated in FIG. 87B as the plane of the page. The tails of the vectors 1972-1976 can go into and past the plane on the page illustrating FIG. 87B, thus all of the navigation vectors 1972-1976 are not coplanar, but they all intersect the single plane P. Each of the vectors 1972-1976 can be formed relative to the plane P rotationally spaced at the RA angle relative to one another around the center 1980 of the instrument 1970.

As discussed above, the navigation vector angle can be selected by forming the windings of the tracking device 1972w-1976w at a selected angle relative to the long axis of the coil winding 1972w-1976w. By changing the positioning of the angle of the rotation of the windings of the various tracking devices, the navigation vectors can be positioned relative to the instrument 1970 in this selected manner. In various embodiments, the vectors 1972-1976 are differently oriented relative to the instrument 1980 by having more than one coil wound at the same winding angle, but being spaced relative to one another with the RA angle.

Figure 88:
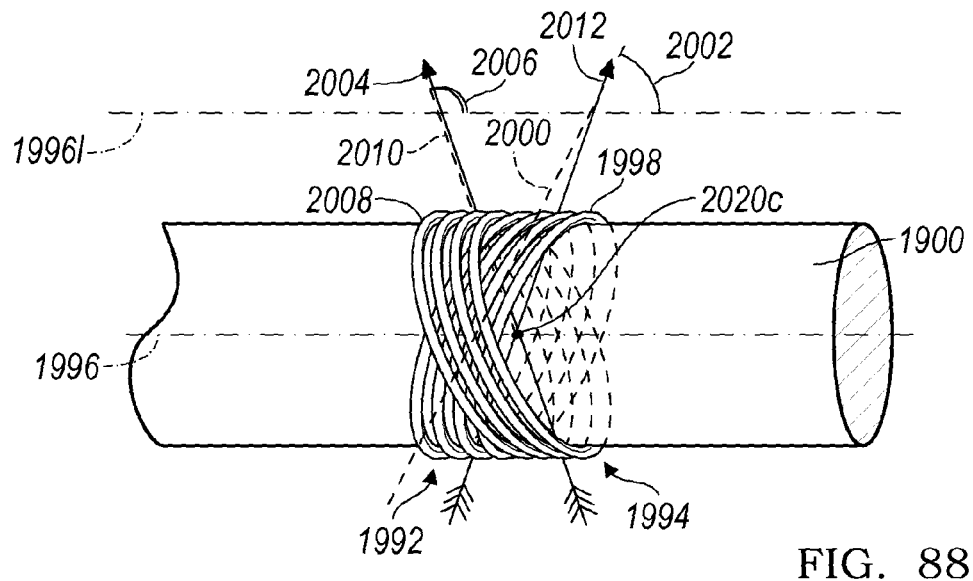
FIG. 88 is a plan view of an instrument with a selected tracking device.

Accordingly, not only can navigation vectors include supplementary angles relative to the long axis of the instrument 1900, as illustrated by the navigation vector angle 1932, 1952, they can also be formed to be at a selected angle relative to a long axis of the instrument 1970, but positioned around the center of the instrument 1980 to have an angle of about 120 degrees to one another. The RA angle between the navigation vectors 1972-1976, however, can be at a selected angle, such as an angle between about 10 degrees to about 180 degrees, including about 90 to about 180 degrees, further including about 120 degrees. It will be further understood that each tracking device that defines the respective navigation vectors 1972-1976 can be formed or defined by tracking devices that are non-overlaid or are sequential along the instrument 1970. Although tracking devices can be positioned sequentially, or non-overlaid on an instrument, tracking devices can be overlaid, as illustrated in FIG. 88, on an instrument 1990. The instrument 1990 can include a first tracking device 1992 and a second tracking device 1994. The instrument 1990 can include or define a long axis 1996 that is illustrated parallel to a line 1996I. As discussed above, the line 1996I is drawn for illustration in FIG. 88 of the current discussion. When overlaid a layer of insulation, either on the wire, between the windings, or both, can be provided between the two tracking portions 1992 and 1994. Also, three or more windings can also be provided.

A first tracking device 1992 can be formed with a first wire winding 1998 similar to the wire 1912 of the first tracking device 1910. The tracking device 1992, having the wire winding 1998, can define a winding axis 2000 that is at an angle 2002 relative to the line 1996I. The first tracking device 1992 can therefore define a navigation vector 2004 that is at an angle 2006 relative to the line 1996I. As discussed above, the angle 2002 and 2006 can be supplementary to each other relative to the line 1996I. In a similar manner, a second tracking device 1994 can include a wire winding 2008 that can define a wire winding axis 2010 having an angle 2011 and a navigation vector 2012 having an angle 2013.

The two tracking devices 1992, 1994 can be similar to the two tracking devices 1910, 1940 discussed above. The navigation vectors 2004, 2012 can be at similar angles to the line 1996 as the navigation vectors 1930, 1950 to the line 1914I. The two tracking devices 1992, 1994, however, can be formed over each other, also referred to as overlaid, on the instrument 1990. Overlaying the two tracking devices 1992, 1994 on one another can be provided to substantially eliminate a possibility of movement between the two tracking devices. However, even if the wire 1998, 2008 of the two tracking devices 1992, 1994 is thin or has a small diameter, the diameter at the tracking devices 1992, 1994 of the wire is doubled by overlaying them. Accordingly, having sequential tracking devices, such as the first and second tracking devices 1910, 1940 on the instrument 1900 illustrated in FIG. 85, can be provided to minimize the diameter of the instrument and tracking devices. Each of the tracking devices 1992, 1994 can be insulated from one another and from the instrument 1900 with insulation. The insulation can be a shrink wrap, insulated wire for the windings, or other selected insulation portions.

Figure 89A:
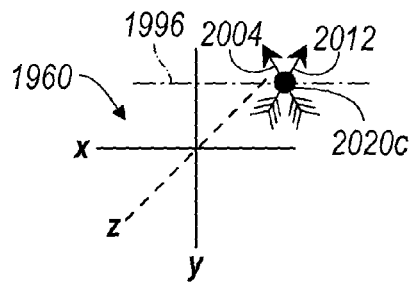
FIGS. 89A and 89B illustrate a representation of navigation vectors.
Figure 89B:
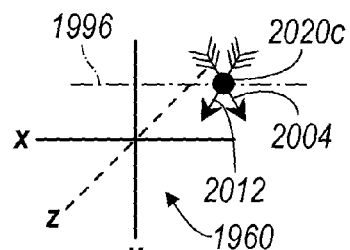

The two tracking devices 1992, 1994, however, can still define multiple navigation vectors relative to a single tracking device center point 2020c. As illustrated in FIGS. 89A and 89B, the navigation vectors 2004, 2012 can both extend through the single center point 2020c in the coordinate system 1960. Again, the plurality of the navigation vectors 2004, 2012 that do not extend at an identical angle from the long axis 1996 of the instrument 1990 can allow for determination of an orientation and a position of the instrument 1990 with six degrees of freedom.

Figure 90:
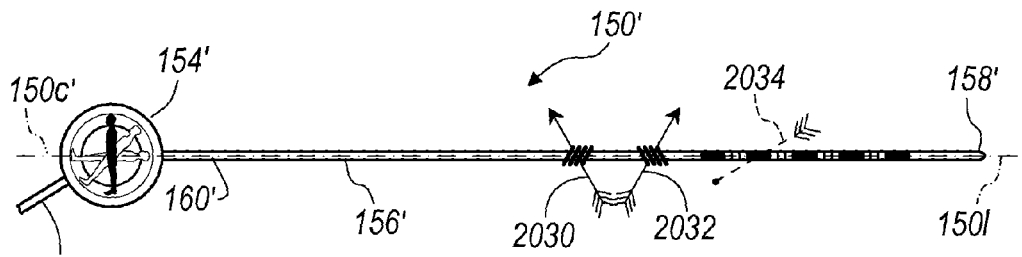
FIG. 90 is a plan view of an instrument with a selected tracking device.

With reference to FIG. 90, and drawing on the description of the stylet 150 above, a stylet 150' is illustrated. The stylet 150' can include portions substantially similar or identical to the portions discussed above, with like reference numerals augmented with a prime in FIG. 90. The stylet 150', however, can include tracking devices such as the tracking devices 1910, 1940 along the length of the stylet 150'. The various tracking devices along the stylet 150' can provide navigation vectors in a plurality of orientations relative to the long axis 1501 of the stylet 150'. Navigation vectors can include a first navigation vector 2030, a second navigation vector 2032, and a third navigation vector 2034. The first navigation vector 2030 can be on the plane of the page and form an angle and be pointed towards a proximal end of the stylet 150'. The second navigation vector 2032 can be substantially parallel to the plane of the page and be pointed towards the distal end of the stylet 150'. The third navigation vector 2034 can extend out of the plane of the page and also have an angle towards the proximal end of the stylet 150.

Figure 91A:
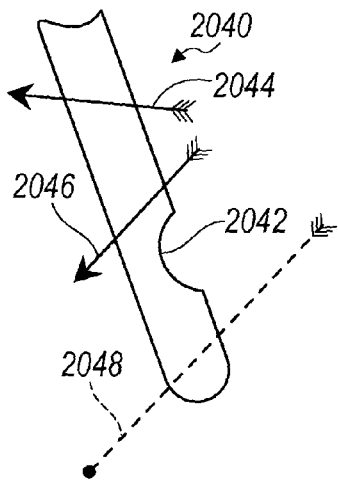
FIG. 91A is a plan detail view of an instrument with a selected tracking device.
Figure 91B:
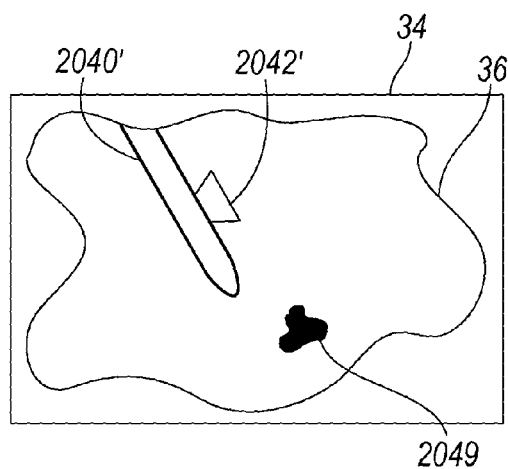
FIG. 91B is a display device view of an instrument and image data.

The various navigation devices can also be positioned on or with other instruments, such as a biopsy needle 2040, illustrated in FIGS. 91A and 91B. A biopsy needle can include an appropriate biopsy needle such as the biopsy needle sold by Medtronic Navigation, Inc. and generally understood in the art. Briefly, the biopsy needle 2040 can include a resection or biopsy port 2042. As is understood by one skilled in the art, a biopsy port 2042 allows for tissue to be drawn in the biopsy needle 2042 for testing and various biopsy procedures.

By positioning the tracking devices on the biopsy needle 2040, a plurality of navigation vectors 2044, 2046, and 2048 can be used to identify the location of the biopsy needle port 2042 on the display device 2034. The location information, again, can include six degrees of freedom information. Thus, complete three-dimensional location information regarding the resection port 2042 can be determined. In knowing the location of the biopsy port 2042, the user 614 can be ensured that the appropriate tissue is being biopsied from within the patient 14.

With reference to FIG. 91B, the display 34 can illustrate image data 36 of the patient 14. The image data 36 can include information, such as of a portion of the patient 14 to be resected 2049. Icons can be displayed on the display device 34 representing the instrument 2040 with an instrument icon 2040'. As discussed above, a window, such as a biopsy window 2042 can be formed in the instrument 2040. The biopsy window 2042 generally includes only a selected cone of resection into which material can be drawn for biopsy. Accordingly, the direction of the cone can be displayed on the display device 34 with a biopsy cone icon 2042'. Because the cone generally extends at only a single angle relative to the instrument 2040, knowing six degrees of freedom information regarding the location of the biopsy window 2042 can assist the user 614 by illustrating the location of the biopsy cone 2042' on the display 34. In this way, the user 614 can view and confirm that the resection cone is aimed or at the tissue to be resected.

In a further example, as illustrated in FIG. 92, an instrument 2050 can be positioned in a heart 2052 of the patient 14. The instrument 2050 can include an ablation or sensing portion 2054 that is positioned at a selected location on the instrument 2050. Again, by providing the plurality of tracking devices on the instrument 2050, the three-dimension location of the ablation portion 2054 can be determined and illustrated on the display device 34 relative to the image data. Alternatively, only the location can be illustrated without reference to other image date just for reference of the location of the instrument 2050. Accordingly, the user 614 can understand the orientation of the instrument 2050 for ensuring an appropriate location of the ablation portion 2054 within the heart 2052.

It is understood that image data and icons representing instruments can be displayed on the display device 34, thus FIG. 92 can be understood to represent image data and icons on the display device 34. The catheter or instrument 2050 can be used to guide a needle or other instrument, such as an ablation needle 2056, through the catheter 2050. The ablation needle 2056 can include an ablation end 2058 which extends through an opening 2060 in the catheter 2050. The opening 2060 in the catheter 2050 can be a single opening, similar to the biopsy window 2042 of the biopsy instrument 2040. The opening 2060 can extend or allow the needle 2058 to extend substantially in only a single direction or position from the catheter 2050. Accordingly, again knowing six degree of freedom information regarding the location of the opening 2060, can assist the user in understanding the location of the ablation portion 2058 within the patient 14. It will be understood that image data of the heart 2052 can be displayed on the display device 34 as can icons representing the location of the various portions, including the ablation needle 2056, the ablation portion 2058, and the opening 2060.

The various tracking devices, as discussed above, can be positioned at a plurality of locations along an instrument, such as an instrument 2070, as illustrated in FIG. 93A. The instrument 2070 can be a selected instrument that has a length and may be flexible or moveable along its length, such as the instrument 2050 illustrated in FIG. 92 including a catheter, ablation probes, or the like. The instrument 2070 can be moved through the patient 14 or any other appropriate subject and can achieve multiple configurations and orientations based upon a movement, either intended or unintended. Therefore, the instrument 2070 can move to a second orientation or location 2070', as illustrated in FIG. 93B.

Positioned along the instrument can be a plurality of tracking devices including a first tracking device 2072, a second tracking device 2074, a third tracking device 2076, and a fourth tracking device 2078. The tracking devices can include the tracking devices discussed above including the first winding 1912 and the second winding 1942. It will be understood that a number of windings or portions can be included for each of the tracking devices and that groups of windings, including three windings, can be used to form each of the tracking devices 2072-2078. As illustrated in FIG. 87, each of the tracking device portions can include a navigation vector that is angled relative to one another, which can allow for the determination of six degrees of freedom. Accordingly, each tracking device can be formed by a plurality of windings that form a tracking device coil having a navigation vector defined through each of the windings.

By providing a plurality of tracking devices 2072-2078 on the single instrument 2070, a location and a relative orientation vector 2072v-2078v can be determined at each of the locations of the tracking devices 2072-2078. The location can be determined with the tracking system. Also, the relative orientation of the various tracking devices 2072-2078, relative to the others or to an initial orientation, can be illustrated. This can allow for a substantially discreet and complex view of a location of different portions of the instrument 2070 within the patient 14.

As illustrated in FIG. 93A, each of the relative orientation vectors 2072v-2078v point generally towards one side of the instrument 2070. It will be understood that the relative orientation vectors 2072v-2078v can relate to a determined orientation based upon the individual navigation vectors of the portions of the tracking devices 2072-2078. Accordingly, it will be understood that each of the tracking devices 2072-2078 can each include a plurality of navigation vectors and the relative orientation vector $2072v$-$2078v$ is based upon the determination of each of the plurality of navigation vectors.

At a selected time, which can be after the time for which the location information is determined and illustrated in FIG. 93A, the instrument can change to a different configuration as illustrated as instrument 2070' illustrated in FIG. 93B. The instrument 2070' still includes each of the tracking devices 2072-2078 and each of the tracking devices can include a relative orientation vector $2072v'$-$2078v'$. Each of the relative orientation vectors $2070v'$-$2078v'$ can be used to determine a new or different location of the instrument 2070 and this information can be used to determine if the instrument 2070 has moved to a selected configuration or has moved from a selected configuration to an unselected configuration. Regardless, the plurality of tracking devices can be provided to determine detailed information for the user 614 regarding the location information for several portions of the instrument 2070.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A method of providing an instrument for a procedure, comprising:
    providing a tracking device configured to be in communication with a navigation system, wherein the instrument extending along a longitudinal axis, by:
        providing a first tracking portion having a first length wrapped around the longitudinal axis for a first distance and includes a plurality of turns wherein each turn of the plurality of turns is formed at a first winding angle relative to the longitudinal axis to define a first wrap axis; and
        providing a second tracking portion having a second length wrapped around the longitudinal axis for a second distance and includes a plurality of turns, wherein each turn of the plurality of turns is formed at a second winding angle relative to the longitudinal axis to define a second wrap axis;
    providing the first tracking portion and the second tracking portion configured to be in communication with the navigation system;
    providing the first tracking portion and the second tacking portion on the instrument to generate all of a first navigation vector and a second navigation vector to intersect near a single point in a single plane.

2. The method of claim 1, further comprising:
    providing the first tracking portion formed of a first material; and
    providing the second tracking portion to be formed of a second material.

3. The method of claim 2, wherein the first material and the second material are the same material and a conductive material;
    and the first plurality of turns and the second plurality of turns are formed around a wall of the instrument.

4. The method of claim 1, further comprising:
    providing the first tracking portion spaced a distance from the second tracking portion along the longitudinal axis.

5. The method of claim 1, further comprising:
    providing the first tracking portion to be formed between the second tracking portion and an outer wall of the instrument.

6. The method of claim 1, further comprising:
    determining with the navigation system:
        a first navigation vector of the first tracking portion and a second navigation vector of the second tracking portion; and
        a location information for the tracking device based on the determined first navigation vector and the determined second navigation vector.

7. The method of claim 1, further comprising:
    providing a third tracking portion wrapped a third length around the longitudinal axis for a third length, wherein the wrapped third length includes a plurality of turns and each turn is formed at a third winding angle relative to the longitudinal axis.

8. The method of claim 1, further comprising:
    providing a plurality of the tracking devices; and
    providing the instrument to be flexible;
    wherein a first tracking device of the plurality of tracking devices is configured to track a first portion of the instrument and a second tracking device of the plurality of the plurality of tracking devices is configured to track a second portion of the instrument.

9. An instrument, comprising:
    a tracking device formed around a longitudinal axis of the instrument, including:
        a first tracking portion formed of a first elongated member having a wrapped first length around the longitudinal axis for a first distance, wherein the wrapped first length includes a plurality of turns and each turn of the plurality of turns of the first elongated member is formed at a first winding angle relative to the longitudinal axis to define a first wrap axis; and
        a second tracking portion formed of a second elongated member having a wrapped second length around the longitudinal axis for a second distance, wherein the wrapped second length includes a plurality of turns and each turn of the plurality of turns of the second elongated member is formed at a second winding angle relative to the longitudinal axis to define a second wrap axis;
        a third tracking portion formed of a third elongated member having a wrapped third length around the longitudinal axis for a third distance, wherein the wrapped third length includes a plurality of turns and each turn of the plurality of turns of the third elongated member is formed at a third winding angle relative to the longitudinal axis to define a third wrap axis;
    wherein the first tracking portion is configured to define a first navigation vector, the second tracking portion is configured to define a second navigation vector, and the third tracking portion is configured to define a third navigation vector.

10. The instrument of claim 9, wherein the first tracking portion is formed of a first material and the second tracking portion is formed of a second material.

11. The instrument of claim 9, wherein the first tracking portion is spaced a distance along the longitudinal axis apart from the second tracking portion.

12. The instrument of claim 9, wherein the first tracking portion is positioned between the second tracking portion and an exterior wall of the instrument.

13. The system of claim 9, wherein at least one of the first winding angle and the second winding angle is about 40 degrees to about 50 degrees.

14. The system of claim 13, further comprising:
a tracking system localizer having a system to induce a voltage in the first tracking portion and the second tracking portion; and
a processor to receive a signal from the first tracking portion, the second tracking portion, and the third tracking portion to compute a location of the first tracking portion, the second tracking portion, and the third tracking portion based on the first navigation vector, the second navigation vector, and the third navigation vector;
wherein a representation of at least a portion of the instrument is operable to be superimposed on an image at the computed location.

15. The system of claim 9, further comprising:
an elongated member forms the instrument extending along the longitudinal axis.

16. The instrument of claim 9, wherein the first winding angle is a non-zero angle relative to the longitudinal axis.

17. A trackable instrument, comprising:
an instrument having at least an elongated portion extending along a longitudinal axis;
a tracking device, including:
a first tracking portion of a first material having a first plurality of turns around the elongated portion, wherein each turn of the first plurality of turns is formed at a first winding angle relative to the longitudinal axis;
a second tracking portion of a second material having a second plurality of turns around the elongated portion, wherein each turn of the second plurality of turns is formed at a second winding angle relative to the longitudinal axis, wherein the second winding angle is different from the first winding angle; and
a third tracking portion of a third material having a third plurality of turns around the elongated portion;
wherein the first tracking portion defines a first navigation vector and the second tracking portion defines a second navigation vector to determine an orientation of at least a first section of the elongated portion;
wherein each turn of the third plurality of turns is formed at a third winding angle relative to the longitudinal axis.

18. The trackable instrument of claim 17, wherein the instrument includes a working portion configured to act at a selected angle relative to the longitudinal axis.

19. The trackable instrument of claim 18, wherein the working portion is selected from a group consisting of an opening, an ablation needle, a biopsy window, an ablation portion, or a sensing portion.

20. The trackable instrument of claim 18, further comprising:
a display device configured to display an icon representative of at least one of an orientation or position of the working portion illustrated relative to an environment in which the elongated portion is placed.

21. The trackable instrument of claim 20, further comprising:
a tracking system localizer having a system to induce a voltage in the first tracking portion and the second tracking portion to determine at least one of a position or an orientation of the first navigation vector and the second navigation vector for display with the display device.

22. The trackable instrument of claim 17, wherein the first material, the second material, and the third material are the same material and a conductive material.

* * * * *